US008158859B2

(12) United States Patent
Allen et al.

(10) Patent No.: US 8,158,859 B2
(45) Date of Patent: Apr. 17, 2012

(54) DROUGHT TOLERANT PLANTS AND RELATED CONSTRUCTS AND METHODS INVOLVING GENE ENCODING FERROCHELATASES

(75) Inventors: Stephen M. Allen, Wilmington, DE (US); Stanley Luck, Wilmington, DE (US); Jeffrey Mullen, Medina, MN (US); Hajime Sakai, Newark, DE (US); Sobhana Sivasankar, Urbandale, IA (US); Scott V. Tingey, Wilmington, DE (US); Robert Wayne Williams, Hockessin, DE (US)

(73) Assignees: E I du Pont de Nemours and Company, Wilmington, DE (US); Pioneer Hi Bred International Inc, Johnston, IA (US)

( * ) Notice: Subject to any disclaimer, the term of this patent is extended or adjusted under 35 U.S.C. 154(b) by 0 days.

(21) Appl. No.: 12/887,724

(22) Filed: Sep. 22, 2010

(65) Prior Publication Data

US 2011/0010798 A1 Jan. 13, 2011

Related U.S. Application Data

(62) Division of application No. 12/326,206, filed on Dec. 2, 2008, now Pat. No. 7,812,223.

(60) Provisional application No. 60/991,859, filed on Dec. 3, 2007.

(51) Int. Cl.
*A01H 1/00* (2006.01)
*C07H 21/04* (2006.01)
*C12N 15/00* (2006.01)
*C12N 15/29* (2006.01)

(52) U.S. Cl. ........ 800/295; 435/6.1; 435/69.1; 435/183; 435/468; 435/410; 435/320.1; 536/23.6; 800/278

(58) Field of Classification Search .................. 435/6.1, 435/69.1, 183, 468, 419, 320.1; 530/370; 536/23.6; 800/278, 295, 320.1, 312
See application file for complete search history.

(56) References Cited

U.S. PATENT DOCUMENTS

| | | | | |
|---|---|---|---|---|
| 7,625,738 | B1 | 12/2009 | CaJacob et al. | |
| 2004/0010815 | A1 | 1/2004 | Lange et al. | |
| 2004/0031072 | A1 | 2/2004 | LaRosa et al. | |
| 2004/0034888 | A1 | 2/2004 | Liu et al. | |
| 2004/0123343 | A1 * | 6/2004 | La Rosa et al. | 800/278 |
| 2006/0150283 | A1 | 7/2006 | Alexandrov et al. | |

FOREIGN PATENT DOCUMENTS

| | | |
|---|---|---|
| JP | 2001190168 | 7/2001 |
| JP | 2005185101 | 7/2005 |
| WO | 2007/030001 A1 | 3/2007 |

OTHER PUBLICATIONS

Jagdish P. Singh et al., Investigatin of the Effects of Atmospheric Conditions on the Quantification of Metal Hydrides Using Laser Induced Breakdown Spectroscopy, Society for Applied Spectroscopy, Jun. 1, 1996, pp. 764-773, vol. 50, No. 6.
Database EMBL, Accession No. D26105, Jan. 6, 1994, XP002517106.
Database EMBL, Accession No. D26106, Jan. 6, 1994, XP002517107.
Cushman et al., Genomic Approaches to Plant Stress Tolerance. Curr. Opin. Plant Biol., vol. 3(2), p. 117-124, 2000.
Bray et al., Molecular Responses to Water Deficit. Plant Physiol., vol, 103, p. 1035-1040, 1993.
Zhu et al., Molecular Aspects of Osmotic Stress in Plants. Critical Reviews in Plant Sciences, vol. 16(3), p. 253-277, 1997.
Thomashow, Plant Cold Acclimation: Freezing Tolerance Genes and Regulatory Mechanisms. Annu Rev Plant Physiol. Plant Mol. Biol., vol. 50, p. 571-599, 1999.
Xiong et al., Molecular and Genetic Aspects of Plant Responses to Osmotic Stress. Plant, Cell and Environment, vol. 25, p. 131-139, 2002.
Weigel et al., Activation Tagging in *Arabidopsis*. Plant Physiol., vol. 122, p. 1003-1013, 2000.
National Center for Biotechnology Information General Identifier No. 511080, Accession No. X73417, Apr. 18, 2005, Smith et al., Isolation of a cDNA Encoding Chloroplast Ferrochelatase from *Arabidopsis thaliana* by Functional Complementation of a Yeast Mutant.
National Center for Biotechnology Information General Identifier No. 511081, Accession No. CAA51819, Apr. 18, 2005, Smith et al., Isolation of a cDNA Encoding Chloroplast Ferrochelatase from *Arabidopsis thaliana* by Functional Complementation of a Yeast Mutant.
National Center for Biotechnology Information General Identifier No. 30684569, Accession No. NM_128592, May 22, 2008, *Arabidopsis thaliana* Ferrochelatase II mRNA, Complete cds.
National Center for Biotechnology Information General Identifier No. 15227742, Accession No. NP_180598, May 22, 2008, Ferrochelatase II (*Arabidopsis thaliana*).
National Center for Biotechnology Information General Identifier No. 2623989, Accession No. Y13156, Apr. 18, 2005, Chow et al., Ferrochelatase is Encoded by two Genes in *Arabidopsis*.
National Center for Biotechnology Information General Identifier No. 2623990, Accession No. CAA73614, Apr. 18, 2005, Chow et al., Ferrochetatase is Encoded by Two Genes in *Arabidopsis*.
National Center for Biotechnology Information General Identifier No. 2460251, Accession No. AAB71887, Oct. 2, 1997, Hansson et al., Six Barley Genes Encoding Enzymes Involved in Chlorophyll and Heme Synthesis: Chromosomal Locations and Genomic Sequence of the Ferrochelatase Gene.
National Center for Biotechnology Information General Identifier No. 113631036, Accession No. BAF24717, May 19, 2007, Matsumoto et al., The Rice Annotation Project Database (RAP-DB): Hub for Oryza Sativa ssp.Japonica Genome Information.
National Center for Biotechnology Information General Identifier No. 147818793, Accession No. CAN67281, Feb. 5, 2008, Velasco et al., A High Quality Draft Consensus Sequence of the Genome of a Heterozygous Grapevine Variety.

(Continued)

*Primary Examiner* — Phuong Bui

(57) ABSTRACT

Isolated polynucleotides and polypeptides and recombinant DNA constructs useful for conferring drought tolerance, compositions (such as plants or seeds) comprising these recombinant DNA constructs, and methods utilizing these recombinant DNA constructs. The recombinant DNA construct comprises a polynucleotide operably linked to a promoter that is functional in a plant, wherein said polynucleotide encodes a ferrochelatase.

9 Claims, 27 Drawing Sheets

OTHER PUBLICATIONS

National Center for Biotechnology Information General Identifier No. 115463419, Accession No. NP_001055309, Feb. 14, 2008, Ohyanagi et al., The Rice Annotation Project Database (RAP-DB): Hub for Oryza Sativa.

National Center for Biotechnology Information General Identifier No. 12082085, Accession No. BAB20760, Feb. 14, 2002, Suzuki et al., Two of Ferrochelatase in Photosynthetic and Nonphotosynthetic Tissues of Cucumber. Their Difference in Phylogeny, Gene Expression and Localization.

National Center for Biotechnology Information General Identifier No. 15147828, Accession No. CAC50871, Aug. 17, 2005, Papenbrock et al., Impaired Expression of the Plastidic Ferrochelatase by Antisense RNA Synthesis Leads to a Necrotic Phenotype of Transformed Tobacco Plants.

National Center for Biotechnology Information General Identifier No. 1708186, Accession No. P54225, Jan. 20, 2009, Kaneko et al., Sequence Analysis of the Genome of the Unicellular Cyanobacterium *Synechocystis* sp. Strain PCC6803. I. Sequence Features in the 1 Mb Region from Map Positions 64% to 92% of the Genome.

Suzuki et al., Two Types of Ferrochelatase in Photosynthetic and Nonphotosynthetic Tissues of Cucumber, The Journal of Biological Chemistry, vol. 277, p. 4731-4737, 2002.

Smith et al., Isolation of a cDNA Encoding Chloroplast Ferrochelatase from *Arabidopsis thaliana* by Functional Complementation of a Yeast Mutant, The Journal of Biological Chemistry, vol. 269, p. 13405-13413, 1994.

Chow et al., Two Different Genes Encode Ferrochelatase in *Arabidopsis*: Mapping, Expression and Subcellular Targeting of the Precursor Proteins, The Plant Journal, vol. 15, p. 531-541, 1998.

Miyamoto et al., Nucleotide Sequences of cDNA Clones Encoding Ferrochelatase from Barley and Cucumber, Plant Physiology, vol. 105, p. 769-770, 1994.

Chow et al., A Single Precursor Protein for Ferrochelatase—I from *Arabidopsis* is Imported in Vitro into both Chloroplasts and Mitchondria, The Journal of Biological Chemistry, vol. 272, p. 27565-27571, 1997.

The Future of Agricultural Biotechnology, Environmental Effects of Transgenic Plants: The Scope and Adequacy of Regulation, Board on Agriculture and Natural Resources (BANR); Chapter 7, 2002.

Shinozaki et al., Gene Expression and Signal Transduction in Water-Stress Response. Plant Physiology, vol. 115, p. 327-334, 1997.

* cited by examiner

Multiple Alignment of Ferrochelatase-I Proteins

Multiple Alignment of Ferrochelatase-I Proteins

Multiple Alignment of Ferrochelatase-I Proteins

FIG. 11
Percent Sequence Identities Between Ferrochelatase-I Proteins

Percent Identity (upper triangle) / Divergence (lower triangle)

| | 1 | 2 | 3 | 4 | 5 | 6 | 7 | 8 | 9 | 10 | 11 | 12 | | |
|---|---|---|---|---|---|---|---|---|---|---|---|---|---|---|
| 1 | | 64.6 | 83.3 | 62.0 | 62.2 | 63.9 | 66.5 | 63.1 | 63.9 | 63.9 | 63.9 | 67.6 | 1 | SEQ ID NO-2.pro |
| 2 | 44.6 | | 63.5 | 64.7 | 63.6 | 65.8 | 68.8 | 65.8 | 64.0 | 64.3 | 65.8 | 72.6 | 2 | SEQ ID NO-4.pro |
| 3 | 14.6 | 47.3 | | 61.2 | 59.9 | 61.8 | 64.2 | 61.6 | 62.7 | 62.7 | 61.8 | 65.8 | 3 | SEQ ID NO-6.pro |
| 4 | 43.7 | 43.3 | 47.2 | | 87.6 | 84.0 | 64.1 | 67.3 | 79.6 | 79.4 | 84.0 | 67.2 | 4 | SEQ ID NO-8.pro |
| 5 | 46.9 | 44.9 | 50.6 | 12.8 | | 81.7 | 64.0 | 67.8 | 77.1 | 77.5 | 81.7 | 67.6 | 5 | SEQ ID NO-10.pro |
| 6 | 42.5 | 41.5 | 45.8 | 16.8 | 19.4 | | 64.4 | 69.5 | 84.6 | 84.9 | 100.0 | 70.3 | 6 | SEQ ID NO-12.pro |
| 7 | 42.5 | 36.3 | 44.5 | 46.5 | 47.5 | 45.4 | | 65.1 | 63.4 | 63.8 | 64.4 | 74.2 | 7 | SEQ ID NO-14.pro |
| 8 | 42.7 | 43.7 | 45.6 | 37.4 | 39.6 | 35.0 | 43.5 | | 68.2 | 68.4 | 69.5 | 67.2 | 8 | SEQ ID NO-16.pro |
| 9 | 43.8 | 44.2 | 45.0 | 20.6 | 24.5 | 14.2 | 48.1 | 36.7 | | 98.3 | 84.6 | 69.0 | 9 | SEQ ID NO-18.pro |
| 10 | 43.8 | 44.6 | 45.0 | 20.9 | 23.9 | 14.0 | 47.3 | 36.4 | 1.7 | | 84.9 | 69.0 | 10 | SEQ ID NO-48.pro |
| 11 | 42.5 | 41.5 | 45.8 | 16.8 | 19.4 | 0.0 | 45.4 | 35.0 | 14.2 | 14.0 | | 70.3 | 11 | SEQ ID NO-49.pro |
| 12 | 36.2 | 31.2 | 38.5 | 38.0 | 39.5 | 35.9 | 27.6 | 36.0 | 37.2 | 36.8 | 35.9 | | 12 | SEQ ID NO-50.pro |
| | 1 | 2 | 3 | 4 | 5 | 6 | 7 | 8 | 9 | 10 | 11 | 12 | | |

Multiple Alignment of Ferrochelatase-II Proteins

Multiple Alignment of Ferrochelatase-II Proteins

Multiple Alignment of Ferrochelatase-II Proteins

FIG. 13

Percent Sequence Identities Between Ferrochelatase-II Proteins

Percent Identity (upper triangle); Divergence (lower triangle)

| | 1 | 2 | 3 | 4 | 5 | 6 | 7 | 8 | 9 | 10 | | |
|---|---|---|---|---|---|---|---|---|---|---|---|---|
| 1 | | 98.8 | 74.5 | 73.6 | 72.9 | 72.5 | 73.4 | 72.7 | 75.7 | 57.4 | 1 | SEQ ID NO-20.pro |
| 2 | 0.6 | | 73.1 | 72.4 | 71.6 | 71.2 | 72.2 | 71.6 | 73.8 | 56.3 | 2 | SEQ ID NO-22.pro |
| 3 | 27.5 | 28.5 | | 76.2 | 75.0 | 75.0 | 77.4 | 78.6 | 78.3 | 50.9 | 3 | SEQ ID NO-24.pro |
| 4 | 29.8 | 30.8 | 23.5 | | 82.7 | 83.1 | 90.5 | 74.6 | 77.3 | 56.1 | 4 | SEQ ID NO-26.pro |
| 5 | 32.3 | 33.3 | 26.9 | 19.2 | | 98.7 | 82.9 | 72.2 | 75.7 | 56.8 | 5 | SEQ ID NO-28.pro |
| 6 | 33.5 | 34.5 | 26.9 | 18.7 | 1.3 | | 83.3 | 72.4 | 75.9 | 56.6 | 6 | SEQ ID NO-30.pro |
| 7 | 31.7 | 32.7 | 24.9 | 9.5 | 19.5 | 19.0 | | 75.7 | 77.9 | 56.1 | 7 | SEQ ID NO-51.pro |
| 8 | 31.7 | 32.1 | 23.0 | 29.7 | 34.2 | 33.3 | 28.3 | | 77.1 | 55.3 | 8 | SEQ ID NO-52.pro |
| 9 | 25.4 | 26.3 | 19.3 | 24.7 | 27.0 | 26.7 | 24.4 | 25.3 | | 53.2 | 9 | SEQ ID NO-53.pro |
| 10 | 54.6 | 54.8 | 59.9 | 57.7 | 56.7 | 57.2 | 57.7 | 58.8 | 57.2 | | 10 | SEQ ID NO-54.pro |
| | 1 | 2 | 3 | 4 | 5 | 6 | 7 | 8 | 9 | 10 | | |

FIG. 14A

Evaluation of Individual Gaspe Flint Derived Maize Lines Transformed with PHP31419*

| Treatment | Event name | % area chg_start chronic - acute2 | % area chg_start chronic - end chronic | % area chg_start chronic - harvest | % area chg_start chronic - recovery 24hr | fv/fm_acute1 | fv/fm_acute2 |
|---|---|---|---|---|---|---|---|
| Reduce Water | EA2392.498.1.2 | ns | ns | ns | ns | ns | ns |
| Reduce Water | EA2392.498.1.3 | ns | ns | ns | ns | 0.089 | ns |
| Reduce Water | EA2392.498.1.5 | ns | ns | ns | ns | ns | ns |
| Reduce Water | EA2392.498.1.6 | 0.034 | 0.072 | 0.0004 | 0.079 | 0.014 | 0.003 |
| Well Water | EA2392.498.1.2 | ns | 0.037 | ns | 0.085 | ns | 0.030 |
| Well Water | EA2392.498.1.3 | ns | ns | 0.093 | (0.032) | ns | ns |
| Well Water | EA2392.498.1.5 | ns | 0.083 | ns | ns | 0.016 | ns |
| Well Water | EA2392.498.1.6 | 0.051 | ns | ns | ns | 0.001 | ns |

* Significant positive effect has P-value less than or equal to 0.1; significant negative effect is in parenthesis; "ns" when difference not significant

FIG. 14B

Evaluation of Individual Gaspe Flint Derived Maize Lines Transformed with PHP31419*

| Treatment | Event name | leaf rolling_ harvest | leaf rolling_ recovery 24hr | psii_acute1 | psii_acute2 | sgr - r2 > 0.9 | shoot dry weight | shoot fresh weight |
|---|---|---|---|---|---|---|---|---|
| Reduce Water | EA2392.498.1.2 | 0.065 | ns | ns | ns | 0.046 | (0.028) | ns |
| Reduce Water | EA2392.498.1.3 | ns | 0.019 | 0.024 | ns | ns | ns | (0.037) |
| Reduce Water | EA2392.498.1.5 | ns | ns | ns | ns | ns | ns | ns |
| Reduce Water | EA2392.498.1.6 | 0.068 | 0.011 | 0.072 | 0.003 | 0.015 | ns | 0.009 |
| Well Water | EA2392.498.1.2 | ns | 0.083 | ns | ns | ns | ns | ns |
| Well Water | EA2392.498.1.3 | ns | ns | ns | ns | ns | (0.047) | (0.031) |
| Well Water | EA2392.498.1.5 | ns | ns | 0.022 | ns | ns | ns | ns |
| Well Water | EA2392.498.1.6 | ns | ns | 0.007 | ns | ns | ns | ns |

* Significant positive effect has P-value less than or equal to 0.1; significant negative effect is in parenthesis; "ns" when difference not significant

FIG. 15

Summary Evaluation of Gaspe Flint Derived Maize Lines Transformed with PHP31419*

| Treatment | % area chg_start chronic - acute2 | % area chg_start chronic - end chronic | % area chg_start chronic - harvest | % area chg_start chronic - recovery 24hr | fv/fm_ acute1 | fv/fm_ acute2 | leaf rolling_ harvest | leaf rolling_ recovery 24hr | psii_ acute1 | psii_ acute2 | sgr - r2 > 0.9 | shoot dry weight | shoot fresh weight |
|---|---|---|---|---|---|---|---|---|---|---|---|---|---|
| Reduce Water | 0.093 | ns | 0.043 | ns | 0.054 | ns | 0.059 | 0.001 | 0.015 | 0.069 | 0.008 | (0.025) | ns |
| Well Water | 0.078 | ns | ns | ns | ns | ns | ns | ns | 0.011 | ns | ns | ns | ns |

* Significant positive effect has P-value less than or equal to 0.1; significant negative effect is in parenthesis; "ns" when difference not significant

FIG. 16A

Evaluation of Individual Gaspe Flint Derived Maize Lines Transformed with PHP33089*

| Treatment | Event name | % area chg_ start chronic - end chronic | % area chg_ start chronic - end severe | % area chg_ start chronic - recovery 48hr | fv/fm_ end severe | fv/fm_ recovery 48hr | fv/fm_ start severe |
|---|---|---|---|---|---|---|---|
| Reduce Water | EA2534.088.2.2 | ns | (0.076) | ns | (0.074) | ns | ns |
| Reduce Water | EA2534.088.2.4 | 0.095 | Ns | ns | (0.025) | 0.041 | ns |
| Reduce Water | EA2534.088.2.5 | 0.068 | 0.063 | ns | 0.065 | ns | 0.036 |
| Reduce Water | EA2534.088.2.8 | ns | (0.012) | (0.032) | ns | ns | ns |
| Well Water | EA2534.088.2.2 | ns | Ns | ns | ns | ns | ns |
| Well Water | EA2534.088.2.4 | 0.030 | Ns | ns | ns | ns | ns |
| Well Water | EA2534.088.2.5 | ns | Ns | ns | 0.01 | ns | ns |
| Well Water | EA2534.088.2.8 | ns | Ns | ns | ns | (0.012) | ns |

* Significant positive effect has P-value less than or equal to 0.1; significant negative effect is in parenthesis; "ns" when difference not significant

FIG. 16B

Evaluation of Individual Gaspe Flint Derived Maize Lines Transformed with PHP33089*

| Treatment | Event name | leaf rolling_ recovery 48hr | Psii_ end severe | psii_ recovery 48hr | psii_ start severe | sgr - r2 > 0.9 | shoot dry weight | shoot fresh weight |
|---|---|---|---|---|---|---|---|---|
| Reduce Water | EA2534.088.2.2 | ns | (0.016) | ns | ns | ns | ns | ns |
| Reduce Water | EA2534.088.2.4 | ns | ns | 0.043 | ns | ns | ns | ns |
| Reduce Water | EA2534.088.2.5 | ns | 0.008 | ns | 0.022 | ns | ns | ns |
| Reduce Water | EA2534.088.2.8 | ns | (0.011) | ns | ns | ns | 0.005 | ns |
| Well Water | EA2534.088.2.2 | ns | ns | ns | 0.058 | ns | ns | ns |
| Well Water | EA2534.088.2.4 | 0.072 | ns | (0.017) | (0.060) | ns | ns | ns |
| Well Water | EA2534.088.2.5 | (0.051) | 0.006 | ns | (0.029) | ns | ns | ns |
| Well Water | EA2534.088.2.8 | ns | ns | (0.048) | ns | ns | ns | ns |

* Significant positive effect has P-value less than or equal to 0.1; significant negative effect is in parenthesis; "ns" when difference not significant

FIG. 17

Summary Evaluation of Gaspe Flint Derived Maize Lines Transformed with PHP33089*

| Treatment | % area chg_ start chronic - end chronic | % area chg_ start chronic - end severe | % area chg_ start chronic - recovery48hr | fv/fm_ end severe | fv/fm_ recovery 48hr | fv/fm_ start severe | leaf rolling_ recovery 48hr | psii_ end severe | psii_ recovery 48hr | psii_ start severe | sgr - r2 > 0.9 | shoot dry weight | shoot fresh weight |
|---|---|---|---|---|---|---|---|---|---|---|---|---|---|
| Reduce Water | ns | ns | ns | ns | ns | ns | ns | ns | ns | ns | ns | 0.027 | ns |
| Well Water | 0.076 | ns | ns | ns | (0.032) | ns | ns | ns | (0.087) | ns | ns | ns | ns |

* Significant positive effect has P-value less than or equal to 0.1; significant negative effect is in parenthesis; "ns" when difference not significant

FIG. 18A

Evaluation of Individual Gaspe Flint Derived Maize Lines Transformed with PHP30829*

| Treatment | Event name | % area chg_start chronic - end chronic | % area chg_start chronic - harvest | % area chg_start chronic - recovery 24hr | % area chg_start chronic - recovery 48hr | fv/fm_acute1 | fv/fm_acute2 |
|---|---|---|---|---|---|---|---|
| Reduce Water | EA2391.472.1.10 | (0.013) | (0.002) | ns | (0.002) | ns | ns |
| Reduce Water | EA2391.472.1.2 | ns | ns | ns | ns | ns | (0.028) |
| Reduce Water | EA2391.472.1.3 | (0.036) | ns | ns | ns | ns | ns |
| Reduce Water | EA2391.472.1.4 | ns | ns | ns | ns | ns | 0.0022 |
| Well Water | EA2391.472.1.10 | ns | 0.001 | ns | ns | (0.007) | ns |
| Well Water | EA2391.472.1.2 | ns | 0.058 | ns | ns | 0.008 | 0.001 |
| Well Water | EA2391.472.1.3 | ns | 0.059 | ns | ns | ns | ns |
| Well Water | EA2391.472.1.4 | ns | ns | ns | ns | 0.006 | 0.095 |

* Significant positive effect has P-value less than or equal to 0.1; significant negative effect is in parenthesis; "ns" when difference not significant

FIG. 18B

Evaluation of Individual Gaspe Flint Derived Maize Lines Transformed with PHP30829*

| Treatment | Event name | leaf rolling_ recovery 24hr | leaf rolling_ recovery 48hr | psii_acute1 | psii_acute2 | sgr - r2 > 0.9 | shoot dry weight | shoot fresh weight |
|---|---|---|---|---|---|---|---|---|
| Reduce Water | EA2391.472.1.10 | ns | (0.012) | ns | ns | (0.025) | ns | ns |
| Reduce Water | EA2391.472.1.2 | ns | ns | ns | (0.021) | ns | ns | ns |
| Reduce Water | EA2391.472.1.3 | ns | (0.096) | ns | ns | ns | (0.079) | (0.056) |
| Reduce Water | EA2391.472.1.4 | (0.081) | ns | ns | 0.012 | (0.058) | ns | ns |
| Well Water | EA2391.472.1.10 | ns | ns | (0.018) | (0.071) | 0.034 | ns | 0.012 |
| Well Water | EA2391.472.1.2 | ns | 0.069 | 0.026 | 0.016 | ns | (0.046) | ns |
| Well Water | EA2391.472.1.3 | 0.091 | ns | ns | ns | ns | ns | ns |
| Well Water | EA2391.472.1.4 | ns | ns | 0.04 | ns | ns | ns | ns |

* Significant positive effect has P-value less than or equal to 0.1; significant negative effect is in parenthesis; "ns" when difference not significant

FIG. 19

Summary Evaluation of Gaspe Flint Derived Maize Lines Transformed with PHP30829

| Treatment | % area chg_ start chronic - end chronic | % area chg_ start chronic - harvest | % area chg_ start chronic - recovery 24hr | % area chg_ start chronic - recovery 48hr | fv/fm_ acute1 | fv/fm_ acute2 | leaf rolling_ recovery 24hr | leaf rolling_ recovery 48hr | psii_ acute1 | psii_ acute2 | sgr - r2 > 0.9 | shoot dry weight | shoot fresh weight |
|---|---|---|---|---|---|---|---|---|---|---|---|---|---|
| Reduce Water | (0.056) | ns | ns | (0.087) | ns | ns | ns | (0.087) | ns | ns | (0.056) | ns | ns |
| Well Water | 0.032 | 0.0002 | ns | ns | 0.027 | ns | ns | ns | ns | ns | 0.081 | ns | ns |

* Significant positive effect has P-value less than or equal to 0.1; significant negative effect is in parenthesis; "ns" when difference not significant

FIG. 20A

Evaluation of Individual Gaspe Flint Derived Maize Lines Transformed with PHP30745*

| Treatment | Event name | % area chg_ start chronic - end chronic | % area chg_start chronic - end severe | % area chg_start chronic - recovery 48hr | fv/fm_ end severe | fv/fm_ recovery 48hr | fv/fm_ start severe |
|---|---|---|---|---|---|---|---|
| Reduce Water | EA2392.447.1.1 | ns | ns | ns | (0.071) | 0.039 | ns |
| Reduce Water | EA2392.447.1.3 | ns | ns | ns | ns | (0.087) | ns |
| Reduce Water | EA2392.447.1.5 | ns | ns | ns | ns | ns | ns |
| Reduce Water | EA2392.447.1.9 | (0.059) | ns | ns | (0.091) | ns | 0.003 |
| Well Water | EA2392.447.1.1 | 0.003 | 0.007 | 0.007 | ns | ns | ns |
| Well Water | EA2392.447.1.3 | (0.054) | (0.037) | (0.025) | ns | (0.004) | (0.001) |
| Well Water | EA2392.447.1.5 | 0.098 | ns | ns | ns | ns | ns |
| Well Water | EA2392.447.1.9 | 0.001 | 0.002 | 0.005 | ns | ns | ns |

* Significant positive effect has P-value less than or equal to 0.1; significant negative effect is in parenthesis; "ns" when difference not significant

FIG. 20B

Evaluation of Individual Gaspe Flint Derived Maize Lines Transformed with PHP30745*

| Treatment | Event name | leaf rolling_ recovery 48hr | psii_ end severe | psii_ recovery 48hr | psii_ start severe | shoot dry weight | shoot fresh weight |
|---|---|---|---|---|---|---|---|
| Reduce Water | EA2392.447.1.1 | ns | ns | 0.01 | 0.054 | ns | 0.006 |
| Reduce Water | EA2392.447.1.3 | ns | ns | ns | ns | (0.028) | (0.081) |
| Reduce Water | EA2392.447.1.5 | ns | ns | ns | ns | ns | ns |
| Reduce Water | EA2392.447.1.9 | ns | ns | ns | 0.019 | (0.096) | (0.012) |
| Well Water | EA2392.447.1.1 | ns | ns | ns | ns | 0.051 | ns |
| Well Water | EA2392.447.1.3 | ns | ns | (0.051) | (0.0003) | 0.0012 | 0.003 |
| Well Water | EA2392.447.1.5 | ns | ns | 0.002 | ns | (0.026) | ns |
| Well Water | EA2392.447.1.9 | ns | ns | (0.014) | ns | ns | 0.066 |

* Significant positive effect has P-value less than or equal to 0.1; significant negative effect is in parenthesis; "ns" when difference not significant

FIG. 21

Summary Evaluation of Gaspe Flint Derived Maize Lines Transformed with PHP30745*

| Treatment | % area chg_ start chronic - end chronic | % area chg_ start chronic - end severe | % area chg_start chronic - recovery 48hr | fv/fm_ end severe | fv/fm_ recovery 48hr | fv/fm_ start severe | leaf rolling_ recovery 48hr | psii_ end severe | psii_ recovery 48hr | psii_ start severe | shoot dry weight | shoot fresh weight |
|---|---|---|---|---|---|---|---|---|---|---|---|---|
| Reduce Water | ns | ns | ns | ns | ns | 0.061 | ns | ns | 0.035 | 0.091 | ns | ns |
| Well Water | ns | ns | ns | 0.034 | (0.098) | ns | ns | 0.083 | ns | ns | ns | ns |

* Significant positive effect has P-value less than or equal to 0.1; significant negative effect is in parenthesis; "ns" when difference not significant

FIG. 22A

Evaluation of Individual Gaspe Flint Derived Maize Lines Transformed with PHP30761*

| Treatment | Event name | % area chg_ start chronic - end chronic | % area chg_ start chronic - end severe | % area chg_ start chronic - recovery 48hr | fv/fm_ end severe | fv/fm_ recovery 48hr | fv/fm_ start severe |
|---|---|---|---|---|---|---|---|
| Reduce Water | EA2392.441.1.1 | ns | ns | ns | ns | ns | ns |
| Reduce Water | EA2392.441.1.2 | ns | ns | ns | ns | ns | ns |
| Reduce Water | EA2392.441.1.4 | ns | ns | ns | 0.02 | 0.038 | ns |
| Reduce Water | EA2392.441.1.7 | (0.034) | (0.054) | ns | 0.047 | 0.042 | ns |
| Well Water | EA2392.441.1.1 | ns | ns | ns | ns | ns | ns |
| Well Water | EA2392.441.1.2 | ns | ns | ns | ns | ns | 0.03 |
| Well Water | EA2392.441.1.4 | (0.004) | ns | ns | 0.000 | 0.008 | 0.001 |
| Well Water | EA2392.441.1.7 | ns | ns | ns | ns | ns | ns |

* Significant positive effect has P-value less than or equal to 0.1; significant negative effect is in parenthesis; "ns" when difference not significant

FIG. 22B

Evaluation of Individual Gaspe Flint Derived Maize Lines Transformed with PHP30761*

| Treatment | Event name | leaf rolling_ recovery 48hr | psii_ end severe | psii_ recovery 48hr | psii_ start severe | sgr - r2 > 0.9 | shoot dry weight | shoot fresh weight |
|---|---|---|---|---|---|---|---|---|
| Reduce Water | EA2392.441.1.1 | ns | ns | ns | ns | ns | ns | ns |
| Reduce Water | EA2392.441.1.2 | ns | ns | ns | ns | ns | ns | ns |
| Reduce Water | EA2392.441.1.4 | 0.058 | 0.071 | 0.072 | ns | ns | ns | ns |
| Reduce Water | EA2392.441.1.7 | ns | 0.098 | 0.037 | 0.068 | ns | (0.001) | ns |
| Well Water | EA2392.441.1.1 | ns | ns | ns | ns | ns | (0.048) | ns |
| Well Water | EA2392.441.1.2 | ns | ns | ns | ns | ns | 0.1 | ns |
| Well Water | EA2392.441.1.4 | 0.001 | 0.002 | 0.000 | 0.006 | (0.0002) | (0.050) | ns |
| Well Water | EA2392.441.1.7 | ns | ns | ns | ns | ns | ns | ns |

* Significant positive effect has P-value less than or equal to 0.1; significant negative effect is in parenthesis; "ns" when difference not significant

FIG. 23

Summary Evaluation of Gaspe Flint Derived Maize Lines Transformed with PHP30761*

| Treatment | % area chg_ start chronic - end chronic | % area chg_ start chronic - end severe | % area chg_ start chronic - recovery 48hr | fv/fm_ end severe | fv/fm_ recovery 48hr | fv/fm_ start severe | leaf rolling_ recovery 48hr | psii_ end severe | psii_ recovery 48hr | psii_ start severe | sgr - r2 > 0.9 | shoot dry weight | shoot fresh weight |
|---|---|---|---|---|---|---|---|---|---|---|---|---|---|
| Reduce Water | (0.050) | ns | ns | 0.065 | 0.000 | ns | ns | ns | 0.000 | 0.024 | ns | ns | ns |
| Well Water | (0.001) | (0.063) | ns | ns | ns | ns | 0.032 | ns | ns | 0.071 | (0.002) | (0.005) | ns |

* Significant positive effect has P-value less than or equal to 0.1; significant negative effect is in parenthesis; "ns" when difference not significant

SEQUENCE LISTING

```
<160> NUMBER OF SEQ ID NOS: 63

<210> SEQ ID NO 1
<211> LENGTH: 1867
<212> TYPE: DNA
<213> ORGANISM: Arabidopsis thaliana

<400> SEQUENCE: 1

agtaatttag cttcattctc tctctctctc tctcacaatt actgatcggt tctgaaattt     60

gtagctatgc aggcaacggc tttatcatct gggttcaatc ctctaacgaa acgtaaagat    120

cacagatttc ccaggtcatg ctctcagaga aattctctgt ctttgattca atgcgatata    180

aaagagagat ctttcggaga gtctatgacg atcacgaatc gtggattgag ttttaagacg    240

aatgtgtttg agcaagctcg ttctgtgact ggagactgtt cttatgatga aacttcagca    300

aaagcacgtt ctcatgttgt tgcagaagat aagattggtg tcttgctttt gaatttaggt    360

ggtcctgaaa ctcttaacga tgttcaacct ttcttgtata atctctttgc tgatccggat    420

attataaggc ttcctagacc atttcagttt cttcaaggga ctatagctaa gtttatatct    480

gttgttcgtg ctccgaaatc taaagaaggg tatgctgcta ttggtggtgg ctctcctttg    540

cgtaaaataa ctgatgagca agcggatgct attaagatgt ctttgcaagc gaagaacatt    600

gctgctaatg tctatgttgg tatgcggtat tggtatccgt tcactgagga ggctgttcag    660

cagataaaga aggacaaaat tactagactt gttgtactgc cattgtatcc tcagtattct    720
```

atctctacaa cgggttcaag catacgcgtt ctccaagatt tattcaggaa agatccgtac 780
ctagctggag tgccggtagc tattataaag tcctggtacc aaaggcgagg ctatgtcaat 840
tctatggctg acctcattga gaaggagctt caaactttct ctgatcctaa ggaggttatg 900
atattcttca gtgcccatgg tgttccggtc agctacgtag agaatgctgg agatccgtac 960
cagaagcaga tggaagagtg tattgacttg ataatggaag agctaaaagc cagaggggtt 1020
cttaacgacc ataaattggc ataccagagt cgtgttggcc ctgttcaatg gctgaagcca 1080
tacaccgatg aggttcttgt cgaccttggt aagagtggtg ttaagagtct actagccgtt 1140
ccagtcagtt tcgtgagtga gcacattgag acacttgagg agatagacat ggagtatagg 1200
gaattagctc ttgagtcagg ggtagagaac tggggacggg tacccgcgct aggtctcaca 1260
ccatccttca tcaccgactt agctgatgca gtgatagaat cacttccttc agcagaagca 1320
atgtcaaacc caaatgcagt ggttgactca gaagatagcg agtcgtcaga tgctttcagt 1380
tacattgtca agatgttctt cggttcgatt ctggctttcg tcctacttct ctccccaaag 1440
atgttccatg cgttccggaa cctatagaat ctcgttggtt ttgtgttaag tcttttcttg 1500
gagaaatgtc ttggttaaat tcaatatata tagtccaatc tattgaagta ctagtacacc 1560
agctctaata agctgatgtg ggtaagtagt tcaatagatt ggactatgta tattaaattt 1620
gactaagaga taaactagag aatgggataa agatgagaac ggtattagaa agttctttga 1680
ggaaatttag atgtatttta aattgaagat gcatttagct ataaacatag tggctacgtt 1740
cctcttagag atgaggagag aattatattc tattattatt tggtttcttt tcttcgtttt 1800
tgtatggttt caatacttaa ttgtcaaaag tatcctataa ttttgttaaa aaaaaaaaaa 1860
aaaaaaa 1867

<210> SEQ ID NO 2
<211> LENGTH: 466
<212> TYPE: PRT
<213> ORGANISM: Arabidopsis thaliana

<400> SEQUENCE: 2

Met Gln Ala Thr Ala Leu Ser Ser Gly Phe Asn Pro Leu Thr Lys Arg
1 5 10 15

Lys Asp His Arg Phe Pro Arg Ser Cys Ser Gln Arg Asn Ser Leu Ser
20 25 30

Leu Ile Gln Cys Asp Ile Lys Glu Arg Ser Phe Gly Glu Ser Met Thr
35 40 45

Ile Thr Asn Arg Gly Leu Ser Phe Lys Thr Asn Val Phe Glu Gln Ala
50 55 60

Arg Ser Val Thr Gly Asp Cys Ser Tyr Asp Glu Thr Ser Ala Lys Ala
65 70 75 80

Arg Ser His Val Val Ala Glu Asp Lys Ile Gly Val Leu Leu Leu Asn
85 90 95

Leu Gly Gly Pro Glu Thr Leu Asn Asp Val Gln Pro Phe Leu Tyr Asn
100 105 110

Leu Phe Ala Asp Pro Asp Ile Ile Arg Leu Pro Arg Pro Phe Gln Phe
115 120 125

Leu Gln Gly Thr Ile Ala Lys Phe Ile Ser Val Val Arg Ala Pro Lys
130 135 140

Ser Lys Glu Gly Tyr Ala Ala Ile Gly Gly Gly Ser Pro Leu Arg Lys
145 150 155 160

Ile Thr Asp Glu Gln Ala Asp Ala Ile Lys Met Ser Leu Gln Ala Lys

```
                165                 170                 175

Asn Ile Ala Ala Asn Val Tyr Val Gly Met Arg Tyr Trp Tyr Pro Phe
            180                 185                 190

Thr Glu Glu Ala Val Gln Gln Ile Lys Lys Asp Lys Ile Thr Arg Leu
        195                 200                 205

Val Val Leu Pro Leu Tyr Pro Gln Tyr Ser Ile Ser Thr Thr Gly Ser
    210                 215                 220

Ser Ile Arg Val Leu Gln Asp Leu Phe Arg Lys Asp Pro Tyr Leu Ala
225                 230                 235                 240

Gly Val Pro Val Ala Ile Ile Lys Ser Trp Tyr Gln Arg Arg Gly Tyr
                245                 250                 255

Val Asn Ser Met Ala Asp Leu Ile Glu Lys Glu Leu Gln Thr Phe Ser
            260                 265                 270

Asp Pro Lys Glu Val Met Ile Phe Phe Ser Ala His Gly Val Pro Val
        275                 280                 285

Ser Tyr Val Glu Asn Ala Gly Asp Pro Tyr Gln Lys Gln Met Glu Glu
    290                 295                 300

Cys Ile Asp Leu Ile Met Glu Glu Leu Lys Ala Arg Gly Val Leu Asn
305                 310                 315                 320

Asp His Lys Leu Ala Tyr Gln Ser Arg Val Gly Pro Val Gln Trp Leu
                325                 330                 335

Lys Pro Tyr Thr Asp Glu Val Leu Val Asp Leu Gly Lys Ser Gly Val
            340                 345                 350

Lys Ser Leu Leu Ala Val Pro Val Ser Phe Val Ser Glu His Ile Glu
        355                 360                 365

Thr Leu Glu Glu Ile Asp Met Glu Tyr Arg Glu Leu Ala Leu Glu Ser
    370                 375                 380

Gly Val Glu Asn Trp Gly Arg Val Pro Ala Leu Gly Leu Thr Pro Ser
385                 390                 395                 400

Phe Ile Thr Asp Leu Ala Asp Ala Val Ile Glu Ser Leu Pro Ser Ala
                405                 410                 415

Glu Ala Met Ser Asn Pro Asn Ala Val Val Asp Ser Glu Asp Ser Glu
            420                 425                 430

Ser Ser Asp Ala Phe Ser Tyr Ile Val Lys Met Phe Phe Gly Ser Ile
        435                 440                 445

Leu Ala Phe Val Leu Leu Leu Ser Pro Lys Met Phe His Ala Phe Arg
    450                 455                 460

Asn Leu
465
```

<210> SEQ ID NO 3
<211> LENGTH: 1848
<212> TYPE: DNA
<213> ORGANISM: Beta vulgaris

<400> SEQUENCE: 3

```
gacttgtaat attattttat atgcccatca aaatccctaa aaattcctcc tttcaacagc     60

ctaaactgcc ttacaggctt ctggatttct gggtatctca taattaacgc catggatgca    120

accacaagct ctgccatgtt ttcgcagata agattatcat ctccctccct tcgaaatttc    180

agaactagat tctttcagtc atgcccacaa acgagagctc acatgcctcc ttgtagatat    240

acatgtaggc attcttcaat tggttcatat gcactattgc cttccaacct tgttgaaatt    300

caaagcagca aaatcagtgg attttcttat tgtcaaccag agaagaaaag acttggagtg    360

gggaaaactt tttgttctgc tgctatacag acaagcacat acaacgagaa cttggctata    420
```

-continued

```
gctccttcac atgttgcaga ggaaaagatt ggggtgcttc ttttgaattt aggaggaccc    480
gaaactctta atgatgtcca accgttcttg tttaatctat ttgctgaccc agacatcatt    540
cgccttccta tgttgttccg ttttctgcaa aggcctctag ctcaattgat ttctaagctt    600
agagccccta aaagcaaaga aggatatgct tctataggag gggttcacc attgcgaaag     660
ataactgacg agcaggcaaa tgcacttaag ttggccttgg aagcaaagaa aaagaatgta    720
tctgtctacg ttgccatgag gtactggtac ccgtttacag aggaggcagt tcagcagata    780
aagaaagacg aggtcacaag gcttgtcgtt cttcctctct atcctcagtt ttctatatct    840
acaacaggtt ctagcctccg cgttctcgaa aacattttca ggaaggatgc atatctatct    900
caccttccca tcgctatcat ccagtcctgg taccagcgag aaggttatgt caagtccatg    960
gctgacttga ttgagaaaga gctgcagtct ttttctatgc cagatgaggt tatgatattc   1020
ttcagtgctc atggcgtgcc agtaagttat gtggaaaacg ctggagatcc atacaaagat   1080
cagatggagg attgcatttt tttaattatg agagaattaa aatctagagg aatcaacaat   1140
gatcatacac ttgcttacca gagtcgggtt ggtccagtgc aatggctgaa accttatact   1200
gatgaagttc ttgttgagct tggcgaaaaa ggagtcaaga gtctgctagc tgttcctgtg   1260
agctttgtga gtgagcacat tgagacactt gaagagatcg atatggagta caaggaattg   1320
gcgcttgaat ctggcattga gaactggggt cgtgttcctg ctcttaactg caattcttct   1380
ttcatcaatg atctagctga tgctgtagct gaagctcttc cttcagcaac tgcaatgtca   1440
actagcacag ctgaagaagt tgataatgat ccagtcaagt atttcataaa attgtttttt   1500
ggttcactgt tggccttcgt cttgcttttg tccccgaaaa tgatttcgc atttaagaac    1560
agccttttgt aaaaatagat ggtagtgttc accagatttt gaagatatac acaaattaga   1620
ctgaaaaatc acactagaat ggatagagga acacaattcg ccacgtaaca tgtagaatta   1680
ctccaagagt atacaacttt gtgtgtacta atttgtagtt tttggattgc gattcacaag   1740
ggatttaatg aattaggtaa caccaaatag cttgtattct tcttaaaaaa aaaaaaaaaa   1800
aaaaaaaaaa aaaaaaaaaa aaaaaaaaaa aaaaaaaaaa aaaaaaaa                1848
```

<210> SEQ ID NO 4
<211> LENGTH: 486
<212> TYPE: PRT
<213> ORGANISM: Beta vulgaris

<400> SEQUENCE: 4

```
Met Asp Ala Thr Thr Ser Ser Ala Met Phe Ser Gln Ile Arg Leu Ser
1               5                   10                  15

Ser Pro Ser Leu Arg Asn Phe Arg Thr Arg Phe Phe Gln Ser Cys Pro
            20                  25                  30

Gln Thr Arg Ala His Met Pro Pro Cys Arg Tyr Thr Cys Arg His Ser
        35                  40                  45

Ser Ile Gly Ser Tyr Ala Leu Leu Pro Ser Asn Leu Val Glu Ile Gln
    50                  55                  60

Ser Ser Lys Ile Ser Gly Phe Ser Tyr Cys Gln Pro Glu Lys Lys Arg
65                  70                  75                  80

Leu Gly Val Gly Lys Thr Phe Cys Ser Ala Ala Ile Gln Thr Ser Thr
                85                  90                  95

Tyr Asn Glu Asn Leu Ala Ile Ala Pro Ser His Val Ala Glu Glu Lys
            100                 105                 110

Ile Gly Val Leu Leu Leu Asn Leu Gly Gly Pro Glu Thr Leu Asn Asp
        115                 120                 125
```

-continued

```
Val Gln Pro Phe Leu Phe Asn Leu Phe Ala Asp Pro Asp Ile Ile Arg
    130                 135                 140

Leu Pro Met Leu Phe Arg Phe Leu Gln Arg Pro Leu Ala Gln Leu Ile
145                 150                 155                 160

Ser Lys Leu Arg Ala Pro Lys Ser Lys Glu Gly Tyr Ala Ser Ile Gly
                165                 170                 175

Gly Gly Ser Pro Leu Arg Lys Ile Thr Asp Glu Gln Ala Asn Ala Leu
            180                 185                 190

Lys Leu Ala Leu Glu Ala Lys Lys Lys Asn Val Ser Val Tyr Val Ala
        195                 200                 205

Met Arg Tyr Trp Tyr Pro Phe Thr Glu Glu Ala Val Gln Gln Ile Lys
    210                 215                 220

Lys Asp Glu Val Thr Arg Leu Val Val Leu Pro Leu Tyr Pro Gln Phe
225                 230                 235                 240

Ser Ile Ser Thr Thr Gly Ser Ser Leu Arg Val Leu Glu Asn Ile Phe
                245                 250                 255

Arg Lys Asp Ala Tyr Leu Ser His Leu Pro Ile Ala Ile Ile Gln Ser
            260                 265                 270

Trp Tyr Gln Arg Glu Gly Tyr Val Lys Ser Met Ala Asp Leu Ile Glu
        275                 280                 285

Lys Glu Leu Gln Ser Phe Ser Met Pro Asp Glu Val Met Ile Phe Phe
    290                 295                 300

Ser Ala His Gly Val Pro Val Ser Tyr Val Glu Asn Ala Gly Asp Pro
305                 310                 315                 320

Tyr Lys Asp Gln Met Glu Asp Cys Ile Phe Leu Ile Met Arg Glu Leu
                325                 330                 335

Lys Ser Arg Gly Ile Asn Asn Asp His Thr Leu Ala Tyr Gln Ser Arg
            340                 345                 350

Val Gly Pro Val Gln Trp Leu Lys Pro Tyr Thr Asp Glu Val Leu Val
        355                 360                 365

Glu Leu Gly Glu Lys Gly Val Lys Ser Leu Leu Ala Val Pro Val Ser
    370                 375                 380

Phe Val Ser Glu His Ile Glu Thr Leu Glu Glu Ile Asp Met Glu Tyr
385                 390                 395                 400

Lys Glu Leu Ala Leu Glu Ser Gly Ile Glu Asn Trp Gly Arg Val Pro
                405                 410                 415

Ala Leu Asn Cys Asn Ser Ser Phe Ile Asn Asp Leu Ala Asp Ala Val
            420                 425                 430

Ala Glu Ala Leu Pro Ser Ala Thr Ala Met Ser Thr Ser Thr Ala Glu
        435                 440                 445

Glu Val Asp Asn Asp Pro Val Lys Tyr Phe Ile Lys Leu Phe Phe Gly
    450                 455                 460

Ser Leu Leu Ala Phe Val Leu Leu Leu Ser Pro Lys Met Ile Phe Ala
465                 470                 475                 480

Phe Lys Asn Ser Leu Leu
                485
```

<210> SEQ ID NO 5
<211> LENGTH: 1979
<212> TYPE: DNA
<213> ORGANISM: Brassica napus

<400> SEQUENCE: 5

```
ttcggcacga ggcctcgtgc cggaaaactg tatggaggcg acggcgttat catctgggct      60
```

-continued

```
tcgtcctctt ccgaacccta acggttacag actcccgagg tcatgttctc agagaaagtc    120

tctgccttta gctcgattcc attcaaagga gacacctttc aagaaacctc aagggtctct    180

cgcgatcact caccaccgtg ggttgagttt caagacgaac gtcttcgagc aagcgcatca    240

tcctgtagct ggagacctct cttacgatga cactagccgt tctaacgttg ctgaggataa    300

gatcggtgtc ttgcttttga acctaggtgg gcctgagacg cttaacgatg tgcagccttt    360

cttgtataat ctgtttgcag acccggtgag aatcatctat aggctttttg agtttttgga    420

gttgttttgg agtgttggtt tttttgatga aatgtggttt gtttgtttgt ttgtgttgca    480

ggatattata cggcttccta gaccgtttca gtttctccaa ggggctatag caaagttcat    540

atctgtggtt cgcgctccga agtcgaaaga agggtatgct gctattggcg gggatctcc    600

tttgcgtaag attactgatg agcaagctga tgctattcgg ttggcgttgc aagctaagaa    660

cgtttctgct gatgtctatg ttgggatgcg gtattggttt cctttcactg aggaggctgt    720

ccaacagatt aagaaggata agattacaag acttgttgta ctaccgttgt accctcagta    780

ttctatctcc acgactggct caagcgtccg cgttctccaa gacttattca ggaaagatcc    840

atacctagct agagtgccgg ttgctattat agagtcctgg taccagagaa gaggctatgt    900

caattccatg gctgacctca ttcagaagga gcttcaaact ttctctgatc ctaaggaggt    960

tatggtgttc ttcagtgccc atggtgttcc agttagctat gtagagaact ctggagatcc   1020

ataccagaaa cagatggaag agtgcattga cttgataatg gaagagctaa aatccagagg   1080

ggttcaaaac aaccatatct tggcttacca gagtcgtgtt gggcctgttc aatggctgaa   1140

gccatacact gatgaggttc ttgtcgacct tggtaagaat ggtgtcaaga gtctactagc   1200

cgttccagtc agttttgtga gtgagcacat tgagacgctt gaagagatag acatggagta   1260

cagggagcta gctttggagt cagggataga gaactggggg cgtgtcccgg cgctaggtct   1320

gacgccatcc ttcatcaccg acttggctga tgcagtgata gagtcgcttc cttcagcaga   1380

agcaatggtg aacccaccaa gtgctggtgt ctcagaggat agcgagtcat cagacgcttt   1440

cggttacata atgaagatgt tcttcggttc ggttctagcc ttcctactgc ttctctcccc   1500

aaagatgttc catgcattcc gcaaccattt tatctaagaa gaaaacctat cgagaatctc   1560

tggatgaata gttggtttta tgttgttttt ttgttgttgg agaaatgtct tggtgaagtg   1620

taacgtatgt agtccaatct attgaagtac tagcacacca tctctagtga gattatgtgg   1680

ttgagtagtt caatacattg gactacatat attacttttg atcaagatgt aaactaggta   1740

agggaaataa tgagggaaga gacaggattc attttgtttt ttagctatga acatagttcc   1800

tcctagagat gaggtaaagg gaatataatc tattagttat tttggttttc ttaaaagcaa   1860

attgtcaaat gcattctttt gtttattaat caagctgcaa aattcatcac taaaaaaaaa   1920

aaaaaaaaaa aaaaaaaaaa aaaaaaaaaa aaaaaaaaaa aaaaaaaaaa aaaaaaaaa    1979
```

<210> SEQ ID NO 6
<211> LENGTH: 469
<212> TYPE: PRT
<213> ORGANISM: Brassica napus

<400> SEQUENCE: 6

```
Met Glu Ala Thr Ala Leu Ser Ser Gly Leu Arg Pro Leu Pro Asn Pro
1               5                   10                  15

Asn Gly Tyr Arg Leu Pro Arg Ser Cys Ser Gln Arg Lys Ser Leu Pro
            20                  25                  30

Leu Ala Arg Phe His Ser Lys Glu Thr Pro Phe Lys Lys Pro Gln Gly
        35                  40                  45
```

-continued

```
Ser Leu Ala Ile Thr His His Arg Gly Leu Ser Phe Lys Thr Asn Val
    50                  55                  60

Phe Glu Gln Ala His His Pro Val Ala Gly Asp Leu Ser Tyr Asp Asp
65                  70                  75                  80

Thr Ser Arg Ser Asn Val Ala Glu Asp Lys Ile Gly Val Leu Leu Leu
                85                  90                  95

Asn Leu Gly Gly Pro Glu Thr Leu Asn Asp Val Gln Pro Phe Leu Tyr
            100                 105                 110

Asn Leu Phe Ala Asp Pro Asp Ile Ile Arg Leu Pro Arg Pro Phe Gln
        115                 120                 125

Phe Leu Gln Gly Ala Ile Ala Lys Phe Ile Ser Val Val Arg Ala Pro
    130                 135                 140

Lys Ser Lys Glu Gly Tyr Ala Ala Ile Gly Gly Gly Ser Pro Leu Arg
145                 150                 155                 160

Lys Ile Thr Asp Glu Gln Ala Asp Ala Ile Arg Leu Ala Leu Gln Ala
                165                 170                 175

Lys Asn Val Ser Ala Asp Val Tyr Val Gly Met Arg Tyr Trp Phe Pro
            180                 185                 190

Phe Thr Glu Glu Ala Val Gln Gln Ile Lys Lys Asp Lys Ile Thr Arg
        195                 200                 205

Leu Val Val Leu Pro Leu Tyr Pro Gln Tyr Ser Ile Ser Thr Thr Gly
    210                 215                 220

Ser Ser Val Arg Val Leu Gln Asp Leu Phe Arg Lys Asp Pro Tyr Leu
225                 230                 235                 240

Ala Arg Val Pro Val Ala Ile Ile Glu Ser Trp Tyr Gln Arg Arg Gly
                245                 250                 255

Tyr Val Asn Ser Met Ala Asp Leu Ile Gln Lys Glu Leu Gln Thr Phe
            260                 265                 270

Ser Asp Pro Lys Glu Val Met Val Phe Phe Ser Ala His Gly Val Pro
        275                 280                 285

Val Ser Tyr Val Glu Asn Ser Gly Asp Pro Tyr Gln Lys Gln Met Glu
    290                 295                 300

Glu Cys Ile Asp Leu Ile Met Glu Glu Leu Lys Ser Arg Gly Val Gln
305                 310                 315                 320

Asn Asn His Ile Leu Ala Tyr Gln Ser Arg Val Gly Pro Val Gln Trp
                325                 330                 335

Leu Lys Pro Tyr Thr Asp Glu Val Leu Val Asp Leu Gly Lys Asn Gly
            340                 345                 350

Val Lys Ser Leu Leu Ala Val Pro Val Ser Phe Val Ser Glu His Ile
        355                 360                 365

Glu Thr Leu Glu Glu Ile Asp Met Glu Tyr Arg Glu Leu Ala Leu Glu
    370                 375                 380

Ser Gly Ile Glu Asn Trp Gly Arg Val Pro Ala Leu Gly Leu Thr Pro
385                 390                 395                 400

Ser Phe Ile Thr Asp Leu Ala Asp Ala Val Ile Glu Ser Leu Pro Ser
                405                 410                 415

Ala Glu Ala Met Val Asn Pro Pro Ser Ala Gly Val Ser Glu Asp Ser
            420                 425                 430

Glu Ser Ser Asp Ala Phe Gly Tyr Ile Met Lys Met Phe Phe Gly Ser
        435                 440                 445

Val Leu Ala Phe Leu Leu Leu Leu Ser Pro Lys Met Phe His Ala Phe
    450                 455                 460

Arg Asn His Phe Ile
```

465

<210> SEQ ID NO 7
<211> LENGTH: 2005
<212> TYPE: DNA
<213> ORGANISM: Zea mays

<400> SEQUENCE: 7
cggaaagcaa atagcagacg gcagacaaca gtcgagggga cacaggaagg cgcgaagaag 60
accgagatcc tcgcccaacg ccatcacgcc actcccccaa tactcaggtg tcaggacagc 120
gagcaggcac aagcagatct cactccacgt tgctccttcc gcccttcctc tccgccgctc 180
cccggaagga tcatggagcg cgggattctt ggctccaggg gcgccgtcca aatcttgggg 240
tcgaagaccg gggccgcgat gtcatgtggc aaaacaacct ctacaagttt tacttgttct 300
accaaacacg agctgaactt gcatgtgaat gttaagccgt tgcaattggc aacagatgga 360
tcctctcgtt tggcatacaa aactccagtg cttaaaaatc agtggaatct ttctgctagt 420
tcttcctctg caaatgtggt taccactttt gatgatgaca aaggtgtacc ttccagtttt 480
gctgaagaaa agatcggagt actgttatta aatcttggtg gtccagaaac cctagacgat 540
gttcaaccat tcttgttcaa cctatttgct gatccagata tcattcgact gcctaggctc 600
ttcaggttcc ttcaaagacc actggccaaa cttatttcta cttttagagc tcctaagagt 660
aaagaagggt atgcttcaat cggtggtggg tcaccattga ggaaaattac tgatgagcag 720
gcaaatgctt tgaagattgc tctggaaaag aaaaaattga acgcaaatat atatgttggg 780
atgcggtatt ggtatccttt cacagaagaa gccattgatc agattaagaa ggataatatt 840
tccaagctcg ttgttcttcc actctaccct cagtactcca tatcaacaag tgggtcaagc 900
attcgtgttc tccaaaatgt tgtcaaggaa gattcatatt tttctggctt gccaatctcc 960
attatcgaat catggtacca acgtgatggc tatgtgaaat caatggctga cctaattgaa 1020
aaagagctat ctgccttttc caatcctgaa gaggtaatga tattcttcag tgcacatggt 1080
gtgccactta cctatgttca ggatgctgga gatccttaca gagatcagat ggaggattgt 1140
atttctttga tcatggggga gctgagatcc agaggaatct taaatggtca cactttggcg 1200
tatcagagtc gggtgggacc agttcaatgg ctgaagccat atactgatga agttttagta 1260
gaacttggtc agaacggtgt gaagagcctc ctggctgttc cagtaagctt cgtgagcgag 1320
cacattgaga cactggaaga aatagacatg gagtacaagg agttggctct ggaatcaggc 1380
attgagaact ggggccgggt ccctgctctt ggatgcactt cgactttcat ctccgacctt 1440
gcagatgcgg ttgtcgaagc cctcccatct gcctcggcgc tgggaaccag aaagcctgaa 1500
gacaccgatt ccagcatgga tctgatgcat tacctgacca agatgttctt cggctcaatc 1560
ttggcattta tcctgctgtt gtcaccaaga ctggtttctg ctttccggaa caccatgctt 1620
taggtggtta ggtaggtaag caaaaaggga atggtgtgat aggtaattct taaaaatttg 1680
agattaataa tggaaaaact ggagagagct tggtgatagt aactagagat cctttaggct 1740
ttgtttgggt actctagtat tgaccctaat ccgtgtgttg agatagattg aggtgtaaat 1800
tagtttaagt tatacctcaa ttcagctcag tacatataga ttgagctcaa tactagaata 1860
ctcaaactag gccttagtgc acgaggtagc agcttgtaat ttgctgtttt tgatattgtt 1920
cacaggaaac attggtctca taaatgaatc tgtgaaagca cataacgtta caaatcaaaa 1980
aaaaaaaaaa aaaaaaaaaa aaaaa 2005

<210> SEQ ID NO 8

-continued

<211> LENGTH: 476
<212> TYPE: PRT
<213> ORGANISM: Zea mays

<400> SEQUENCE: 8

```
Met Glu Arg Gly Ile Leu Gly Ser Arg Gly Ala Val Gln Ile Leu Gly
1               5                   10                  15

Ser Lys Thr Gly Ala Ala Met Ser Cys Gly Lys Thr Thr Ser Thr Ser
            20                  25                  30

Phe Thr Cys Ser Thr Lys His Glu Leu Asn Leu His Val Asn Val Lys
        35                  40                  45

Pro Leu Gln Leu Ala Thr Asp Gly Ser Ser Arg Leu Ala Tyr Lys Thr
    50                  55                  60

Pro Val Leu Lys Asn Gln Trp Asn Leu Ser Ala Ser Ser Ser Ser Ala
65                  70                  75                  80

Asn Val Val Thr Thr Phe Asp Asp Asp Lys Gly Val Pro Ser Ser Phe
                85                  90                  95

Ala Glu Glu Lys Ile Gly Val Leu Leu Leu Asn Leu Gly Gly Pro Glu
            100                 105                 110

Thr Leu Asp Asp Val Gln Pro Phe Leu Phe Asn Leu Phe Ala Asp Pro
        115                 120                 125

Asp Ile Ile Arg Leu Pro Arg Leu Phe Arg Phe Leu Gln Arg Pro Leu
    130                 135                 140

Ala Lys Leu Ile Ser Thr Phe Arg Ala Pro Lys Ser Lys Glu Gly Tyr
145                 150                 155                 160

Ala Ser Ile Gly Gly Gly Ser Pro Leu Arg Lys Ile Thr Asp Glu Gln
                165                 170                 175

Ala Asn Ala Leu Lys Ile Ala Leu Glu Lys Lys Lys Leu Asn Ala Asn
            180                 185                 190

Ile Tyr Val Gly Met Arg Tyr Trp Tyr Pro Phe Thr Glu Glu Ala Ile
        195                 200                 205

Asp Gln Ile Lys Lys Asp Asn Ile Ser Lys Leu Val Val Leu Pro Leu
    210                 215                 220

Tyr Pro Gln Tyr Ser Ile Ser Thr Ser Gly Ser Ser Ile Arg Val Leu
225                 230                 235                 240

Gln Asn Val Val Lys Glu Asp Ser Tyr Phe Ser Gly Leu Pro Ile Ser
                245                 250                 255

Ile Ile Glu Ser Trp Tyr Gln Arg Asp Gly Tyr Val Lys Ser Met Ala
            260                 265                 270

Asp Leu Ile Glu Lys Glu Leu Ser Ala Phe Ser Asn Pro Glu Glu Val
        275                 280                 285

Met Ile Phe Phe Ser Ala His Gly Val Pro Leu Thr Tyr Val Gln Asp
    290                 295                 300

Ala Gly Asp Pro Tyr Arg Asp Gln Met Glu Asp Cys Ile Ser Leu Ile
305                 310                 315                 320

Met Gly Glu Leu Arg Ser Arg Gly Ile Leu Asn Gly His Thr Leu Ala
                325                 330                 335

Tyr Gln Ser Arg Val Gly Pro Val Gln Trp Leu Lys Pro Tyr Thr Asp
            340                 345                 350

Glu Val Leu Val Glu Leu Gly Gln Asn Gly Val Lys Ser Leu Leu Ala
        355                 360                 365

Val Pro Val Ser Phe Val Ser Glu His Ile Glu Thr Leu Glu Glu Ile
    370                 375                 380

Asp Met Glu Tyr Lys Glu Leu Ala Leu Glu Ser Gly Ile Glu Asn Trp
385                 390                 395                 400
```

-continued

```
Gly Arg Val Pro Ala Leu Gly Cys Thr Ser Thr Phe Ile Ser Asp Leu
                405                 410                 415

Ala Asp Ala Val Val Glu Ala Leu Pro Ser Ala Ser Ala Leu Gly Thr
            420                 425                 430

Arg Lys Pro Glu Asp Thr Asp Ser Ser Met Asp Leu Met His Tyr Leu
        435                 440                 445

Thr Lys Met Phe Phe Gly Ser Ile Leu Ala Phe Ile Leu Leu Leu Ser
    450                 455                 460

Pro Arg Leu Val Ser Ala Phe Arg Asn Thr Met Leu
465                 470                 475


<210> SEQ ID NO 9
<211> LENGTH: 1760
<212> TYPE: DNA
<213> ORGANISM: Zea mays

<400> SEQUENCE: 9

ccgatcgacc gttcacctcg cccgacggcc caagcagccc atgtcttcgt cgggcccctc     60

cccggcgacg ggaatccacg cgtcgccgcc gttgggcctt ttgccggcga cgggaaccca    120

tcacaccagg tcatggggca aaacaacctc cacaagtttt actggttcta ccaccaaaca    180

tgagcagagc ttgcatggaa atgttaagcc gttgcaattg gcggcaaatg aatcctctcg    240

tttggcttac agaagtccag cacttaaaaa ccagtggaat cttcctgcta gttcttcctc    300

cactaatgtg gttaccacct ttgatgataa cgaacacgtg tcttccagtg ttattgaaga    360

aaaagttgga gtactgttat taaaccttgg tggtccagag acacttgacg atgttcaacc    420

atttttattc aacctatttg ctgatccaga tatcattcga ctccctaggc tcttcaggtt    480

tcttcaaaga ccactggcca aacttatttc tacttttaga gctcctaaga gtaaagaagg    540

gtatgcttca attggtggtg ggtcgccgtt aaggaaaatt actgatgaac aggcgaatgc    600

tttgaagatt gccctggaaa agaaaaaatt gaacgcaaac atatatgttg ggatgcggta    660

ttggtaccct ttcacagaag aggccattga tcaaattaaa aaggataaga ttaccaagct    720

cgttgttctt ccccctttacc ctcagtactc catatcaaca agtgggtcaa gcattcgtgt    780

tctccaagac attgtcaagg aagattcata tttttctggt ttgccaattt ccattattga    840

atcatggtac caacgagatg gctatgtgaa atcaatgtct gacctaattg aaaaggagct    900

ctccgccttc tccaatcctg aagaggttat gatattcttc agtgcacatg gtgtgccact    960

tacctatgtt gaggatgctg gagatcctta cagagatcag atggaggatt gtattgcttt   1020

gatcatgggg gagttaagat caagaggaat cttaaatagt cacactttgg cgtaccagag   1080

tcgggtgggg ccagttcaat ggctgaagcc atatactgat gaagttttag tagaacttgg   1140

tcaaaagggt gtgaagagcc tcctggctgt tccagtaagc tttgtgagtg agcacatcga   1200

gacattggaa gaaattgaca tggagtacaa ggagttggct ctggaatcag gcatcaagaa   1260

ctggggtcgg gttcctgctc ttggatgcac ttcaacattc atctccgacc ttgcagatgc   1320

tgtcgtcgaa gccctgccct ctgcttcagc gctcgcgacc agaaagcctg acgacatcga   1380

ttccagcatg gacctgacgc attacctcac caagatgctg tttggctcaa tcttggcatt   1440

tgtcctgctg ctatcaccaa ggctagtttc cgccttccgg agcaccatgc tttaagtttt   1500

tctccaaagc actaaatttg agattgagaa tgagatattt cattttggac cttttttttcc   1560

tccttaatag aatgatgtgc agttcttctg ctcgttccag agaaaaaaat aactgctagg   1620

aactcacaag gtagtagggg attgcaaaag ggatgtgaac agctgttttg atcgaagttg   1680
```

tctataaata ccgtgctcac ggactctgta ttttaaaaaa aaaaaaaaaa aaaaaaaaaa 1740
aaaaaaaaaa aaaaaaaaaa 1760

<210> SEQ ID NO 10
<211> LENGTH: 484
<212> TYPE: PRT
<213> ORGANISM: Zea mays

<400> SEQUENCE: 10

Met Ser Ser Ser Gly Pro Ser Pro Ala Thr Gly Ile His Ala Ser Pro
1 5 10 15

Pro Leu Gly Leu Leu Pro Ala Thr Gly Thr His His Thr Arg Ser Trp
20 25 30

Gly Lys Thr Thr Ser Thr Ser Phe Thr Gly Ser Thr Thr Lys His Glu
35 40 45

Gln Ser Leu His Gly Asn Val Lys Pro Leu Gln Leu Ala Ala Asn Glu
50 55 60

Ser Ser Arg Leu Ala Tyr Arg Ser Pro Ala Leu Lys Asn Gln Trp Asn
65 70 75 80

Leu Pro Ala Ser Ser Ser Ser Thr Asn Val Val Thr Thr Phe Asp Asp
85 90 95

Asn Glu His Val Ser Ser Ser Val Ile Glu Glu Lys Val Gly Val Leu
100 105 110

Leu Leu Asn Leu Gly Gly Pro Glu Thr Leu Asp Asp Val Gln Pro Phe
115 120 125

Leu Phe Asn Leu Phe Ala Asp Pro Asp Ile Ile Arg Leu Pro Arg Leu
130 135 140

Phe Arg Phe Leu Gln Arg Pro Leu Ala Lys Leu Ile Ser Thr Phe Arg
145 150 155 160

Ala Pro Lys Ser Lys Glu Gly Tyr Ala Ser Ile Gly Gly Gly Ser Pro
165 170 175

Leu Arg Lys Ile Thr Asp Glu Gln Ala Asn Ala Leu Lys Ile Ala Leu
180 185 190

Glu Lys Lys Lys Leu Asn Ala Asn Ile Tyr Val Gly Met Arg Tyr Trp
195 200 205

Tyr Pro Phe Thr Glu Glu Ala Ile Asp Gln Ile Lys Lys Asp Lys Ile
210 215 220

Thr Lys Leu Val Val Leu Pro Leu Tyr Pro Gln Tyr Ser Ile Ser Thr
225 230 235 240

Ser Gly Ser Ser Ile Arg Val Leu Gln Asp Ile Val Lys Glu Asp Ser
245 250 255

Tyr Phe Ser Gly Leu Pro Ile Ser Ile Ile Glu Ser Trp Tyr Gln Arg
260 265 270

Asp Gly Tyr Val Lys Ser Met Ser Asp Leu Ile Glu Lys Glu Leu Ser
275 280 285

Ala Phe Ser Asn Pro Glu Glu Val Met Ile Phe Phe Ser Ala His Gly
290 295 300

Val Pro Leu Thr Tyr Val Glu Asp Ala Gly Asp Pro Tyr Arg Asp Gln
305 310 315 320

Met Glu Asp Cys Ile Ala Leu Ile Met Gly Glu Leu Arg Ser Arg Gly
325 330 335

Ile Leu Asn Ser His Thr Leu Ala Tyr Gln Ser Arg Val Gly Pro Val
340 345 350

Gln Trp Leu Lys Pro Tyr Thr Asp Glu Val Leu Val Glu Leu Gly Gln
355 360 365

Lys Gly Val Lys Ser Leu Leu Ala Val Pro Val Ser Phe Val Ser Glu
    370                 375                 380

His Ile Glu Thr Leu Glu Glu Ile Asp Met Glu Tyr Lys Glu Leu Ala
385                 390                 395                 400

Leu Glu Ser Gly Ile Lys Asn Trp Gly Arg Val Pro Ala Leu Gly Cys
                405                 410                 415

Thr Ser Thr Phe Ile Ser Asp Leu Ala Asp Ala Val Val Glu Ala Leu
            420                 425                 430

Pro Ser Ala Ser Ala Leu Ala Thr Arg Lys Pro Asp Asp Ile Asp Ser
        435                 440                 445

Ser Met Asp Leu Thr His Tyr Leu Thr Lys Met Leu Phe Gly Ser Ile
    450                 455                 460

Leu Ala Phe Val Leu Leu Leu Ser Pro Arg Leu Val Ser Ala Phe Arg
465                 470                 475                 480

Ser Thr Met Leu

<210> SEQ ID NO 11
<211> LENGTH: 1971
<212> TYPE: DNA
<213> ORGANISM: Oryza sativa

<400> SEQUENCE: 11
cttacagggc aacgaatgcg aacctacttc tcctagtata ctgcttttac tttagccatc      60
gccaccaccg ccattcctgg aacccccttc cctcttcctc cctcggatct ctcctcgctc     120
gcgcgttcgc gccgccgcct tccccccttcc cccgttgatt gattgggagg aggatcaatg     180
gagtgcgtcc gctccggctc cggggttctt gatcccaggt gctctccgcg gttcctgggg     240
aagaagggtg gttcgctcac gtcatgtggt aaagccactt ctacaaatct tgccatttgt     300
accaaacacg agcaaaactt gcatgggaat gttaaaccct cacagttagc agcaagtgga     360
tcctcttatt ctgttcacag aagtccagtg cttaagcaga gacagaatct ttctgctagg     420
tctacctctg cagatgtata tactactttt gatgaaaatg tcagagctgt atcttcacat     480
gctgctgaag aaaaggttgg agtactctta ttaaaccttg gtggcccaga gacactggat     540
gatgttcagc catttctatt caacctgttt gctgacccag atatcatccg tttgccaagg     600
ctgttcaggt ttcttcaaag accattggcc aagcttatct ccacttttag agctccaaag     660
agtaaggagg ggtacgcttc aatcggtgga ggatcacctt tgcggaaaat tactgatgag     720
caggcaaatg ctttgaaggt ggcactgaaa aagaagaatt tgaatgctaa tatatatgtt     780
ggaatgcgat actggtaccc ttttacagaa gaagccattg atcagattaa gaaggataag     840
attacaaagc ttgtcgttct tccactgtac cctcaatact ccatatcgac aagtggatca     900
agcatccgtg ttctccaaaa cattgtcaag gaggattcat attttgctgg attgccaatt     960
tccattatcg aatcatggta ccaacgtgac ggttatgtga aatcaatggc tgacttaatt    1020
gaaaaggaac tgtcaatttt ttccaatcct gaagaggtta tgatattctt cagtgcacat    1080
ggagtaccac ttacctatgt tacggatgct ggagatcctt acagagatca gatggaggac    1140
tgcattgctt tgatcatggg agagttaaaa tccagaggaa tcttaaacag ccatactctg    1200
gcttaccaga gtcgagtggg gccagttcag tggctgaaac catatactga tgaagttcta    1260
gttgaactag gtcaacaggg tgtaaagagc ctcctggctg ttccagtaag ctttgtgagc    1320
gagcacatcg agaccttgga agaaatcgac atggagtaca aggagctggc tctagaatcg    1380
ggcatcgaga actggggaag ggttccagct cttggatgca cctcatcctt catctccgac    1440

-continued

```
cttgctgatg cagtggtcga agccctgccc tccgcttccg ctctcgtgac gaagaaggtg   1500

gacgagagcg attccgacat ggacctgatg cactacctga gcaagatgtt cttcggctcc   1560

atcttggcgt tcgtcctcct attgtcgcca aggctgattt ccgctttccg gaacaccctg   1620

ttgtaggtga tggtggcttc ttttgtttgg ttttttgcac taggggtttg gcttgagtaa   1680

gtagaaaggc aggctcgtgg gatgatagtg aatagtgatg gttaaagttc ccctttttta   1740

cagaagtaat atgcatgaag tcattgcaag gtagcttaag tggtggtttt aagcaaggag   1800

cctctagggg taaattgcca gtctgtacca gttttcttgt gctggtacaa ggcaagccta   1860

tccttttttt tcttttttttt tctttttgtt acatgagcac attgataaaa catcattgat   1920

atattactaa tgcataaaca ccaaaaaaaa aaaaaaaaaa aaaaaaaaaa a            1971


<210> SEQ ID NO 12
<211> LENGTH: 482
<212> TYPE: PRT
<213> ORGANISM: Oryza sativa

<400> SEQUENCE: 12

Met Glu Cys Val Arg Ser Gly Ser Gly Val Leu Asp Pro Arg Cys Ser
1               5                   10                  15

Pro Arg Phe Leu Gly Lys Lys Gly Gly Ser Leu Thr Ser Cys Gly Lys
            20                  25                  30

Ala Thr Ser Thr Asn Leu Ala Ile Cys Thr Lys His Glu Gln Asn Leu
        35                  40                  45

His Gly Asn Val Lys Pro Ser Gln Leu Ala Ala Ser Gly Ser Ser Tyr
    50                  55                  60

Ser Val His Arg Ser Pro Val Leu Lys Gln Arg Gln Asn Leu Ser Ala
65                  70                  75                  80

Arg Ser Thr Ser Ala Asp Val Tyr Thr Thr Phe Asp Glu Asn Val Arg
                85                  90                  95

Ala Val Ser Ser His Ala Ala Glu Glu Lys Val Gly Val Leu Leu Leu
            100                 105                 110

Asn Leu Gly Gly Pro Glu Thr Leu Asp Asp Val Gln Pro Phe Leu Phe
        115                 120                 125

Asn Leu Phe Ala Asp Pro Asp Ile Ile Arg Leu Pro Arg Leu Phe Arg
    130                 135                 140

Phe Leu Gln Arg Pro Leu Ala Lys Leu Ile Ser Thr Phe Arg Ala Pro
145                 150                 155                 160

Lys Ser Lys Glu Gly Tyr Ala Ser Ile Gly Gly Gly Ser Pro Leu Arg
                165                 170                 175

Lys Ile Thr Asp Glu Gln Ala Asn Ala Leu Lys Val Ala Leu Lys Lys
            180                 185                 190

Lys Asn Leu Asn Ala Asn Ile Tyr Val Gly Met Arg Tyr Trp Tyr Pro
        195                 200                 205

Phe Thr Glu Glu Ala Ile Asp Gln Ile Lys Lys Asp Lys Ile Thr Lys
    210                 215                 220

Leu Val Val Leu Pro Leu Tyr Pro Gln Tyr Ser Ile Ser Thr Ser Gly
225                 230                 235                 240

Ser Ser Ile Arg Val Leu Gln Asn Ile Val Lys Glu Asp Ser Tyr Phe
                245                 250                 255

Ala Gly Leu Pro Ile Ser Ile Ile Glu Ser Trp Tyr Gln Arg Asp Gly
            260                 265                 270

Tyr Val Lys Ser Met Ala Asp Leu Ile Glu Lys Glu Leu Ser Ile Phe
        275                 280                 285
```

```
Ser Asn Pro Glu Glu Val Met Ile Phe Phe Ser Ala His Gly Val Pro
    290                 295                 300

Leu Thr Tyr Val Thr Asp Ala Gly Asp Pro Tyr Arg Asp Gln Met Glu
305                 310                 315                 320

Asp Cys Ile Ala Leu Ile Met Gly Glu Leu Lys Ser Arg Gly Ile Leu
                325                 330                 335

Asn Ser His Thr Leu Ala Tyr Gln Ser Arg Val Gly Pro Val Gln Trp
            340                 345                 350

Leu Lys Pro Tyr Thr Asp Glu Val Leu Val Glu Leu Gly Gln Gln Gly
        355                 360                 365

Val Lys Ser Leu Leu Ala Val Pro Val Ser Phe Val Ser Glu His Ile
    370                 375                 380

Glu Thr Leu Glu Glu Ile Asp Met Glu Tyr Lys Glu Leu Ala Leu Glu
385                 390                 395                 400

Ser Gly Ile Glu Asn Trp Gly Arg Val Pro Ala Leu Gly Cys Thr Ser
                405                 410                 415

Ser Phe Ile Ser Asp Leu Ala Asp Ala Val Val Glu Ala Leu Pro Ser
            420                 425                 430

Ala Ser Ala Leu Val Thr Lys Lys Val Asp Glu Ser Asp Ser Asp Met
        435                 440                 445

Asp Leu Met His Tyr Leu Ser Lys Met Phe Phe Gly Ser Ile Leu Ala
    450                 455                 460

Phe Val Leu Leu Leu Ser Pro Arg Leu Ile Ser Ala Phe Arg Asn Thr
465                 470                 475                 480

Leu Leu
```

<210> SEQ ID NO 13
<211> LENGTH: 1756
<212> TYPE: DNA
<213> ORGANISM: Glycine max

<400> SEQUENCE: 13

```
cttttctttg ccaacactcc ttcgattagg ggtttcgatc ccaaattaca aattggtcgc     60

catgaacgca acctcatact ctgctcttcc ttctacgttc cgcagtctcc atcatcggaa    120

tttctcagcg ttttgttctg atatccaaaa tcctggctat gttgattgcc attcaaattg    180

taataagtct acatctcaag cgtctttgtt tttgtgttcc gactccaaca gtagaagaaa    240

tggtgttttt ggtagaccac tttgtgtgaa cccctctggc aggagaaacc tagttggtcc    300

agctttttat tctctggaga ctagtgctta tgacgtggct gctttagaat ctccttcccg    360

tgttgcagaa gaaaaagttg gtgtgctgct tctcaatcta ggaggaccag agacattgag    420

tgacgtgcaa ccttttctgt ttaatctttt tgcagatcct gatatcattc gtcttccaag    480

gttgtttcgg tttctccagc gaccattggc aaaattgatt tctgtacttc gggctcctaa    540

atccaaggaa gggtatgctg ctattggtgg tggctctcct ttacgaaaaa ttacagatga    600

ccaggcactt gcaattaaaa tggctttgga agcaaagggc atctcttcaa atgtctacgt    660

tgggatgcga tactggtacc catttactga agaagcaatt cagcaaatta agagggacag    720

aataacaagg cttgtggtac taccccttta tccccagttt tctatatcca caactggatc    780

aagcatccgt gttcttgagc atatattcag ggaagatgcc tacttgtcta agctccctgt    840

ttccattata aactcttggt atcaacgaga aggttatatt aagtcaatgg ctaacttaat    900

tcagaaagag ctccagagtt tttctgaacc aaaagaggta atgatatttt tcagtgccca    960

tggtgtacct gtcagttacg ttgaggaagc tggggatcca taccgagacc aaatggagga   1020
```

```
gtgcatcttc ttgatcatgc aagagttgaa agctagagga attagtaatg agcacactct   1080

tgcttatcag agtcgagtgg gtcctgtaca gtggctgaaa ccatatactg atgaagttct   1140

cgttgagctt ggccaaaaag gtgtgaagag tcttttagct gttccagtga gttttgtgag   1200

tgagcatatt gaaacccttg aagaaattga catggagtac aaggaattgg ctcttgaatc   1260

tggcatcaag aattgggcac gtgtacctgc ccttggtgtt acccccttcct tcattacaga   1320

tttagcagat gcagtaatag aagctctccc atcagcaaca gcaatatatg caccgaccag   1380

aacctctgaa gatgttgatc atgacccagt tagatatttt atcaagatgt tctttggttc   1440

aatcttggca ttcatcttgt tcttgtcacc caaaatgatc acggcattca ggaatcatgt   1500

catttagaag aattaaatcc tgcttgctga attcaatctg caagcatata gatgaagcct   1560

attgatagca acaaagtata ctttgatttt ttgtctttgt tttacttatt tcaacctcta   1620

ctgtatacag cacagagcta taaggaagca atttttcgca cttgattata atgagaactt   1680

gcacctcggc ttaaagagga ttcaaagaat aataattgta gaccaggatc tattcaggaa   1740

aaaaaaaaaa aaaaaa                                                   1756


<210> SEQ ID NO 14
<211> LENGTH: 481
<212> TYPE: PRT
<213> ORGANISM: Glycine max

<400> SEQUENCE: 14

Met Asn Ala Thr Ser Tyr Ser Ala Leu Pro Ser Thr Phe Arg Ser Leu
1               5                   10                  15

His His Arg Asn Phe Ser Ala Phe Cys Ser Asp Ile Gln Asn Pro Gly
            20                  25                  30

Tyr Val Asp Cys His Ser Asn Cys Asn Lys Ser Thr Ser Gln Ala Ser
        35                  40                  45

Leu Phe Leu Cys Ser Asp Ser Asn Ser Arg Arg Asn Gly Val Phe Gly
    50                  55                  60

Arg Pro Leu Cys Val Asn Pro Ser Gly Arg Arg Asn Leu Val Gly Pro
65                  70                  75                  80

Ala Phe Tyr Ser Leu Glu Thr Ser Ala Tyr Asp Val Ala Ala Leu Glu
                85                  90                  95

Ser Pro Ser Arg Val Ala Glu Glu Lys Val Gly Val Leu Leu Leu Asn
            100                 105                 110

Leu Gly Gly Pro Glu Thr Leu Ser Asp Val Gln Pro Phe Leu Phe Asn
        115                 120                 125

Leu Phe Ala Asp Pro Asp Ile Ile Arg Leu Pro Arg Leu Phe Arg Phe
    130                 135                 140

Leu Gln Arg Pro Leu Ala Lys Leu Ile Ser Val Leu Arg Ala Pro Lys
145                 150                 155                 160

Ser Lys Glu Gly Tyr Ala Ala Ile Gly Gly Gly Ser Pro Leu Arg Lys
                165                 170                 175

Ile Thr Asp Asp Gln Ala Leu Ala Ile Lys Met Ala Leu Glu Ala Lys
            180                 185                 190

Gly Ile Ser Ser Asn Val Tyr Val Gly Met Arg Tyr Trp Tyr Pro Phe
        195                 200                 205

Thr Glu Glu Ala Ile Gln Gln Ile Lys Arg Asp Arg Ile Thr Arg Leu
    210                 215                 220

Val Val Leu Pro Leu Tyr Pro Gln Phe Ser Ile Ser Thr Thr Gly Ser
225                 230                 235                 240

Ser Ile Arg Val Leu Glu His Ile Phe Arg Glu Asp Ala Tyr Leu Ser
```

```
                245                 250                 255

Lys Leu Pro Val Ser Ile Ile Asn Ser Trp Tyr Gln Arg Glu Gly Tyr
            260                 265                 270

Ile Lys Ser Met Ala Asn Leu Ile Gln Lys Glu Leu Gln Ser Phe Ser
        275                 280                 285

Glu Pro Lys Glu Val Met Ile Phe Phe Ser Ala His Gly Val Pro Val
    290                 295                 300

Ser Tyr Val Glu Glu Ala Gly Asp Pro Tyr Arg Asp Gln Met Glu Glu
305                 310                 315                 320

Cys Ile Phe Leu Ile Met Gln Glu Leu Lys Ala Arg Gly Ile Ser Asn
                325                 330                 335

Glu His Thr Leu Ala Tyr Gln Ser Arg Val Gly Pro Val Gln Trp Leu
            340                 345                 350

Lys Pro Tyr Thr Asp Glu Val Leu Val Glu Leu Gly Gln Lys Gly Val
        355                 360                 365

Lys Ser Leu Leu Ala Val Pro Val Ser Phe Val Ser Glu His Ile Glu
    370                 375                 380

Thr Leu Glu Glu Ile Asp Met Glu Tyr Lys Glu Leu Ala Leu Glu Ser
385                 390                 395                 400

Gly Ile Lys Asn Trp Ala Arg Val Pro Ala Leu Gly Val Thr Pro Ser
                405                 410                 415

Phe Ile Thr Asp Leu Ala Asp Ala Val Ile Glu Ala Leu Pro Ser Ala
            420                 425                 430

Thr Ala Ile Tyr Ala Pro Thr Arg Thr Ser Glu Asp Val Asp His Asp
        435                 440                 445

Pro Val Arg Tyr Phe Ile Lys Met Phe Phe Gly Ser Ile Leu Ala Phe
    450                 455                 460

Ile Leu Phe Leu Ser Pro Lys Met Ile Thr Ala Phe Arg Asn His Val
465                 470                 475                 480

Ile


<210> SEQ ID NO 15
<211> LENGTH: 1651
<212> TYPE: DNA
<213> ORGANISM: Tulip

<400> SEQUENCE: 15

gaaaagtcca gcgaagcctt ttccccgttt gaccgcgctc ctccaccccc gacgtggctc      60

ccaaatcccc cacattcccc cttcctctcc gatctcaaaa ccctaaccct agctccgcaa     120

ttccccaacc tcctccgcca tggaagccct cacctccggc gcctcccagc tcagcctcgc     180

cgcccaccgc cgccgccgca ccgccgccca cctctccagg ccgagggggt tcgtctcctg     240

tgcggcggcg ccggcccgat cggcgccggg gctggtgagt cggagggatg cgaggggcgc     300

ggtggcttgc ggttccaagg cgtgcacgta tgacgaggcg atcgccgggt ttggggaaag     360

cgtggcggag gagaaggtcg gggtgttgtt gctgaatctc ggggggccgg atacgctcca     420

ggatgtccag ccgtttctct ttaatctctt cgctgatccg gatattattc ggcttccaag     480

gctgttccgg tttcttcaac gaccactagc acaactaata tcagttgtca gagcccccaa     540

aagccaagaa ggatatgctg ctattggtgg tggatcacct ttgcggagaa taacaaatga     600

acaggcgcag gcacttaaaa tggcactgga gaagaagaac ctggatgtca atgtttatgt     660

tgcaatgaga tattggcatc cattcactga ggaagctgta catcagataa agaaggataa     720

cgttacaaag cttgtcattc taccacttta tcctcagtac tccatatcca caagtgggtc     780
```

-continued

```
aagcattcgt cttcttcaga atatcttcag ggaagactcc tattttgcag gaattccagt     840

ttctgttatt gaatattggt atcaacgtga gggttatgtc aaatcaatgt cagatttgat     900

tgaaaaggag ctatcgtgtt tctcgaatcc tgaagaggtt atgatatttt ttagcgcaca     960

tggggttcca gtgagctata ttgaggcagg agatccttat agagatcaga tggaggactg    1020

tattagtttg atcatggatg agttgaagtc aaggggagtc tccaatcagc acactcttgc    1080

ttatcagagt cgagttgggc ctgttcagtg gttgaagcct tacacggatg aagttatagt    1140

tgagcttggt cagaaaggtg taaagagtct tctggcggtt ccagtaagct ttgtgagtga    1200

acacatcgag actttggaag aaattgatat ggagtaccgg gagttggctc ttgaatctgg    1260

tatagagaat tggggcaggg taccagctct agggtgcaag tcttccttca ttaccgatct    1320

ggcggatgct gtaattgaat ccctcccttc tgcttctgtt atgtcaactg ccaaaagcac    1380

ctccaatgac ggcaatacag accttgtgca gtatgtagtg aacttgtttt ttgggtcgat    1440

tttcgccttc gtgttgctgt tttcacctag attgatttcc ggtatcagaa attttcttta    1500

acttattcat agtgctgcag atctttgtat aagtggtaac aataaaacaa tacctcatag    1560

attttacgtg gaacatacaa ctgaagggtg taagcctttt ttcccctcaa tagaatcaca    1620

aagtagtatt aataaaaaaa aaaaaaaaaa a                                   1651
```

```
<210> SEQ ID NO 16
<211> LENGTH: 453
<212> TYPE: PRT
<213> ORGANISM: Tulip

<400> SEQUENCE: 16

Met Glu Ala Leu Thr Ser Gly Ala Ser Gln Leu Ser Leu Ala Ala His
1               5                   10                  15

Arg Arg Arg Arg Thr Ala Ala His Leu Ser Arg Pro Arg Gly Phe Val
            20                  25                  30

Ser Cys Ala Ala Ala Pro Ala Arg Ser Ala Pro Gly Leu Val Ser Arg
        35                  40                  45

Arg Asp Ala Arg Gly Ala Val Ala Cys Gly Ser Lys Ala Cys Thr Tyr
    50                  55                  60

Asp Glu Ala Ile Ala Gly Phe Gly Glu Ser Val Ala Glu Glu Lys Val
65                  70                  75                  80

Gly Val Leu Leu Leu Asn Leu Gly Gly Pro Asp Thr Leu Gln Asp Val
                85                  90                  95

Gln Pro Phe Leu Phe Asn Leu Phe Ala Asp Pro Asp Ile Ile Arg Leu
            100                 105                 110

Pro Arg Leu Phe Arg Phe Leu Gln Arg Pro Leu Ala Gln Leu Ile Ser
        115                 120                 125

Val Val Arg Ala Pro Lys Ser Gln Glu Gly Tyr Ala Ala Ile Gly Gly
    130                 135                 140

Gly Ser Pro Leu Arg Arg Ile Thr Asn Glu Gln Ala Gln Ala Leu Lys
145                 150                 155                 160

Met Ala Leu Glu Lys Lys Asn Leu Asp Val Asn Val Tyr Val Ala Met
                165                 170                 175

Arg Tyr Trp His Pro Phe Thr Glu Glu Ala Val His Gln Ile Lys Lys
            180                 185                 190

Asp Asn Val Thr Lys Leu Val Ile Leu Pro Leu Tyr Pro Gln Tyr Ser
        195                 200                 205

Ile Ser Thr Ser Gly Ser Ser Ile Arg Leu Leu Gln Asn Ile Phe Arg
    210                 215                 220
```

```
Glu Asp Ser Tyr Phe Ala Gly Ile Pro Val Ser Val Ile Glu Tyr Trp
225                 230                 235                 240

Tyr Gln Arg Glu Gly Tyr Val Lys Ser Met Ser Asp Leu Ile Glu Lys
                245                 250                 255

Glu Leu Ser Cys Phe Ser Asn Pro Glu Glu Val Met Ile Phe Phe Ser
            260                 265                 270

Ala His Gly Val Pro Val Ser Tyr Ile Glu Ala Gly Asp Pro Tyr Arg
        275                 280                 285

Asp Gln Met Glu Asp Cys Ile Ser Leu Ile Met Asp Glu Leu Lys Ser
    290                 295                 300

Arg Gly Val Ser Asn Gln His Thr Leu Ala Tyr Gln Ser Arg Val Gly
305                 310                 315                 320

Pro Val Gln Trp Leu Lys Pro Tyr Thr Asp Glu Val Ile Val Glu Leu
                325                 330                 335

Gly Gln Lys Gly Val Lys Ser Leu Leu Ala Val Pro Val Ser Phe Val
            340                 345                 350

Ser Glu His Ile Glu Thr Leu Glu Glu Ile Asp Met Glu Tyr Arg Glu
        355                 360                 365

Leu Ala Leu Glu Ser Gly Ile Glu Asn Trp Gly Arg Val Pro Ala Leu
    370                 375                 380

Gly Cys Lys Ser Ser Phe Ile Thr Asp Leu Ala Asp Ala Val Ile Glu
385                 390                 395                 400

Ser Leu Pro Ser Ala Ser Val Met Ser Thr Ala Lys Ser Thr Ser Asn
                405                 410                 415

Asp Gly Asn Thr Asp Leu Val Gln Tyr Val Val Asn Leu Phe Phe Gly
            420                 425                 430

Ser Ile Phe Ala Phe Val Leu Leu Phe Ser Pro Arg Leu Ile Ser Gly
        435                 440                 445

Ile Arg Asn Phe Leu
    450
```

<210> SEQ ID NO 17
<211> LENGTH: 1748
<212> TYPE: DNA
<213> ORGANISM: Triticum aestivum

<400> SEQUENCE: 17

```
gctttgattc cagaaaggga gaggagagag gggaagaaga cgccagagtc gcaacccgcc      60

gcagatctcc tccgtcctcc gcgcccagcc ccgctctgtc ctccatggag tgcgtccgct     120

ccggagctct tgatctgggg cgctccggga atttcttggg gaagagcggc tccacgacgt     180

catgtggtaa agtcagatgt tctacaaacc ttgctggttc taccaaatgc gagcaaaact     240

tgcatgggaa ggttaaaccc ttgctgttgt cagcaagtgg aaaagcaagg ggaacctctg     300

gtttggttca cagaagtgca gtacttaaac atcagcacca tctttctgtg agatccacct     360

ctaccgatgt atgtactact tttgatgaag atgtcaaagg tgtatcttca catgctgttg     420

aggaaaagat tggagtgctg ttactaaatc ttggtggtcc agagaccctc aatgatgttc     480

aaccattttt gttcaacctc tttgctgatc cagatatcat ccgactccct aggctgttca     540

ggtttcttca aagaccactg gccaaactta tttctacttt tagagctcct aagagtaaag     600

aggggtatgc ctcaattggt ggtggatcac ctctgcggaa aattaccgac gagcaggcaa     660

atgctttgaa ggttgcacta aaaagtaaga acttggaagc agatatatat gttggaatgc     720

gttattggta cccattcacc gaagaagcca tcgatcagat taagaaggat aaaattacga     780

agcttgtggt tcttccacta taccctcaat actccatatc aacaagcggg tctagtatcc     840
```

```
gcgttctcca aaacattgtc aaggaagatc aatactttgc tggcttgcca atttccatta    900

ttgaatcttg gtaccagcgc gagggctatg tgaaatcaat ggctgactta attgagaagg    960

aactatcagt ttttacgaat cctgaagagg ttatgatatt cttcagtgca catggagtac   1020

cacttaccta tgttaaggat gctggagatc catacagaga tcagatggaa gactgcattg   1080

ctttgatcat ggaggagttg aaatccagag gaaccttgaa tgaccatact ctggcttacc   1140

agagtcgcgt gggaccagtt caatggctta agccatatac tgatgaagtt ttagttgaac   1200

ttggtcaaaa gggtgtaaag agtctcctgg ctgtcccagt aagcttcgtt agcgagcata   1260

ttgagacact ggaggaaatc gacatggagt acagggagtt ggctctagag tcgggcattg   1320

agaactgggg cagggttcca gctcttggat gcacttcatc cttcatctcg gatcttgctg   1380

atgctgtcgt cgaagccctt ccatctgcct ctgcgatgac gaccagaaag gtcaaggata   1440

ctgactctga catggatatg atgcattacc tgaccaagat gttcttcggc tcggtcctgg   1500

ccttcttcct gctgttatca ccgaggctag tttccgcttt ccggaatact cttcattgag   1560

ctgcttattt ttatcgatgc tccgtggtta accattttgg cgattgtaac tagaaaccgt   1620

atacaggata atatctgggc gagaaagaaa ggaagagttt gtttcactta tgtcttgccc   1680

ataacatatc gacatgcccg ttgtatgaag gagtcatgta ccaccagcat gtataatggc   1740

agatgctt                                                            1748
```

```
<210> SEQ ID NO 18
<211> LENGTH: 484
<212> TYPE: PRT
<213> ORGANISM: Triticum aestivum

<400> SEQUENCE: 18

Met Glu Cys Val Arg Ser Gly Ala Leu Asp Leu Gly Arg Ser Gly Asn
1               5                   10                  15

Phe Leu Gly Lys Ser Gly Ser Thr Thr Ser Cys Gly Lys Val Arg Cys
            20                  25                  30

Ser Thr Asn Leu Ala Gly Ser Thr Lys Cys Glu Gln Asn Leu His Gly
        35                  40                  45

Lys Val Lys Pro Leu Leu Leu Ser Ala Ser Gly Lys Ala Arg Gly Thr
    50                  55                  60

Ser Gly Leu Val His Arg Ser Ala Val Leu Lys His Gln His His Leu
65                  70                  75                  80

Ser Val Arg Ser Thr Ser Thr Asp Val Cys Thr Thr Phe Asp Glu Asp
                85                  90                  95

Val Lys Gly Val Ser Ser His Ala Val Glu Glu Lys Ile Gly Val Leu
            100                 105                 110

Leu Leu Asn Leu Gly Gly Pro Glu Thr Leu Asn Asp Val Gln Pro Phe
        115                 120                 125

Leu Phe Asn Leu Phe Ala Asp Pro Asp Ile Ile Arg Leu Pro Arg Leu
    130                 135                 140

Phe Arg Phe Leu Gln Arg Pro Leu Ala Lys Leu Ile Ser Thr Phe Arg
145                 150                 155                 160

Ala Pro Lys Ser Lys Glu Gly Tyr Ala Ser Ile Gly Gly Gly Ser Pro
                165                 170                 175

Leu Arg Lys Ile Thr Asp Glu Gln Ala Asn Ala Leu Lys Val Ala Leu
            180                 185                 190

Lys Ser Lys Asn Leu Glu Ala Asp Ile Tyr Val Gly Met Arg Tyr Trp
        195                 200                 205
```

```
Tyr Pro Phe Thr Glu Glu Ala Ile Asp Gln Ile Lys Lys Asp Lys Ile
    210                 215                 220

Thr Lys Leu Val Val Leu Pro Leu Tyr Pro Gln Tyr Ser Ile Ser Thr
225                 230                 235                 240

Ser Gly Ser Ser Ile Arg Val Leu Gln Asn Ile Val Lys Glu Asp Gln
                245                 250                 255

Tyr Phe Ala Gly Leu Pro Ile Ser Ile Ile Glu Ser Trp Tyr Gln Arg
            260                 265                 270

Glu Gly Tyr Val Lys Ser Met Ala Asp Leu Ile Glu Lys Glu Leu Ser
        275                 280                 285

Val Phe Thr Asn Pro Glu Glu Val Met Ile Phe Phe Ser Ala His Gly
    290                 295                 300

Val Pro Leu Thr Tyr Val Lys Asp Ala Gly Asp Pro Tyr Arg Asp Gln
305                 310                 315                 320

Met Glu Asp Cys Ile Ala Leu Ile Met Glu Glu Leu Lys Ser Arg Gly
                325                 330                 335

Thr Leu Asn Asp His Thr Leu Ala Tyr Gln Ser Arg Val Gly Pro Val
            340                 345                 350

Gln Trp Leu Lys Pro Tyr Thr Asp Glu Val Leu Val Glu Leu Gly Gln
        355                 360                 365

Lys Gly Val Lys Ser Leu Leu Ala Val Pro Val Ser Phe Val Ser Glu
    370                 375                 380

His Ile Glu Thr Leu Glu Glu Ile Asp Met Glu Tyr Arg Glu Leu Ala
385                 390                 395                 400

Leu Glu Ser Gly Ile Glu Asn Trp Gly Arg Val Pro Ala Leu Gly Cys
                405                 410                 415

Thr Ser Ser Phe Ile Ser Asp Leu Ala Asp Ala Val Val Glu Ala Leu
            420                 425                 430

Pro Ser Ala Ser Ala Met Thr Thr Arg Lys Val Lys Asp Thr Asp Ser
        435                 440                 445

Asp Met Asp Met Met His Tyr Leu Thr Lys Met Phe Phe Gly Ser Val
    450                 455                 460

Leu Ala Phe Phe Leu Leu Leu Ser Pro Arg Leu Val Ser Ala Phe Arg
465                 470                 475                 480

Asn Thr Leu His
```

<210> SEQ ID NO 19
<211> LENGTH: 1859
<212> TYPE: DNA
<213> ORGANISM: Arabidopsis thaliana

<400> SEQUENCE: 19

```
aaaaaataaa acaaattcga agaaatataa atgagatttt tgtagctagc tcctccaaat     60

ccaaatcgtt gcgttaaggt ttcttcaagt ttcaatcttt ttgcaatgaa ttgcccagcc    120

atgactgctt ctccttcttc ttcctcttct tcttcctact caacgtttcg tcctcctcct    180

ccactcttgc cacaattgag taacgattca caaagatctg ttgttatgca ctgcacaaga    240

ttaccctttg aagcatttgc tgctacttca tcaaaccggc ttcttgggaa acattcattg    300

cctttgagag cagctttggt tacttcgaac cctttaaaca tttcatcttc ctcagttatc    360

tctgatgcca tttcatcttc ctctgttatc actgatgatg ccaaaattgg tgtcttgtta    420

ttaaaccttg gaggtcctga gactttagat gatgtacaac cctttttgtt taacctcttc    480

gccgacccgg acattatacg gttgccgccg gtattccagt ttcttcagaa gccattagca    540

cagtttatat cagtagcaag agcacccaaa agcaaggaag gatatgcatc tattggtgga    600
```

ggttctcctc ttcgccacat aactgatgca caggctgaag aattaagaaa atgcctttgg 660
gaaaaaaatg taccagcaaa ggtatatgtt ggtatgcggt attggcatcc attcactgag 720
gaagccattg aacagataaa aagagatgga attacaaaac tagttgttct accactttat 780
cctcaatttt ctatatcaac tagtggttca agcctaagac tcttggagag aatatttcga 840
gaggacgagt atcttgttaa catgcaacat actgttatac catcgtggta tcagcgggag 900
ggatatataa aggcaatggc aaatctaatc caaagcgagt tgggaaaatt tggttctcct 960
aatcaggttg taatattttt cagtgcacat ggcgtgcctc ttgcatatgt cgaagaagcc 1020
ggtgatcctt acaaggcaga gatggaagaa tgtgttgatc taatcatgga ggaattagac 1080
aagagaaaga taactaatgc ttacactctt gcttatcaga gcagagttgg accagttgaa 1140
tggctgaaac catacactga agaagccatt actgaacttg gtaaaaaagg tgttgaaaat 1200
cttctggctg tacccataag ttttgtgagc gagcacattg aaactctgga ggagatagat 1260
gttgagtata aagagttggc tttgaagtct ggtatcaaaa actgggggcg agtacctgct 1320
ctaggaacag aacctatgtt tatatctgac ttggcagatg ctgttgtgga aagtcttcca 1380
tacgttggtg ctatggctgt ctcaaacctt gaagctcgac agtcgttagt tccgctcggg 1440
agtgtagaag aattattagc aacgtatgat tcacagagaa gggagttacc agcaccggtg 1500
acaatgtggg aatggggatg gacaaaaagt gcagaaacat ggaacggaag agcagcaatg 1560
ttagcggtgc tagcactctt ggtgctcgaa gtcaccaccg gaaaagggtt tctgcatcag 1620
tggggcatct tgccttcatt ataataaaga taacgtatag tctttttctc tatgaaaacc 1680
caatccaaga atccaaatgt gagctttcac atgtggaata aggccagcta tgttattatg 1740
ctctcttctt ctctgttgta gaaatgttga catttaaata cttcatactg tatcttcata 1800
aaacattaaa tgttgacatt ttaatcggca tgctttttcg caacgtgaat gtttgagtc 1859

<210> SEQ ID NO 20
<211> LENGTH: 512
<212> TYPE: PRT
<213> ORGANISM: Arabidopsis thaliana

<400> SEQUENCE: 20

Met Asn Cys Pro Ala Met Thr Ala Ser Pro Ser Ser Ser Ser Ser Ser
1               5                   10                  15

Ser Tyr Ser Thr Phe Arg Pro Pro Pro Pro Leu Leu Pro Gln Leu Ser
            20                  25                  30

Asn Asp Ser Gln Arg Ser Val Val Met His Cys Thr Arg Leu Pro Phe
        35                  40                  45

Glu Ala Phe Ala Ala Thr Ser Ser Asn Arg Leu Leu Gly Lys His Ser
    50                  55                  60

Leu Pro Leu Arg Ala Ala Leu Val Thr Ser Asn Pro Leu Asn Ile Ser
65                  70                  75                  80

Ser Ser Ser Val Ile Ser Asp Ala Ile Ser Ser Ser Ser Val Ile Thr
                85                  90                  95

Asp Asp Ala Lys Ile Gly Val Leu Leu Leu Asn Leu Gly Gly Pro Glu
            100                 105                 110

Thr Leu Asp Asp Val Gln Pro Phe Leu Phe Asn Leu Phe Ala Asp Pro
        115                 120                 125

Asp Ile Ile Arg Leu Pro Pro Val Phe Gln Phe Leu Gln Lys Pro Leu
    130                 135                 140

Ala Gln Phe Ile Ser Val Ala Arg Ala Pro Lys Ser Lys Glu Gly Tyr
145                 150                 155                 160

```
Ala Ser Ile Gly Gly Gly Ser Pro Leu Arg His Ile Thr Asp Ala Gln
                165                 170                 175

Ala Glu Glu Leu Arg Lys Cys Leu Trp Glu Lys Asn Val Pro Ala Lys
            180                 185                 190

Val Tyr Val Gly Met Arg Tyr Trp His Pro Phe Thr Glu Glu Ala Ile
        195                 200                 205

Glu Gln Ile Lys Arg Asp Gly Ile Thr Lys Leu Val Val Leu Pro Leu
    210                 215                 220

Tyr Pro Gln Phe Ser Ile Ser Thr Ser Gly Ser Ser Leu Arg Leu Leu
225                 230                 235                 240

Glu Arg Ile Phe Arg Glu Asp Glu Tyr Leu Val Asn Met Gln His Thr
                245                 250                 255

Val Ile Pro Ser Trp Tyr Gln Arg Glu Gly Tyr Ile Lys Ala Met Ala
            260                 265                 270

Asn Leu Ile Gln Ser Glu Leu Gly Lys Phe Gly Ser Pro Asn Gln Val
        275                 280                 285

Val Ile Phe Phe Ser Ala His Gly Val Pro Leu Ala Tyr Val Glu Glu
    290                 295                 300

Ala Gly Asp Pro Tyr Lys Ala Glu Met Glu Glu Cys Val Asp Leu Ile
305                 310                 315                 320

Met Glu Glu Leu Asp Lys Arg Lys Ile Thr Asn Ala Tyr Thr Leu Ala
                325                 330                 335

Tyr Gln Ser Arg Val Gly Pro Val Glu Trp Leu Lys Pro Tyr Thr Glu
            340                 345                 350

Glu Ala Ile Thr Glu Leu Gly Lys Lys Gly Val Glu Asn Leu Leu Ala
        355                 360                 365

Val Pro Ile Ser Phe Val Ser Glu His Ile Glu Thr Leu Glu Glu Ile
    370                 375                 380

Asp Val Glu Tyr Lys Glu Leu Ala Leu Lys Ser Gly Ile Lys Asn Trp
385                 390                 395                 400

Gly Arg Val Pro Ala Leu Gly Thr Glu Pro Met Phe Ile Ser Asp Leu
                405                 410                 415

Ala Asp Ala Val Val Glu Ser Leu Pro Tyr Val Gly Ala Met Ala Val
            420                 425                 430

Ser Asn Leu Glu Ala Arg Gln Ser Leu Val Pro Leu Gly Ser Val Glu
        435                 440                 445

Glu Leu Leu Ala Thr Tyr Asp Ser Gln Arg Arg Glu Leu Pro Ala Pro
    450                 455                 460

Val Thr Met Trp Glu Trp Gly Trp Thr Lys Ser Ala Glu Thr Trp Asn
465                 470                 475                 480

Gly Arg Ala Ala Met Leu Ala Val Leu Ala Leu Leu Val Leu Glu Val
                485                 490                 495

Thr Thr Gly Lys Gly Phe Leu His Gln Trp Gly Ile Leu Pro Ser Leu
            500                 505                 510
```

<210> SEQ ID NO 21
<211> LENGTH: 1797
<212> TYPE: DNA
<213> ORGANISM: Arabidopsis thaliana

<400> SEQUENCE: 21

```
gtttcttcaa gtttcaatct ttttgcaatg aattgcccag ccatgactgc ttctccttct      60

tcttcctctt cttcttccta ctcaacgttt cgtcctcctc ctccactctt gccacaattg     120

agtaacgatt cacaaagatc tgttgttatg cactgcacaa gattaccctt tgaagcattt     180
```

gctgctactt catcaaaccg gcttcttggg aaacattcat tgcctttgag agcagctttg 240
gttacttcga accctttaaa catttcatct tcctcagtta tctctgatgc catttcatct 300
tcctctgtta tcactgatga tgccaaaatt ggtgtcttgt tattaaacct tggaggccct 360
gagactttag atgatgtaca accctttttg tttaacctct tcgccgaccc ggacattata 420
cggttgccgc cggtattcca gtttcttcag aagccattag cacagtttat atcagtagca 480
agagcaccaa aagcaagaag atatgcatct attggtggag gttctcctct tcgccacata 540
actgatgcac aggctgaaga attaagaaaa tgcctttggg aaaaaaatgt accagcaaag 600
gtatatgttg gtatgcggta ttggcatcca ttcactgagg aagccattga acagataaaa 660
agagatggaa ttacaaaact agttgttcta ccactttatc ctcaatttc tatatcaact 720 agtggttcaa gcctaagact cttggagaga atatttcgag aggacgagta tcttgttaac 780
atgcaacata ctgttatacc atcgtggtat cagcgggagg gatatataaa ggcaatggca 840
aatctaatcc aaagcgagtt gggaaaattt ggttctccta atcaggttgt aatattttc 900 agtgcacatg gcgtgcctct tgcatatgtc gaagaagccg gtgatcctta caaggcagag 960
atggaagaat gtgttgatct aatcatggag gaattagaca agagaaagat aactaatgct 1020
tacactcttg cttatcagag cagagttgga ccagttgaat ggctgaaacc atacactgaa 1080
gaagccatta ctgaacttgg taaaaaaggt gttgaaaatc ttctggctgt acccataagt 1140
tttgtgagcg agcacattga aactctggag gagatagatg ttgagtataa agagttggct 1200
ttgaagtctg gtatcaaaaa ctgggggcga gtacctgctc taggaacaga acctatgttt 1260
atatctgact tggcagatgc tgttgtggaa agtcttccat acgttggtgc tatggctgtc 1320
tcaaaccttg aagctcgaca gtcgttagtt ccgctcggga gtgtagaaga actattagca 1380
acgtatgatt cacagagaag ggagttacca gcaccggtga caatgtggga atggggatgg 1440
acaaaaagtg cagaaacatg gaacggaaga gcagcaatgt tagcggtgct agcactcttg 1500
gtgctcgaag tcaccaccgg aaaagggttt ctgcatcagt ggggcatctt gccttcatta 1560
taataaagat aacgtatagt ctttttctct atgaaaaccc aatccaagaa tccaaatgtg 1620
agctttcaca tgtggaataa ggccagctat gttattatgc tctcttcttc tctgtgtaga 1680
aatgtgacat ttaaatactt catactgtat cttcataaaa cattaaatgt tgacatttta 1740
aaaaaaaaaa aaaaaaaaaa aaaaaaaaaa aaaaaaaaaa aaaaaaaaaa aaaaaaa 1797

<210> SEQ ID NO 22
<211> LENGTH: 511
<212> TYPE: PRT
<213> ORGANISM: Arabidopsis thaliana

<400> SEQUENCE: 22

Met Asn Cys Pro Ala Met Thr Ala Ser Pro Ser Ser Ser Ser Ser Ser
1               5                   10                  15

Ser Tyr Ser Thr Phe Arg Pro Pro Pro Pro Leu Leu Pro Gln Leu Ser
            20                  25                  30

Asn Asp Ser Gln Arg Ser Val Val Met His Cys Thr Arg Leu Pro Phe
        35                  40                  45

Glu Ala Phe Ala Ala Thr Ser Ser Asn Arg Leu Leu Gly Lys His Ser
    50                  55                  60

Leu Pro Leu Arg Ala Ala Leu Val Thr Ser Asn Pro Leu Asn Ile Ser
65                  70                  75                  80

Ser Ser Ser Val Ile Ser Asp Ala Ile Ser Ser Ser Ser Val Ile Thr
                85                  90                  95

```
Asp Asp Ala Lys Ile Gly Val Leu Leu Leu Asn Leu Gly Gly Pro Glu
            100                 105                 110

Thr Leu Asp Asp Val Gln Pro Phe Leu Phe Asn Leu Phe Ala Asp Pro
        115                 120                 125

Asp Ile Ile Arg Leu Pro Pro Val Phe Gln Phe Leu Gln Lys Pro Leu
    130                 135                 140

Ala Gln Phe Ile Ser Val Ala Arg Ala Pro Lys Ala Arg Arg Tyr Ala
145                 150                 155                 160

Ser Ile Gly Gly Gly Ser Pro Leu Arg His Ile Thr Asp Ala Gln Ala
                165                 170                 175

Glu Glu Leu Arg Lys Cys Leu Trp Glu Lys Asn Val Pro Ala Lys Val
            180                 185                 190

Tyr Val Gly Met Arg Tyr Trp His Pro Phe Thr Glu Glu Ala Ile Glu
        195                 200                 205

Gln Ile Lys Arg Asp Gly Ile Thr Lys Leu Val Val Leu Pro Leu Tyr
    210                 215                 220

Pro Gln Phe Ser Ile Ser Thr Ser Gly Ser Ser Leu Arg Leu Leu Glu
225                 230                 235                 240

Arg Ile Phe Arg Glu Asp Glu Tyr Leu Val Asn Met Gln His Thr Val
                245                 250                 255

Ile Pro Ser Trp Tyr Gln Arg Glu Gly Tyr Ile Lys Ala Met Ala Asn
            260                 265                 270

Leu Ile Gln Ser Glu Leu Gly Lys Phe Gly Ser Pro Asn Gln Val Val
        275                 280                 285

Ile Phe Phe Ser Ala His Gly Val Pro Leu Ala Tyr Val Glu Glu Ala
    290                 295                 300

Gly Asp Pro Tyr Lys Ala Glu Met Glu Glu Cys Val Asp Leu Ile Met
305                 310                 315                 320

Glu Glu Leu Asp Lys Arg Lys Ile Thr Asn Ala Tyr Thr Leu Ala Tyr
                325                 330                 335

Gln Ser Arg Val Gly Pro Val Glu Trp Leu Lys Pro Tyr Thr Glu Glu
            340                 345                 350

Ala Ile Thr Glu Leu Gly Lys Lys Gly Val Glu Asn Leu Leu Ala Val
        355                 360                 365

Pro Ile Ser Phe Val Ser Glu His Ile Glu Thr Leu Glu Glu Ile Asp
    370                 375                 380

Val Glu Tyr Lys Glu Leu Ala Leu Lys Ser Gly Ile Lys Asn Trp Gly
385                 390                 395                 400

Arg Val Pro Ala Leu Gly Thr Glu Pro Met Phe Ile Ser Asp Leu Ala
                405                 410                 415

Asp Ala Val Val Glu Ser Leu Pro Tyr Val Gly Ala Met Ala Val Ser
            420                 425                 430

Asn Leu Glu Ala Arg Gln Ser Leu Val Pro Leu Gly Ser Val Glu Glu
        435                 440                 445

Leu Leu Ala Thr Tyr Asp Ser Gln Arg Arg Glu Leu Pro Ala Pro Val
    450                 455                 460

Thr Met Trp Glu Trp Gly Trp Thr Lys Ser Ala Glu Thr Trp Asn Gly
465                 470                 475                 480

Arg Ala Ala Met Leu Ala Val Leu Ala Leu Leu Val Leu Glu Val Thr
                485                 490                 495

Thr Gly Lys Gly Phe Leu His Gln Trp Gly Ile Leu Pro Ser Leu
            500                 505                 510
```

-continued

<210> SEQ ID NO 23
<211> LENGTH: 2116
<212> TYPE: DNA
<213> ORGANISM: Nepeta racemosa

<400> SEQUENCE: 23

```
gcacaatttc atttattttt ttgtgaataa tctcttctct acattatcga aatgaaccaa     60

tcttccatga atatacgaat tcaagctcct tctccatctc tactactgcc acgagccaaa    120

gtatgcccat gcataagggt gcaactggag agttttccca atcctaatct tttgaaaaca    180

tccatagttg caagatgccc cttggggtgg tccaagacat catctgtatt tgcagagcac    240

tcgatcaagc attcaacacg accagaagcc ctggttaccg ctggctctca agaaacgtcc    300

acacctgccc tggttggtaa tgataagatt ggagtgttat tgcttaacct tggaggtcca    360

gagactctgg atgacgtgca gcctttcttg tttaatcttt ttgcagatcc agatattatt    420

cgattgccaa gattattccg gtttcttcag aagcccttgg cccaattcat atctgtagct    480

agatcctcga agagcaaaga aggatatgct gcaattggtg gtggctcgcc actgcgtcgt    540

atcactgatg ctcaggctga ggagttgaga aaggcactgt gtgacaagaa tgtccctgca    600

aaagtgtatg ttggtatgcg ctactggcat cctttcactg aagaagcgat tgaacagatt    660

aaggtagatg gaatttcaaa acttgtcgtg cttcctctct acccacaatt ctcaatctca    720

actagtggtt caagtcttcg gcttctggag agtatattca gggaggatga atatctagtc    780

aacatgcagc atactgtaat tccttcatgg taccagcggg gaggatatat aaaagctatg    840

gcagatttga ttgaaaagga gttgggaaag tttgattgtt ctgaggaggt gatgattttc    900

tttagtgctc atggggtacc actggcctat gttgaggaag ctggtgatcc atacaaagct    960

gagatggagg agtgtgttga cttgatcatg gaagaactag aaaacagaaa gataaataat   1020

gcatataccc ttgcatatca gagcagagtt ggacctgtag aatggttgaa accctacaca   1080

gatgatacaa tcgttgaact tggagaaaag ggagtgaaga gtcttctagc tgttccaatt   1140

agttttgtga gcgaacatat tgaaacattg gaagaaatgg atgttgaata caaagaattg   1200

gctctaaagt ctggcataga aaagtgggga cgagttcctg cactaggttg cgagcctact   1260

tttatttcag atttggctga tgctgttata gaaagtcttc catatgttgg agctatggct   1320

gtctcaaatc tcgaagctcg acagtcttta gtcccactcg gcagtgtaga agagctattg   1380

gccgcatatg attcacagcg cagagagctt cctcccctg tggtagtttg ggaatggggt   1440

tggacgaaaa gtgctgaaac atggaatggc agagcagcga tgctggcggt tcttgtcctg   1500

ctcgtgctcg aggtgactac tggagaaggt tttcttcacc agtggggtat attgcccttg   1560

gttccgtgac cacaatttcc cctacttcct tcacttcctt catcctctct ctaacctctg   1620

tatacataaa ctctctgcaa tatatatgga ccctgcataa gaaagatact acaaagtttg   1680

gaggaaaatc agaaacaaaa aatgtcaaga gttatctgta caagttggat atgcacgtct   1740

cgatcctcac gtgtaggatc tggttcgaat tgagctggat aaggagaaat cagaaagtga   1800

gaagtttcgg aaattgagag ctcacggttt tgaggatcgc ttgaggtaga ggttactttc   1860

tagaaatgga cgtgtgagat tcgacttttg aagcagagct ttctctcagt ctgtttagtt   1920

tttcctcttc ttttttttt tgatacggaa cgaacaagat gttgttgtat acacctccga   1980

cattcatatg tatgctggct tatgaattta tcaagttgta tcaatgaaaa ttatgaatgt   2040

ggtaggtgca tttttacaaa aaaaaaaaaa aaaaaaaaaa aaaaaaaaaa aaaaaaaaaa   2100

aaaaaaaaaa aaaaaa                                                   2116
```

<210> SEQ ID NO 24
<211> LENGTH: 505
<212> TYPE: PRT
<213> ORGANISM: Nepeta racemosa

<400> SEQUENCE: 24

```
Met Asn Gln Ser Ser Met Asn Ile Arg Ile Gln Ala Pro Ser Pro Ser
1               5                   10                  15

Leu Leu Leu Pro Arg Ala Lys Val Cys Pro Cys Ile Arg Val Gln Leu
            20                  25                  30

Glu Ser Phe Pro Asn Pro Asn Leu Leu Lys Thr Ser Ile Val Ala Arg
        35                  40                  45

Cys Pro Leu Gly Trp Ser Lys Thr Ser Ser Val Phe Ala Glu His Ser
    50                  55                  60

Ile Lys His Ser Thr Arg Pro Glu Ala Leu Val Thr Ala Gly Ser Gln
65                  70                  75                  80

Glu Thr Ser Thr Pro Ala Leu Val Gly Asn Asp Lys Ile Gly Val Leu
                85                  90                  95

Leu Leu Asn Leu Gly Gly Pro Glu Thr Leu Asp Asp Val Gln Pro Phe
            100                 105                 110

Leu Phe Asn Leu Phe Ala Asp Pro Asp Ile Ile Arg Leu Pro Arg Leu
        115                 120                 125

Phe Arg Phe Leu Gln Lys Pro Leu Ala Gln Phe Ile Ser Val Ala Arg
    130                 135                 140

Ser Ser Lys Ser Lys Glu Gly Tyr Ala Ala Ile Gly Gly Gly Ser Pro
145                 150                 155                 160

Leu Arg Arg Ile Thr Asp Ala Gln Ala Glu Glu Leu Arg Lys Ala Leu
                165                 170                 175

Cys Asp Lys Asn Val Pro Ala Lys Val Tyr Val Gly Met Arg Tyr Trp
            180                 185                 190

His Pro Phe Thr Glu Glu Ala Ile Glu Gln Ile Lys Val Asp Gly Ile
        195                 200                 205

Ser Lys Leu Val Val Leu Pro Leu Tyr Pro Gln Phe Ser Ile Ser Thr
    210                 215                 220

Ser Gly Ser Ser Leu Arg Leu Leu Glu Ser Ile Phe Arg Glu Asp Glu
225                 230                 235                 240

Tyr Leu Val Asn Met Gln His Thr Val Ile Pro Ser Trp Tyr Gln Arg
                245                 250                 255

Gly Gly Tyr Ile Lys Ala Met Ala Asp Leu Ile Glu Lys Glu Leu Gly
            260                 265                 270

Lys Phe Asp Cys Ser Glu Glu Val Met Ile Phe Phe Ser Ala His Gly
        275                 280                 285

Val Pro Leu Ala Tyr Val Glu Glu Ala Gly Asp Pro Tyr Lys Ala Glu
    290                 295                 300

Met Glu Glu Cys Val Asp Leu Ile Met Glu Glu Leu Glu Asn Arg Lys
305                 310                 315                 320

Ile Asn Asn Ala Tyr Thr Leu Ala Tyr Gln Ser Arg Val Gly Pro Val
                325                 330                 335

Glu Trp Leu Lys Pro Tyr Thr Asp Asp Thr Ile Val Glu Leu Gly Glu
            340                 345                 350

Lys Gly Val Lys Ser Leu Leu Ala Val Pro Ile Ser Phe Val Ser Glu
        355                 360                 365

His Ile Glu Thr Leu Glu Glu Met Asp Val Glu Tyr Lys Glu Leu Ala
    370                 375                 380

Leu Lys Ser Gly Ile Glu Lys Trp Gly Arg Val Pro Ala Leu Gly Cys
```

385 390 395 400

Glu Pro Thr Phe Ile Ser Asp Leu Ala Asp Ala Val Ile Glu Ser Leu
405 410 415

Pro Tyr Val Gly Ala Met Ala Val Ser Asn Leu Glu Ala Arg Gln Ser
420 425 430

Leu Val Pro Leu Gly Ser Val Glu Glu Leu Leu Ala Ala Tyr Asp Ser
435 440 445

Gln Arg Arg Glu Leu Pro Pro Pro Val Val Val Trp Glu Trp Gly Trp
450 455 460

Thr Lys Ser Ala Glu Thr Trp Asn Gly Arg Ala Ala Met Leu Ala Val
465 470 475 480

Leu Val Leu Leu Val Leu Glu Val Thr Thr Gly Glu Gly Phe Leu His
485 490 495

Gln Trp Gly Ile Leu Pro Leu Val Pro
500 505

<210> SEQ ID NO 25
<211> LENGTH: 2072
<212> TYPE: DNA
<213> ORGANISM: Zea mays

<400> SEQUENCE: 25
gtcccatact cccgtcctgt ccgtcttcac ctgcgttccc cgggtcccga cacgccgctg 60
taccagtccc gcccgcctgc gcacttctcc cacccccgcg ccgcctccgg cgccggcgag 120
ccctcccgac gctcctcgaa cgatccgtcc ctgtcgcggc ccttctctct gccgcttcca 180
gcccaagggg aggagaggga gaggatgtgg tcgtcgagcc aggcgagcac gaggggcgtc 240
gtggagatgg ggagggtgga ggccgggccg tcgcatttcc ctaagagacc cgcgcctcag 300
aactccgcca gggtcaatct gtcaaggaca cacacagtca aacctacctc tgctggcgac 360
cgttcaggaa tttctgttaa atgcaacttg gggtggtctt ctcaaccatc gcctgacttg 420
aggcatcact ttagaggata ctcatcagca tcagaggcag ttcttacttc ccaatctgat 480
gtgagaaaac tgtttgttgg caatgaaaaa atcggtgttc tcttgctgaa tcttgggggc 540
ccagagactc ttgacgatgt gcagcctttc ttgtttaatc tttttgcaga tccggacatt 600
atccgtcttc ctaggctctt tcgctttctg cagaagccac ttgcaaaatt catatcagaa 660
gtgagagcac caaaaagtaa ggaaggttat gcatccatag gtggcggttc tcctctacga 720
caaattactg atgcacaggc tgaagcactt agggaggcat tacatgggaa agatgttcct 780
gccaacgtgt atgttggaat gcggtattgg catcccttca ctgaagaagc catagaacaa 840
ataaaacggg atggaatcac gaaacttgtt gtgttgcctc tataccctca gttctccata 900
tcaactagtg gttcaagtct ccgtttattg gagagcatat tcagagagga tgagtatctc 960
gtgaatatgc aacatacagt tataccttcc tggtaccaac gtgaaggata tatcaaggct 1020
atggcaactt tgattgaaaa cgaattgaca aaatttcaag aaccccaaaa ggttatgata 1080
tttttcagtg ctcatggagt tcctctggca tatgttgaag aagctggtga tccatataaa 1140
gcagaaatgg aagagtgtat cgatcttatc atggaagaac tggaaaaaag aggaataaca 1200
aatccgtgca tacttgctta tcagagccga gttggaccag tggaatggct gaaaccgtac 1260
actgatgaga caattattga gcttgggcag aaaggggtaa agagcctgct tgctgttccc 1320
attagttttg ttagcgaaca cattgaaact ttggaagaaa tcgatgtgga gtacaaagag 1380
ttggctttag aatctggcat caagcactgg ggacgggttc cagcactagg ttgcgaaccc 1440
acattcattt cggatcttgc tgatgctgtt attgaaagcc taccttatgt tggcgcaatg 1500

```
gcagtttcca atcttgaggc tcggcagtct ctcgtacccc tcgggagcgt ggaggagctg   1560

ctagcagcat acgactcgaa gcgcgatgag ctccctccac cggtaatcgt gtgggagtgg   1620

ggctggacaa agagcgcgga gacctggaat ggtcgtgcgg cgatgctggc cgtgctggct   1680

ctcctggtgc tggaagtgac caccggcgaa gggttcctgc atcaatgggg aatcctgcct   1740

ctgttccgct gagccgacag ttctgttcat gatggggtca taattttgct gcagccgaag   1800

gaagttttga acttctgatg ctgtatatga atcaatttgc cttaaatcgt cgatgggaaa   1860

agaggagaaa atggtaaaat atggacagaa ttcgacggta tatcatgtta tattgtacct   1920

acctacatga catgggacat gaaatagggc tcagacatgc gctatggaac ttggaataca   1980

cacaaaccta acacgccaaa aaaaaaaaaa aaaaaaaaaa aaaaaaaaaa aaaaaaaaaa   2040

aaaaaaaaaa aaaaaaaaaa aaaaaaaaaa aa                                 2072


<210> SEQ ID NO 26
<211> LENGTH: 515
<212> TYPE: PRT
<213> ORGANISM: Zea mays

<400> SEQUENCE: 26

Met Trp Ser Ser Ser Gln Ala Ser Thr Arg Gly Val Val Glu Met Gly
1               5                   10                  15

Arg Val Glu Ala Gly Pro Ser His Phe Pro Lys Arg Pro Ala Pro Gln
            20                  25                  30

Asn Ser Ala Arg Val Asn Leu Ser Arg Thr His Thr Val Lys Pro Thr
        35                  40                  45

Ser Ala Gly Asp Arg Ser Gly Ile Ser Val Lys Cys Asn Leu Gly Trp
    50                  55                  60

Ser Ser Gln Pro Ser Pro Asp Leu Arg His His Phe Arg Gly Tyr Ser
65                  70                  75                  80

Ser Ala Ser Glu Ala Val Leu Thr Ser Gln Ser Asp Val Arg Lys Leu
                85                  90                  95

Phe Val Gly Asn Glu Lys Ile Gly Val Leu Leu Leu Asn Leu Gly Gly
            100                 105                 110

Pro Glu Thr Leu Asp Asp Val Gln Pro Phe Leu Phe Asn Leu Phe Ala
        115                 120                 125

Asp Pro Asp Ile Ile Arg Leu Pro Arg Leu Phe Arg Phe Leu Gln Lys
    130                 135                 140

Pro Leu Ala Lys Phe Ile Ser Glu Val Arg Ala Pro Lys Ser Lys Glu
145                 150                 155                 160

Gly Tyr Ala Ser Ile Gly Gly Gly Ser Pro Leu Arg Gln Ile Thr Asp
                165                 170                 175

Ala Gln Ala Glu Ala Leu Arg Glu Ala Leu His Gly Lys Asp Val Pro
            180                 185                 190

Ala Asn Val Tyr Val Gly Met Arg Tyr Trp His Pro Phe Thr Glu Glu
        195                 200                 205

Ala Ile Glu Gln Ile Lys Arg Asp Gly Ile Thr Lys Leu Val Val Leu
    210                 215                 220

Pro Leu Tyr Pro Gln Phe Ser Ile Ser Thr Ser Gly Ser Ser Leu Arg
225                 230                 235                 240

Leu Leu Glu Ser Ile Phe Arg Glu Asp Glu Tyr Leu Val Asn Met Gln
                245                 250                 255

His Thr Val Ile Pro Ser Trp Tyr Gln Arg Glu Gly Tyr Ile Lys Ala
            260                 265                 270
```

```
Met Ala Thr Leu Ile Glu Asn Glu Leu Thr Lys Phe Gln Glu Pro Gln
        275                 280                 285

Lys Val Met Ile Phe Phe Ser Ala His Gly Val Pro Leu Ala Tyr Val
    290                 295                 300

Glu Glu Ala Gly Asp Pro Tyr Lys Ala Glu Met Glu Glu Cys Ile Asp
305                 310                 315                 320

Leu Ile Met Glu Glu Leu Glu Lys Arg Gly Ile Thr Asn Pro Cys Ile
                325                 330                 335

Leu Ala Tyr Gln Ser Arg Val Gly Pro Val Glu Trp Leu Lys Pro Tyr
            340                 345                 350

Thr Asp Glu Thr Ile Ile Glu Leu Gly Gln Lys Gly Val Lys Ser Leu
        355                 360                 365

Leu Ala Val Pro Ile Ser Phe Val Ser Glu His Ile Glu Thr Leu Glu
    370                 375                 380

Glu Ile Asp Val Glu Tyr Lys Glu Leu Ala Leu Glu Ser Gly Ile Lys
385                 390                 395                 400

His Trp Gly Arg Val Pro Ala Leu Gly Cys Glu Pro Thr Phe Ile Ser
                405                 410                 415

Asp Leu Ala Asp Ala Val Ile Glu Ser Leu Pro Tyr Val Gly Ala Met
            420                 425                 430

Ala Val Ser Asn Leu Glu Ala Arg Gln Ser Leu Val Pro Leu Gly Ser
        435                 440                 445

Val Glu Glu Leu Leu Ala Ala Tyr Asp Ser Lys Arg Asp Glu Leu Pro
    450                 455                 460

Pro Pro Val Ile Val Trp Glu Trp Gly Trp Thr Lys Ser Ala Glu Thr
465                 470                 475                 480

Trp Asn Gly Arg Ala Ala Met Leu Ala Val Leu Ala Leu Leu Val Leu
                485                 490                 495

Glu Val Thr Thr Gly Glu Gly Phe Leu His Gln Trp Gly Ile Leu Pro
            500                 505                 510

Leu Phe Arg
        515
```

<210> SEQ ID NO 27
<211> LENGTH: 1946
<212> TYPE: DNA
<213> ORGANISM: Triticum aestivum

<400> SEQUENCE: 27

```
ggttctcttg tacctccgcg cttccaagga tttgatttct tcgctcgttg cggatttccc      60

tactggctga gtaccaattt cgctcggttt cacaacaaat ttggatatcc atgctccacg     120

tcaggctcgc tcctgggcct gcaccgcgta atttatctag gagatgggat accagcgcat     180

acctacatag ctggtgttcc gttccttgtc caagcaggct cagtctctcg aggacatatt     240

caattaaatc ttctttgatt ggtagcgcca cgggactttg tcttgggcaa tgttgccgca     300

tcaagccttt gtcctgcaaa tgcaagctag gtaggtcttc tcagccgcca cctgactcga     360

ggcaacattt tagtgcatct tcatccgcat cagaggcggt tctcactgcg cagtctgata     420

tccggaaact ttttgttgcc aatgagaaaa tcggcgttct gctgctaaac cttggaggcc     480

cagagaccct tgatgatgtc cagcctttct tgtttaatct ctttgctgat ccggatatca     540

tccgtcttcc tagggcgttc cgctttctgc agaagccgct agcacaattc atttctgttg     600

caagagcgcc aaagagcaag gaaggttatg catccatagg tggtggttca cctcttcgac     660

aaattactga tgcgcaggga gaagcactta tggaggcact atgtggaaag gatatccctg     720
```

```
ctaaggtgta cgtgggaatg cggtattggc atcccttcac cgaggaagct atagaacaaa    780
taaaaaagga tggaatcaca aaacttgttg tactacctct ttacccccag ttctccatat    840
cgaccagtgg ttcaagtctc cgtcttctgg agagcatatt cagagaggat gagtatctgg    900
tcaatatgca acatacggtt attccttctt ggtatcagcg tgaaggatat attaaggcca    960
tggcaacttt gatcgagaag gagttgttga aatttccaaa accgcagaag gttatgatat   1020
ttttcagtgc tcatggagtt cctctggcat acgttgaaga agctggtgat ccgtataaag   1080
cagagatgga agagtgcgtg gatcttatca tggaggagct cgaaaaaaga ggaatggcaa   1140
atccatctac acttgcttat cagagccgag taggaccagt ggaatggctg aaaccctaca   1200
ctgacgagac aattattgct cttgggcaga gaggggtaaa gagccttcta gcagttccca   1260
ttagttttgt cagcgaacac attgagacgt tagaagaaat tgacgtcgaa tacaaggagc   1320
tggctttgca atctggtatc aagcactggg gacgagttcc cgctttaggt tgtgagccca   1380
cattcatttc agatctggcg gatgctgtta tcgaaagcct gccttatgtt ggcgcaatgg   1440
cagtttccaa ccttgaggct cggcagtcac tggtgccact tggaagcgtg gaggagctgc   1500
tagcaaccta cgactcgaaa cgcgacatgc tgcctcctcc ggtgattgtg tgggagtggg   1560
gctggacgaa gagcgccgag acatggaatg gacgtgctgc tatgctggcc gtgttggctc   1620
tcctggtgct ggaggtaaca accggacagg ggctcttgca ccagtggggt atattgccac   1680
ctctcccttg acaagcgggg atggatggat ggatggattt caggtctccc cttgagggga   1740
tctgatcgta attttggttc atttggggaa tgccctgatg ctatatatga tggatcgatt   1800
tgccttacgc caagaaagga aaatatggac tgtattcgcc ggtgtaaata tgctagactg   1860
aagagagctt tacattatta ttattaacca ataagagctg tcgaatcgtt ggctaaaaaa   1920
aaaaaaaaaa aaaaaaaaaa aaaaaa                                        1946
```

<210> SEQ ID NO 28
<211> LENGTH: 526
<212> TYPE: PRT
<213> ORGANISM: Triticum aestivum

<400> SEQUENCE: 28

```
Met Leu His Val Arg Leu Ala Pro Gly Pro Ala Pro Arg Asn Leu Ser
1               5                   10                  15

Arg Arg Trp Asp Thr Ser Ala Tyr Leu His Ser Trp Cys Ser Val Pro
            20                  25                  30

Cys Pro Ser Arg Leu Ser Leu Ser Arg Thr Tyr Ser Ile Lys Ser Ser
        35                  40                  45

Leu Ile Gly Ser Ala Thr Gly Leu Cys Leu Gly Gln Cys Cys Arg Ile
    50                  55                  60

Lys Pro Leu Ser Cys Lys Cys Lys Leu Gly Arg Ser Ser Gln Pro Pro
65                  70                  75                  80

Pro Asp Ser Arg Gln His Phe Ser Ala Ser Ser Ser Ala Ser Glu Ala
                85                  90                  95

Val Leu Thr Ala Gln Ser Asp Ile Arg Lys Leu Phe Val Ala Asn Glu
            100                 105                 110

Lys Ile Gly Val Leu Leu Leu Asn Leu Gly Gly Pro Glu Thr Leu Asp
        115                 120                 125

Asp Val Gln Pro Phe Leu Phe Asn Leu Phe Ala Asp Pro Asp Ile Ile
    130                 135                 140

Arg Leu Pro Arg Ala Phe Arg Phe Leu Gln Lys Pro Leu Ala Gln Phe
145                 150                 155                 160
```

```
Ile Ser Val Ala Arg Ala Pro Lys Ser Lys Glu Gly Tyr Ala Ser Ile
                165                 170                 175

Gly Gly Gly Ser Pro Leu Arg Gln Ile Thr Asp Ala Gln Gly Glu Ala
            180                 185                 190

Leu Met Glu Ala Leu Cys Gly Lys Asp Ile Pro Ala Lys Val Tyr Val
        195                 200                 205

Gly Met Arg Tyr Trp His Pro Phe Thr Glu Glu Ala Ile Glu Gln Ile
    210                 215                 220

Lys Lys Asp Gly Ile Thr Lys Leu Val Val Leu Pro Leu Tyr Pro Gln
225                 230                 235                 240

Phe Ser Ile Ser Thr Ser Gly Ser Ser Leu Arg Leu Leu Glu Ser Ile
                245                 250                 255

Phe Arg Glu Asp Glu Tyr Leu Val Asn Met Gln His Thr Val Ile Pro
            260                 265                 270

Ser Trp Tyr Gln Arg Glu Gly Tyr Ile Lys Ala Met Ala Thr Leu Ile
        275                 280                 285

Glu Lys Glu Leu Leu Lys Phe Pro Lys Pro Gln Lys Val Met Ile Phe
    290                 295                 300

Phe Ser Ala His Gly Val Pro Leu Ala Tyr Val Glu Glu Ala Gly Asp
305                 310                 315                 320

Pro Tyr Lys Ala Glu Met Glu Glu Cys Val Asp Leu Ile Met Glu Glu
                325                 330                 335

Leu Glu Lys Arg Gly Met Ala Asn Pro Ser Thr Leu Ala Tyr Gln Ser
            340                 345                 350

Arg Val Gly Pro Val Glu Trp Leu Lys Pro Tyr Thr Asp Glu Thr Ile
        355                 360                 365

Ile Ala Leu Gly Gln Arg Gly Val Lys Ser Leu Leu Ala Val Pro Ile
    370                 375                 380

Ser Phe Val Ser Glu His Ile Glu Thr Leu Glu Glu Ile Asp Val Glu
385                 390                 395                 400

Tyr Lys Glu Leu Ala Leu Gln Ser Gly Ile Lys His Trp Gly Arg Val
                405                 410                 415

Pro Ala Leu Gly Cys Glu Pro Thr Phe Ile Ser Asp Leu Ala Asp Ala
            420                 425                 430

Val Ile Glu Ser Leu Pro Tyr Val Gly Ala Met Ala Val Ser Asn Leu
        435                 440                 445

Glu Ala Arg Gln Ser Leu Val Pro Leu Gly Ser Val Glu Glu Leu Leu
    450                 455                 460

Ala Thr Tyr Asp Ser Lys Arg Asp Met Leu Pro Pro Pro Val Ile Val
465                 470                 475                 480

Trp Glu Trp Gly Trp Thr Lys Ser Ala Glu Thr Trp Asn Gly Arg Ala
                485                 490                 495

Ala Met Leu Ala Val Leu Ala Leu Leu Val Leu Glu Val Thr Thr Gly
            500                 505                 510

Gln Gly Leu Leu His Gln Trp Gly Ile Leu Pro Pro Leu Pro
        515                 520                 525


<210> SEQ ID NO 29
<211> LENGTH: 2014
<212> TYPE: DNA
<213> ORGANISM: Triticum aestivum

<400> SEQUENCE: 29

gctcgcttcc ttccgctgcc acttgccact tcgtccttcc gcttcttccc ccgaagcccg     60

aatcctctct ctcctccccg tcataaacag ggacctcaaa caagttctct tgtacctccg    120
```

-continued

```
cgcctcctcg gatttgattt cttcgttcgt tgcggatttc cctcccgtct gagtactaat    180
ttcgctcggt ttcccaacaa atttcgatat ccatgctcca cgtcaggctc gctcctgggc    240
ctgcaccgcg taatttatct aggagatggg attccagcgc atacctacat agctggtgtt    300
ccgttccttg tccaagcagg ctcagtctct cgagggcata ttcaattaaa tcttcttcga    360
ttggtagcgc cacgggactt tgtcttgggc aatgttgccg catcaagcct ttgtcctgca    420
aatgcaagct aggtaggtct tctcagccgc cacctgactc gaggcaacat tttagtgcat    480
cttcatccgc atcagaggcg gttctcactg cgcagtccga tatccggaaa ctttttgttg    540
ccaatgagaa aatcggcgtt ctgctgctaa accttggagg cccagagacc cttgatgatg    600
tccagccttt cttgtttaat ctctttgctg atccggatat catccgtctt cctagggcgt    660
tccgctttct gcagaagccg ctagcacaat tcatttctgt tgcaagagcg ccaaagagca    720
aggaaggtta tgcatccata ggtggtggtt cacctcttcg acaaattact gatgcgcagg    780
gagaagcact tatggaagca ttatgtggaa aggatatccc tgctaaggtg tacgtgggaa    840
tgcggtactg gcatcccttc accgaggaag ctatagaaca aataaaaaag gatggaatca    900
caaaacttgt tgtactacct ctttaccccc agttctccat atcgaccagt ggttcaagtc    960
tccgtcttct ggagagcata ttcagagagg atgagtatct ggtcaatatg caacatacgg   1020
ttattccttc ttggtatcag cgtgaaggat atattaaggc catgacaact ttgatcgaga   1080
aggagttgtt gaaatttcca aaaccgcaga aggttatgat atttttcagt gctcatggag   1140
ttcctctggc atacgttgaa gaagctggtg atccgtataa agcagagatg gaagagtgcg   1200
tggatcttat catggaggag ctcgaaaaaa gaggaatggc aaatccatgt acacttgctt   1260
atcagagccg agtaggacca gtggaatggc tgaaacccta cactgacgag acaattattg   1320
ctcttgggca gagggggtta aagagtcttc tagcagttcc cattagtttt gtcagcgaac   1380
acattgagac gttagaagaa attgacgtcg aatacaagga gctggctttg caatctggta   1440
tcaagcactg ggacgagtt cccgctttag gttgtgagcc cacattcatt tcagatctgg   1500
cggatgctgt tatcgaaagc ctgccttatg ttggcgcaat ggcagtttcc aaccttgagg   1560
ctcgacagtc actggtgcca cttggaagcg tggaggagct gctagcagcc tacgactcga   1620
aacgcgacat gctgcctcct ccggtgattg tgtgggagtg gggctggacg aagagcgccg   1680
agacatggaa tggacgtgct gctatgctgg ccgtgttggc tctcctggtg ctggaggtaa   1740
caaccggaca ggggctcttg caccagtggg gtattttgcc acctttccct taacaagcgg   1800
ggatggatgg atggatggat ttcaggtctc cccttgaggg gatctgatcg taattttggt   1860
tcatttgggg aatgtcctga tgctatatat gatggatcga tttgccttac gccaagaaag   1920
gaaaatatgg actcaattcg ccggtgtaaa tatgctagac tgaagagagc tttacattat   1980
tattaaccaa aaaaaaaaaa aaaaaaaaaa aaaa                               2014
```

<210> SEQ ID NO 30
<211> LENGTH: 526
<212> TYPE: PRT
<213> ORGANISM: Triticum aestivum

<400> SEQUENCE: 30

```
Met Leu His Val Arg Leu Ala Pro Gly Pro Ala Pro Arg Asn Leu Ser
1               5                   10                  15

Arg Arg Trp Asp Ser Ser Ala Tyr Leu His Ser Trp Cys Ser Val Pro
            20                  25                  30

Cys Pro Ser Arg Leu Ser Leu Ser Arg Ala Tyr Ser Ile Lys Ser Ser
```

-continued

```
        35                  40                  45

Ser Ile Gly Ser Ala Thr Gly Leu Cys Leu Gly Gln Cys Cys Arg Ile
    50                  55                  60

Lys Pro Leu Ser Cys Lys Cys Lys Leu Gly Arg Ser Ser Gln Pro Pro
65                  70                  75                  80

Pro Asp Ser Arg Gln His Phe Ser Ala Ser Ser Ser Ala Ser Glu Ala
                85                  90                  95

Val Leu Thr Ala Gln Ser Asp Ile Arg Lys Leu Phe Val Ala Asn Glu
            100                 105                 110

Lys Ile Gly Val Leu Leu Leu Asn Leu Gly Gly Pro Glu Thr Leu Asp
        115                 120                 125

Asp Val Gln Pro Phe Leu Phe Asn Leu Phe Ala Asp Pro Asp Ile Ile
    130                 135                 140

Arg Leu Pro Arg Ala Phe Arg Phe Leu Gln Lys Pro Leu Ala Gln Phe
145                 150                 155                 160

Ile Ser Val Ala Arg Ala Pro Lys Ser Lys Glu Gly Tyr Ala Ser Ile
                165                 170                 175

Gly Gly Gly Ser Pro Leu Arg Gln Ile Thr Asp Ala Gln Gly Glu Ala
            180                 185                 190

Leu Met Glu Ala Leu Cys Gly Lys Asp Ile Pro Ala Lys Val Tyr Val
        195                 200                 205

Gly Met Arg Tyr Trp His Pro Phe Thr Glu Glu Ala Ile Glu Gln Ile
    210                 215                 220

Lys Lys Asp Gly Ile Thr Lys Leu Val Val Leu Pro Leu Tyr Pro Gln
225                 230                 235                 240

Phe Ser Ile Ser Thr Ser Gly Ser Ser Leu Arg Leu Leu Glu Ser Ile
                245                 250                 255

Phe Arg Glu Asp Glu Tyr Leu Val Asn Met Gln His Thr Val Ile Pro
            260                 265                 270

Ser Trp Tyr Gln Arg Glu Gly Tyr Ile Lys Ala Met Thr Thr Leu Ile
        275                 280                 285

Glu Lys Glu Leu Leu Lys Phe Pro Lys Pro Gln Lys Val Met Ile Phe
    290                 295                 300

Phe Ser Ala His Gly Val Pro Leu Ala Tyr Val Glu Glu Ala Gly Asp
305                 310                 315                 320

Pro Tyr Lys Ala Glu Met Glu Glu Cys Val Asp Leu Ile Met Glu Glu
                325                 330                 335

Leu Glu Lys Arg Gly Met Ala Asn Pro Cys Thr Leu Ala Tyr Gln Ser
            340                 345                 350

Arg Val Gly Pro Val Glu Trp Leu Lys Pro Tyr Thr Asp Glu Thr Ile
        355                 360                 365

Ile Ala Leu Gly Gln Arg Gly Val Lys Ser Leu Leu Ala Val Pro Ile
    370                 375                 380

Ser Phe Val Ser Glu His Ile Glu Thr Leu Glu Glu Ile Asp Val Glu
385                 390                 395                 400

Tyr Lys Glu Leu Ala Leu Gln Ser Gly Ile Lys His Trp Gly Arg Val
                405                 410                 415

Pro Ala Leu Gly Cys Glu Pro Thr Phe Ile Ser Asp Leu Ala Asp Ala
            420                 425                 430

Val Ile Glu Ser Leu Pro Tyr Val Gly Ala Met Ala Val Ser Asn Leu
        435                 440                 445

Glu Ala Arg Gln Ser Leu Val Pro Leu Gly Ser Val Glu Glu Leu Leu
    450                 455                 460
```

```
Ala Ala Tyr Asp Ser Lys Arg Asp Met Leu Pro Pro Pro Val Ile Val
465                 470                 475                 480

Trp Glu Trp Gly Trp Thr Lys Ser Ala Glu Thr Trp Asn Gly Arg Ala
                485                 490                 495

Ala Met Leu Ala Val Leu Ala Leu Leu Val Leu Glu Val Thr Thr Gly
            500                 505                 510

Gln Gly Leu Leu His Gln Trp Gly Ile Leu Pro Pro Phe Pro
        515                 520                 525


<210> SEQ ID NO 31
<211> LENGTH: 18491
<212> TYPE: DNA
<213> ORGANISM: Artificial
<220> FEATURE:
<223> OTHER INFORMATION: pHSbarENDs2 activation tagging vector

<400> SEQUENCE: 31

catgaatcaa acaaacatac acagcgactt attcacacga gctcaaatta caacggtata     60

tatcctgccg tcgacaacca tggtctagac aggatccccg ggtaccgagc tcgaatttgc    120

aggtcgactg cgtcatccct tacgtcagtg gagatatcac atcaatccac ttgctttgaa    180

gacgtggttg gaacgtcttc tttttccacg atgctcctcg tgggtggggg tccatctttg    240

ggaccactgt cggcagaggc atcttgaacg atagcctttc ctttatcgca atgatggcat    300

ttgtaggtgc caccttcctt ttctactgtc cttttgatga agtgacagat agctgggcaa    360

tggaatccga ggaggtttcc cgatattacc ctttgttgaa aagtctcaat tgccctttgg    420

tcttctgaga ctgttgcgtc atcccttacg tcagtggaga tatcacatca atccacttgc    480

tttgaagacg tggttggaac gtcttctttt tccacgatgc tcctcgtggg tgggggtcca    540

tctttgggac cactgtcggc agaggcatct tgaacgatag cctttccttt atcgcaatga    600

tggcatttgt aggtgccacc ttccttttct actgtccttt tgatgaagtg acagatagct    660

gggcaatgga atccgaggag gtttcccgat attacccttt gttgaaaagt ctcagttaac    720

ccgcgatcct gcgtcatccc ttacgtcagt ggagatatca catcaatcca cttgctttga    780

agacgtggtt ggaacgtctt ctttttccac gatgctcctc gtgggtgggg gtccatcttt    840

gggaccactg tcggcagagg catcttgaac gatagccttt cctttatcgc aatgatggca    900

tttgtaggtg ccaccttcct tttctactgt ccttttgatg aagtgacaga tagctgggca    960

atggaatccg aggaggtttc ccgatattac cctttgttga aaagtctcaa ttgccctttg   1020

gtcttctgag actgttgcgt catcccttac gtcagtggag atatcacatc aatccacttg   1080

ctttgaagac gtggttggaa cgtcttcttt ttccacgatg ctcctcgtgg gtgggggtcc   1140

atctttggga ccactgtcgg cagaggcatc ttgaacgata gcctttcctt tatcgcaatg   1200

atggcatttg taggtgccac cttccttttc tactgtcctt ttgatgaagt gacagatagc   1260

tgggcaatgg aatccgagga ggtttcccga tattaccctt tgttgaaaag tctcagttaa   1320

cccgcaattc actggccgtc gttttacaac gtcgtgactg ggaaaaccct ggcgttaccc   1380

aacttaatcg ccttgcagca catccccctt tcgccagctg gcgtaatagc gaagaggccc   1440

gcaccgatcg cccttcccaa cagttgcgca gcctgaatgg cgaatggatc gatccgtcga   1500

tcgaccaaag cggccatcgt gcctccccac tcctgcagtt cgggggcatg gatgcgcgga   1560

tagccgctgc tggtttcctg gatgccgacg gatttgcact gccggtagaa ctccgcgagg   1620

tcgtccagcc tcaggcagca gctgaaccaa ctcgcgaggg gatcgagccc ctgctgagcc   1680

tcgacatgtt gtcgcaaaat tcgccctgga cccgcccaac gatttgtcgt cactgtcaag   1740
```

-continued

```
gtttgacctg cacttcattt ggggcccaca tacaccaaaa aaatgctgca taattctcgg   1800
ggcagcaagt cggttacccg gccgccgtgc tggaccgggt tgaatggtgc ccgtaacttt   1860
cggtagagcg gacggccaat actcaacttc aaggaatctc acccatgcgc gccggcgggg   1920
aaccggagtt cccttcagtg aacgttatta gttcgccgct cggtgtgtcg tagatactag   1980
cccctggggc cttttgaaat ttgaataaga tttatgtaat cagtctttta ggtttgaccg   2040
gttctgccgc ttttttttaaa attggatttg taataataaa acgcaattgt ttgttattgt   2100
ggcgctctat catagatgtc gctataaacc tattcagcac aatatattgt tttcatttta   2160
atattgtaca tataagtagt agggtacaat cagtaaattg aacggagaat attattcata   2220
aaaatacgat agtaacgggt gatatattca ttagaatgaa ccgaaaccgg cggtaaggat   2280
ctgagctaca catgctcagg tttttttacaa cgtgcacaac agaattgaaa gcaaatatca   2340
tgcgatcata ggcgtctcgc atatctcatt aaagcagggg gtgggcgaag aactccagca   2400
tgagatcccc gcgctggagg atcatccagc cggcgtcccg gaaaacgatt ccgaagccca   2460
acctttcata gaaggcggcg gtggaatcga aatctcgtga tggcaggttg ggcgtcgctt   2520
ggtcggtcat ttcgaacccc agagtcccgc tcagaagaac tcgtcaagaa ggcgatagaa   2580
ggcgatgcgc tgcgaatcgg gagcggcgat accgtaaagc acgaggaagc ggtcagccca   2640
ttcgccgcca agctcttcag caatatcacg ggtagccaac gctatgtcct gatagcggtc   2700
cgccacaccc agccggccac agtcgatgaa tccagaaaag cggccatttt ccaccatgat   2760
attcggcaag caggcatcgc catgggtcac gacgagatcc tcgccgtcgg gcatgccccc   2820
caattcactg gccgtcgttt tacaacgtcg tgactgggaa aaccctggcg ttacccaact   2880
taatcgcctt gcagcacatc ccccttttcgc cagctggcgt aatagcgaag aggcccgcac   2940
cgatcgccct tcccaacagt tgcgcagcct gaatggcgaa tggcgcctga tgcggtattt   3000
tctccttacg catctgtgcg gtatttcaca ccgcatatgg tgcactctca gtacaatctg   3060
ctctgatgcc gcatagttaa gccagccccg acacccgcca acacccgctg acgcgccctg   3120
acgggcttgt ctgctcccgg catccgctta cagacaagct gtgaccgtct ccgggagctg   3180
catgtgtcag aggttttcac cgtcatcacc gaaacgcgcg agacgaaagg gcctcgtgat   3240
acgcctattt ttataggtta atgtcatgat aataatggtt tcttagacgt caggtggcac   3300
ttttcgggga aatgtgcgcg gaacccctat ttgtttattt ttctaaatac attcaaatat   3360
gtatccgctc atgagacaat aaccctgata aatgcttcaa taatattgaa aaaggaagag   3420
tatgagtatt caacatttcc gtgtcgccct tattcccttt tttgcggcat tttgccttcc   3480
tgtttttgct cacccagaaa cgctggtgaa agtaaaagat gctgaagatc agttgggtgc   3540
acgagtgggt tacatcgaac tggatctcaa cagcggtaag atccttgaga gttttcgccc   3600
cgaagaacgt tttccaatga tgagcacttt taaagttctg ctatgtggcg cggtattatc   3660
ccgtattgac gccgggcaag agcaactcgg tcgccgcata cactattctc agaatgactt   3720
ggttgagtac tcaccagtca cagaaaagca tcttacggat ggcatgacag taagagaatt   3780
atgcagtgct gccataacca tgagtgataa cactgcggcc aacttacttc tgacaacgat   3840
cggaggaccg aaggagctaa ccgctttttt gcacaacatg ggggatcatg taactcgcct   3900
tgatcgttgg gaaccggagc tgaatgaagc cataccaaac gacgagcgtg acaccacgat   3960
gcctgtagca atggcaacaa cgttgcgcaa actattaact ggcgaactac ttactctagc   4020
ttcccggcaa caattaatag actggatgga ggcggataaa gttgcaggac cacttctgcg   4080
ctcggccctt ccggctggct ggtttattgc tgataaatct ggagccggtg agcgtgggtc   4140
```

-continued

```
tcgcggtatc attgcagcac tggggccaga tggtaagccc tcccgtatcg tagttatcta   4200
cacgacgggg agtcaggcaa ctatggatga acgaaataga cagatcgctg agataggtgc   4260
ctcactgatt aagcattggt aactgtcaga ccaagtttac tcatatatac tttagattga   4320
tttaaaactt catttttaat ttaaaaggat ctaggtgaag atcctttttg ataatctcat   4380
gaccaaaatc ccttaacgtg agttttcgtt ccactgagcg tcagaccccg tagaaaagat   4440
caaaggatct tcttgagatc cttttttt ct gcgcgtaatc tgctgcttgc aaacaaaaaa   4500
accaccgcta ccagcggtgg tttgtttgcc ggatcaagag ctaccaactc tttttccgaa   4560
ggtaactggc ttcagcagag cgcagatacc aaatactgtc cttctagtgt agccgtagtt   4620
aggccaccac ttcaagaact ctgtagcacc gcctacatac ctcgctctgc taatcctgtt   4680
accagtggct gctgccagtg gcgataagtc gtgtcttacc gggttggact caagacgata   4740
gttaccggat aaggcgcagc ggtcgggctg aacggggggt tcgtgcacac agcccagctt   4800
ggagcgaacg acctacaccg aactgagata cctacagcgt gagcattgag aaagcgccac   4860
gcttcccgaa gggagaaagg cggacaggta tccggtaagc ggcagggtcg gaacaggaga   4920
gcgcacgagg gagcttccag ggggaaacgc ctggtatctt tatagtcctg tcgggtttcg   4980
ccacctctga cttgagcgtc gatttttgtg atgctcgtca ggggggcgga gcctatggaa   5040
aaacgccagc aacgcggcct ttttacggtt cctggccttt tgctggcctt ttgctcacat   5100
gttctttcct gcgttatccc ctgattctgt ggataaccgt attaccgcct ttgagtgagc   5160
tgataccgct cgccgcagcc gaacgaccga gcgcagcgag tcagtgagcg aggaagcgga   5220
agagcgccca atacgcaaac cgcctctccc cgcgcgttgg ccgattcatt aatgcagctg   5280
gcacgacagg tttcccgact ggaaagcggg cagtgagcgc aacgcaatta atgtgagtta   5340
gctcactcat taggcacccc aggctttaca ctttatgctt ccggctcgta tgttgtgtgg   5400
aattgtgagc ggataacaat ttcacacagg aaacagctat gaccatgatt acgccaagct   5460
ttctaggggg ggggtaccga tctgagatcg gtaacgaaaa cgaacgggta gggatgaaaa   5520
cggtcggtaa cggtcggtaa aatacctcta ccgttttcat tttcatattt aacttgcggg   5580
acggaaacga aaacgggata taccggtaac gaaaacgaac gggataaata cggtaatcga   5640
aaaccgatac gatccggtcg ggttaaagtc gaaatcggac gggaaccggt atttttgttc   5700
ggtaaaatca cacatgaaaa catatattca aaacttaaaa acaaatataa aaaattgtaa   5760
acacaagtct taatgatcac tagtggcgcg cctaggagat ctcgagtagg gataacaggg   5820
taatacatag ataaaatcca tataaatctg gagcacacat agtttaatgt agcacataag   5880
tgataagtct tgggctcttg gctaacataa gaagccatat aagtctacta gcacacatga   5940
cacaatataa agtttaaaac acatattcat aatcacttgc tcacatctgg atcacttagc   6000
atgctacagc tagtgcaata ttagacactt tccaatattt ctcaaacttt tcactcattg   6060
caacggccat tctcctaatg acaaattttt catgaacaca ccattggtca atcaaatcct   6120
ttatctcaca gaaacctttg taaaataaat ttgcagtgga atattgagta ccagatagga   6180
gttcagtgag atcaaaaaac ttcttcaaac acttaaaaag agttaatgcc atcttccact   6240
cctcggcttt aggacaaatt gcatcgtacc tacaataatt gacatttgat taattgagaa   6300
tttataatga tgacatgtac aacaattgag acaaacatac ctgcgaggat cacttgtttt   6360
aagccgtgtt agtgcaggct tataatataa ggcatccctc aacatcaaat aggttgaatt   6420
ccatctagtt gagacatcat atgagatccc tttagattta tccaagtcac attcactagc   6480
acacttcatt agttcttccc actgcaaagg agaagatttt acagcaagaa caatcgcttt   6540
```

-continued

```
gattttctca attgttcctg caattacagc caagccatcc tttgcaacca agttcagtat   6600
gtgacaagca cacctcacat gaaagaaagc accatcacaa actagatttg aatcagtgtc   6660
ctgcaaatcc tcaattatat cgtgcacagc tacttcattt gcactagcat tatccaaaga   6720
caaggcaaac aatttttct caatgttcca cttaaccatg attgcagtga aggtttgtga   6780
taacctttgg ccagtgtggc gcccttcaac atgaaaaaag ccaacaattc tttttggag   6840
acaccaatca tcatcaatcc aatggatggt gacacacatg tatgacttat tttgacaaga   6900
tgtccacata tccatagttg tactgaagcg agactgaaca tcttttagtt ttccatacaa   6960
cttttctttt tcttccaaat acaaatccat gatatatttt ctagcagtga cacgggactt   7020
tattggaaag tgagggcgca gagacttaac aaactcaaca aagtactcat gttctacaat   7080
attgaaagga tattcatgca tgattattgc caaatgaagc ttctttaggc taaccacttc   7140
atcgtactta taaggctcaa tgagatttat gtctttgcca tgatcctttt cactttttag   7200
acacaactga cctttaacta aactatgtga tgttctcaag tgatttcgaa atccgcttgt   7260
tccatgatga ccctcagccc tatacttagc cttgcaatta ggaaagttgc aatgtcccca   7320
tacctgaacg tatttctttc catcgacctc cacttcaatt tccttcttgg tgaaatgctg   7380
ccatacatcc gatgtgcact tctttgccct cttctgtggt gcttcttctt cgggttcagg   7440
ttgtggctgt ggttgtggtt ctggttgtgg ttgtggttgt ggttgtggtt catgaacaat   7500
agccatatca tcttgactcg gatctgtagc tgtaccattt gcattactac tgcttacact   7560
ctgaataaaa tgcctctcgg cctcagctgt tgatgatgat ggtgatgtgc ggccacatcc   7620
atgcccacgc gcacgtgcac gtacattctg aatccgacta gaagaggctt cagcttttct   7680
tttcaaccct gttataaaca gatttttcgt attattctac agtcaatatg atgcttccca   7740
atctacaacc aattagtaat gctaatgcta ttgctactgt ttttctaata tataccttga   7800
gcatatgcag agaatacgga atttgttttg cgagtagaag gcgctcttgt ggtagacatc   7860
aacttggcca atcttatggc tgagcctgag ggaggattat ttccaaccgg aggcgtcatc   7920
tgaggaatgg agtcgtagcc ggctagccga agtggagagc agagccctgg acagcaggtg   7980
ttcagcaatc agcttggtgc tgtactgctg tgacttgtga gcacctggac ggctggacag   8040
caatcagcag gtgttgcaga gcccctggac agcacacaaa tgacacaaca gcttggtgca   8100
atggtgctga cgtgctgtac tgctaagtgc tgtgagcctg tgagcagccg tggagacagg   8160
gagaccgcgg atggccggat gggcgagcgc cgagcagtgg aggtctggag gaccgctgac   8220
cgcagatggc ggatggcgga tgggcggacc gcggatgggc gagcagtgga gtggaggtct   8280
gggcggatgg gcggaccgcg gcgcggatgg gcgagtcgcg agcagtggag tggagggcgg   8340
accgtggatg gcggcgtctg cgtccggcgt gccgcgtcac ggccgtcacc gcgtgtggtg   8400
cctggtgcag cccagcggcc ggccggctgg gagacaggga gagtcggaga gagcaggcga   8460
gagcgagacg cgtcgccggc gtcggcgtgc ggctggcggc gtccggactc cggcgtgggc   8520
gcgtggcggc gtgtgaatgt gtgatgctgt tactcgtgtg gtgcctggcc gcctgggaga   8580
gaggcagagc agcgttcgct aggtatttct tacatgggct gggcctcagt ggttatggat   8640
gggagttgga gctggccata ttgcagtcat cccgaattag aaaatacggt aacgaaacgg   8700
gatcatcccg attaaaaacg ggatcccggt gaaacggtcg ggaaactagc tctaccgttt   8760
ccgtttccgt ttaccgtttt gtatatcccg tttccgttcc gttttcgttt tttacctcgg   8820
gttcgaaatc gatcgggata aaactaacaa aatcggttat acgataacgg tcggtacggg   8880
attttcccat cctactttca tccctgagat tattgtcgtt tctttcgcag atcggtaccc   8940
```

-continued

```
ccccccctaga gtcgacatcg atctagtaac atagatgaca ccgcgcgcga taatttatcc   9000
tagtttgcgc gctatatttt gttttctatc gcgtattaaa tgtataattg cgggactcta   9060
atcataaaaa cccatctcat aaataacgtc atgcattaca tgttaattat tacatgctta   9120
acgtaattca acagaaatta tatgataatc atcgcaagac cggcaacagg attcaatctt   9180
aagaaacttt attgccaaat gtttgaacga tctgcttcga cgcactcctt ctttaggtac   9240
ggactagatc tcggtgacgg gcaggaccgg acggggcggt accggcaggc tgaagtccag   9300
ctgccagaaa cccacgtcat gccagttccc gtgcttgaag ccggccgccc gcagcatgcc   9360
gcggggggca tatccgagcg cctcgtgcat gcgcacgctc gggtcgttgg gcagcccgat   9420
gacagcgacc acgctcttga agccctgtgc ctccagggac ttcagcaggt gggtgtagag   9480
cgtggagccc agtcccgtcc gctggtggcg gggggagacg tacacggtcg actcggccgt   9540
ccagtcgtag gcgttgcgtg ccttccaggg gcccgcgtag gcgatgccgg cgacctcgcc   9600
gtccacctcg gcgacgagcc agggatagcg ctcccgcaga cggacgaggt cgtccgtcca   9660
ctcctgcggt tcctgcggct cggtacggaa gttgaccgtg cttgtctcga tgtagtggtt   9720
gacgatggtg cagaccgccg gcatgtccgc ctcggtggca cggcggatgt cggccgggcg   9780
tcgttctggg ctcatggatc tggattgaga gtgaatatga gactctaatt ggataccgag   9840
gggaatttat ggaacgtcag tggagcattt ttgacaagaa atatttgcta gctgatagtg   9900
accttaggcg acttttgaac gcgcaataat ggtttctgac gtatgtgctt agctcattaa   9960
actccagaaa cccgcggctg agtggctcct tcaatcgttg cggttctgtc agttccaaac  10020
gtaaaacggc ttgtcccgcg tcatcggcgg gggtcataac gtgactccct taattctccg  10080
ctcatgatcc ccgggtaccg agctcgaatt gcggctgagt ggctccttca atcgttgcgg  10140
ttctgtcagt tccaaacgta aaacggcttg tcccgcgtca tcggcggggg tcataacgtg  10200
actcccttaa ttctccgctc atgatcttga tcccctgcgc catcagatcc ttggcggcaa  10260
gaaagccatc cagtttactt tgcagggctt cccaacctta ccagagggcg ccccagctgg  10320
caattccggt tcgcttgctg tatcgatatg gtggatttat cacaaatggg acccgccgcc  10380
gacagaggtg tgatgttagg ccaggacttt gaaaatttgc gcaactatcg tatagtggcc  10440
gacaaattga cgccgagttg acagactgcc tagcatttga gtgaattatg tgaggtaatg  10500
ggctacactg aattggtagc tcaaactgtc agtatttatg tatatgagtg tatattttcg  10560
cataatctca gaccaatctg aagatgaaat gggtatctgg gaatggcgaa atcaaggcat  10620
cgatcgtgaa gtttctcatc taagccccca tttggacgtg aatgtagaca cgtcgaaata  10680
aagatttccg aattagaata atttgtttat tgctttcgcc tataaatacg acggatcgta  10740
atttgtcgtt ttatcaaaat gtactttcat tttataataa cgctgcggac atctacattt  10800
ttgaattgaa aaaaaattgg taattactct ttcttttttct ccatattgac catcatactc  10860
attgctgatc catgtagatt tcccggacat gaagccattt acaattgaat atatcctgcc  10920
gccgctgccg ctttgcaccc ggtggagctt gcatgttggt ttctacgcag aactgagccg  10980
gttaggcaga taatttccat tgagaactga gccatgtgca ccttcccccc aacacggtga  11040
gcgacggggc aacggagtga tccacatggg acttttaaac atcatccgtc ggatggcgtt  11100
gcgagagaag cagtcgatcc gtgagatcag ccgacgcacc gggcaggcgc gcaacacgat  11160
cgcaaagtat ttgaacgcag gtacaatcga gccgacgttc accgtcaccc tggatgctgt  11220
aggcataggc ttggttatgc cggtactgcc gggcctcttg cgggatatcg tccattccga  11280
cagcatcgcc agtcactatg gcgtgctgct agcgctatat gcgttgatgc aatttctatg  11340
```

-continued

```
cgcacccgtt ctcggagcac tgtccgaccg ctttggccgc cgcccagtcc tgctcgcttc  11400
gctacttgga gccactatcg actacgcgat catggcgacc acacccgtcc tgtggtccaa  11460
cccctccgct gctatagtgc agtcggcttc tgacgttcag tgcagccgtc ttctgaaaac  11520
gacatgtcgc acaagtccta agttacgcga caggctgccg ccctgccctt ttcctggcgt  11580
tttcttgtcg cgtgttttag tcgcataaag tagaatactt gcgactagaa ccggagacat  11640
tacgccatga acaagagcgc cgccgctggc ctgctgggct atgcccgcgt cagcaccgac  11700
gaccaggact tgaccaacca acgggccgaa ctgcacgcgg ccggctgcac caagctgttt  11760
tccgagaaga tcaccggcac caggcgcgac cgcccggagc tggccaggat gcttgaccac  11820
ctacgccctg gcgacgttgt gacagtgacc aggctagacc gcctggcccg cagcacccgc  11880
gacctactgg acattgccga gcgcatccag gaggccggcg cgggcctgcg tagcctggca  11940
gagccgtggg ccgacaccac cacgccggcc ggccgcatgg tgttgaccgt gttcgccggc  12000
attgccgagt tcgagcgttc cctaatcatc gaccgcaccc ggagcgggcg cgaggccgcc  12060
aaggcccgag gcgtgaagtt tggcccccgc cctaccctca ccccggcaca gatcgcgcac  12120
gcccgcgagc tgatcgacca ggaaggccgc accgtgaaag aggcggctgc actgcttggc  12180
gtgcatcgct cgaccctgta ccgcgcactt gagcgcagcg aggaagtgac gcccaccgag  12240
gccaggcggc gcggtgcctt ccgtgaggac gcattgaccg aggccgacgc cctggcggcc  12300
gccgagaatg aacgccaaga ggaacaagca tgaaaccgca ccaggacggc caggacgaac  12360
cgtttttcat taccgaagag atcgaggcgg agatgatcgc ggccgggtac gtgttcgagc  12420
cgcccgcgca cgtctcaacc gtgcggctgc atgaaatcct ggccggtttg tctgatgcca  12480
agctggcggc ctggccggcc agcttggccg ctgaagaaac cgagcgccgc cgtctaaaaa  12540
ggtgatgtgt atttgagtaa aacagcttgc gtcatgcggt cgctgcgtat atgatgcgat  12600
gagtaaataa acaaatacgc aagggaacgc atgaagttat cgctgtactt aaccagaaag  12660
gcgggtcagg caagacgacc atcgcaaccc atctagcccg cgccctgcaa ctcgccgggg  12720
ccgatgttct gttagtcgat tccgatcccc agggcagtgc ccgcgattgg gcggccgtgc  12780
gggaagatca accgctaacc gttgtcggca tcgaccgccc gacgattgac cgcgacgtga  12840
aggccatcgg ccggcgcgac ttcgtagtga tcgacggagc gccccaggcg gcggacttgg  12900
ctgtgtccgc gatcaaggca gccgacttcg tgctgattcc ggtgcagcca agcccttacg  12960
acatatgggc caccgccgac ctggtggagc tggttaagca gcgcattgag gtcacggatg  13020
gaaggctaca agcggccttt gtcgtgtcgc gggcgatcaa aggcacgcgc atcggcggtg  13080
aggttgccga ggcgctggcc gggtacgagc tgcccattct tgagtcccgt atcacgcagc  13140
gcgtgagcta cccaggcact gccgccgccg gcacaaccgt tcttgaatca gaacccgagg  13200
gcgacgctgc ccgcgaggtc caggcgctgg ccgctgaaat taaatcaaaa ctcatttgag  13260
ttaatgaggt aaagagaaaa tgagcaaaag cacaaacacg ctaagtgccg gccgtccgag  13320
cgcacgcagc agcaaggctg caacgttggc cagcctggca gacacgccag ccatgaagcg  13380
ggtcaacttt cagttgccgg cggaggatca caccaagctg aagatgtacg cggtacgcca  13440
aggcaagacc attaccgagc tgctatctga atacatcgcg cagctaccag agtaaatgag  13500
caaatgaata aatgagtaga tgaattttag cggctaaagg aggcggcatg gaaaatcaag  13560
aacaaccagg caccgacgcc gtggaatgcc ccatgtgtgg aggaacgggc ggttggccag  13620
gcgtaagcgg ctgggttgtc tgccggccct gcaatggcac tggaaccccc aagcccgagg  13680
aatcggcgtg agcggtcgca aaccatccgg cccggtacaa atcggcgcgg cgctgggtga  13740
```

-continued

```
tgacctggtg gagaagttga aggccgcgca ggccgcccag cggcaacgca tcgaggcaga  13800
agcacgcccc ggtgaatcgt ggcaagcggc cgctgatcga atccgcaaag aatcccggca  13860
accgccggca gccggtgcgc cgtcgattag gaagccgccc aagggcgacg agcaaccaga  13920
tttttcgtt ccgatgctct atgacgtggg cacccgcgat agtcgcagca tcatggacgt  13980
ggccgttttc cgtctgtcga agcgtgaccg acgagctggc gaggtgatcc gctacgagct  14040
tccagacggg cacgtagagg tttccgcagg gccggccggc atggccagtg tgtgggatta  14100
cgacctggta ctgatggcgg tttcccatct aaccgaatcc atgaaccgat accgggaagg  14160
gaagggagac aagcccggcc gcgtgttccg tccacacgtt gcggacgtac tcaagttctg  14220
ccggcgagcc gatggcggaa agcagaaaga cgacctggta gaaacctgca ttcggttaaa  14280
caccacgcac gttgccatgc agcgtacgaa gaaggccaag aacggccgcc tggtgacggt  14340
atccgagggt gaagccttga ttagccgcta caagatcgta aagagcgaaa ccgggcggcc  14400
ggagtacatc gagatcgagc tagctgattg gatgtaccgc gagatcacag aaggcaagaa  14460
cccggacgtg ctgacggttc accccgatta ctttttgatc gatcccggca tcggccgttt  14520
tctctaccgc ctggcacgcc gcgccgcagg caaggcagaa gccagatggt tgttcaagac  14580
gatctacgaa cgcagtggca gcgccggaga gttcaagaag ttctgtttca ccgtgcgcaa  14640
gctgatcggg tcaaatgacc tgccggagta cgatttgaag gaggaggcgg ggcaggctgg  14700
cccgatccta gtcatgcgct accgcaacct gatcgagggc gaagcatccg ccggttccta  14760
atgtacggag cagatgctag ggcaaattgc cctagcaggg gaaaaaggtc gaaaaggtct  14820
ctttcctgtg gatagcacgt acattgggaa cccaaagccg tacattggga accggaaccc  14880
gtacattggg aacccaaagc cgtacattgg gaaccggtca cacatgtaag tgactgatat  14940
aaaagagaaa aaaggcgatt tttccgccta aaactcttta aaacttatta aaactcttaa  15000
aacccgcctg gcctgtgcat aactgtctgg ccagcgcaca gccgaagagc tgcaaaaagc  15060
gcctaccctt cggtcgctgc gctccctacg ccccgccgct tcgcgtcggc ctatcgcggc  15120
cgctggccgc tcaaaaatgg ctggcctacg gccaggcaat ctaccagggc gcggacaagc  15180
cgcgccgtcg ccactcgacc gccggcgccc acatcaaggc accctgcctc gcgcgtttcg  15240
gtgatgacgg tgaaaacctc tgacacatgc agctcccgga gacggtcaca gcttgtctgt  15300
aagcggatgc cgggagcaga caagcccgtc agggcgcgtc agcgggtgtt ggcgggtgtc  15360
ggggcgcagc catgacccag tcacgtagcg atagcggagt gtatactggc ttaactatgc  15420
ggcatcagag cagattgtac tgagagtgca ccatatgcgg tgtgaaatac cgcacagatg  15480
cgtaaggaga aaataccgca tcaggcgctc ttccgcttcc tcgctcactg actcgctgcg  15540
ctcggtcgtt cggctgcggc gagcggtatc agctcactca aaggcggtaa tacggttatc  15600
cacagaatca ggggataacg caggaaagaa catgtgagca aaaggccagc aaaaggccag  15660
gaaccgtaaa aaggccgcgt tgctggcgtt tttccatagg ctccgccccc ctgacgagca  15720
tcacaaaaat cgacgctcaa gtcagaggtg gcgaaacccg acaggactat aaagatacca  15780
ggcgtttccc cctggaagct ccctcgtgcg ctctcctgtt ccgaccctgc cgcttaccgg  15840
atacctgtcc gcctttctcc cttcgggaag cgtggcgctt tctcatagct cacgctgtag  15900
gtatctcagt tcggtgtagg tcgttcgctc caagctgggc tgtgtgcacg aaccccccgt  15960
tcagcccgac cgctgcgcct tatccggtaa ctatcgtctt gagtccaacc cggtaagaca  16020
cgacttatcg ccactggcag cagccactgg taacaggatt agcagagcga ggtatgtagg  16080
cggtgctaca gagttcttga agtggtggcc taactacggc tacactagaa ggacagtatt  16140
```

-continued

```
tggtatctgc gctctgctga agccagttac cttcggaaaa agagttggta gctcttgatc  16200
cggcaaacaa accaccgctg gtagcggtgg tttttttgtt tgcaagcagc agattacgcg  16260
cagaaaaaaa ggatctcaag aagatccttt gatcttttct acggggtctg acgctcagtg  16320
gaacgaaaac tcacgttaag ggattttggt catgagatta tcaaaaagga tcttcaccta  16380
gatcctttta aattaaaaat gaagttttaa atcaatctaa agtatatatg agtaaacttg  16440
gtctgacagt taccaatgct taatcagtga ggcacctatc tcagcgatct gtctatttcg  16500
ttcatccata gttgcctgac tccccgtcgt gtagataact acgatacggg agggcttacc  16560
atctggcccc agtgctgcaa tgataccgcg agacccacgc tcaccggctc cagatttatc  16620
agcaataaac cagccagccg gaagggccga gcgcagaagt ggtcctgcaa ctttatccgc  16680
ctccatccag tctattaatt gttgccggga agctagagta agtagttcgc cagttaatag  16740
tttgcgcaac gttgttgcca ttgctacagg catcgtggtg tcacgctcgt cgtttggtat  16800
ggcttcattc agctccggtt cccaacgatc aaggcgagtt acatgatccc ccatgttgtg  16860
caaaaaagcg gttagctcct tcggtcctcc gatcgttgtc agaagtaagt tggccgcagt  16920
gttatcactc atggttatgg cagcactgca taattctctt actgtcatgc catccgtaag  16980
atgcttttct gtgactggtg agtactcaac caagtcattc tgagaatagt gtatgcggcg  17040
accgagttgc tcttgcccgg cgtcaacacg ggataatacc gcgccacata gcagaacttt  17100
aaaagtgctc atcattggaa aagacctgca gggggggggg ggaaagccac gttgtgtctc  17160
aaaatctctg atgttacatt gcacaagata aaaatatatc atcatgaaca ataaaactgt  17220
ctgcttacat aaacagtaat acaaggggtg ttatgagcca tattcaacgg gaaacgtctt  17280
gctcgaggcc gcgattaaat tccaacatgg atgctgattt atatgggtat aaatgggctc  17340
gcgataatgt cgggcaatca ggtgcgacaa tctatcgatt gtatgggaag cccgatgcgc  17400
cagagttgtt tctgaaacat ggcaaaggta gcgttgccaa tgatgttaca gatgagatgg  17460
tcagactaaa ctggctgacg gaatttatgc ctcttccgac catcaagcat tttatccgta  17520
ctcctgatga tgcatggtta ctcaccactg cgatccccgg gaaaacagca ttccaggtat  17580
tagaagaata tcctgattca ggtgaaaata ttgttgatgc gctggcagtg ttcctgcgcc  17640
ggttgcattc gattcctgtt tgtaattgtc cttttaacag cgatcgcgta tttcgtctcg  17700
ctcaggcgca atcacgaatg aataacggtt tggttgatgc gagtgatttt gatgacgagc  17760
gtaatggctg gcctgttgaa caagtctgga aagaaatgca taagcttttg ccattctcac  17820
cggattcagt cgtcactcat ggtgatttct cacttgataa ccttattttt gacgagggga  17880
aattaatagg ttgtattgat gttggacgag tcggaatcgc agaccgatac caggatcttg  17940
ccatcctatg gaactgcctc ggtgagtttt ctccttcatt acagaaacgg ctttttcaaa  18000
aatatggtat tgataatcct gatatgaata aattgcagtt tcatttgatg ctcgatgagt  18060
ttttctaatc agaattggtt aattggttgt aacactggca gagcattacg ctgacttgac  18120
gggacggcgg ctttgttgaa taaatcgaac ttttgctgag ttgaaggatc agatcacgca  18180
tcttcccgac aacgcagacc gttccgtggc aaagcaaaag ttcaaaatca ccaactggtc  18240
cacctacaac aaagctctca tcaaccgtgg ctccctcact ttctggctgg atgatggggc  18300
gattcaggcc tggtatgagt cagcaacacc ttcttcacga ggcagacctc agcgcccccc  18360
ccccctgca ggtcaattcg gtcgatatgg ctattacgaa gaaggctcgt gcgcggagtc  18420
ccgtgaactt tcccacgcaa caagtgaacc gcaccgggtt tgccggaggc catttcgtta  18480
aaatgcgcag c                                                        18491
```

<210> SEQ ID NO 32
<211> LENGTH: 4291
<212> TYPE: DNA
<213> ORGANISM: Artificial
<220> FEATURE:
<223> OTHER INFORMATION: Donor vector pDONR/Zeo

<400> SEQUENCE: 32
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacacattg atgagcaatg cttttttata atgccaactt tgtacaaaaa 660
agctgaacga gaaacgtaaa atgatataaa tatcaatata ttaaattaga ttttgcataa 720
aaaacagact acataatact gtaaaacaca acatatccag tcactatgaa tcaactactt 780
agatggtatt agtgacctgt agtcgaccga cagccttcca aatgttcttc gggtgatgct 840
gccaacttag tcgaccgaca gccttccaaa tgttcttctc aaacggaatc gtcgtatcca 900
gcctactcgc tattgtcctc aatgccgtat taaatcataa aaagaaataa gaaaaagagg 960
tgcgagcctc ttttttgtgt gacaaaataa aaacatctac ctattcatat acgctagtgt 1020
catagtcctg aaaatcatct gcatcaagaa caatttcaca actcttatac ttttctctta 1080
caagtcgttc ggcttcatct ggattttcag cctctatact tactaaacgt gataaagttt 1140
ctgtaatttc tactgtatcg acctgcagac tggctgtgta taagggagcc tgacatttat 1200
attccccaga acatcaggtt aatggcgttt ttgatgtcat tttcgcggtg gctgagatca 1260
gccacttctt ccccgataac ggagaccggc acactggcca tatcggtggt catcatgcgc 1320
cagctttcat ccccgatatg caccaccggg taaagttcac gggagacttt atctgacagc 1380
agacgtgcac tggccagggg gatcaccatc cgtcgcccgg gcgtgtcaat aatatcactc 1440
tgtacatcca caaacagacg ataacggctc tctcttttat aggtgtaaac cttaaactgc 1500
atttcaccag cccctgttct cgtcagcaaa agagccgttc atttcaataa accgggcgac 1560
ctcagccatc ccttcctgat ttccgcttt ccagcgttcg gcacgcagac gacgggcttc 1620
attctgcatg gttgtgctta ccagaccgga gatattgaca tcatatatgc cttgagcaac 1680
tgatagctgt cgctgtcaac tgtcactgta atacgctgct tcatagcata cctctttttg 1740
acatacttcg ggtatacata tcagtatata ttcttatacc gcaaaaatca gcgcgcaaat 1800
acgcatactg ttatctggct tttagtaagc cggatccacg cggcgtttac gccccgccct 1860
gccactcatc gcagtactgt tgtaattcat taagcattct gccgacatgg aagccatcac 1920
agacggcatg atgaacctga atcgccagcg gcatcagcac cttgtcgcct tgcgtataat 1980
atttgcccat ggtgaaaacg ggggcgaaga agttgtccat attggccacg tttaaatcaa 2040
aactggtgaa actcacccag ggattggctg agacgaaaaa catattctca ataaaccctt 2100

-continued

```
tagggaaata ggccaggttt tcaccgtaac acgccacatc ttgcgaatat atgtgtagaa   2160
actgccggaa atcgtcgtgg tattcactcc agagcgatga aaacgtttca gtttgctcat   2220
ggaaaacggt gtaacaaggg tgaacactat cccatatcac cagctcaccg tctttcattg   2280
ccatacggaa ttccggatga gcattcatca ggcgggcaag aatgtgaata aaggccggat   2340
aaaacttgtg cttatttttc tttacggtct ttaaaaaggc cgtaatatcc agctgaacgg   2400
tctggttata ggtacattga gcaactgact gaaatgcctc aaaatgttct ttacgatgcc   2460
attgggatat atcaacggtg gtatatccag tgattttttt ctccatttta gcttccttag   2520
ctcctgaaaa tctcgataac tcaaaaaata cgcccggtag tgatcttatt tcattatggt   2580
gaaagttgga acctcttacg tgccgatcaa cgtctcattt tcgccaaaag ttggcccagg   2640
gcttcccggt atcaacaggg acaccaggat ttatttattc tgcgaagtga tcttccgtca   2700
caggtattta ttcggcgcaa agtgcgtcgg gtgatgctgc caacttagtc gactacaggt   2760
cactaatacc atctaagtag ttgattcata gtgactggat atgttgtgtt ttacagtatt   2820
atgtagtctg tttttatgc aaaatctaat ttaatatatt gatatttata tcattttacg    2880
tttctcgttc agctttcttg tacaaagttg gcattataag aaagcattgc ttatcaattt   2940
gttgcaacga acaggtcact atcagtcaaa ataaaatcat tatttgccat ccagctgata   3000
tcccctatag tgagtcgtat tacatggtca tagctgtttc ctggcagctc tggcccgtgt   3060
ctcaaaatct ctgatgttac attgcacaag ataaaaataat atcatcatga tcagtcctgc  3120
tcctcggcca cgaagtgcac gcagttgccg gccgggtcgc gcagggcgaa ctcccgcccc   3180
cacggctgct cgccgatctc ggtcatggcc ggcccggagg cgtcccggaa gttcgtggac   3240
acgacctccg accactcggc gtacagctcg tccaggccgc gcacccacac ccaggccagg   3300
gtgttgtccg gcaccacctg gtcctggacc gcgctgatga acagggtcac gtcgtcccgg   3360
accacaccgg cgaagtcgtc ctccacgaag tcccgggaga acccgagccg gtcggtccag   3420
aactcgaccg ctccggcgac gtcgcgcgcg gtgagcaccg gaacggcact ggtcaacttg   3480
gccatggttt agttcctcac cttgtcgtat tatactatgc cgatatacta tgccgatgat   3540
taattgtcaa cacgtgctga tcatgaccaa aatcccttaa cgtgagttac gcgtcgttcc   3600
actgagcgtc agaccccgta gaaaagatca aaggatcttc ttgagatcct ttttttctgc   3660
gcgtaatctg ctgcttgcaa acaaaaaaac caccgctacc agcggtggtt tgtttgccgg   3720
atcaagagct accaactctt tttccgaagg taactggctt cagcagagcg cagataccaa   3780
atactgttct tctagtgtag ccgtagttag gccaccactt caagaactct gtagcaccgc   3840
ctacatacct cgctctgcta atcctgttac cagtggctgc tgccagtggc gataagtcgt   3900
gtcttaccgg gttggactca agacgatagt taccggataa ggcgcagcgg tcgggctgaa   3960
cggggggttc gtgcacacag cccagcttgg agcgaacgac ctacaccgaa ctgagatacc   4020
tacagcgtga gctatgagaa agcgccacgc ttcccgaagg gagaaaggcg gacaggtatc   4080
cggtaagcgg cagggtcgga acaggagagc gcacgaggga gcttccaggg ggaaacgcct   4140
ggtatcttta tagtcctgtc gggtttcgcc acctctgact tgagcgtcga tttttgtgat   4200
gctcgtcagg ggggcggagc ctatggaaaa acgccagcaa cgcggccttt ttacggttcc   4260
tggccttttg ctggcctttt gctcacatgt t                                  4291
```

<210> SEQ ID NO 33
<211> LENGTH: 4762
<212> TYPE: DNA
<213> ORGANISM: Artificial
<220> FEATURE:

<223> OTHER INFORMATION: Donor vector pDONR221

<400> SEQUENCE: 33
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacacattg atgagcaatg cttttttata atgccaactt tgtacaaaaa 660
agctgaacga gaaacgtaaa atgatataaa tatcaatata ttaaattaga ttttgcataa 720
aaaacagact acataatact gtaaaacaca acatatccag tcactatgaa tcaactactt 780
agatggtatt agtgacctgt agtcgaccga cagccttcca aatgttcttc gggtgatgct 840
gccaacttag tcgaccgaca gccttccaaa tgttcttctc aaacggaatc gtcgtatcca 900
gcctactcgc tattgtcctc aatgccgtat taaatcataa aaagaaataa gaaaaagagg 960
tgcgagcctc ttttttgtgt gacaaaataa aaacatctac ctattcatat acgctagtgt 1020
catagtcctg aaaatcatct gcatcaagaa caatttcaca actcttatac ttttctctta 1080
caagtcgttc ggcttcatct ggattttcag cctctatact tactaaacgt gataaagttt 1140
ctgtaatttc tactgtatcg acctgcagac tggctgtgta taagggagcc tgacatttat 1200
attccccaga acatcaggtt aatggcgttt ttgatgtcat tttcgcggtg gctgagatca 1260
gccacttctt ccccgataac ggagaccggc acactggcca tatcggtggt catcatgcgc 1320
cagctttcat ccccgatatg caccaccggg taaagttcac gggagacttt atctgacagc 1380
agacgtgcac tggccagggg gatcaccatc cgtcgcccgg gcgtgtcaat aatatcactc 1440
tgtacatcca caaacagacg ataacggctc tctcttttat aggtgtaaac cttaaactgc 1500
atttcaccag cccctgttct cgtcagcaaa agagccgttc atttcaataa accgggcgac 1560
ctcagccatc ccttcctgat tttccgcttt ccagcgttcg gcacgcagac gacgggcttc 1620
attctgcatg gttgtgctta ccagaccgga gatattgaca tcatatatgc cttgagcaac 1680
tgatagctgt cgctgtcaac tgtcactgta atacgctgct tcatagcata cctcttttg 1740
acatacttcg ggtatacata tcagtatata ttcttatacc gcaaaaatca gcgcgcaaat 1800
acgcatactg ttatctggct tttagtaagc cggatccacg cggcgtttac gccccgccct 1860
gccactcatc gcagtactgt tgtaattcat taagcattct gccgacatgg aagccatcac 1920
agacggcatg atgaacctga atcgccagcg gcatcagcac cttgtcgcct tgcgtataat 1980
atttgcccat ggtgaaaacg ggggcgaaga agttgtccat attggccacg tttaaatcaa 2040
aactggtgaa actcacccag ggattggctg agacgaaaaa catattctca ataaaccctt 2100
tagggaaata ggccaggttt tcaccgtaac acgccacatc ttgcgaatat atgtgtagaa 2160
actgccggaa atcgtcgtgg tattcactcc agagcgatga aaacgtttca gtttgctcat 2220
ggaaaacggt gtaacaaggg tgaacactat cccatatcac cagctcaccg tctttcattg 2280

-continued

```
ccatacggaa ttccggatga gcattcatca ggcgggcaag aatgtgaata aaggccggat   2340
aaaacttgtg cttatttttc tttacggtct ttaaaaaggc cgtaatatcc agctgaacgg   2400
tctggttata ggtacattga gcaactgact gaaatgcctc aaaatgttct ttacgatgcc   2460
attgggatat atcaacggtg gtatatccag tgattttttt ctccatttta gcttccttag   2520
ctcctgaaaa tctcgataac tcaaaaaata cgcccggtag tgatcttatt tcattatggt   2580
gaaagttgga acctcttacg tgccgatcaa cgtctcattt tcgccaaaag ttggcccagg   2640
gcttcccggt atcaacaggg acaccaggat ttatttattc tgcgaagtga tcttccgtca   2700
caggtattta ttcggcgcaa agtgcgtcgg gtgatgctgc caacttagtc gactacaggt   2760
cactaatacc atctaagtag ttgattcata gtgactggat atgttgtgtt ttacagtatt   2820
atgtagtctg tttttatgc aaaatctaat ttaatatatt gatatttata tcattttacg   2880
tttctcgttc agctttcttg tacaaagttg gcattataag aaagcattgc ttatcaattt   2940
gttgcaacga acaggtcact atcagtcaaa ataaaatcat tatttgccat ccagctgata   3000
tcccctatag tgagtcgtat tacatggtca tagctgtttc ctggcagctc tggcccgtgt   3060
ctcaaaatct ctgatgttac attgcacaag ataaaaataat atcatcatga acaataaaac   3120
tgtctgctta cataaacagt aatacaaggg gtgttatgag ccatattcaa cgggaaacgt   3180
cgaggccgcg attaaattcc aacatggatg ctgatttata tgggtataaa tgggctcgcg   3240
ataatgtcgg gcaatcaggt gcgacaatct atcgcttgta tgggaagccc gatgcgccag   3300
agttgtttct gaaacatggc aaaggtagcg ttgccaatga tgttacagat gagatggtca   3360
gactaaactg gctgacggaa tttatgcctc ttccgaccat caagcatttt atccgtactc   3420
ctgatgatgc atggttactc accactgcga tccccggaaa aacagcattc caggtattag   3480
aagaatatcc tgattcaggt gaaaatattg ttgatgcgct ggcagtgttc ctgcgccggt   3540
tgcattcgat tcctgtttgt aattgtcctt ttaacagcga tcgcgtattt cgtctcgctc   3600
aggcgcaatc acgaatgaat aacggtttgg ttgatgcgag tgattttgat gacgagcgta   3660
atggctggcc tgttgaacaa gtctggaaag aaatgcataa acttttgcca ttctcaccgg   3720
attcagtcgt cactcatggt gatttctcac ttgataacct tatttttgac gaggggaaat   3780
taataggttg tattgatgtt ggacgagtcg gaatcgcaga ccgataccag gatcttgcca   3840
tcctatggaa ctgcctcggt gagttttctc cttcattaca gaaacggctt tttcaaaaat   3900
atggtattga taatcctgat atgaataaat tgcagtttca tttgatgctc gatgagtttt   3960
tctaatcaga attggttaat tggttgtaac actggcagag cattacgctg acttgacggg   4020
acggcgcaag ctcatgacca aaatccctta acgtgagtta cgcgtcgttc cactgagcgt   4080
cagaccccgt agaaaagatc aaaggatctt cttgagatcc tttttttctg cgcgtaatct   4140
gctgcttgca aacaaaaaaa ccaccgctac cagcggtggt ttgtttgccg gatcaagagc   4200
taccaactct ttttccgaag gtaactggct tcagcagagc gcagatacca aatactgttc   4260
ttctagtgta gccgtagtta ggccaccact tcaagaactc tgtagcaccg cctacatacc   4320
tcgctctgct aatcctgtta ccagtggctg ctgccagtgg cgataagtcg tgtcttaccg   4380
ggttggactc aagacgatag ttaccggata aggcgcagcg gtcgggctga acggggggtt   4440
cgtgcacaca gcccagcttg gagcgaacga cctacaccga actgagatac ctacagcgtg   4500
agctatgaga aagcgccacg cttcccgaag ggagaaaggc ggacaggtat ccggtaagcg   4560
gcagggtcgg aacaggagag cgcacgaggg agcttccagg gggaaacgcc tggtatcttt   4620
atagtcctgt cgggtttcgc cacctctgac ttgagcgtcg atttttgtga tgctcgtcag   4680
```

-continued gggggcggag cctatggaaa aacgccagca acgcggcctt tttacggttc ctggcctttt 4740
gctggccttt tgctcacatg tt 4762

<210> SEQ ID NO 34
<211> LENGTH: 16843
<212> TYPE: DNA
<213> ORGANISM: Artificial
<220> FEATURE:
<223> OTHER INFORMATION: Destination vector pBC-yellow

<400> SEQUENCE: 34
ccgggctggt tgccctcgcc gctgggctgg cggccgtcta tggccctgca aacgcgccag 60
aaacgccgtc gaagccgtgt gcgagacacc gcggccgccg gcgttgtgga tacctcgcgg 120
aaaacttggc cctcactgac agatgagggg cggacgttga cacttgaggg gccgactcac 180
ccggcgcggc gttgacagat gaggggcagg ctcgatttcg gccggcgacg tggagctggc 240
cagcctcgca aatcggcgaa aacgcctgat tttacgcgag tttcccacag atgatgtgga 300
caagcctggg gataagtgcc ctgcggtatt gacacttgag gggcgcgact actgacagat 360
gaggggcgcg atccttgaca cttgaggggc agagtgctga cagatgaggg gcgcacctat 420
tgacatttga ggggctgtcc acaggcagaa aatccagcat ttgcaagggt ttccgcccgt 480
ttttcggcca ccgctaacct gtcttttaac ctgcttttaa accaatattt ataaaccttg 540
tttttaacca gggctgcgcc ctgtgcgcgt gaccgcgcac gccgaagggg ggtgcccccc 600
cttctcgaac cctcccggcc cgctaacgcg ggcctcccat ccccccaggg gctgcgcccc 660
tcggccgcga acggcctcac cccaaaaatg gcagcgctgg cagtccttgc cattgccggg 720
atcggggcag taacgggatg ggcgatcagc ccgagcgcga cgcccggaag cattgacgtg 780
ccgcaggtgc tggcatcgac attcagcgac caggtgccgg gcagtgaggg cggcggcctg 840
ggtggcggcc tgcccttcac ttcggccgtc ggggcattca cggacttcat ggcggggccg 900
gcaattttta ccttgggcat tcttggcata gtggtcgcgg gtgccgtgct cgtgttcggg 960
ggtgcgataa acccagcgaa ccatttgagg tgataggtaa gattataccg aggtatgaaa 1020
acgagaattg gacctttaca gaattactct atgaagcgcc atatttaaaa agctaccaag 1080
acgaagagga tgaagaggat gaggaggcag attgccttga atatattgac aatactgata 1140
agataatata tcttttatat agaagatatc gccgtatgta aggatttcag ggggcaaggc 1200
ataggcagcg cgcttatcaa tatatctata gaatgggcaa agcataaaaa cttgcatgga 1260
ctaatgcttg aaacccagga caataacctt atagcttgta aattctatca taattgggta 1320
atgactccaa cttattgata gtgttttatg ttcagataat gcccgatgac tttgtcatgc 1380
agctccaccg attttgagaa cgacagcgac ttccgtccca gccgtgccag gtgctgcctc 1440
agattcaggt tatgccgctc aattcgctgc gtatatcgct tgctgattac gtgcagcttt 1500
cccttcaggc gggattcata cagcggccag ccatccgtca tccatatcac cacgtcaaag 1560
ggtgacagca ggctcataag acgccccagc gtcgccatag tgcgttcacc gaatacgtgc 1620
gcaacaaccg tcttccggag actgtcatac gcgtaaaaca gccagcgctg gcgcgattta 1680
gccccgacat agccccactg ttcgtccatt tccgcgcaga cgatgacgtc actgcccggc 1740
tgtatgcgcg aggttaccga ctgcggcctg agtttttttaa gtgacgtaaa atcgtgttga 1800
ggccaacgcc cataatgcgg gctgttgccc ggcatccaac gccattcatg gccatatcaa 1860
tgattttctg gtgcgtaccg ggttgagaag cggtgtaagt gaactgcagt tgccatgttt 1920
tacggcagtg agagcagaga tagcgctgat gtccggcggt gcttttgccg ttacgcacca 1980

-continued

```
ccccgtcagt agctgaacag gagggacagc tgatagacac agaagccact ggagcacctc   2040
aaaaacacca tcatacacta aatcagtaag ttggcagcat cacccataat tgtggtttca   2100
aaatcggctc cgtcgatact atgttatacg ccaactttga aaacaacttt gaaaaagctg   2160
ttttctggta tttaaggttt tagaatgcaa ggaacagtga attggagttc gtcttgttat   2220
aattagcttc ttggggtatc tttaaatact gtagaaaaga ggaaggaaat aataaatggc   2280
taaaatgaga atatcaccgg aattgaaaaa actgatcgaa aaataccgct gcgtaaaaga   2340
tacggaagga atgtctcctg ctaaggtata taagctggtg ggagaaaatg aaaacctata   2400
tttaaaaatg acggacagcc ggtataaagg gaccacctat gatgtggaac gggaaaagga   2460
catgatgcta tggctggaag gaaagctgcc tgttccaaag gtcctgcact ttgaacggca   2520
tgatggctgg agcaatctgc tcatgagtga ggccgatggc gtcctttgct cggaagagta   2580
tgaagatgaa caaagccctg aaaagattat cgagctgtat gcggagtgca tcaggctctt   2640
tcactccatc gacatatcgg attgtcccta tacgaatagc ttagacagcc gcttagccga   2700
attggattac ttactgaata acgatctggc cgatgtggat tgcgaaaact gggaagaaga   2760
cactccattt aaagatccgc gcgagctgta tgattttta aagacggaaa agcccgaaga   2820
ggaacttgtc ttttcccacg gcgacctggg agacagcaac atctttgtga aagatggcaa   2880
agtaagtggc tttattgatc ttgggagaag cggcagggcg gacaagtggt atgacattgc   2940
cttctgcgtc cggtcgatca gggaggatat cggggaagaa cagtatgtcg agctattttt   3000
tgacttactg gggatcaagc ctgattggga gaaaataaaa tattatattt tactggatga   3060
attgttttag tacctagatg tggcgcaacg atgccggcga caagcaggag cgcaccgact   3120
tcttccgcat caagtgtttt ggctctcagg ccgaggccca cggcaagtat ttgggcaagg   3180
ggtcgctggt attcgtgcag ggcaagattc ggaataccaa gtacgagaag gacggccaga   3240
cggtctacgg gaccgacttc attgccgata aggtggatta tctggacacc aaggcaccag   3300
gcgggtcaaa tcaggaataa gggcacattg ccccggcgtg agtcggggca atcccgcaag   3360
gagggtgaat gaatcggacg tttgaccgga aggcatacag gcaagaactg atcgacgcgg   3420
ggttttccgc cgaggatgcc gaaaccatcg caagccgcac cgtcatgcgt gcgccccgcg   3480
aaaccttcca gtccgtcggc tcgatggtcc agcaagctac ggccaagatc gagcgcgaca   3540
gcgtgcaact ggctcccct gccctgcccg cgccatcggc cgccgtggag cgttcgcgtc   3600
gtctcgaaca ggaggcggca ggtttggcga agtcgatgac catcgacacg cgaggaacta   3660
tgacgaccaa gaagcgaaaa accgccggcg aggacctggc aaaacaggtc agcgaggcca   3720
agcaggccgc gttgctgaaa cacacgaagc agcagatcaa ggaaatgcag ctttccttgt   3780
tcgatattgc gccgtggccg gacacgatgc gagcgatgcc aaacgacacg gcccgctctg   3840
ccctgttcac cacgcgcaac aagaaaatcc cgcgcgaggc gctgcaaaac aaggtcattt   3900
tccacgtcaa caaggacgtg aagatcacct acaccggcgt cgagctgcgg gccgacgatg   3960
acgaactggt gtggcagcag gtgttggagt acgcgaagcg cacccctatc ggcgagccga   4020
tcaccttcac gttctacgag ctttgccagg acctgggctg gtcgatcaat ggccggtatt   4080
acacgaaggc cgaggaatgc ctgtcgcgcc tacaggcgac ggcgatgggc ttcacgtccg   4140
accgcgttgg gcacctggaa tcggtgtcgc tgctgcaccg cttccgcgtc ctggaccgtg   4200
gcaagaaaac gtcccgttgc caggtcctga tcgacgagga aatcgtcgtg ctgtttgctg   4260
gcgaccacta cacgaaattc atatgggaga agtaccgcaa gctgtcgccg acggcccgac   4320
ggatgttcga ctatttcagc tcgcaccggg agccgtaccc gctcaagctg gaaaccttcc   4380
```

```
gcctcatgtg cggatcggat tccacccgcg tgaagaagtg gcgcgagcag gtcggcgaag   4440
cctgcgaaga gttgcgaggc agcggcctgg tggaacacgc ctgggtcaat gatgacctgg   4500
tgcattgcaa acgctagggc cttgtggggt cagttccggc tgggggttca gcagccagcg   4560
ctttactggc atttcaggaa caagcgggca ctgctcgacg cacttgcttc gctcagtatc   4620
gctcgggacg cacggcgcgc tctacgaact gccgataaac agaggattaa aattgacaat   4680
tgtgattaag gctcagattc gacggcttgg agcggccgac gtgcaggatt tccgcgagat   4740
ccgattgtcg gccctgaaga aagctccaga gatgttcggg tccgtttacg agcacgagga   4800
gaaaaagccc atggaggcgt tcgctgaacg gttgcgagat gccgtggcat tcggcgccta   4860
catcgacggc gagatcattg ggctgtcggt cttcaaacag gaggacggcc ccaaggacgc   4920
tcacaaggcg catctgtccg gcgttttcgt ggagcccgaa cagcgaggcc gaggggtcgc   4980
cggtatgctg ctgcgggcgt tgccggcggg tttattgctc gtgatgatcg tccgacagat   5040
tccaacggga atctggtgga tgcgcatctt catcctcggc gcacttaata tttcgctatt   5100
ctggagcttg ttgtttattt cggtctaccg cctgccgggc ggggtcgcgg cgacggtagg   5160
cgctgtgcag ccgctgatgg tcgtgttcat ctctgccgct ctgctaggta gcccgatacg   5220
attgatggcg gtcctggggg ctatttgcgg aactgcgggc gtggcgctgt tggtgttgac   5280
accaaacgca gcgctagatc ctgtcggcgt cgcagcgggc ctggcggggg cggtttccat   5340
ggcgttcgga accgtgctga cccgcaagtg gcaacctccc gtgcctctgc tcacctttac   5400
cgcctggcaa ctggcggccg gaggacttct gctcgttcca gtagctttag tgtttgatcc   5460
gccaatcccg atgcctacag gaaccaatgt tctcggcctg gcgtggctcg gcctgatcgg   5520
agcgggttta acctacttcc tttggttccg ggggatctcg cgactcgaac ctacagttgt   5580
ttccttactg ggctttctca gccccagatc tggggtcgat cagccgggga tgcatcaggc   5640
cgacagtcgg aacttcgggt ccccgacctg taccattcgg tgagcaatgg ataggggagt   5700
tgatatcgtc aacgttcact tctaaagaaa tagcgccact cagcttcctc agcggcttta   5760
tccagcgatt tcctattatg tcggcatagt tctcaagatc gacagcctgt cacggttaag   5820
cgagaaatga ataagaaggc tgataattcg gatctctgcg agggagatga tatttgatca   5880
caggcagcaa cgctctgtca tcgttacaat caacatgcta ccctccgcga gatcatccgt   5940
gtttcaaacc cggcagctta gttgccgttc ttccgaatag catcggtaac atgagcaaag   6000
tctgccgcct tacaacggct ctcccgctga cgccgtcccg gactgatggg ctgcctgtat   6060
cgagtggtga ttttgtgccg agctgccggt cggggagctg ttggctggct ggtggcagga   6120
tatattgtgg tgtaaacaaa ttgacgctta gacaacttaa taacacattg cggacgtttt   6180
taatgtactg gggtggtttt tcttttcacc agtgagacgg gcaacagctg attgcccttc   6240
accgcctggc cctgagagag ttgcagcaag cggtccacgc tggtttgccc cagcaggcga   6300
aaatcctgtt tgatggtggt tccgaaatcg gcaaaatccc ttataaatca aaagaatagc   6360
ccgagatagg gttgagtgtt gttccagttt ggaacaagag tccactatta aagaacgtgg   6420
actccaacgt caaagggcga aaaaccgtct atcagggcga tggcccacta cctgtatggc   6480
cgcattcgca aaacacacct agactagatt tgttttgcta acccaattga tattaattat   6540
atatgattaa tatttatatg tatatggatt tggttaatga aatgcatctg gttcatcaaa   6600
gaattataaa gacacgtgac attcatttag gataagaaat atggatgatc tctttctctt   6660
ttattcagat aactagtaat tacacataac acacaacttt gatgcccaca ttatagtgat   6720
tagcatgtca ctatgtgtgc atccttttat ttcatacatt aattaagttg gccaatccag   6780
```

-continued

```
aagatggaca agtctaggtt aaccatgtgg tacctacgcg ttcgaatatc catgggccgc   6840
ttcaggccag ggcgctgggg aaggcgatgg cgtgctcggt cagctgccac ttctggttct   6900
tggcgtcgct ccggtcctcc cgcagcagct tgtgctggat gaagtgccac tcgggcatct   6960
tgctgggcac gctcttggcc ttgtacacgg tgtcgaactg gcaccggtac cggccgccgt   7020
ccttcagcag caggtacatg ctcacgtcgc ccttcaggat gccctgctta ggcacgggca   7080
tgatcttctc gcagctggcc tcccagttgg tggtcatctt cttcatcacg gggccgtcgg   7140
cggggaagtt cacgccgttg aagatgctct tgtggtagat gcagttctcc ttcacgctca   7200
cggtgatgtc cacgttacag atgcacacgg cgccgtcctc gaacaggaag ctccggcccc   7260
aggtgtagcc ggcggggcag ctgttcttga agtagtccac gatgtcctgg gggtactcgg   7320
tgaagatccg gtcgccgtac ttgaagccgg cgctcaggat gtcctcgctg aagggcaggg   7380
ggccgccctc gatcacgcac aggttgatgg tctgcttgcc cttgaagggg tagccgatgc   7440
cctcgccggt gatcacgaac ttgtggccgt tcacgcagcc ctccatgtgg tacttcatgg   7500
tcatctcctc cttcaggccg tgcttgctgt gggccatggt ggcgaccggt gaattcgagc   7560
tcggtacccg gggatcctga gtaaaacaga ggagggtctc actaagttta tagagagact   7620
gagagagata aagggacacg tatgaagcgt ctgttttcgt ggtgtgacgt caaagtcatt   7680
ttgctctcta cgcgtgtctg tgtcggcttg atcttttttt ttgctttttg gaactcatgt   7740
cggtagtata tcttttattt atttttcttt tttttccctt ttctttcaaa ctgatgtcgg   7800
tatgatattt attccatcct aaaatgtaac ttactattat tagtagtcgg tccatgtcta   7860
ttggcccatc atgtggtcat tttacgttta cgtcgtgtgg ctgtttatta taacaaacgg   7920
cacatccttc tcattcgaat tgtatttctc cttaatcgtt ctaataggta tgatctttta   7980
ttttatacgt aaaattaaaa ttgaatgatg tcaagaacga aaattaattt gtatttacaa   8040
aggagctaaa tattgtttat tcctctactg gtagaagata aaagaagtag atgaaataat   8100
gatcttacta gagaatattc ctcatttaca ctagtcaaat ggaaatcttg taaactttta   8160
caataattta tcctgaaaat atgaaaaaat agaagaaaat gtttacctcc tctctcctct   8220
taattcacct acgatcggtg cgggcctctt cgctattacg ccagctggcg aaagggggat   8280
gtgctgcaag gcgattaagt tgggtaacgc cagggttttc ccagtcacga cgttgtaaaa   8340
cgacggccag tgaattcgag ctcggtaccc ggggatcctc tagagtcgac ctgcaggcat   8400
gcaagcttgt tgaaacatcc ctgaagtgtc tcattttatt ttatttattc tttgctgata   8460
aaaaaataaa ataaaagaag ctaagcacac ggtcaaccat tgctctactg ctaaaagggt   8520
tatgtgtagt gttttactgc ataaattatg cagcaaacaa gacaactcaa attaaaaaat   8580
ttcctttgct tgtttttttg ttgtctctga cttgactttc ttgtggaagt tggttgtata   8640
aggattggga cacaccattg tccttcttaa tttaatttta tttctttgct gataaaaaaa   8700
aaaaatttca tatagtgtta aataataatt tgttaaataa ccaaaaagtc aaatatgttt   8760
actctcgttt aaataattga gagtcgtcca gcaaggctaa acgattgtat agatttatga   8820
caatatttac tttttttatag ataaatgtta tattataata aatttatata catatattat   8880
atgttattta ttatttatta ttattttaaa tccttcaata ttttatcaaa ccaactcata   8940
attttttttt tatctgtaag aagcaataaa attaaataga cccactttaa ggatgatcca   9000
acctttatac agagtaagag agttcaaata gtaccctttc atatacatat caactaaaat   9060
attagaaata tcatggatca aaccttataa agacattaaa taagtggata agtataatat   9120
ataaatgggt agtatataat atataaatgg atacaaactt ctctctttat aattgttatg   9180
```

-continued

```
tctccttaac atcctaatat aatacataag tgggtaatat ataatatata aatggagaca   9240
aacttcttcc attataattg ttatgtcttc ttaacactta tgtctcgttc acaatgctaa   9300
agttagaatt gtttagaaag tcttatagta cacatttgtt tttgtactat ttgaagcatt   9360
ccataagccg tcacgattca gatgatttat aataataaga ggaaatttat catagaacaa   9420
taaggtgcat agatagagtg ttaatatatc ataacatcct ttgtttattc atagaagaag   9480
tgagatggag ctcagttatt atactgttac atggtcggat acaatattcc atgctctcca   9540
tgagctctta cacctacatg cattttagtt catacttcat gcacgtggcc atcacagcta   9600
gctgcagcta catatttaca ttttacaaca ccaggagaac tgccctgtta gtgcataaca   9660
atcagaagat ggccgtggct actcgagtta tcgaaccact ttgtacaaga aagctgaacg   9720
agaaacgtaa aatgatataa atatcaatat attaaattag attttgcata aaaaacagac   9780
tacataatac tgtaaaacac aacatatcca gtcactatgg tcgacctgca gactggctgt   9840
gtataaggga gcctgacatt tatattcccc agaacatcag gttaatggcg tttttgatgt   9900
cattttcgcg gtggctgaga tcagccactt cttccccgat aacggagacc ggcacactgg   9960
ccatatcggt ggtcatcatg cgccagcttt catccccgat atgcaccacc gggtaaagtt  10020
cacgggagac tttatctgac agcagacgtg cactggccag ggggatcacc atccgtcgcc  10080
cgggcgtgtc aataatatca ctctgtacat ccacaaacag acgataacgg ctctctcttt  10140
tataggtgta aaccttaaac tgcatttcac cagtccctgt tctcgtcagc aaaagagccg  10200
ttcatttcaa taaaccgggc gacctcagcc atcccttcct gattttccgc tttccagcgt  10260
tcggcacgca gacgacgggc ttcattctgc atggttgtgc ttaccagacc ggagatattg  10320
acatcatata tgccttgagc aactgatagc tgtcgctgtc aactgtcact gtaatacgct  10380
gcttcatagc acacctcttt ttgacatact tcgggtatac atatcagtat atattcttat  10440
accgcaaaaa tcagcgcgca aatacgcata ctgttatctg gcttttagta agccggatcc  10500
tctagattac gccccgccct gccactcatc gcagtactgt tgtaattcat taagcattct  10560
gccgacatgg aagccatcac agacggcatg atgaacctga atcgccagcg gcatcagcac  10620
cttgtcgcct tgcgtataat atttgcccat ggtgaaaacg ggggcgaaga agttgtccat  10680
attggccacg tttaaatcaa aactggtgaa actcacccag ggattggctg agacgaaaaa  10740
catattctca ataaaccctt tagggaaata ggccaggttt tcaccgtaac acgccacatc  10800
ttgcgaatat atgtgtagaa actgccggaa atcgtcgtgg tattcactcc agagcgatga  10860
aaacgtttca gtttgctcat ggaaaacggt gtaacaaggg tgaacactat cccatatcac  10920
cagctcaccg tctttcattg ccatacggaa ttccggatga gcattcatca ggcgggcaag  10980
aatgtgaata aaggccggat aaaacttgtg cttatttttc tttacggtct ttaaaaaggc  11040
cgtaatatcc agctgaacgg tctggttata ggtacattga gcaactgact gaaatgcctc  11100
aaaatgttct ttacgatgcc attgggatat atcaacggtg gtatatccag tgattttttt  11160
ctccatttta gcttccttag ctcctgaaaa tctcgccgga tcctaactca aaatccacac  11220
attatacgag ccggaagcat aaagtgtaaa gcctggggtg cctaatgcgg ccgccatagt  11280
gactggatat gttgtgtttt acagtattat gtagtctgtt ttttatgcaa aatctaattt  11340
aatatattga tatttatatc attttacgtt tctcgttcag ctttttttgta caaacttgtt  11400
tgataaccgg tactagtgtg cacgtcgagc gtgtcctctc caaatgaaat gaacttcctt  11460
atatagagga agggtcttgc gaaggatagt gggattgtgc gtcatccctt acgtcagtgg  11520
agatgtcaca tcaatccact tgctttgaag acgtggttgg aacgtcttct ttttccacga  11580
```

-continued

```
tgctcctcgt gggtgggggt ccatctttgg gaccactgtc ggcagaggca tcttgaatga  11640
tagcctttcc tttatcgcaa tgatggcatt tgtaggagcc accttccttt tctactgtcc  11700
tttcgatgaa gtgacagata gctgggcaat ggaatccgag gaggtttccc gaaattatcc  11760
tttgttgaaa agtctcaata gccctttggt cttctgagac tgtatctttg acatttttgg  11820
agtagaccag agtgtcgtgc tccaccatgt tgacgaagat tttcttcttg tcattgagtc  11880
gtaaaagact ctgtatgaac tgttcgccag tcttcacggc gagttctgtt agatcctcga  11940
tttgaatctt agactccatg catggcctta gattcagtag gaactacctt tttagagact  12000
ccaatctcta ttacttgcct tggtttatga agcaagcctt gaatcgtcca tactggaata  12060
gtacttctga tcttgagaaa tatgtctttc tctgtgttct tgatgcaatt agtcctgaat  12120
cttttgactg catctttaac cttcttggga aggtatttga tctcctggag attgttactc  12180
gggtagatcg tcttgatgag acctgctgcg taggcctctc taaccatctg tgggtcagca  12240
ttctttctga aattgaagag gctaaccttc tcattatcag tggtgaacat agtgtcgtca  12300
ccttcacctt cgaacttcct tcctagatcg taaagataga ggaaatcgtc cattgtaatc  12360
tccggggcaa aggagatctc ttttggggct ggatcactgc tgggcctttt ggttcctagc  12420
gtgagccagt gggctttttg ctttggtggg cttgttaggg ccttagcaaa gctcttgggc  12480
ttgagttgag cttctccttt ggggatgaag ttcaacctgt ctgtttgctg acttgttgtg  12540
tacgcgtcag ctgctgctct tgcctctgta atagtggcaa atttcttgtg tgcaactccg  12600
ggaacgccgt ttgttgccgc ctttgtacaa ccccagtcat cgtatatacc ggcatgtgga  12660
ccgttataca caacgtagta gttgatatga gggtgttgaa tacccgattc tgctctgaga  12720
ggagcaactg tgctgttaag ctcagatttt tgtgggattg gaattggatc ctctagagca  12780
aagcttggcg taatcatggt catagctgtt tcctgtgtga aattgttatc cgctcacaat  12840
tccacacaac atacgagccg gaagcataaa gtgtaaagcc tggggtgcct aatgagtgag  12900
ctaactcaca ttaattgcgt tgcgctcact gcccgctttc cagtcgggaa acctgtcgtg  12960
ccagctgcat taatgaatcg gccaacgcgc ggggagaggc ggtttgcgta ttgggccaaa  13020
gacaaaaggg cgacattcaa ccgattgagg gagggaaggt aaatattgac ggaaattatt  13080
cattaaaggt gaattatcac cgtcaccgac ttgagccatt tgggaattag agccagcaaa  13140
atcaccagta gcaccattac cattagcaag gccggaaacg tcaccaatga aaccatcatc  13200
tagtaacata gatgacaccg cgcgcgataa tttatcctag tttgcgcgct atattttgtt  13260
ttctatcgcg tattaaatgt ataattgcgg gactctaatc ataaaaaccc atctcataaa  13320
taacgtcatg cattacatgt taattattac atgcttaacg taattcaaca gaaattatat  13380
gataatcatc gcaagaccgg caacaggatt caatcttaag aaactttatt gccaaatgtt  13440
tgaacgatct gcttcgacgc actccttctt taggtacgga ctagatctcg gtgacgggca  13500
ggaccggacg gggcggtacc ggcaggctga agtccagctg ccagaaaccc acgtcatgcc  13560
agttcccgtg cttgaagccg gccgcccgca gcatgccgcg gggggcatat ccgagcgcct  13620
cgtgcatgcg cacgctcggg tcgttgggca gcccgatgac agcgaccacg ctcttgaagc  13680
cctgtgcctc cagggacttc agcaggtggg tgtagagcgt ggagcccagt cccgtccgct  13740
ggtggcgggg ggagacgtac acggtcgact cggccgtcca gtcgtaggcg ttgcgtgcct  13800
tccaggggcc cgcgtaggcg atgccggcga cctcgccgtc cacctcggcg acgagccagg  13860
gatagcgctc ccgcagacgg acgaggtcgt ccgtccactc ctgcggttcc tgcggctcgg  13920
tacggaagtt gaccgtgctt gtctcgatgt agtggttgac gatggtgcag accgccggca  13980
```

tgtccgcctc ggtggcacgg cggatgtcgg ccgggcgtcg ttctgggctc atggatctgg 14040
attgagagtg aatatgagac tctaattgga taccgagggg aatttatgga acgtcagtgg 14100
agcatttttg acaagaaata tttgctagct gatagtgacc ttaggcgact tttgaacgcg 14160
caataatggt ttctgacgta tgtgcttagc tcattaaact ccagaaaccc gcggctgagt 14220
ggctccttca acgttgcggt tctgtcagtt ccaaacgtaa aacggcttgt cccgcgtcat 14280
cggcgggggt cataacgtga ctcccttaat tctccgctca tgatcagatt gtcgtttccc 14340
gccttcagtt taaactatca gtgtttgaca ggatatattg gcgggtaaac ctaagagaaa 14400
agagcgttta ttagaataat cggatattta aaagggcgtg aaaaggttta tccgttcgtc 14460
catttgtatg tgcatgccaa ccacagggtt ccccagatct ggcgccggcc agcgagacga 14520
gcaagattgg ccgccgcccg aaacgatccg acagcgcgcc cagcacaggt gcgcaggcaa 14580
attgcaccaa cgcatacagc gccagcagaa tgccatagtg ggcggtgacg tcgttcgagt 14640
gaaccagatc gcgcaggagg cccggcagca ccggcataat caggccgatg ccgacagcgt 14700
cgagcgcgac agtgctcaga attacgatca ggggtatgtt gggtttcacg tctggcctcc 14760
ggaccagcct ccgctggtcc gattgaacgc gcggattctt tatcactgat aagttggtgg 14820
acatattatg tttatcagtg ataaagtgtc aagcatgaca aagttgcagc cgaatacagt 14880
gatccgtgcc gccctggacc tgttgaacga ggtcggcgta gacggtctga cgacacgcaa 14940
actggcggaa cggttggggg ttcagcagcc ggcgctttac tggcacttca ggaacaagcg 15000
ggcgctgctc gacgcactgg ccgaagccat gctggcggag aatcatacgc attcggtgcc 15060
gagagccgac gacgactggc gctcatttct gatcgggaat gcccgcagct tcaggcaggc 15120
gctgctcgcc taccgcgatg gcgcgcgcat ccatgccggc acgcgaccgg gcgcaccgca 15180
gatggaaacg gccgacgcgc agcttcgctt cctctgcgag gcgggttttt cggccgggga 15240
cgccgtcaat gcgctgatga caatcagcta cttcactgtt ggggccgtgc ttgaggagca 15300
ggccggcgac agcgatgccg gcgagcgcgg cggcaccgtt gaacaggctc cgctctcgcc 15360
gctgttgcgg gccgcgatag acgccttcga cgaagccggt ccggacgcag cgttcgagca 15420
gggactcgcg gtgattgtcg atggattggc gaaaaggagg ctcgttgtca ggaacgttga 15480
aggaccgaga aagggtgacg attgatcagg accgctgccg gagcgcaacc cactcactac 15540
agcagagcca tgtagacaac atcccctccc cctttccacc gcgtcagacg cccgtagcag 15600
cccgctacgg gctttttcat gccctgccct agcgtccaag cctcacggcc gcgctcggcc 15660
tctctggcgg ccttctggcg ctcttccgct tcctcgctca ctgactcgct gcgctcggtc 15720
gttcggctgc ggcgagcggt atcagctcac tcaaaggcgg taatacggtt atccacagaa 15780
tcaggggata acgcaggaaa gaacatgtga gcaaaaggcc agcaaaaggc caggaaccgt 15840
aaaaaggccg cgttgctggc gtttttccat aggctccgcc cccctgacga gcatcacaaa 15900
aatcgacgct caagtcagag gtggcgaaac ccgacaggac tataaagata ccaggcgttt 15960
ccccctggaa gctccctcgt gcgctctcct gttccgaccc tgccgcttac cggatacctg 16020
tccgcctttc tcccttcggg aagcgtggcg ctttttccgct gcataaccct gcttcggggt 16080
cattatagcg attttttcgg tatatccatc ctttttcgca cgatatacag gattttgcca 16140
aagggttcgt gtagactttc cttggtgtat ccaacggcgt cagccgggca ggataggtga 16200
agtaggccca cccgcgagcg ggtgttcctt cttcactgtc ccttattcgc acctggcggt 16260
gctcaacggg aatcctgctc tgcgaggctg gccggctacc gccggcgtaa cagatgaggg 16320
caagcggatg gctgatgaaa ccaagccaac caggaagggc agcccaccta tcaaggtgta 16380

```
ctgccttcca gacgaacgaa gagcgattga ggaaaaggcg gcggcggccg gcatgagcct  16440

gtcggcctac ctgctggccg tcggccaggg ctacaaaatc acgggcgtcg tggactatga  16500

gcacgtccgc gagctggccc gcatcaatgg cgacctgggc cgcctgggcg gcctgctgaa  16560

actctggctc accgacgacc cgcgcacggc gcggttcggt gatgccacga tcctcgccct  16620

gctggcgaag atcgaagaga agcaggacga gcttggcaag gtcatgatgg gcgtggtccg  16680

cccgagggca gagccatgac tttttttagcc gctaaaacgg ccgggggggtg cgcgtgattg  16740

ccaagcacgt ccccatgcgc tccatcaaga agagcgactt cgcggagctg gtgaagtaca  16800

tcaccgacga gcaaggcaag accgagcgcc tttgcgacgc tca                    16843
```

<210> SEQ ID NO 35
<211> LENGTH: 9142
<212> TYPE: DNA
<213> ORGANISM: Artificial
<220> FEATURE:
<223> OTHER INFORMATION: Destination vector PHP27840

<400> SEQUENCE: 35

```
ctagttatct gaataaaaga gaaagagatc atccatattt cttatcctaa atgaatgtca     60

cgtgtcttta taattctttg atgaaccaga tgcatttcat taaccaaatc catatacata    120

taaatattaa tcatatataa ttaatatcaa ttgggttagc aaaacaaatc tagtctaggt    180

gtgttttgcg aattcgatat caagcttgat gggtaccggc gcgcccgatc atccggatat    240

agttcctcct ttcagcaaaa aacccctcaa gacccgttta gaggccccaa ggggttatgc    300

tagttattgc tcagcggtgg cagcagccaa ctcagcttcc tttcgggctt tgttagcagc    360

cggatcgatc caagctgtac ctcactattc ctttgccctc ggacgagtgc tggggcgtcg    420

gtttccacta tcggcgagta cttctacaca gccatcggtc cagacggccg cgcttctgcg    480

ggcgatttgt gtacgcccga cagtcccggc tccggatcgg acgattgcgt cgcatcgacc    540

ctgcgcccaa gctgcatcat cgaaattgcc gtcaaccaag ctctgataga gttggtcaag    600

accaatgcgg agcatatacg cccggagccg cggcgatcct gcaagctccg gatgcctccg    660

ctcgaagtag cgcgtctgct gctccataca agccaaccac ggcctccaga agaagatgtt    720

ggcgacctcg tattgggaat ccccgaacat cgcctcgctc cagtcaatga ccgctgttat    780

gcggccattg tccgtcagga cattgttgga gccgaaatcc gcgtgcacga ggtgccggac    840

ttcggggcag tcctcggccc aaagcatcag ctcatcgaga gcctgcgcga cggacgcact    900

gacggtgtcg tccatcacag tttgccagtg atacacatgg ggatcagcaa tcgcgcatat    960

gaaatcacgc catgtagtgt attgaccgat tccttgcggt ccgaatgggc cgaacccgct   1020

cgtctggcta agatcggccg cagcgatcgc atccatagcc tccgcgaccg gctgcagaac   1080

agcgggcagt tcggtttcag gcaggtcttg caacgtgaca ccctgtgcac ggcgggagat   1140

gcaataggtc aggctctcgc tgaattcccc aatgtcaagc acttccggaa tcgggagcgc   1200

ggccgatgca aagtgccgat aaacataacg atctttgtag aaaccatcgg cgcagctatt   1260

tacccgcagg acatatccac gccctcctac atcgaagctg aaagcacgag attcttcgcc   1320

ctccgagagc tgcatcaggt cggagacgct gtcgaacttt tcgatcagaa acttctcgac   1380

agacgtcgcg gtgagttcag gcttttccat gggtatatct ccttcttaaa gttaaacaaa   1440

attatttcta gagggaaacc gttgtggtct ccctatagtg agtcgtatta atttcgcggg   1500

atcgagatct gatcaacctg cattaatgaa tcggccaacg cgcggggaga ggcggtttgc   1560

gtattgggcg ctcttccgct tcctcgctca ctgactcgct gcgctcggtc gttcggctgc   1620
```

-continued

```
ggcgagcggt atcagctcac tcaaaggcgg taatacggtt atccacagaa tcaggggata   1680
acgcaggaaa gaacatgtga gcaaaaggcc agcaaaaggc caggaaccgt aaaaaggccg   1740
cgttgctggc gtttttccat aggctccgcc cccctgacga gcatcacaaa aatcgacgct   1800
caagtcagag gtggcgaaac ccgacaggac tataaagata ccaggcgttt ccccctggaa   1860
gctccctcgt gcgctctcct gttccgaccc tgccgcttac cggatacctg tccgcctttc   1920
tcccttcggg aagcgtggcg ctttctcaat gctcacgctg taggtatctc agttcggtgt   1980
aggtcgttcg ctccaagctg ggctgtgtgc acgaaccccc cgttcagccc gaccgctgcg   2040
ccttatccgg taactatcgt cttgagtcca acccggtaag acacgactta tcgccactgg   2100
cagcagccac tggtaacagg attagcagag cgaggtatgt aggcggtgct acagagttct   2160
tgaagtggtg gcctaactac ggctacacta gaaggacagt atttggtatc tgcgctctgc   2220
tgaagccagt taccttcgga aaaagagttg gtagctcttg atccggcaaa caaaccaccg   2280
ctggtagcgg tggttttttt gtttgcaagc agcagattac gcgcagaaaa aaaggatctc   2340
aagaagatcc tttgatcttt tctacggggt ctgacgctca gtggaacgaa aactcacgtt   2400
aagggatttt ggtcatgaca ttaacctata aaaataggcg tatcacgagg ccctttcgtc   2460
tcgcgcgttt cggtgatgac ggtgaaaacc tctgacacat gcagctcccg gagacggtca   2520
cagcttgtct gtaagcggat gccgggagca gacaagcccg tcagggcgcg tcagcgggtg   2580
ttggcgggtg tcggggctgg cttaactatg cggcatcaga gcagattgta ctgagagtgc   2640
accatatgga catattgtcg ttagaacgcg gctacaatta atacataacc ttatgtatca   2700
tacacatacg atttaggtga cactatagaa cggcgcgcca agctgggtct agaactagaa   2760
acgtgatgcc acttgttatt gaagtcgatt acagcatcta ttctgtttta ctatttataa   2820
ctttgccatt tctgactttt gaaaactatc tctggatttc ggtatcgctt tgtgaagatc   2880
gagcaaaaga gacgttttgt ggacgcaatg gtccaaatcc gttctacatg aacaaattgg   2940
tcacaatttc cactaaaagt aaataaatgg caagttaaaa aaggaatatg cattttactg   3000
attgcctagg tgagctccaa gagaagttga atctacacgt ctaccaaccg ctaaaaaaag   3060
aaaaacattg aatatgtaac ctgattccat tagcttttga cttcttcaac agattctcta   3120
cttagatttc taacagaaat attattacta gcacatcatt ttcagtctca ctacagcaaa   3180
aaatccaacg gcacaataca gacaacagga gatatcagac tacagagata gatagatgct   3240
actgcatgta gtaagttaaa taaaaggaaa ataaaatgtc ttgctaccaa aactactaca   3300
gactatgatg ctcaccacag gccaaatcct gcaactagga cagcattatc ttatatatat   3360
tgtacaaaac aagcatcaag gaacatttgg tctaggcaat cagtacctcg ttctaccatc   3420
accctcagtt atcacatcct tgaaggatcc attactggga atcatcggca acacatgctc   3480
ctgatggggc acaatgacat caagaaggta ggggccaggg gtgtccaaca ttctctgaat   3540
tgccgctcta agctcttcct tcttcgtcac tcgcgctgcc ggtatcccac aagcatcagc   3600
aaacttgagc atgtttggga atatctcgct ctcgctagac ggatctccaa gataggtgtg   3660
agctctattg gacttgtaga acctatcctc caactgaacc accataccca aatgctgatt   3720
gttcaacaac aatatcttaa ctgggagatt ctccactctt atagtggcca actcctgaac   3780
attcatgatg aaactaccat ccccatcaat gtcaaccaca acagccccag ggttagcaac   3840
agcagcacca atagccgcag gcaatccaaa acccatggct ccaagacccc ctgaggtcaa   3900
ccactgcctc ggtctcttgt acttgtaaaa ctgcgcagcc cacatttgat gctgcccaac   3960
cccagtacta acaatagcat ctccattagt caactcatca agaacctcga tagcatgctg   4020
```

-continued

```
cggagaaatc gcgtcctgga atgtcttgta acccaatgga aacttgtgtt tctgcacatt   4080
aatctcttct ctccaacctc caagatcaaa cttaccctcc actcctttct cctccaaaat   4140
catattaatt cccttcaagg ccaacttcaa atccgcgcaa accgacacgt gcgcctgctt   4200
gttcttccca atctcggcag aatcaatatc aatgtgaaca atcttagccc tactagcaaa   4260
agcctcaagc ttcccagtaa cacggtcatc aaaccttacc ccaaaggcaa gcaacaaatc   4320
actattgtca acagcatagt tagcataaac agtaccatgc atacccagca tctgaaggga   4380
atattcatca ccaataggaa aagttccaag acccattaaa gtgctagcaa cgggaatacc   4440
agtgagttca acaaagcgcc tcaattcagc actggaattc aaactgccac cgccgacgta   4500
gagaacgggc ttttgggcct ccatgatgag tctgacaatg tgttccaatt gggcctcggc   4560
ggggggcctg ggcagcctgg cgaggtaacc ggggaggtta acgggctcgt cccaattagg   4620
cacggcgagt tgctgctgaa cgtctttggg aatgtcgatg aggaccggac cggggcggcc   4680
ggaggtggcg acgaagaaag cctcggcgac gacgcggggg atgtcgtcga cgtcgaggat   4740
gaggtagttg tgcttcgtga tggatctgct cacctccacg atcggggttt cttggaaggc   4800
gtcggtgccg atcatccggc gggcgacctg gccggtgatg gcgacgactg ggacgctgtc   4860
cattaaagcg tcggcgaggc cgctcacgag gttggtggcg ccggggccgg aggtggcaat   4920
gcagacgccg gggaggccgg aggaacgcgc gtagccttcg gcggcgaaga cgccgccctg   4980
ctcgtggcgc gggagcacgt tgcggatggc ggcggagcgc gtgagcgcct ggtggatctc   5040
catcgacgca ccgccggggt acgcgaacac cgtcgtcacg ccctgcctct ccagcgcctc   5100
cacaaggatg tccgcgccct tgcgaggttc gccggaggcg aaccgtgaca cgaagggctc   5160
cgtggtcggc gcttccttgg tgaagggcgc cgccgtgggg ggtttggaga tggaacattt   5220
gattttgaga gcgtggttgg gtttggtgag ggtttgatga gagagaggga gggtggatct   5280
agtaatgcgt ttggggaagg tggggtgtga agaggaagaa gagaatcggg tggttctgga   5340
agcggtggcc gccattgtgt tgtgtggcat ggttatactt caaaaactgc acaacaagcc   5400
tagagttagt acctaaacag taaatttaca acagagagca aagacacatg caaaaatttc   5460
agccataaaa aaagttataa tagaatttaa agcaaaagtt tcatttttta aacatatata   5520
caaacaaact ggatttgaag gaagggatta attcccctgc tcaaagtttg aattcctatt   5580
gtgacctata ctcgaataaa attgaagcct aaggaatgta tgagaaacaa gaaaacaaaa   5640
caaaactaca gacaaacaag tacaattaca aaattcgcta aaattctgta atcaccaaac   5700
cccatctcag tcagcacaag gcccaaggtt tattttgaaa taaaaaaaaa gtgattttat   5760
ttctcataag ctaaaagaaa gaaaggcaat tatgaaatga tttcgactag atctgaaagt   5820
caaacgcgta ttccgcagat attaaagaaa gagtagagtt tcacatggat cctagatgga   5880
cccagttgag gaaaaagcaa ggcaaagcaa accagaagtg caagatccga aattgaacca   5940
cggaatctag gatttggtag agggagaaga aaagtacctt gagaggtaga agagaagaga   6000
agagcagaga gatatatgaa cgagtgtgtc ttggtctcaa ctctgaagcg atacgagttt   6060
agaggggagc attgagttcc aatttatagg gaaaccgggt ggcaggggtg agttaatgac   6120
ggaaaagccc ctaagtaacg agattggatt gtgggttaga ttcaaccgtt tgcatccgcg   6180
gcttagattg gggaagtcag agtgaatctc aaccgttgac tgagttgaaa attgaatgta   6240
gcaaccaatt gagccaaccc cagcctttgc cctttgattt tgatttgttt gttgcatact   6300
ttttatttgt cttctggttc tgactctctt tctctcgttt caatgccagg ttgcctactc   6360
ccacaccact cacaagaaga ttctactgtt agtattaaat attttttaat gtattaaatg   6420
```

atgaatgctt ttgtaaacag aacaagacta tgtctaataa gtgtcttgca acatttttta 6480
agaaattaaa aaaaatatat ttattatcaa aatcaaatgt atgaaaaatc atgaataata 6540
taattttata catttttta aaaaatcttt taatttctta attaatatct taaaaataat 6600
gattaatatt taacccaaaa taattagtat gattggtaag gaagatatcc atgttatgtt 6660
tggatgtgag tttgatctag agcaaagctt actagagtcg acctgcagcc cctccaccgc 6720
ggtggcggcc gctctagaga tccgtcaaca tggtggagca cgacactctc gtctactcca 6780
agaatatcaa agatacagtc tcagaagacc aaagggctat tgagactttt caacaaaggg 6840
taatatcggg aaacctcctc ggattccatt gcccagctat ctgtcacttc atcaaaagga 6900
cagtagaaaa ggaaggtggc acctacaaat gccatcattg cgataaagga aaggctatcg 6960
ttcaagatgc ctctgccgac agtggtccca aagatggacc cccacccacg aggagcatcg 7020
tggaaaaaga agacgttcca accacgtctt caaagcaagt ggattgatgt gatgatccta 7080
tgcgtatggt atgacgtgtg ttcaagatga tgacttcaaa cctacctatg acgtatggta 7140
tgacgtgtgt cgactgatga cttagatcca ctcgagcggc tataaatacg tacctacgca 7200
ccctgcgcta ccatccctag agctgcagct tatttttaca acaattacca acaacaacaa 7260
acaacaaaca acattacaat tactatttac aattacagtc gacccatcaa caagtttgta 7320
caaaaaagct gaacgagaaa cgtaaaatga tataaatatc aatatattaa attagatttt 7380
gcataaaaaa cagactacat aatactgtaa aacacaacat atccagtcat attggcggcc 7440
gcattaggca ccccaggctt tacactttat gcttccggct cgtataatgt gtggattttg 7500
agttaggatc cgtcgagatt ttcaggagct aaggaagcta aaatggagaa aaaaatcact 7560
ggatatacca ccgttgatat atcccaatgg catcgtaaag aacattttga ggcatttcag 7620
tcagttgctc aatgtaccta taaccagacc gttcagctgg atattacggc ctttttaaag 7680
accgtaaaga aaaataagca caagttttat ccggccttta ttcacattct tgcccgcctg 7740
atgaatgctc atccggaatt ccgtatggca atgaaagacg gtgagctggt gatatgggat 7800
agtgttcacc cttgttacac cgttttccat gagcaaactg aaacgttttc atcgctctgg 7860
agtgaatacc acgacgattt ccggcagttt ctacacatat attcgcaaga tgtggcgtgt 7920
tacggtgaaa acctggccta tttccctaaa gggtttattg agaatatgtt tttcgtctca 7980
gccaatccct gggtgagttt caccagtttt gatttaaacg tggccaatat ggacaacttc 8040
ttcgcccccg ttttcaccat gggcaaatat tatacgcaag gcgacaaggt gctgatgccg 8100
ctggcgattc aggttcatca tgccgtttgt gatggcttcc atgtcggcag aatgcttaat 8160
gaattacaac agtactgcga tgagtggcag ggcggggcgt aaagatctgg atccggctta 8220
ctaaaagcca gataacagta tgcgtatttg cgcgctgatt tttgcggtat aagaatatat 8280
actgatatgt atacccgaag tatgtcaaaa agaggtatgc tatgaagcag cgtattacag 8340
tgacagttga cagcgacagc tatcagttgc tcaaggcata tatgatgtca atatctccgg 8400
tctggtaagc acaaccatgc agaatgaagc ccgtcgtctg cgtgccgaac gctggaaagc 8460
ggaaaatcag gaagggatgg ctgaggtcgc ccggtttatt gaaatgaacg gctcttttgc 8520
tgacgagaac aggggctggt gaaatgcagt ttaaggttta cacctataaa agagagagcc 8580
gttatcgtct gtttgtggat gtacagagtg atattattga cacgcccggg cgacggatgg 8640
tgatccccct ggccagtgca cgtctgctgt cagataaagt ctcccgtgaa ctttacccgg 8700
tggtgcatat cggggatgaa agctggcgca tgatgaccac cgatatggcc agtgtgccgg 8760
tctccgttat cggggaagaa gtggctgatc tcagccaccg cgaaaatgac atcaaaaacg 8820
ccattaacct gatgttctgg ggaatataaa tgtcaggctc ccttatacac agccagtctg 8880
caggtcgacc atagtgactg gatatgttgt gttttacagt attatgtagt ctgtttttta 8940
tgcaaaatct aatttaatat attgatattt atatcatttt acgtttctcg ttcagctttc 9000
ttgtacaaag tggttgataa cctagacttg tccatcttct ggattggcca acttaattaa 9060
tgtatgaaat aaaaggatgc acacatagtg acatgctaat cactataatg tgggcatcaa 9120
agttgtgtgt tatgtgtaat ta 9142

<210> SEQ ID NO 36
<211> LENGTH: 49911
<212> TYPE: DNA
<213> ORGANISM: Artificial
<220> FEATURE:
<223> OTHER INFORMATION: Destination vector PHP23236

<400> SEQUENCE: 36
gtgcagcgtg acccggtcgt gcccctctct agagataatg agcattgcat gtctaagtta 60
taaaaaatta ccacatattt tttttgtcac acttgtttga agtgcagttt atctatcttt 120
atacatatat ttaaacttta ctctacgaat aatataatct atagtactac aataatatca 180
gtgttttaga gaatcatata aatgaacagt tagacatggt ctaaaggaca attgagtatt 240
ttgacaacag gactctacag ttttatcttt ttagtgtgca tgtgttctcc tttttttttg 300
caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gtttttttat ttaataattt agatataaaa 480
tagaataaaa taaagtgact aaaaattaaa caaataccct ttaagaaatt aaaaaaacta 540
aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcacggca gctacggggg attcctttcc caccgctcct 840
tcgctttccc ttcctcgccc gccgtaataa atagacaccc cctccacacc ctctttcccc 900
aacctcgtgt tgttcggagc gcacacacac acaaccagat ctcccccaaa tccacccgtc 960
ggcacctccg cttcaaggta cgccgctcgt cctccccccc cccccctctc taccttctct 1020
agatcggcgt tccggtccat ggttagggcc cggtagttct acttctgttc atgtttgtgt 1080
tagatccgtg tttgtgttag atccgtgctg ctagcgttcg tacacggatg cgacctgtac 1140
gtcagacacg ttctgattgc taacttgcca gtgtttctct ttggggaatc ctgggatggc 1200
tctagccgtt ccgcagacgg gatcgatttc atgatttttt ttgtttcgtt gcatagggtt 1260
tggtttgccc ttttccttta tttcaatata tgccgtgcac ttgtttgtcg ggtcatcttt 1320
tcatgctttt ttttgtcttg gttgtgatga tgtggtctgg ttgggcggtc gttctagatc 1380
ggagtagaat tctgtttcaa actacctggt ggatttatta attttggatc tgtatgtgtg 1440
tgccatacat attcatagtt acgaattgaa gatgatggat ggaaatatcg atctaggata 1500
ggtatacatg ttgatgcggg ttttactgat gcatatacag agatgctttt tgttcgcttg 1560
gttgtgatga tgtggtgtgg ttgggcggtc gttcattcgt tctagatcgg agtagaatac 1620
tgtttcaaac tacctggtgt atttattaat tttggaactg tatgtgtgtg tcatacatct 1680
tcatagttac gagtttaaga tggatggaaa tatcgatcta ggataggtat acatgttgat 1740
gtgggtttta ctgatgcata tacatgatgg catatgcagc atctattcat atgctctaac 1800
cttgagtacc tatctattat aataaacaag tatgttttat aattattttg atcttgatat 1860
acttggatga tggcatatgc agcagctata tgtggatttt tttagccctg ccttcatacg 1920
ctatttattt gcttggtact gtttcttttg tcgatgctca ccctgttgtt tggtgttact 1980
tctgcaggtc gactctagag gatccacaag tttgtacaaa aaagctgaac gagaaacgta 2040
aaatgatata aatatcaata tattaaatta gattttgcat aaaaaacaga ctacataata 2100
ctgtaaaaca caacatatcc agtcactatg gcggccgcat taggcacccc aggctttaca 2160
ctttatgctt ccggctcgta taatgtgtgg attttgagtt aggatttaaa tacgcgttga 2220
tccggcttac taaaagccag ataacagtat gcgtatttgc gcgctgattt ttgcggtata 2280
agaatatata ctgatatgta tacccgaagt atgtcaaaaa gaggtatgct atgaagcagc 2340
gtattacagt gacagttgac agcgacagct atcagttgct caaggcatat atgatgtcaa 2400
tatctccggt ctggtaagca caaccatgca gaatgaagcc cgtcgtctgc gtgccgaacg 2460
ctggaaagcg gaaaatcagg aagggatggc tgaggtcgcc cggtttattg aaatgaacgg 2520
ctcttttgct gacgagaaca ggggctggtg aaatgcagtt taaggtttac acctataaaa 2580
gagagagccg ttatcgtctg tttgtggatg tacagagtga tatcattgac acgcccggtc 2640
gacggatggt gatccccctg gccagtgcac gtctgctgtc agataaagtc tcccgtgaac 2700
tttacccggt ggtgcatatc ggggatgaaa gctggcgcat gatgaccacc gatatggcca 2760
gtgtgccggt ctccgttatc ggggaagaag tggctgatct cagccaccgc gaaaatgaca 2820
tcaaaaacgc cattaacctg atgttctggg gaatataaat gtcaggctcc cttatacaca 2880
gccagtctgc aggtcgacca tagtgactgg atatgttgtg ttttacagta ttatgtagtc 2940 tgtttttat gcaaaatcta atttaatata ttgatattta tatcatttta cgtttctcgt 3000
tcagctttct tgtacaaagt ggtgttaacc tagacttgtc catcttctgg attggccaac 3060
ttaattaatg tatgaaataa aaggatgcac acatagtgac atgctaatca ctataatgtg 3120
ggcatcaaag ttgtgtgtta tgtgtaatta ctagttatct gaataaaaga gaaagagatc 3180
atccatattt cttatcctaa atgaatgtca cgtgtcttta taattctttg atgaaccaga 3240
tgcatttcat taaccaaatc catatacata taaatattaa tcatatataa ttaatatcaa 3300
ttgggttagc aaaacaaatc tagtctaggt gtgttttgcg aattgcggcc gccaccgcgg 3360
tggagctcga attccggtcc gggtcacctt tgtccaccaa gatggaactg cggccgctca 3420
ttaattaagt caggcgcgcc tctagttgaa gacacgttca tgtcttcatc gtaagaagac 3480
actcagtagt cttcggccag aatggccatc tggattcagc aggcctagaa ggccatttaa 3540
atcctgagga tctggtcttc ctaaggaccc gggatatcgg accgattaaa ctttaattcg 3600
gtccgaagct tgcatgcctg cagtgcagcg tgacccggtc gtgcccctct ctagagataa 3660
tgagcattgc atgtctaagt tataaaaaat taccacatat ttttttgtc acacttgttt 3720 gaagtgcagt ttatctatct ttatacatat atttaaactt tactctacga ataatataat 3780
ctatagtact acaataatat cagtgtttta gagaatcata taaatgaaca gttagacatg 3840
gtctaaagga caattgagta ttttgacaac aggactctac agttttatct ttttagtgtg 3900
catgtgttct cctttttttt tgcaaatagc ttcacctata taatacttca tccattttat 3960
tagtacatcc atttagggtt tagggttaat ggtttttata gactaatttt tttagtacat 4020
ctattttatt ctattttagc ctctaaatta agaaaactaa aactctattt tagttttttt 4080
atttaataat ttagatataa aatagaataa aataaagtga ctaaaaatta aacaaatacc 4140

-continued

```
ctttaagaaa ttaaaaaaac taaggaaaca tttttcttgt ttcgagtaga taatgccagc   4200
ctgttaaacg ccgtcgacga gtctaacgga caccaaccag cgaaccagca gcgtcgcgtc   4260
gggccaagcg aagcagacgg cacggcatct ctgtcgctgc ctctggaccc ctctcgagag   4320
ttccgctcca ccgttggact tgctccgctg tcggcatcca gaaattgcgt ggcggagcgg   4380
cagacgtgag ccggcacggc aggcggcctc ctcctcctct cacggcaccg gcagctacgg   4440
gggattcctt tcccaccgct ccttcgcttt cccttcctcg cccgccgtaa taaatagaca   4500
ccccctccac accctctttc cccaacctcg tgttgttcgg agcgcacaca cacacaacca   4560
gatctccccc aaatccaccc gtcggcacct ccgcttcaag gtacgccgct cgtcctcccc   4620
cccccccctc tctaccttct ctagatcggc gttccggtcc atgcatggtt agggcccggt   4680
agttctactt ctgttcatgt ttgtgttaga tccgtgtttg tgttagatcc gtgctgctag   4740
cgttcgtaca cggatgcgac ctgtacgtca gacacgttct gattgctaac ttgccagtgt   4800
ttctctttgg ggaatcctgg gatggctcta gccgttccgc agacgggatc gatttcatga   4860
ttttttttgt ttcgttgcat agggtttggt ttgccctttt cctttatttc aatatatgcc   4920
gtgcacttgt ttgtcgggtc atcttttcat gctttttttt gtcttggttg tgatgatgtg   4980
gtctggttgg gcggtcgttc tagatcggag tagaattctg tttcaaacta cctggtggat   5040
ttattaattt tggatctgta tgtgtgtgcc atacatattc atagttacga attgaagatg   5100
atggatggaa atatcgatct aggataggta tacatgttga tgcgggtttt actgatgcat   5160
atacagagat gctttttgtt cgcttggttg tgatgatgtg gtgtggttgg gcggtcgttc   5220
attcgttcta gatcggagta gaatactgtt tcaaactacc tggtgtattt attaattttg   5280
gaactgtatg tgtgtgtcat acatcttcat agttacgagt ttaagatgga tggaaatatc   5340
gatctaggat aggtatacat gttgatgtgg gttttactga tgcatataca tgatggcata   5400
tgcagcatct attcatatgc tctaaccttg agtacctatc tattataata aacaagtatg   5460
ttttataatt attttgatct tgatatactt ggatgatggc atatgcagca gctatatgtg   5520
gattttttta gccctgcctt catacgctat ttatttgctt ggtactgttt cttttgtcga   5580
tgctcaccct gttgtttggt gttacttctg caggtcgact ttaacttagc ctaggatcca   5640
cacgacacca tgtcccccga gcgccgcccc gtcgagatcc gcccggccac cgccgccgac   5700
atggccgccg tgtgcgacat cgtgaaccac tacatcgaga cctccaccgt gaacttccgc   5760
accgagccgc agaccccgca ggagtggatc gacgacctgg agcgcctcca ggaccgctac   5820
ccgtggctcg tggccgaggt ggagggcgtg gtggccggca tcgcctacgc cggcccgtgg   5880
aaggcccgca acgcctacga ctggaccgtg gagtccaccg tgtacgtgtc ccaccgccac   5940
cagcgcctcg gcctcggctc caccctctac acccacctcc tcaagagcat ggaggcccag   6000
ggcttcaagt ccgtggtggc cgtgatcggc ctcccgaacg acccgtccgt gcgcctccac   6060
gaggccctcg gctacaccgc ccgcggcacc ctccgcgccg ccggctacaa gcacggcggc   6120
tggcacgacg tcggcttctg gcagcgcgac ttcgagctgc cggccccgcc gcgcccggtg   6180
cgcccggtga cgcagatctg agtcgaaacc tagacttgtc catcttctgg attggccaac   6240
ttaattaatg tatgaaataa aaggatgcac acatagtgac atgctaatca ctataatgtg   6300
ggcatcaaag ttgtgtgtta tgtgtaatta ctagttatct gaataaaaga gaaagagatc   6360
atccatattt cttatcctaa atgaatgtca cgtgtcttta taattctttg atgaaccaga   6420
tgcatttcat taaccaaatc catatacata taaatattaa tcatatataa ttaatatcaa   6480
ttgggttagc aaaacaaatc tagtctaggt gtgttttgcg aattgcggcc gccaccgcgg   6540
```

-continued tggagctcga attcattccg attaatcgtg gcctcttgct cttcaggatg aagagctatg 6600
tttaaacgtg caagcgctac tagacaattc agtacattaa aaacgtccgc aatgtgttat 6660
taagttgtct aagcgtcaat ttggtttaca ccacaatata tcctgccacc agccagccaa 6720
cagctccccg accggcagct cggcacaaaa tcaccactcg atacaggcag cccatcagtc 6780
cgggacggcg tcagcgggag agccgttgta aggcggcaga ctttgctcat gttaccgatg 6840
ctattcggaa gaacggcaac taagctgccg ggtttgaaac acggatgatc tcgcggaggg 6900
tagcatgttg attgtaacga tgacagagcg ttgctgcctg tgatcaaata tcatctccct 6960
cgcagagatc cgaattatca gccttcttat tcatttctcg cttaaccgtg acaggctgtc 7020
gatcttgaga actatgccga cataatagga aatcgctgga taaagccgct gaggaagctg 7080
agtggcgcta tttctttaga agtgaacgtt gacgatcgtc gaccgtaccc cgatgaatta 7140
attcggacgt acgttctgaa cacagctgga tacttacttg ggcgattgtc atacatgaca 7200
tcaacaatgt acccgtttgt gtaaccgtct cttggaggtt cgtatgacac tagtggttcc 7260
cctcagcttg cgactagatg ttgaggccta acattttatt agagagcagg ctagttgctt 7320
agatacatga tcttcaggcc gttatctgtc agggcaagcg aaaattggcc atttatgacg 7380
accaatgccc cgcagaagct cccatctttg ccgccataga cgccgcgccc cccttttggg 7440
gtgtagaaca tccttttgcc agatgtggaa aagaagttcg ttgtcccatt gttggcaatg 7500
acgtagtagc cggcgaaagt gcgagaccca tttgcgctat atataagcct acgatttccg 7560
ttgcgactat tgtcgtaatt ggatgaacta ttatcgtagt tgctctcaga gttgtcgtaa 7620
tttgatggac tattgtcgta attgcttatg gagttgtcgt agttgcttgg agaaatgtcg 7680
tagttggatg gggagtagtc atagggaaga cgagcttcat ccactaaaac aattggcagg 7740
tcagcaagtg cctgccccga tgccatcgca agtacgaggc ttagaaccac cttcaacaga 7800
tcgcgcatag tcttccccag ctctctaacg cttgagttaa gccgcgccgc gaagcggcgt 7860
cggcttgaac gaattgttag acattatttg ccgactacct tggtgatctc gcctttcacg 7920
tagtgaacaa attcttccaa ctgatctgcg cgcgaggcca agcgatcttc ttgtccaaga 7980
taagcctgcc tagcttcaag tatgacgggc tgatactggg ccggcaggcg ctccattgcc 8040
cagtcggcag cgacatcctt cggcgcgatt ttgccggtta ctgcgctgta ccaaatgcgg 8100
gacaacgtaa gcactacatt tcgctcatcg ccagcccagt cgggcggcga gttccatagc 8160
gttaaggttt catttagcgc ctcaaataga tcctgttcag gaaccggatc aaagagttcc 8220
tccgccgctg gacctaccaa ggcaacgcta tgttctcttg cttttgtcag caagatagcc 8280
agatcaatgt cgatcgtggc tggctcgaag atacctgcaa gaatgtcatt gcgctgccat 8340
tctccaaatt gcagttcgcg cttagctgga taacgccacg gaatgatgtc gtcgtgcaca 8400
acaatggtga cttctacagc gcggagaatc tcgctctctc caggggaagc cgaagtttcc 8460
aaaaggtcgt tgatcaaagc tcgccgcgtt gtttcatcaa gccttacagt caccgtaacc 8520
agcaaatcaa tatcactgtg tggcttcagg ccgccatcca ctgcggagcc gtacaaatgt 8580
acggccagca acgtcggttc gagatggcgc tcgatgacgc caactacctc tgatagttga 8640
gtcgatactt cggcgatcac cgcttccctc atgatgttta actcctgaat taagccgcgc 8700
cgcgaagcgg tgtcggcttg aatgaattgt taggcgtcat cctgtgctcc cgagaaccag 8760
taccagtaca tcgctgtttc gttcgagact tgaggtctag ttttatacgt gaacaggtca 8820
atgccgccga gagtaaagcc acattttgcg tacaaattgc aggcaggtac attgttcgtt 8880
tgtgtctcta atcgtatgcc aaggagctgt ctgcttagtg cccacttttt cgcaaattcg 8940

-continued atgagactgt gcgcgactcc tttgcctcgg tgcgtgtgcg acacaacaat gtgttcgata 9000
gaggctagat cgttccatgt tgagttgagt tcaatcttcc cgacaagctc ttggtcgatg 9060
aatgcgccat agcaagcaga gtcttcatca gagtcatcat ccgagatgta atccttccgg 9120
taggggctca cacttctggt agatagttca aagccttggt cggataggtg cacatcgaac 9180
acttcacgaa caatgaaatg gttctcagca tccaatgttt ccgccacctg ctcagggatc 9240
accgaaatct tcatatgacg cctaacgcct ggcacagcgg atcgcaaacc tggcgcggct 9300
tttggcacaa aaggcgtgac aggtttgcga atccgttgct gccacttgtt aacccttttg 9360
ccagatttgg taactataat ttatgttaga ggcgaagtct tgggtaaaaa ctggcctaaa 9420
attgctgggg atttcaggaa agtaaacatc accttccggc tcgatgtcta ttgtagatat 9480
atgtagtgta tctacttgat cgggggatct gctgcctcgc gcgtttcggt gatgacggtg 9540
aaaacctctg acacatgcag ctcccggaga cggtcacagc ttgtctgtaa gcggatgccg 9600
ggagcagaca agcccgtcag ggcgcgtcag cgggtgttgg cgggtgtcgg ggcgcagcca 9660
tgacccagtc acgtagcgat agcggagtgt atactggctt aactatgcgg catcagagca 9720
gattgtactg agagtgcacc atatgcggtg tgaaataccg cacagatgcg taaggagaaa 9780
ataccgcatc aggcgctctt ccgcttcctc gctcactgac tcgctgcgct cggtcgttcg 9840
gctgcggcga gcggtatcag ctcactcaaa ggcggtaata cggttatcca cagaatcagg 9900
ggataacgca ggaaagaaca tgtgagcaaa aggccagcaa aaggccagga accgtaaaaa 9960
ggccgcgttg ctggcgtttt tccataggct ccgcccccct gacgagcatc acaaaaatcg 10020
acgctcaagt cagaggtggc gaaacccgac aggactataa agataccagg cgtttccccc 10080
tggaagctcc ctcgtgcgct ctcctgttcc gaccctgccg cttaccggat acctgtccgc 10140
ctttctccct tcgggaagcg tggcgctttc tcatagctca cgctgtaggt atctcagttc 10200
ggtgtaggtc gttcgctcca agctgggctg tgtgcacgaa ccccccgttc agcccgaccg 10260
ctgcgcctta tccggtaact atcgtcttga gtccaacccg gtaagacacg acttatcgcc 10320
actggcagca gccactggta acaggattag cagagcgagg tatgtaggcg gtgctacaga 10380
gttcttgaag tggtggccta actacggcta cactagaagg acagtatttg gtatctgcgc 10440
tctgctgaag ccagttacct tcggaaaaag agttggtagc tcttgatccg gcaaacaaac 10500
caccgctggt agcggtggtt tttttgtttg caagcagcag attacgcgca gaaaaaaagg 10560
atctcaagaa gatcctttga tcttttctac ggggtctgac gctcagtgga acgaaaactc 10620
acgttaaggg attttggtca tgagattatc aaaaaggatc ttcacctaga tccttttaaa 10680
ttaaaaatga agttttaaat caatctaaag tatatatgag taaacttggt ctgacagtta 10740
ccaatgctta atcagtgagg cacctatctc agcgatctgt ctatttcgtt catccatagt 10800
tgcctgactc cccgtcgtgt agataactac gatacgggag ggcttaccat ctggccccag 10860
tgctgcaatg ataccgcgag acccacgctc accggctcca gatttatcag caataaacca 10920
gccagccgga agggccgagc gcagaagtgg tcctgcaact ttatccgcct ccatccagtc 10980
tattaattgt tgccgggaag ctagagtaag tagttcgcca gttaatagtt tgcgcaacgt 11040
tgttgccatt gctgcagggg gggggggggg gggggacttc cattgttcat tccacggaca 11100
aaaacagaga aaggaaacga cagaggccaa aaagcctcgc tttcagcacc tgtcgtttcc 11160
tttcttttca gagggtattt taaataaaaa cattaagtta tgacgaagaa gaacggaaac 11220
gccttaaacc ggaaaatttt cataaatagc gaaaacccgc gaggtcgccg ccccgtaacc 11280
tacctgtcgg atcaccggaa aggacccgta aagtgataat gattatcatc tacatatcac 11340
aacgtgcgtg gaggccatca aaccacgtca aataatcaat tatgacgcag gtatcgtatt 11400
aattgatctg catcaactta acgtaaaaac aacttcagac aatacaaatc agcgacactg 11460
aatacggggc aacctcatgt cccccccccc cccccccctg caggcatcgt ggtgtcacgc 11520
tcgtcgtttg gtatggcttc attcagctcc ggttcccaac gatcaaggcg agttacatga 11580
tcccccatgt tgtgcaaaaa agcggttagc tccttcggtc ctccgatcgt tgtcagaagt 11640
aagttggccg cagtgttatc actcatggtt atggcagcac tgcataattc tcttactgtc 11700
atgccatccg taagatgctt ttctgtgact ggtgagtact caaccaagtc attctgagaa 11760
tagtgtatgc ggcgaccgag ttgctcttgc ccggcgtcaa cacgggataa taccgcgcca 11820
catagcagaa ctttaaaagt gctcatcatt ggaaaacgtt cttcggggcg aaaactctca 11880
aggatcttac cgctgttgag atccagttcg atgtaaccca ctcgtgcacc caactgatct 11940
tcagcatctt ttactttcac cagcgtttct gggtgagcaa aaacaggaag gcaaaatgcc 12000
gcaaaaaagg gaataagggc gacacggaaa tgttgaatac tcatactctt cctttttcaa 12060
tattattgaa gcatttatca gggttattgt ctcatgagcg gatacatatt tgaatgtatt 12120
tagaaaaata aacaaatagg ggttccgcgc acatttcccc gaaaagtgcc acctgacgtc 12180
taagaaacca ttattatcat gacattaacc tataaaaata ggcgtatcac gaggcccttt 12240
cgtcttcaag aattcggagc ttttgccatt ctcaccggat tcagtcgtca ctcatggtga 12300
tttctcactt gataacctta tttttgacga ggggaaatta ataggttgta ttgatgttgg 12360
acgagtcgga atcgcagacc gataccagga tcttgccatc ctatggaact gcctcggtga 12420
gttttctcct tcattacaga aacggctttt tcaaaaatat ggtattgata atcctgatat 12480
gaataaattg cagtttcatt tgatgctcga tgagtttttc taatcagaat tggttaattg 12540
gttgtaacac tggcagagca ttacgctgac ttgacgggac ggcggctttg ttgaataaat 12600
cgaacttttg ctgagttgaa ggatcagatc acgcatcttc ccgacaacgc agaccgttcc 12660
gtggcaaagc aaaagttcaa aatcaccaac tggtccacct acaacaaagc tctcatcaac 12720
cgtggctccc tcactttctg gctggatgat ggggcgattc aggcctggta tgagtcagca 12780
acaccttctt cacgaggcag acctcagcgc cagaaggccg ccagagaggc cgagcgcggc 12840
cgtgaggctt ggacgctagg gcagggcatg aaaaagcccg tagcgggctg ctacgggcgt 12900
ctgacgcggt ggaaaggggg aggggatgtt gtctacatgg ctctgctgta gtgagtgggt 12960
tgcgctccgg cagcggtcct gatcaatcgt cacccttttct cggtccttca acgttcctga 13020
caacgagcct ccttttcgcc aatccatcga caatcaccgc gagtccctgc tcgaacgctg 13080
cgtccggacc ggcttcgtcg aaggcgtcta tcgcggcccg caacagcggc gagagcggag 13140
cctgttcaac ggtgccgccg cgctcgccgg catcgctgtc gccggcctgc tcctcaagca 13200
cggccccaac agtgaagtag ctgattgtca tcagcgcatt gacggcgtcc ccggccgaaa 13260
aacccgcctc gcagaggaag cgaagctgcg cgtcggccgt ttccatctgc ggtgcgcccg 13320
gtcgcgtgcc ggcatggatg cgcgcgccat cgcggtaggc gagcagcgcc tgcctgaagc 13380
tgcgggcatt cccgatcaga aatgagcgcc agtcgtcgtc ggctctcggc accgaatgcg 13440
tatgattctc cgccagcatg gcttcggcca gtgcgtcgag cagcgcccgc ttgttcctga 13500
agtgccagta aagcgccggc tgctgaaccc ccaaccgttc cgccagtttg cgtgtcgtca 13560
gaccgtctac gccgacctcg ttcaacaggt ccagggcggc acggatcact gtattcggct 13620
gcaactttgt catgcttgac actttatcac tgataaacat aatatgtcca ccaacttatc 13680
agtgataaag aatccgcgcg ttcaatcgga ccagcggagg ctggtccgga ggccagacgt 13740
gaaacccaac ataccccctga tcgtaattct gagcactgtc gcgctcgacg ctgtcggcat 13800
cggcctgatt atgccggtgc tgccgggcct cctgcgcgat ctggttcact cgaacgacgt 13860
caccgcccac tatggcattc tgctggcgct gtatgcgttg gtgcaatttg cctgcgcacc 13920
tgtgctgggc gcgctgtcgg atcgtttcgg gcggcggcca atcttgctcg tctcgctggc 13980
cggcgccact gtcgactacg ccatcatggc gacagcgcct ttcctttggg ttctctatat 14040
cgggcggatc gtggccggca tcaccggggc gactggggcg gtagccggcg cttatattgc 14100
cgatatcact gatggcgatg agcgcgcgcg gcacttcggc ttcatgagcg cctgtttcgg 14160
gttcgggatg gtcgcgggac ctgtgctcgg tgggctgatg ggcggtttct ccccccacgc 14220
tccgttcttc gccgcggcag ccttgaacgg cctcaatttc ctgacgggct gtttcctttt 14280
gccggagtcg cacaaaggcg aacgccggcc gttacgccgg gaggctctca acccgctcgc 14340
ttcgttccgg tgggcccggg gcatgaccgt cgtcgccgcc ctgatggcgg tcttcttcat 14400
catgcaactt gtcggacagg tgccggccgc gctttgggtc attttcggcg aggatcgctt 14460
tcactgggac gcgaccacga tcggcatttc gcttgccgca tttggcattc tgcattcact 14520
cgcccaggca atgatcaccg gccctgtagc cgccccggctc ggcgaaaggc gggcactcat 14580
gctcggaatg attgccgacg gcacaggcta catcctgctt gccttcgcga cacggggatg 14640
gatggcgttc ccgatcatgg tcctgcttgc ttcgggtggc atcggaatgc cggcgctgca 14700
agcaatgttg tccaggcagg tggatgagga acgtcagggg cagctgcaag gctcactggc 14760
ggcgctcacc agcctgacct cgatcgtcgg acccctcctc ttcacggcga tctatgcggc 14820
ttctataaca acgtggaacg ggtgggcatg gattgcaggc gctgccctct acttgctctg 14880
cctgccggcg ctgcgtcgcg ggctttggag cggcgcaggg caacgagccg atcgctgatc 14940
gtggaaacga taggcctatg ccatgcgggt caaggcgact tccggcaagc tatacgcgcc 15000
ctaggagtgc ggttggaacg ttggcccagc cagatactcc cgatcacgag caggacgccg 15060
atgatttgaa gcgcactcag cgtctgatcc aagaacaacc atcctagcaa cacggcggtc 15120
cccgggctga gaaagcccag taaggaaaca actgtaggtt cgagtcgcga gatcccccgg 15180
aaccaaagga agtaggttaa acccgctccg atcaggccga gccacgccag gccgagaaca 15240
ttggttcctg taggcatcgg gattggcgga tcaaacacta aagctactgg aacgagcaga 15300
agtcctccgg ccgccagttg ccaggcggta aaggtgagca gaggcacggg aggttgccac 15360
ttgcgggtca gcacggttcc gaacgccatg gaaaccgccc ccgccaggcc cgctgcgacg 15420
ccgacaggat ctagcgctgc gtttggtgtc aacaccaaca gcgccacgcc cgcagttccg 15480
caaatagccc ccaggaccgc catcaatcgt atcgggctac ctagcagagc ggcagagatg 15540
aacacgacca tcagcggctg cacagcgcct accgtcgccg cgaccccgcc cggcaggcgg 15600
tagaccgaaa taaacaacaa gctccagaat agcgaaatat taagtgcgcc gaggatgaag 15660
atgcgcatcc accagattcc cgttggaatc tgtcggacga tcatcacgag caataaaccc 15720
gccggcaacg cccgcagcag cataccggcg acccctcggc ctcgctgttc gggctccacg 15780
aaaacgccgg acagatgcgc cttgtgagcg tccttggggc cgtcctcctg tttgaagacc 15840
gacagcccaa tgatctcgcc gtcgatgtag gcgccgaatg ccacggcatc tcgcaaccgt 15900
tcagcgaacg cctccatggg ctttttctcc tcgtgctcgt aaacggaccc gaacatctct 15960
ggagctttct tcagggccga caatcggatc tcgcggaaat cctgcacgtc ggccgctcca 16020
agccgtcgaa tctgagcctt aatcacaatt gtcaatttta atcctctgtt tatcggcagt 16080
tcgtagagcg cgccgtgcgt cccgagcgat actgagcgaa gcaagtgcgt cgagcagtgc 16140

-continued

```
ccgcttgttc ctgaaatgcc agtaaagcgc tggctgctga acccccagcc ggaactgacc  16200
ccacaaggcc ctagcgtttg caatgcacca ggtcatcatt gacccaggcg tgttccacca  16260
ggccgctgcc tcgcaactct tcgcaggctt cgccgacctg ctcgcgccac ttcttcacgc  16320
gggtggaatc cgatccgcac atgaggcgga aggtttccag cttgagcggg tacggctccc  16380
ggtgcgagct gaaatagtcg aacatccgtc gggccgtcgg cgacagcttg cggtacttct  16440
cccatatgaa tttcgtgtag tggtcgccag caaacagcac gacgatttcc tcgtcgatca  16500
ggacctggca acgggacgtt ttcttgccac ggtccaggac gcggaagcgg tgcagcagcg  16560
acaccgattc caggtgccca acgcggtcgg acgtgaagcc catcgccgtc gcctgtaggc  16620
gcgacaggca ttcctcggcc ttcgtgtaat accggccatt gatcgaccag cccaggtcct  16680
ggcaaagctc gtagaacgtg aaggtgatcg gctcgccgat aggggtgcgc ttcgcgtact  16740
ccaacacctg ctgccacacc agttcgtcat cgtcggcccg cagctcgacg ccggtgtagg  16800
tgatcttcac gtccttgttg acgtggaaaa tgaccttgtt ttgcagcgcc tcgcgcggga  16860
ttttcttgtt gcgcgtggtg aacagggcag agcgggccgt gtcgtttggc atcgctcgca  16920
tcgtgtccgg ccacggcgca atatcgaaca aggaaagctg catttccttg atctgctgct  16980
tcgtgtgttt cagcaacgcg gcctgcttgg cctcgctgac ctgttttgcc aggtcctcgc  17040
cggcggtttt tcgcttcttg gtcgtcatag ttcctcgcgt gtcgatggtc atcgacttcg  17100
ccaaacctgc cgcctcctgt tcgagacgac gcgaacgctc cacggcggcc gatggcgcgg  17160
gcagggcagg gggagccagt tgcacgctgt cgcgctcgat cttggccgta gcttgctgga  17220
ccatcgagcc gacggactgg aaggtttcgc ggggcgcacg catgacggtg cggcttgcga  17280
tggtttcggc atcctcggcg gaaaaccccg cgtcgatcag ttcttgcctg tatgccttcc  17340
ggtcaaacgt ccgattcatt caccctcctt gcgggattgc cccgactcac gccggggcaa  17400
tgtgccctta ttcctgattt gacccgcctg gtgccttggt gtccagataa tccaccttat  17460
cggcaatgaa gtcggtcccg tagaccgtct ggccgtcctt ctcgtacttg gtattccgaa  17520
tcttgccctg cacgaatacc agcgacccct tgcccaaata cttgccgtgg gcctcggcct  17580
gagagccaaa acacttgatg cggaagaagt cggtgcgctc ctgcttgtcg ccggcatcgt  17640
tgcgccactc ttcattaacc gctatatcga aaattgcttg cggcttgtta gaattgccat  17700
gacgtacctc ggtgtcacgg gtaagattac cgataaactg gaactgatta tggctcatat  17760
cgaaagtctc cttgagaaag gagactctag tttagctaaa cattggttcc gctgtcaaga  17820
actttagcgg ctaaaatttt gcgggccgcg accaaaggtg cgaggggcgg cttccgctgt  17880
gtacaaccag atatttttca ccaacatcct tcgtctgctc gatgagcggg gcatgacgaa  17940
acatgagctg tcggagaggg caggggtttc aatttcgttt ttatcagact taaccaacgg  18000
taaggccaac ccctcgttga aggtgatgga ggccattgcc gacgccctgg aaactcccct  18060
acctcttctc ctggagtcca ccgaccttga ccgcgaggca ctcgcggaga ttgcgggtca  18120
tcctttcaag agcagcgtgc cgcccggata cgaacgcatc agtgtggttt tgccgtcaca  18180
taaggcgttt atcgtaaaga aatggggcga cgacacccga aaaaagctgc gtggaaggct  18240
ctgacgccaa gggttagggc ttgcacttcc ttctttagcc gctaaaacgg ccccttctct  18300
gcgggccgtc ggctcgcgca tcatatcgac atcctcaacg gaagccgtgc cgcgaatggc  18360
atcgggcggg tgcgctttga cagttgtttt ctatcagaac ccctacgtcg tgcggttcga  18420
ttagctgttt gtcttgcagg ctaaacactt tcggtatatc gtttgcctgt gcgataatgt  18480
tgctaatgat ttgttgcgta ggggttactg aaaagtgagc gggaaagaag agtttcagac  18540
```

catcaaggag cgggccaagc gcaagctgga acgcgacatg ggtgcggacc tgttggccgc 18600
gctcaacgac ccgaaaaccg ttgaagtcat gctcaacgcg gacggcaagg tgtggcacga 18660
acgccttggc gagccgatgc ggtacatctg cgacatgcgg cccagccagt cgcaggcgat 18720
tatagaaacg gtggccggat tccacggcaa agaggtcacg cggcattcgc ccatcctgga 18780
aggcgagttc cccttggatg gcagccgctt tgccggccaa ttgccgccgg tcgtggccgc 18840
gccaaccttt gcgatccgca agcgcgcggt cgccatcttc acgctggaac agtacgtcga 18900
ggcgggcatc atgacccgcg agcaatacga ggtcattaaa agcgccgtcg cggcgcatcg 18960
aaacatcctc gtcattggcg gtactggctc gggcaagacc acgctcgtca acgcgatcat 19020
caatgaaatg gtcgccttca acccgtctga gcgcgtcgtc atcatcgagg acaccggcga 19080
aatccagtgc gccgcagaga acgccgtcca ataccacacc agcatcgacg tctcgatgac 19140
gctgctgctc aagacaacgc tgcgtatgcg ccccgaccgc atcctggtcg gtgaggtacg 19200
tggccccgaa gcccttgatc tgttgatggc ctggaacacc gggcatgaag gaggtgccgc 19260
caccctgcac gcaaacaacc ccaaagcggg cctgagccgg ctcgccatgc ttatcagcat 19320
gcacccggat tcaccgaaac ccattgagcc gctgattggc gaggcggttc atgtggtcgt 19380
ccatatcgcc aggaccccta gcggccgtcg agtgcaagaa attctcgaag ttcttggtta 19440
cgagaacggc cagtacatca ccaaaaccct gtaaggagta tttccaatga caacggctgt 19500
tccgttccgt ctgaccatga atcgcggcat tttgttctac cttgccgtgt tcttcgttct 19560
cgctctcgcg ttatccgcgc atccggcgat ggcctcggaa ggcaccggcg gcagcttgcc 19620
atatgagagc tggctgacga acctgcgcaa ctccgtaacc ggcccggtgg ccttcgcgct 19680
gtccatcatc ggcatcgtcg tcgccggcgg cgtgctgatc ttcggcggcg aactcaacgc 19740
cttcttccga accctgatct tcctggttct ggtgatggcg ctgctggtcg gcgcgcagaa 19800
cgtgatgagc accttcttcg gtcgtggtgc cgaaatcgcg gccctcggca acggggcgct 19860
gcaccaggtg caagtcgcgg cggcggatgc cgtgcgtgcg gtagcggctg gacggctcgc 19920
ctaatcatgg ctctgcgcac gatccccatc cgtcgcgcag gcaaccgaga aaacctgttc 19980
atgggtggtg atcgtgaact ggtgatgttc tcgggcctga tggcgtttgc gctgattttc 20040
agcgcccaag agctgcgggc caccgtggtc ggtctgatcc tgtggttcgg ggcgctctat 20100
gcgttccgaa tcatggcgaa ggccgatccg aagatgcggt tcgtgtacct gcgtcaccgc 20160
cggtacaagc cgtattaccc ggcccgctcg accccgttcc gcgagaacac caatagccaa 20220
gggaagcaat accgatgatc caagcaattg cgattgcaat cgcgggcctc ggcgcgcttc 20280
tgttgttcat cctctttgcc cgcatccgcg cggtcgatgc cgaactgaaa ctgaaaaagc 20340
atcgttccaa ggacgccggc ctggccgatc tgctcaacta cgccgctgtc gtcgatgacg 20400
gcgtaatcgt gggcaagaac ggcagcttta tggctgcctg gctgtacaag ggcgatgaca 20460
acgcaagcag caccgaccag cagcgcgaag tagtgtccgc ccgcatcaac caggccctcg 20520
cgggcctggg aagtgggtgg atgatccatg tggacgccgt gcggcgtcct gctccgaact 20580
acgcggagcg gggcctgtcg gcgttccctg accgtctgac ggcagcgatt gaagaagagc 20640
gctcggtctt gccttgctcg tcggtgatgt acttcaccag ctccgcgaag tcgctcttct 20700
tgatggagcg catggggacg tgcttggcaa tcacgcgcac cccccggccg ttttagcggc 20760
taaaaaagtc atggctctgc cctcgggcgg accacgccca tcatgacctt gccaagctcg 20820
tcctgcttct cttcgatctt cgccagcagg gcgaggatcg tggcatcacc gaaccgcgcc 20880
gtgcgcgggt cgtcggtgag ccagagtttc agcaggccgc ccaggcggcc caggtcgcca 20940
ttgatgcggg ccagctcgcg gacgtgctca tagtccacga cgcccgtgat tttgtagccc 21000
tggccgacgg ccagcaggta ggccgacagg ctcatgccgg ccgccgccgc cttttcctca 21060
atcgctcttc gttcgtctgg aaggcagtac accttgatag gtgggctgcc cttcctggtt 21120
ggcttggttt catcagccat ccgcttgccc tcatctgtta cgccggcggt agccggccag 21180
cctcgcagag caggattccc gttgagcacc gccaggtgcg aataagggac agtgaagaag 21240
gaacacccgc tcgcgggtgg gcctacttca cctatcctgc ccggctgacg ccgttggata 21300
caccaaggaa agtctacacg aaccctttgg caaaatcctg tatatcgtgc gaaaaaggat 21360
ggatataccg aaaaaatcgc tataatgacc ccgaagcagg gttatgcagc ggaaaagcgc 21420
tgcttccctg ctgttttgtg gaatatctac cgactggaaa caggcaaatg caggaaatta 21480
ctgaactgag gggacaggcg agagacgatg ccaaagagct acaccgacga gctggccgag 21540
tgggttgaat cccgcgcggc caagaagcgc cggcgtgatg aggctgcggt tgcgttcctg 21600
gcggtgaggg cggatgtcga ggcggcgtta gcgtccggct atgcgctcgt caccatttgg 21660
gagcacatgc gggaaacggg gaaggtcaag ttctcctacg agacgttccg ctcgcacgcc 21720
aggcggcaca tcaaggccaa gcccgccgat gtgcccgcac cgcaggccaa ggctgcggaa 21780
cccgcgccgg cacccaagac gccggagcca cggcggccga agcagggggg caaggctgaa 21840
aagccggccc ccgctgcggc cccgaccggc ttcaccttca acccaacacc ggacaaaaag 21900
gatctactgt aatggcgaaa attcacatgg ttttgcaggg caagggcggg gtcggcaagt 21960
cggccatcgc cgcgatcatt gcgcagtaca agatggacaa ggggcagaca cccttgtgca 22020
tcgacaccga cccggtgaac gcgacgttcg agggctacaa ggccctgaac gtccgccggc 22080
tgaacatcat ggccggcgac gaaattaact cgcgcaactt cgacaccctg gtcgagctga 22140
ttgcgccgac caaggatgac gtggtgatcg acaacggtgc cagctcgttc gtgcctctgt 22200
cgcattacct catcagcaac caggtgccgg ctctgctgca agaaatgggg catgagctgg 22260
tcatccatac cgtcgtcacc ggcggccagg ctctcctgga cacggtgagc ggcttcgccc 22320
agctcgccag ccagttcccg gccgaagcgc ttttcgtggt ctggctgaac ccgtattggg 22380
ggcctatcga gcatgagggc aagagctttg agcagatgaa ggcgtacacg gccaacaagg 22440
cccgcgtgtc gtccatcatc cagattccgg ccctcaagga agaaacctac ggccgcgatt 22500
tcagcgacat gctgcaagag cggctgacgt tcgaccaggc gctggccgat gaatcgctca 22560
cgatcatgac gcggcaacgc ctcaagatcg tgcggcgcgg cctgtttgaa cagctcgacg 22620
cggcggccgt gctatgagcg accagattga agagctgatc cgggagattg cggccaagca 22680
cggcatcgcc gtcggccgcg acgacccggt gctgatcctg cataccatca acgcccggct 22740
catggccgac agtgcggcca agcaagagga aatccttgcc gcgttcaagg aagagctgga 22800
agggatcgcc catcgttggg gcgaggacgc caaggccaaa gcggagcgga tgctgaacgc 22860
ggccctggcg gccagcaagg acgcaatggc gaaggtaatg aaggacagcg ccgcgcaggc 22920
ggccgaagcg atccgcaggg aaatcgacga cggccttggc cgccagctcg cggccaaggt 22980
cgcggacgcg cggcgcgtgg cgatgatgaa catgatcgcc ggcggcatgg tgttgttcgc 23040
ggccgccctg gtggtgtggg cctcgttatg aatcgcagag gcgcagatga aaaagcccgg 23100
cgttgccggg ctttgttttt gcgttagctg ggcttgtttg acaggcccaa gctctgactg 23160
cgcccgcgct cgcgctcctg ggcctgtttc ttctcctgct cctgcttgcg catcagggcc 23220
tggtgccgtc gggctgcttc acgcatcgaa tcccagtcgc cggccagctc gggatgctcc 23280
gcgcgcatct tgcgcgtcgc cagttcctcg atcttgggcg cgtgaatgcc catgccttcc 23340

-continued

```
ttgatttcgc gcaccatgtc cagccgcgtg tgcagggtct gcaagcgggc ttgctgttgg  23400
gcctgctgct gctgccaggc ggcctttgta cgcggcaggg acagcaagcc gggggcattg  23460
gactgtagct gctgcaaacg cgcctgctga cggtctacga gctgttctag gcggtcctcg  23520
atgcgctcca cctggtcatg ctttgcctgc acgtagagcg caagggtctg ctggtaggtc  23580
tgctcgatgg gcgcggattc taagagggcc tgctgttccg tctcggcctc ctgggccgcc  23640
tgtagcaaat cctcgccgct gttgccgctg gactgcttta ctgccgggga ctgctgttgc  23700
cctgctcgcg ccgtcgtcgc agttcggctt gcccccactc gattgactgc ttcatttcga  23760
gccgcagcga tgcgatctcg gattgcgtca acggacgggg cagcgcggag gtgtccggct  23820
tctccttggg tgagtcggtc gatgccatag ccaaaggttt ccttccaaaa tgcgtccatt  23880
gctggaccgt gtttctcatt gatgcccgca agcatcttcg gcttgaccgc caggtcaagc  23940
gcgccttcat gggcggtcat gacggacgcc gccatgacct tgccgccgtt gttctcgatg  24000
tagccgcgta atgaggcaat ggtgccgccc atcgtcagcg tgtcatcgac aacgatgtac  24060
ttctggccgg ggatcacctc cccctcgaaa gtcgggttga acgccaggcg atgatctgaa  24120
ccggctccgg ttcgggcgac cttctcccgc tgcacaatgt ccgtttcgac ctcaaggcca  24180
aggcggtcgg ccagaacgac cgccatcatg gccggaatct tgttgttccc cgccgcctcg  24240
acggcgagga ctggaacgat gcggggcttg tcgtcgccga tcagcgtctt gagctgggca  24300
acagtgtcgt ccgaaatcag gcgctcgacc aaattaagcg ccgcttccgc gtcgccctgc  24360
ttcgcagcct ggtattcagg ctcgttggtc aaagaaccaa ggtcgccgtt gcgaaccacc  24420
ttcgggaagt ctccccacgg tgcgcgctcg gctctgctgt agctgctcaa gacgcctccc  24480
tttttagccg ctaaaactct aacgagtgcg cccgcgactc aacttgacgc tttcggcact  24540
tacctgtgcc ttgccacttg cgtcataggt gatgcttttc gcactcccga tttcaggtac  24600
tttatcgaaa tctgaccggg cgtgcattac aaagttcttc cccacctgtt ggtaaatgct  24660
gccgctatct gcgtggacga tgctgccgtc gtggcgctgc gacttatcgg ccttttgggc  24720
catatagatg ttgtaaatgc caggtttcag ggccccggct ttatctacct tctggttcgt  24780
ccatgcgcct tggttctcgg tctggacaat tctttgccca ttcatgacca ggaggcggtg  24840
tttcattggg tgactcctga cggttgcctc tggtgttaaa cgtgtcctgg tcgcttgccg  24900
gctaaaaaaa agccgacctc ggcagttcga ggccggcttt ccctagagcc gggcgcgtca  24960
aggttgttcc atctatttta gtgaactgcg ttcgatttat cagttacttt cctcccgctt  25020
tgtgtttcct cccactcgtt tccgcgtcta gccgacccct caacatagcg gcctcttctt  25080
gggctgcctt tgcctcttgc cgcgcttcgt cacgctcggc ttgcaccgtc gtaaagcgct  25140
cggcctgcct ggccgcctct tgcgccgcca acttcctttg ctcctggtgg gcctcggcgt  25200
cggcctgcgc cttcgctttc accgctgcca actccgtgcg caaactctcc gcttcgcgcc  25260
tggtggcgtc gcgctcgccg cgaagcgcct gcatttcctg gttggccgcg tccagggtct  25320
tgcggctctc ttctttgaat gcgcgggcgt cctggtgagc gtagtccagc tcggcgcgca  25380
gctcctgcgc tcgacgctcc acctcgtcgg cccgctgcgt cgccagcgcg gcccgctgct  25440
cggctcctgc cagggcggtg cgtgcttcgg ccagggcttg ccgctggcgt gcggccagct  25500
cggccgcctc ggcggcctgc tgctctagca atgtaacgcg cgcctgggct tcttccagct  25560
cgcgggcctg cgcctcgaag gcgtcggcca gctccccgcg cacggcttcc aactcgttgc  25620
gctcacgatc ccagccggct tgcgctgcct gcaacgattc attggcaagg gcctgggcgg  25680
cttgccagag ggcggccacg gcctggttgc cggcctgctg caccgcgtcc ggcacctgga  25740
```

```
ctgccagcgg ggcggcctgc gccgtgcgct ggcgtcgcca ttcgcgcatg ccggcgctgg  25800
cgtcgttcat gttgacgcgg gcggccttac gcactgcatc cacggtcggg aagttctccc  25860
ggtcgccttg ctcgaacagc tcgtccgcag ccgcaaaaat gcggtcgcgc gtctctttgt  25920
tcagttccat gttggctccg gtaattggta agaataataa tactcttacc taccttatca  25980
gcgcaagagt ttagctgaac agttctcgac ttaacggcag gttttttagc ggctgaaggg  26040
caggcaaaaa aagccccgca cggtcggcgg gggcaaaggg tcagcgggaa ggggattagc  26100
gggcgtcggg cttcttcatg cgtcggggcc gcgcttcttg ggatggagca cgacgaagcg  26160
cgcacgcgca tcgtcctcgg ccctatcggc ccgcgtcgcg gtcaggaact tgtcgcgcgc  26220
taggtcctcc ctggtgggca ccaggggcat gaactcggcc tgctcgatgt aggtccactc  26280
catgaccgca tcgcagtcga ggccgcgttc cttcaccgtc tcttgcaggt cgcggtacgc  26340
ccgctcgttg agcggctggt aacgggccaa ttggtcgtaa atggctgtcg gccatgagcg  26400
gcctttcctg ttgagccagc agccgacgac gaagccggca atgcaggccc ctggcacaac  26460
caggccgacg ccgggggcag gggatggcag cagctcgcca accaggaacc ccgccgcgat  26520
gatgccgatg ccggtcaacc agcccttgaa actatccggc cccgaaacac ccctgcgcat  26580
tgcctggatg ctgcgccgga tagcttgcaa catcaggagc cgtttctttt gttcgtcagt  26640
catggtccgc cctcaccagt tgttcgtatc ggtgtcggac gaactgaaat cgcaagagct  26700
gccggtatcg gtccagccgc tgtccgtgtc gctgctgccg aagcacggcg aggggtccgc  26760
gaacgccgca gacggcgtat ccggccgcag cgcatcgccc agcatggccc cggtcagcga  26820
gccgccggcc aggtagccca gcatggtgct gttggtcgcc ccggccacca gggccgacgt  26880
gacgaaatcg ccgtcattcc ctctggattg ttcgctgctc ggcggggcag tgcgccgcgc  26940
cggcggcgtc gtggatggct cgggttggct ggcctgcgac ggccggcgaa aggtgcgcag  27000
cagctcgtta tcgaccggct gcggcgtcgg ggccgccgcc ttgcgctgcg gtcggtgttc  27060
cttcttcggc tcgcgcagct tgaacagcat gatcgcggaa accagcagca acgccgcgcc  27120
tacgcctccc gcgatgtaga acagcatcgg attcattctt cggtcctcct tgtagcggaa  27180
ccgttgtctg tgcggcgcgg gtggcccgcg ccgctgtctt tggggatcag ccctcgatga  27240
gcgcgaccag tttcacgtcg gcaaggttcg cctcgaactc ctggccgtcg tcctcgtact  27300
tcaaccaggc atagccttcc gccggcggcc gacggttgag gataaggcgg gcagggcgct  27360
cgtcgtgctc gacctggacg atggcctttt tcagcttgtc cgggtccggc tccttcgcgc  27420
ccttttcctt ggcgtcctta ccgtcctggt cgccgtcctc gccgtcctgg ccgtcgccgg  27480
cctccgcgtc acgctcggca tcagtctggc cgttgaaggc atcgacggtg ttgggatcgc  27540
ggcccttctc gtccaggaac tcgcgcagca gcttgaccgt gccgcgcgtg atttcctggg  27600
tgtcgtcgtc aagccacgcc tcgacttcct ccgggcgctt cttgaaggcc gtcaccagct  27660
cgttcaccac ggtcacgtcg cgcacgcggc cggtgttgaa cgcatcggcg atcttctccg  27720
gcaggtccag cagcgtgacg tgctgggtga tgaacgccgg cgacttgccg atttccttgg  27780
cgatatcgcc tttcttcttg cccttcgcca gctcgcggcc aatgaagtcg gcaatttcgc  27840
gcggggtcag ctcgttgcgt tgcaggttct cgataacctg gtcggcttcg ttgtagtcgt  27900
tgtcgatgaa cgccgggatg gacttcttgc cggcccactt cgagccacgg tagcggcggg  27960
cgccgtgatt gatgatatag cggcccggct gctcctggtt ctcgcgcacc gaaatgggtg  28020
acttcacccc gcgctctttg atcgtggcac cgatttccgc gatgctctcc ggggaaaagc  28080
cggggttgtc ggccgtccgc ggctgatgcg gatcttcgtc gatcaggtcc aggtccagct  28140
```

-continued

```
cgatagggcc ggaaccgccc tgagacgccg caggagcgtc caggaggctc gacaggtcgc  28200
cgatgctatc caaccccagg ccggacggct gcgccgcgcc tgcggcttcc tgagcggccg  28260
cagcggtgtt tttcttggtg gtcttggctt gagccgcagt cattgggaaa tctccatctt  28320
cgtgaacacg taatcagcca gggcgcgaac ctctttcgat gccttgcgcg cggccgtttt  28380
cttgatcttc cagaccggca caccggatgc gagggcatcg gcgatgctgc tgcgcaggcc  28440
aacggtggcc ggaatcatca tcttggggta cgcggccagc agctcggctt ggtggcgcgc  28500
gtggcgcgga ttccgcgcat cgaccttgct gggcaccatg ccaaggaatt gcagcttggc  28560
gttcttctgg cgcacgttcg caatggtcgt gaccatcttc ttgatgccct ggatgctgta  28620
cgcctcaagc tcgatggggg acagcacata gtcggccgcg aagagggcgg ccgccaggcc  28680
gacgccaagg gtcggggccg tgtcgatcag gcacacgtcg aagccttggt tcgccagggc  28740
cttgatgttc gccccgaaca gctcgcgggc gtcgtccagc gacagccgtt cggcgttcgc  28800
cagtaccggg ttggactcga tgagggcgag gcgcgcggcc tggccgtcgc cggctgcggg  28860
tgcggtttcg gtccagccgc cggcagggac agcgccgaac agcttgcttg catgcaggcc  28920
ggtagcaaag tccttgagcg tgtaggacgc attgccctgg gggtccaggt cgatcacggc  28980
aacccgcaag ccgcgctcga aaaagtcgaa ggcaagatgc acaagggtcg aagtcttgcc  29040
gacgccgcct ttctggttgg ccgtgaccaa agttttcatc gtttggtttc ctgtttttc  29100
ttggcgtccg cttcccactt ccggacgatg tacgcctgat gttccggcag aaccgccgtt  29160
acccgcgcgt acccctcggg caagttcttg tcctcgaacg cggcccacac gcgatgcacc  29220
gcttgcgaca ctgcgcccct ggtcagtccc agcgacgttg cgaacgtcgc ctgtggcttc  29280
ccatcgacta agacgccccg cgctatctcg atggtctgct gccccacttc cagcccctgg  29340
atcgcctcct ggaactggct ttcggtaagc cgtttcttca tggataacac ccataatttg  29400
ctccgcgcct tggttgaaca tagcggtgac agccgccagc acatgagaga agtttagcta  29460
aacatttctc gcacgtcaac acctttagcc gctaaaactc gtccttggcg taacaaaaca  29520
aaagcccgga aaccgggctt tcgtctcttg ccgcttatgg ctctgcaccc ggctccatca  29580
ccaacaggtc gcgcacgcgc ttcactcggt tgcggatcga cactgccagc ccaacaaagc  29640
cggttgccgc cgccgccagg atcgcgccga tgatgccggc cacaccggcc atcgcccacc  29700
aggtcgccgc cttccggttc cattcctgct ggtactgctt cgcaatgctg gacctcggct  29760
caccataggc tgaccgctcg atggcgtatg ccgcttctcc ccttggcgta aaacccagcg  29820
ccgcaggcgg cattgccatg ctgcccgccg ctttcccgac cacgacgcgc gcaccaggct  29880
tgcggtccag accttcggcc acggcgagct gcgcaaggac ataatcagcc gccgacttgg  29940
ctccacgcgc ctcgatcagc tcttgcactc gcgcgaaatc cttggcctcc acggccgcca  30000
tgaatcgcgc acgcggcgaa ggctccgcag ggccggcgtc gtgatcgccg ccgagaatgc  30060
ccttcaccaa gttcgacgac acgaaaatca tgctgacggc tatcaccatc atgcagacgg  30120
atcgcacgaa cccgctgaat tgaacacgag cacggcaccc gcgaccacta tgccaagaat  30180
gcccaaggta aaaattgccg gccccgccat gaagtccgtg aatgccccga cggccgaagt  30240
gaagggcagg ccgccaccca ggccgccgcc ctcactgccc ggcacctggt cgctgaatgt  30300
cgatgccagc acctgcggca cgtcaatgct tccgggcgtc gcgctcgggc tgatcgccca  30360
tcccgttact gccccgatcc cggcaatggc aaggactgcc agcgctgcca tttttggggt  30420
gaggccgttc gcggccgagg ggcgcagccc ctggggggat gggaggcccg cgttagcggg  30480
ccgggagggt tcgagaaggg ggggcacccc ccttcggcgt gcgcggtcac gcgcacaggg  30540
```

-continued

```
cgcagccctg gttaaaaaca aggtttataa atattggttt aaaagcaggt taaaagacag  30600
gttagcggtg gccgaaaaac gggcggaaac ccttgcaaat gctggatttt ctgcctgtgg  30660
acagcccctc aaatgtcaat aggtgcgccc ctcatctgtc agcactctgc ccctcaagtg  30720
tcaaggatcg cgcccctcat ctgtcagtag tcgcgcccct caagtgtcaa taccgcaggg  30780
cacttatccc caggcttgtc cacatcatct gtgggaaact cgcgtaaaat caggcgtttt  30840
cgccgatttg cgaggctggc cagctccacg tcgccggccg aaatcgagcc tgcccctcat  30900
ctgtcaacgc cgcgccgggt gagtcggccc ctcaagtgtc aacgtccgcc cctcatctgt  30960
cagtgagggc caagttttcc gcgaggtatc cacaacgccg gcggccgcgg tgtctcgcac  31020
acggcttcga cggcgtttct ggcgcgtttg cagggccata gacggccgcc agcccagcgg  31080
cgagggcaac cagcccggtg agcgtcggaa aggcgctgga agccccgtag cgacgcggag  31140
aggggcgaga caagccaagg gcgcaggctc gatgcgcagc acgacatagc cggttctcgc  31200
aaggacgaga atttccctgc ggtgcccctc aagtgtcaat gaaagtttcc aacgcgagcc  31260
attcgcgaga gccttgagtc cacgctagat gagagctttg ttgtaggtgg accagttggt  31320
gattttgaac ttttgctttg ccacggaacg gtctgcgttg tcgggaagat gcgtgatctg  31380
atccttcaac tcagcaaaag ttcgatttat tcaacaaagc cacgttgtgt ctcaaaatct  31440
ctgatgttac attgcacaag ataaaaatat atcatcatga acaataaaac tgtctgctta  31500
cataaacagt aatacaaggg gtgttatgag ccatattcaa cgggaaacgt cttgctcgac  31560
tctagagctc gttcctcgag gaacggtacc tgcggggaag cttacaataa tgtgtgttgt  31620
taagtcttgt tgcctgtcat cgtctgactg actttcgtca taaatcccgg cctccgtaac  31680
ccagctttgg gcaagctcac ggatttgatc cggcggaacg ggaatatcga gatgccgggc  31740
tgaacgctgc agttccagct ttccctttcg ggacaggtac tccagctgat tgattatctg  31800
ctgaagggtc ttggttccac ctcctggcac aatgcgaatg attacttgag cgcgatcggg  31860
catccaattt tctcccgtca ggtgcgtggt caagtgctac aaggcacctt tcagtaacga  31920
gcgaccgtcg atccgtcgcc gggatacgga caaaatggag cgcagtagtc catcgagggc  31980
ggcgaaagcc tcgccaaaag caatacgttc atctcgcaca gcctccagat ccgatcgagg  32040
gtcttcggcg taggcagata gaagcatgga tacattgctt gagagtattc cgatggactg  32100
aagtatggct tccatctttt ctcgtgtgtc tgcatctatt tcgagaaagc cccgatgcg  32160
gcgcaccgca acgcgaattg ccatactatc cgaaagtccc agcaggcgcg cttgatagga  32220
aaaggtttca tactcggccg atcgcagacg ggcactcacg accttgaacc cttcaacttt  32280
cagggatcga tgctggttga tggtagtctc actcgacgtg gctctggtgt gttttgacat  32340
agcttcctcc aaagaaagcg gaaggtctgg atactccagc acgaaatgtg cccgggtaga  32400
cggatggaag tctagccctg ctcaatatga aatcaacagt acatttacag tcaatactga  32460
atatacttgc tacatttgca attgtcttat aacgaatgtg aaataaaaat agtgtaacaa  32520
cgcttttact catcgataat cacaaaaaca tttatacgaa caaaaataca aatgcactcc  32580
ggtttcacag gataggcggg atcagaatat gcaacttttg acgttttgtt ctttcaaagg  32640
gggtgctggc aaaaccaccg cactcatggg cctttgcgct gctttggcaa atgacggtaa  32700
acgagtggcc ctctttgatg ccgacgaaaa ccggcctctg acgcgatgga gagaaaacgc  32760
cttacaaagc agtactggga tcctcgctgt gaagtctatt ccgccgacga aatgcccctt  32820
cttgaagcag cctatgaaaa tgccgagctc gaaggatttg attatgcgtt ggccgatacg  32880
cgtggcggct cgagcgagct caacaacaca atcatcgcta gctcaaacct gcttctgatc  32940
```

-continued cccaccatgc taacgccgct cgacatcgat gaggcactat ctacctaccg ctacgtcatc 33000
gagctgctgt tgagtgaaaa tttggcaatt cctacagctg ttttgcgcca acgcgtcccg 33060
gtcggccgat tgacaacatc gcaacgcagg atgtcagaga cgctagagag ccttccagtt 33120
gtaccgtctc ccatgcatga aagagatgca tttgccgcga tgaaagaacg cggcatgttg 33180
catcttacat tactaaacac gggaactgat ccgacgatgc gcctcataga gaggaatctt 33240
cggattgcga tggaggaagt cgtggtcatt tcgaaactga tcagcaaaat cttggaggct 33300
tgaagatggc aattcgcaag cccgcattgt cggtcggcga agcacggcgg cttgctggtg 33360
ctcgacccga gatccaccat cccaacccga cacttgttcc ccagaagctg gacctccagc 33420
acttgcctga aaaagccgac gagaaagacc agcaacgtga gcctctcgtc gccgatcaca 33480
tttacagtcc cgatcgacaa cttaagctaa ctgtggatgc ccttagtcca cctccgtccc 33540
cgaaaaagct ccaggttttt ctttcagcgc gaccgcccgc gcctcaagtg tcgaaaacat 33600
atgacaacct cgttcggcaa tacagtccct cgaagtcgct acaaatgatt ttaaggcgcg 33660
cgttggacga tttcgaaagc atgctggcag atggatcatt tcgcgtggcc ccgaaaagtt 33720
atccgatccc ttcaactaca gaaaaatccg ttctcgttca gacctcacgc atgttcccgg 33780
ttgcgttgct cgaggtcgct cgaagtcatt ttgatccgtt ggggttggag accgctcgag 33840
ctttcggcca caagctggct accgccgcgc tcgcgtcatt ctttgctgga gagaagccat 33900
cgagcaattg gtgaagaggg acctatcgga accccctcacc aaatattgag tgtaggtttg 33960
aggccgctgg ccgcgtcctc agtcaccttt tgagccagat aattaagagc caaatgcaat 34020
tggctcaggc tgccatcgtc cccccgtgcg aaacctgcac gtccgcgtca aagaaataac 34080
cggcacctct tgctgttttt atcagttgag ggcttgacgg atccgcctca agtttgcggc 34140
gcagccgcaa aatgagaaca tctatactcc tgtcgtaaac ctcctcgtcg cgtactcgac 34200
tggcaatgag aagttgctcg cgcgatagaa cgtcgcgggg tttctctaaa aacgcgagga 34260
gaagattgaa ctcacctgcc gtaagtttca cctcaccgcc agcttcggac atcaagcgac 34320
gttgcctgag attaagtgtc cagtcagtaa aacaaaaaga ccgtcggtct ttggagcgga 34380
caacgttggg gcgcacgcgc aaggcaaccc gaatgcgtgc aagaaactct ctcgtactaa 34440
acggcttagc gataaaatca cttgctccta gctcgagtgc aacaacttta tccgtctcct 34500
caaggcggtc gccactgata attatgattg gaatatcaga ctttgccgcc agatttcgaa 34560
cgatctcaag cccatcttca cgacctaaat ttagatcaac aaccacgaca tcgaccgtcg 34620
cggaagagag tactctagtg aactgggtgc tgtcggctac cgcggtcact ttgaaggcgt 34680
ggatcgtaag gtattcgata ataagatgcc gcatagcgac atcgtcatcg ataagaagaa 34740
cgtgtttcaa cggctcacct ttcaatctaa aatctgaacc cttgttcaca gcgcttgaga 34800
aattttcacg tgaaggatgt acaatcatct ccagctaaat gggcagttcg tcagaattgc 34860
ggctgaccgc ggatgacgaa aatgcgaacc aagtatttca attttatgac aaaagttctc 34920
aatcgttgtt acaagtgaaa cgcttcgagg ttacagctac tattgattaa ggagatcgcc 34980
tatggtctcg ccccggcgtc gtgcgtccgc cgcgagccag atctcgccta cttcataaac 35040
gtcctcatag gcacggaatg gaatgatgac atcgatcgcc gtagagagca tgtcaatcag 35100
tgtgcgatct tccaagctag caccttgggc gctacttttg acaagggaaa acagtttctt 35160
gaatccttgg attggattcg cgccgtgtat tgttgaaatc gatcccggat gtcccgagac 35220
gacttcactc agataagccc atgctgcatc gtcgcgcatc tcgccaagca atatccggtc 35280
cggccgcata cgcagacttg cttggagcaa gtgctcggcg ctcacagcac ccagcccagc 35340

-continued accgttcttg gagtagagta gtctaacatg attatcgtgt ggaatgacga gttcgagcgt 35400
atcttctatg gtgattagcc tttcctgggg ggggatggcg ctgatcaagg tcttgctcat 35460
tgttgtcttg ccgcttccgg tagggccaca tagcaacatc gtcagtcggc tgacgacgca 35520
tgcgtgcaga aacgcttcca aatccccgtt gtcaaaatgc tgaaggatag cttcatcatc 35580
ctgattttgg cgtttccttc gtgtctgcca ctggttccac ctcgaagcat cataacggga 35640
ggagacttct ttaagaccag aaacacgcga gcttggccgt cgaatggtca agctgacggt 35700
gcccgaggga acggtcggcg gcagacagat ttgtagtcgt tcaccaccag gaagttcagt 35760
ggcgcagagg gggttacgtg gtccgacatc ctgctttctc agcgcgcccg ctaaaatagc 35820
gatatcttca agatcatcat aagagacggg caaaggcatc ttggtaaaaa tgccggcttg 35880
gcgcacaaat gcctctccag gtcgattgat cgcaatttct tcagtcttcg ggtcatcgag 35940
ccattccaaa atcggcttca gaagaaagcg tagttgcgga tccacttcca tttacaatgt 36000
atcctatctc taagcggaaa tttgaattca ttaagagcgg cggttcctcc cccgcgtggc 36060
gccgccagtc aggcggagct ggtaaacacc aaagaaatcg aggtcccgtg ctacgaaaat 36120
ggaaacggtg tcaccctgat tcttcttcag ggttggcggt atgttgatgg ttgccttaag 36180
ggctgtctca gttgtctgct caccgttatt ttgaaagctg ttgaagctca tcccgccacc 36240
cgagctgccg gcgtaggtgc tagctgcctg gaaggcgcct tgaacaacac tcaagagcat 36300
agctccgcta aaacgctgcc agaagtggct gtcgaccgag cccggcaatc ctgagcgacc 36360
gagttcgtcc gcgcttggcg atgttaacga gatcatcgca tggtcaggtg tctcggcgcg 36420
atcccacaac acaaaaacgc gcccatctcc ctgttgcaag ccacgctgta tttcgccaac 36480
aacggtggtg ccacgatcaa gaagcacgat attgttcgtt gttccacgaa tatcctgagg 36540
caagacacac tttacatagc ctgccaaatt tgtgtcgatt gcggtttgca agatgcacgg 36600
aattattgtc ccttgcgtta ccataaaatc ggggtgcggc aagagcgtgg cgctgctggg 36660
ctgcagctcg gtgggtttca tacgtatcga caaatcgttc tcgccggaca cttcgccatt 36720
cggcaaggag ttgtcgtcac gcttgccttc ttgtcttcgg cccgtgtcgc cctgaatggc 36780
gcgtttgctg accccttgat cgccgctgct atatgcaaaa atcggtgttt cttccggccg 36840
tggctcatgc cgctccggtt cgcccctcgg cggtagagga gcagcaggct gaacagcctc 36900
ttgaaccgct ggaggatccg gcggcacctc aatcggagct ggatgaaatg gcttggtgtt 36960
tgttgcgatc aaagttgacg gcgatgcgtt ctcattcacc ttcttttggc gcccacctag 37020
ccaaatgagg cttaatgata acgcgagaac gacacctccg acgatcaatt tctgagaccc 37080
cgaaagacgc cggcgatgtt tgtcggagac cagggatcca gatgcatcaa cctcatgtgc 37140
cgcttgctga ctatcgttat tcatcccttc gccccccttca ggacgcgttt cacatcgggc 37200
ctcaccgtgc ccgtttgcgg cctttggcca acgggatcgt aagcggtgtt ccagatacat 37260
agtactgtgt ggccatccct cagacgccaa cctcgggaaa ccgaagaaat ctcgacatcg 37320
ctccctttaa ctgaatagtt ggcaacagct tccttgccat caggattgat ggtgtagatg 37380
gagggtatgc gtacattgcc cggaaagtgg aataccgtcg taaatccatt gtcgaagact 37440
tcgagtggca acagcgaacg atcgccttgg gcgacgtagt gccaattact gtccgccgca 37500
ccaagggctg tgacaggctg atccaataaa ttctcagctt tccgttgata ttgtgcttcc 37560
gcgtgtagtc tgtccacaac agccttctgt tgtgcctccc ttcgccgagc cgccgcatcg 37620
tcggcggggt aggcgaattg gacgctgtaa tagagatcgg gctgctcttt atcgaggtgg 37680
gacagagtct tggaacttat actgaaaaca taacggcgca tcccggagtc gcttgcggtt 37740

```
agcacgatta ctggctgagg cgtgaggacc tggcttgcct tgaaaaatag ataatttccc  37800
cgcggtaggg ctgctagatc tttgctattt gaaacggcaa ccgctgtcac cgtttcgttc  37860
gtggcgaatg ttacgaccaa agtagctcca accgccgtcg agaggcgcac cacttgatcg  37920
ggattgtaag ccaaataacg catgcgcgga tctagcttgc ccgccattgg agtgtcttca  37980
gcctccgcac cagtcgcagc ggcaaataaa catgctaaaa tgaaaagtgc ttttctgatc  38040
atggttcgct gtggcctacg tttgaaacgg tatcttccga tgtctgatag gaggtgacaa  38100
ccagacctgc cgggttggtt agtctcaatc tgccgggcaa gctggtcacc ttttcgtagc  38160
gaactgtcgc ggtccacgta ctcaccacag gcattttgcc gtcaacgacg agggtccttt  38220
tatagcgaat ttgctgcgtg cttggagtta catcatttga agcgatgtgc tcgacctcca  38280
ccctgccgcg tttgccaaga atgacttgag gcgaactggg attgggatag ttgaagaatt  38340
gctggtaatc ctggcgcact gttggggcac tgaagttcga taccaggtcg taggcgtact  38400
gagcggtgtc ggcatcataa ctctcgcgca ggcgaacgta ctcccacaat gaggcgttaa  38460
cgacggcctc ctcttgagtt gcaggcaatc gcgagacaga cacctcgctg tcaacggtgc  38520
cgtccggccg tatccataga tatacgggca caagcctgct caacggcacc attgtggcta  38580
tagcgaacgc ttgagcaaca tttcccaaaa tcgcgatagc tgcgacagct gcaatgagtt  38640
tggagagacg tcgcgccgat ttcgctcgcg cggtttgaaa ggcttctact tccttatagt  38700
gctcggcaag gctttcgcgc gccactagca tggcatattc aggccccgtc atagcgtcca  38760
cccgaattgc cgagctgaag atctgacgga gtaggctgcc atcgccccac attcagcggg  38820
aagatcgggc ctttgcagct cgctaatgtg tcgtttgtct ggcagccgct caaagcgaca  38880
actaggcaca gcaggcaata cttcatagaa ttctccattg aggcgaattt ttgcgcgacc  38940
tagcctcgct caacctgagc gaagcgacgg tacaagctgc tggcagattg ggttgcgccg  39000
ctccagtaac tgcctccaat gttgccggcg atcgccggca aagcgacaat gagcgcatcc  39060
cctgtcagaa aaaacatatc gagttcgtaa agaccaatga tcttggccgc ggtcgtaccg  39120
gcgaaggtga ttacaccaag cataagggtg agcgcagtcg cttcggttag gatgacgatc  39180
gttgccacga ggtttaagag gagaagcaag agaccgtagg tgataagttg cccgatccac  39240
ttagctgcga tgtcccgcgt gcgatcaaaa atatatccga cgaggatcag aggcccgatc  39300
gcgagaagca ctttcgtgag aattccaacg gcgtcgtaaa ctccgaaggc agaccagagc  39360
gtgccgtaaa ggacccactg tgccccttgg aaagcaagga tgtcctggtc gttcatcgga  39420
ccgatttcgg atgcgatttt ctgaaaaacg gcctgggtca cggcgaacat tgtatccaac  39480
tgtgccggaa cagtctgcag aggcaagccg gttacactaa actgctgaac aaagtttggg  39540
accgtctttt cgaagatgga aaccacatag tcttggtagt tagcctgccc aacaattaga  39600
gcaacaacga tggtgaccgt gatcacccga gtgataccgc tacgggtatc gacttcgccg  39660
cgtatgacta aaataccctg aacaataatc caaagagtga cacaggcgat caatggcgca  39720
ctcaccgcct cctggatagt ctcaagcatc gagtccaagc ctgtcgtgaa ggctacatcg  39780
aagatcgtat gaatggccgt aaacggcgcc ggaatcgtga aattcatcga ttggacctga  39840
acttgactgg tttgtcgcat aatgttggat aaaatgagct cgcattcggc gaggatgcgg  39900
gcggatgaac aaatcgccca gccttagggg agggcaccaa agatgacagc ggtcttttga  39960
tgctccttgc gttgagcggc cgcctcttcc gcctcgtgaa ggccggcctg cgcggtagtc  40020
atcgttaata ggcttgtcgc ctgtacattt tgaatcattg cgtcatggat ctgcttgaga  40080
agcaaaccat tggtcacggt tgcctgcatg atattgcgag atcgggaaag ctgagcagac  40140
```

-continued

```
gtatcagcat tcgccgtcaa gcgtttgtcc atcgtttcca gattgtcagc cgcaatgcca  40200
gcgctgtttg cggaaccggt gatctgcgat cgcaacaggt ccgcttcagc atcactaccc  40260
acgactgcac gatctgtatc gctggtgatc gcacgtgccg tggtcgacat tggcattcgc  40320
ggcgaaaaca tttcattgtc taggtccttc gtcgaaggat actgattttt ctggttgagc  40380
gaagtcagta gtccagtaac gccgtaggcc gacgtcaaca tcgtaaccat cgctatagtc  40440
tgagtgagat tctccgcagt cgcgagcgca gtcgcgagcg tctcagcctc cgttgccggg  40500
tcgctaacaa caaactgcgc ccgcgcgggc tgaatatata gaaagctgca ggtcaaaact  40560
gttgcaataa gttgcgtcgt cttcatcgtt tcctacctta tcaatcttct gcctcgtggt  40620
gacgggccat gaattcgctg agccagccag atgagttgcc ttcttgtgcc tcgcgtagtc  40680
gagttgcaaa gcgcaccgtg ttggcacgcc ccgaaagcac ggcgacatat tcacgcatat  40740
cccgcagatc aaattcgcag atgacgcttc cactttctcg tttaagaaga aacttacggc  40800
tgccgaccgt catgtcttca cggatcgcct gaaattcctt ttcggtacat ttcagtccat  40860
cgacataagc cgatcgatct gcggttggtg atggatagaa aatcttcgtc atacattgcg  40920
caaccaagct ggctcctagc ggcgattcca gaacatgctc tggttgctgc gttgccagta  40980
ttagcatccc gttgtttttt cgaacggtca ggaggaattt gtcgacgaca gtcgaaaatt  41040
tagggtttaa caaataggcg cgaaactcat cgcagctcat cacaaaacgg cggccgtcga  41100
tcatggctcc aatccgatgc aggagatatg ctgcagcggg agcgcatact tcctcgtatt  41160
cgagaagatg cgtcatgtcg aagccggtaa tcgacggatc taactttact tcgtcaactt  41220
cgccgtcaaa tgcccagcca agcgcatggc cccggcacca gcgttggagc cgcgctcctg  41280
cgccttcggc gggcccatgc aacaaaaatt cacgtaaccc cgcgattgaa cgcatttgtg  41340
gatcaaacga gagctgacga tggataccac ggaccagacg gcggttctct tccggagaaa  41400
tcccaccccg accatcactc tcgatgagag ccacgatcca ttcgcgcaga aaatcgtgtg  41460
aggctgctgt gttttctagg ccacgcaacg gcgccaaccc gctgggtgtg cctctgtgaa  41520
gtgccaaata tgttcctcct gtggcgcgaa ccagcaattc gccaccccgg tccttgtcaa  41580
agaacacgac cgtacctgca cggtcgacca tgctctgttc gagcatggct agaacaaaca  41640
tcatgagcgt cgtcttaccc ctcccgatag gcccgaatat tgccgtcatg ccaacatcgt  41700
gctcatgcgg gatatagtcg aaaggcgttc cgccattggt acgaaatcgg gcaatcgcgt  41760
tgccccagtg gcctgagctg gcgccctctg gaaagttttc gaaagagaca aaccctgcga  41820
aattgcgtga agtgattgcg ccagggcgtg tgcgccactt aaaattcccc ggcaattggg  41880
accaataggc cgcttccata ccaatacctt cttggacaac cacggcacct gcatccgcca  41940
ttcgtgtccg agcccgcgcg cccctgtccc caagactatt gagatcgtct gcatagacgc  42000
aaaggctcaa atgatgtgag cccataacga attcgttgct cgcaagtgcg tcctcagcct  42060
cggataattt gccgatttga gtcacggctt tatcgccgga actcagcatc tggctcgatt  42120
tgaggctaag tttcgcgtgc gcttgcgggc gagtcaggaa cgaaaaactc tgcgtgagaa  42180
caagtggaaa atcgagggat agcagcgcgt tgagcatgcc cggccgtgtt tttgcagggt  42240
attcgcgaaa cgaatagatg gatccaacgt aactgtcttt tggcgttctg atctcgagtc  42300
ctcgcttgcc gcaaatgact ctgtcggtat aaatcgaagc gccgagtgag ccgctgacga  42360
ccggaaccgg tgtgaaccga ccagtcatga tcaaccgtag cgcttcgcca atttcggtga  42420
agagcacacc ctgcttctcg cggatgccaa gacgatgcag gccatacgct ttaagagagc  42480
cagcgacaac atgccaaaga tcttccatgt tcctgatctg gcccgtgaga tcgttttccc  42540
```

-continued

```
tttttccgct tagcttggtg aacctcctct ttaccttccc taaagccgcc tgtgggtaga  42600
caatcaacgt aaggaagtgt tcattgcgga ggagttggcc ggagagcacg cgctgttcaa  42660
aagcttcgtt caggctagcg gcgaaaacac tacggaagtg tcgcggcgcc gatgatggca  42720
cgtcggcatg acgtacgagg tgagcatata ttgacacatg atcatcagcg atattgcgca  42780
acagcgtgtt gaacgcacga caacgcgcat tgcgcatttc agtttcctca agctcgaatg  42840
caacgccatc aattctcgca atggtcatga tcgatccgtc ttcaagaagg acgatatggt  42900
cgctgaggtg gccaatataa gggagataga tctcaccgga tctttcggtc gttccactcg  42960
cgccgagcat cacaccattc ctctccctcg tgggggaacc ctaattggat ttgggctaac  43020
agtagcgccc ccccaaactg cactatcaat gcttcttccc gcggtccgca aaaatagcag  43080
gacgacgctc gccgcattgt agtctcgctc cacgatgagc cgggctgcaa accataacgg  43140
cacgagaacg acttcgtaga gcgggttctg aacgataacg atgacaaagc cggcgaacat  43200
catgaataac cctgccaatg tcagtggcac cccaagaaac aatgcgggcc gtgtggctgc  43260
gaggtaaagg gtcgattctt ccaaacgatc agccatcaac taccgccagt gagcgtttgg  43320
ccgaggaagc tcgccccaaa catgataaca atgccgccga cgacgccggc aaccagccca  43380
agcgaagccc gcccgaacat ccaggagatc ccgatagcga caatgccgag aacagcgagt  43440
gactggccga acggaccaag gataaacgtg catatattgt taaccattgt ggcggggtca  43500
gtgccgccac ccgcagattg cgctgcggcg ggtccggatg aggaaatgct ccatgcaatt  43560
gcaccgcaca agcttggggc gcagctcgat atcacgcgca tcatcgcatt cgagagcgag  43620
aggcgattta gatgtaaacg gtatctctca aagcatcgca tcaatgcgca cctccttagt  43680
ataagtcgaa taagacttga ttgtcgtctg cggatttgcc gttgtcctgg tgtggcggtg  43740
gcggagcgat taaaccgcca gcgccatcct cctgcgagcg gcgctgatat gacccccaaa  43800
catcccacgt ctcttcggat tttagcgcct cgtgatcgtc ttttggaggc tcgattaacg  43860
cgggcaccag cgattgagca gctgtttcaa cttttcgcac gtagccgttt gcaaaaccgc  43920
cgatgaaatt accggtgttg taagcggaga tcgcccgacg aagcgcaaat tgcttctcgt  43980
caatcgtttc gccgcctgca taacgacttt tcagcatgtt tgcagcggca gataatgatg  44040
tgcacgcctg gagcgcaccg tcaggtgtca gaccgagcat agaaaaattt cgagagttta  44100
tttgcatgag gccaacatcc agcgaatgcc gtgcatcgag acggtgcctg acgacttggg  44160
ttgcttggct gtgatcttgc cagtgaagcg tttcgccggt cgtgttgtca tgaatcgcta  44220
aaggatcaaa gcgactctcc accttagcta tcgccgcaag cgtagatgtc gcaactgatg  44280
gggcacactt gcgagcaaca tggtcaaact cagcagatga gagtggcgtg gcaaggctcg  44340
acgaacagaa ggagaccatc aaggcaagag aaagcgaccc cgatctctta agcatacctt  44400
atctccttag ctcgcaacta acaccgcctc tcccgttgga agaagtgcgt tgttttatgt  44460
tgaagattat cgggagggtc ggttactcga aaattttcaa ttgcttcttt atgatttcaa  44520
ttgaagcgag aaacctcgcc cggcgtcttg gaacgcaaca tggaccgaga accgcgcatc  44580
catgactaag caaccggatc gacctattca ggccgcagtt ggtcaggtca ggctcagaac  44640
gaaaatgctc ggcgaggtta cgctgtctgt aaacccattc gatgaacggg aagcttcctt  44700
ccgattgctc ttggcaggaa tattggccca tgcctgcttg cgctttgcaa atgctcttat  44760
cgcgttggta tcatatgcct tgtccgccag cagaaacgca ctctaagcga ttatttgtaa  44820
aaatgtttcg gtcatgcggc ggtcatgggc ttgacccgct gtcagcgcaa gacggatcgg  44880
tcaaccgtcg gcatcgacaa cagcgtgaat cttggtggtc aaaccgccac gggaacgtcc  44940
```

-continued catacagcca tcgtcttgat cccgctgttt cccgtcgccg catgttggtg gacgcggaca 45000
caggaactgt caatcatgac gacattctat cgaaagcctt ggaaatcaca ctcagaatat 45060
gatcccagac gtctgcctca cgccatcgta caaagcgatt gtagcaggtt gtacaggaac 45120
cgtatcgatc aggaacgtct gcccagggcg ggcccgtccg gaagcgccac aagatgacat 45180
tgatcacccg cgtcaacgcg cggcacgcga cgcggcttat ttgggaacaa aggactgaac 45240
aacagtccat tcgaaatcgg tgacatcaaa gcggggacgg gttatcagtg gcctccaagt 45300
caagcctcaa tgaatcaaaa tcagaccgat ttgcaaacct gatttatgag tgtgcggcct 45360
aaatgatgaa atcgtccttc tagatcgcct ccgtggtgta gcaacacctc gcagtatcgc 45420
cgtgctgacc ttggccaggg aattgactgg caagggtgct ttcacatgac cgctcttttg 45480
gccgcgatag atgatttcgt tgctgctttg ggcacgtaga aggagagaag tcatatcgga 45540
gaaattcctc ctggcgcgag agcctgctct atcgcgacgg catcccactg tcgggaacag 45600
accggatcat tcacgaggcg aaagtcgtca acacatgcgt tataggcatc ttcccttgaa 45660
ggatgatctt gttgctgcca atctggaggt gcggcagccg caggcagatg cgatctcagc 45720
gcaacttgcg gcaaaacatc tcactcacct gaaaaccact agcgagtctc gcgatcagac 45780
gaaggccttt tacttaacga cacaatatcc gatgtctgca tcacaggcgt cgctatccca 45840
gtcaatacta aagcggtgca ggaactaaag attactgatg acttaggcgt gccacgaggc 45900
ctgagacgac gcgcgtagac agtttttttga aatcattatc aaagtgatgg cctccgctga 45960
agcctatcac ctctgcgccg gtctgtcgga gagatgggca agcattatta cggtcttcgc 46020
gcccgtacat gcattggacg attgcagggt caatggatct gagatcatcc agaggattgc 46080
cgcccttacc ttccgtttcg agttggagcc agcccctaaa tgagacgaca tagtcgactt 46140
gatgtgacaa tgccaagaga gagatttgct taacccgatt tttttgctca agcgtaagcc 46200
tattgaagct tgccggcatg acgtccgcgc cgaaagaata tcctacaagt aaaacattct 46260
gcacaccgaa atgcttggtg tagacatcga ttatgtgacc aagatcctta gcagtttcgc 46320
ttggggaccg ctccgaccag aaataccgaa gtgaactgac gccaatgaca ggaatccctt 46380
ccgtctgcag ataggtacca tcgatagatc tgctgcctcg cgcgtttcgg tgatgacggt 46440
gaaaacctct gacacatgca gctcccggag acggtcacag cttgtctgta agcggatgcc 46500
gggagcagac aagcccgtca gggcgcgtca gcgggtgttg gcgggtgtcg gggcgcagcc 46560
atgacccagt cacgtagcga tagcggagtg tatactggct taactatgcg gcatcagagc 46620
agattgtact gagagtgcac catatgcggt gtgaaatacc gcacagatgc gtaaggagaa 46680
aataccgcat caggcgctct tccgcttcct cgctcactga ctcgctgcgc tcggtcgttc 46740
ggctgcggcg agcggtatca gctcactcaa aggcggtaat acggttatcc acagaatcag 46800
gggataacgc aggaaagaac atgtgagcaa aaggccagca aaaggccagg aaccgtaaaa 46860
aggccgcgtt gctggcgttt ttccataggc tccgcccccc tgacgagcat cacaaaaatc 46920
gacgctcaag tcagaggtgg cgaaacccga caggactata aagataccag gcgtttcccc 46980
ctggaagctc cctcgtgcgc tctcctgttc cgaccctgcc gcttaccgga tacctgtccg 47040
cctttctccc ttcgggaagc gtggcgcttt ctcatagctc acgctgtagg tatctcagtt 47100
cggtgtaggt cgttcgctcc aagctgggct gtgtgcacga accccccgtt cagcccgacc 47160
gctgcgcctt atccggtaac tatcgtcttg agtccaaccc ggtaagacac gacttatcgc 47220
cactggcagc agccactggt aacaggatta gcagagcgag gtatgtaggc ggtgctacag 47280
agttcttgaa gtggtggcct aactacggct acactagaag gacagtattt ggtatctgcg 47340

-continued ctctgctgaa gccagttacc ttcggaaaaa gagttggtag ctcttgatcc ggcaaacaaa 47400
ccaccgctgg tagcggtggt ttttttgttt gcaagcagca gattacgcgc agaaaaaaag 47460
gatctcaaga agatcctttg atcttttcta cggggtctga cgctcagtgg aacgaaaact 47520
cacgttaagg gattttggtc atgagattat caaaaaggat cttcacctag atccttttaa 47580
attaaaaatg aagttttaaa tcaatctaaa gtatatatga gtaaacttgg tctgacagtt 47640
accaatgctt aatcagtgag gcacctatct cagcgatctg tctatttcgt tcatccatag 47700
ttgcctgact ccccgtcgtg tagataacta cgatacggga gggcttacca tctggcccca 47760
gtgctgcaat gataccgcga gacccacgct caccggctcc agatttatca gcaataaacc 47820
agccagccgg aagggccgag cgcagaagtg gtcctgcaac tttatccgcc tccatccagt 47880
ctattaattg ttgccgggaa gctagagtaa gtagttcgcc agttaatagt ttgcgcaacg 47940
ttgttgccat tgctgcaggg gggggggggg ggggggactt ccattgttca ttccacggac 48000
aaaaacagag aaaggaaacg acagaggcca aaaagcctcg ctttcagcac ctgtcgtttc 48060
ctttcttttc agagggtatt ttaaataaaa acattaagtt atgacgaaga agaacggaaa 48120
cgccttaaac cggaaaattt tcataaatag cgaaaacccg cgaggtcgcc gccccgtagt 48180
cggatcaccg gaaaggaccc gtaaagtgat aatgattatc atctacatat cacaacgtgc 48240
gtggaggcca tcaaaccacg tcaaataatc aattatgacg caggtatcgt attaattgat 48300
ctgcatcaac ttaacgtaaa aacaacttca gacaatacaa atcagcgaca ctgaatacgg 48360
ggcaacctca tgtccccccc cccccccccc ctgcaggcat cgtggtgtca cgctcgtcgt 48420
ttggtatggc ttcattcagc tccggttccc aacgatcaag gcgagttaca tgatccccca 48480
tgttgtgcaa aaaagcggtt agctccttcg gtcctccgat cgttgtcaga agtaagttgg 48540
ccgcagtgtt atcactcatg gttatggcag cactgcataa ttctcttact gtcatgccat 48600
ccgtaagatg cttttctgtg actggtgagt actcaaccaa gtcattctga gaatagtgta 48660
tgcggcgacc gagttgctct tgcccggcgt caacacggga taataccgcg ccacatagca 48720
gaactttaaa agtgctcatc attggaaaac gttcttcggg gcgaaaactc tcaaggatct 48780
taccgctgtt gagatccagt tcgatgtaac ccactcgtgc acccaactga tcttcagcat 48840
cttttacttt caccagcgtt tctgggtgag caaaaacagg aaggcaaaat gccgcaaaaa 48900
agggaataag ggcgacacgg aaatgttgaa tactcatact cttccttttt caatattatt 48960
gaagcattta tcagggttat tgtctcatga gcggatacat atttgaatgt atttagaaaa 49020
ataaacaaat aggggttccg cgcacatttc cccgaaaagt gccacctgac gtctaagaaa 49080
ccattattat catgacatta acctataaaa ataggcgtat cacgaggccc tttcgtcttc 49140
aagaattggt cgacgatctt gctgcgttcg gatattttcg tggagttccc gccacagacc 49200
cggattgaag gcgagatcca gcaactcgcg ccagatcatc ctgtgacgga actttggcgc 49260
gtgatgactg gccaggacgt cggccgaaag agcgacaagc agatcacgct tttcgacagc 49320
gtcggatttg cgatcgagga tttttcggcg ctgcgctacg tccgcgaccg cgttgaggga 49380
tcaagccaca gcagcccact cgaccttcta gccgacccag acgagccaag ggatcttttt 49440
ggaatgctgc tccgtcgtca ggctttccga cgtttgggtg gttgaacaga agtcattatc 49500
gtacggaatg ccaagcactc ccgaggggaa ccctgtggtt ggcatgcaca tacaaatgga 49560
cgaacggata aacctttca cgccctttta aatatccgtt attctaataa acgctctttt 49620
ctcttaggtt tacccgccaa tatatcctgt caaacactga tagtttaaac tgaaggcggg 49680
aaacgacaat ctgatcatga gcggagaatt aagggagtca cgttatgacc cccgccgatg 49740
acgcgggaca agccgtttta cgtttggaac tgacagaacc gcaacgttga aggagccact 49800
cagcaagctg gtacgattgt aatacgactc actatagggc gaattgagcg ctgtttaaac 49860
gctcttcaac tggaagagcg gttacccgga ccgaagcttg catgcctgca g 49911

<210> SEQ ID NO 37
<211> LENGTH: 36909
<212> TYPE: DNA
<213> ORGANISM: Artificial
<220> FEATURE:
<223> OTHER INFORMATION: Vector PHP10523

<400> SEQUENCE: 37
tctagagctc gttcctcgag gcctcgaggc ctcgaggaac ggtacctgcg gggaagctta 60
caataatgtg tgttgttaag tcttgttgcc tgtcatcgtc tgactgactt tcgtcataaa 120
tcccggcctc cgtaacccag ctttgggcaa gctcacggat ttgatccggc ggaacgggaa 180
tatcgagatg ccgggctgaa cgctgcagtt ccagctttcc ctttcgggac aggtactcca 240
gctgattgat tatctgctga agggtcttgg ttccacctcc tggcacaatg cgaatgatta 300
cttgagcgcg atcgggcatc caattttctc ccgtcaggtg cgtggtcaag tgctacaagg 360
cacctttcag taacgagcga ccgtcgatcc gtcgccggga tacggacaaa atggagcgca 420
gtagtccatc gagggcggcg aaagcctcgc caaaagcaat acgttcatct cgcacagcct 480
ccagatccga tcgagggtct tcggcgtagg cagatagaag catggataca ttgcttgaga 540
gtattccgat ggactgaagt atggcttcca tcttttctcg tgtgtctgca tctatttcga 600
gaaagccccc gatgcggcgc accgcaacgc gaattgccat actatccgaa agtcccagca 660
ggcgcgcttg ataggaaaag gtttcatact cggccgatcg cagacgggca ctcacgacct 720
tgaacccttc aactttcagg gatcgatgct ggttgatggt agtctcactc gacgtggctc 780
tggtgtgttt tgacatagct tcctccaaag aaagcggaag gtctggatac tccagcacga 840
aatgtgcccg ggtagacgga tggaagtcta gccctgctca atatgaaatc aacagtacat 900
ttacagtcaa tactgaatat acttgctaca tttgcaattg tcttataacg aatgtgaaat 960
aaaaatagtg taacaacgct tttactcatc gataatcaca aaaacattta tacgaacaaa 1020
aatacaaatg cactccggtt tcacaggata ggcgggatca gaatatgcaa cttttgacgt 1080
tttgttcttt caaagggggt gctggcaaaa ccaccgcact catgggcctt tgcgctgctt 1140
tggcaaatga cggtaaacga gtggccctct ttgatgccga cgaaaaccgg cctctgacgc 1200
gatggagaga aaacgcctta caaagcagta ctgggatcct cgctgtgaag tctattccgc 1260
cgacgaaatg cccccttcttg aagcagccta tgaaaatgcc gagctcgaag gatttgatta 1320
tgcgttggcc gatacgcgtg gcggctcgag cgagctcaac aacacaatca tcgctagctc 1380
aaacctgctt ctgatcccca ccatgctaac gccgctcgac atcgatgagg cactatctac 1440
ctaccgctac gtcatcgagc tgctgttgag tgaaaatttg gcaattccta cagctgtttt 1500
gcgccaacgc gtcccggtcg gccgattgac aacatcgcaa cgcaggatgt cagagacgct 1560
agagagcctt ccagttgtac cgtctcccat gcatgaaaga gatgcatttg ccgcgatgaa 1620
agaacgcggc atgttgcatc ttacattact aaacacggga actgatccga cgatgcgcct 1680
catagagagg aatcttcgga ttgcgatgga ggaagtcgtg gtcatttcga aactgatcag 1740
caaaatcttg gaggcttgaa gatggcaatt cgcaagcccg cattgtcggt cggcgaagca 1800
cggcggcttg ctggtgctcg acccgagatc caccatccca acccgacact tgttccccag 1860
aagctggacc tccagcactt gcctgaaaaa gccgacgaga aagaccagca acgtgagcct 1920
ctcgtcgccg atcacattta cagtcccgat cgacaactta agctaactgt ggatgccctt 1980
agtccacctc cgtccccgaa aaagctccag gtttttcttt cagcgcgacc gcccgcgcct 2040
caagtgtcga aaacatatga caacctcgtt cggcaataca gtccctcgaa gtcgctacaa 2100
atgattttaa ggcgcgcgtt ggacgatttc gaaagcatgc tggcagatgg atcatttcgc 2160
gtggccccga aaagttatcc gatcccttca actacagaaa aatccgttct cgttcagacc 2220
tcacgcatgt tcccggttgc gttgctcgag gtcgctcgaa gtcattttga tccgttgggg 2280
ttggagaccg ctcgagcttt cggccacaag ctggctaccg ccgcgctcgc gtcattcttt 2340
gctggagaga agccatcgag caattggtga agagggacct atcggaaccc ctcaccaaat 2400
attgagtgta ggtttgaggc cgctggccgc gtcctcagtc accttttgag ccagataatt 2460
aagagccaaa tgcaattggc tcaggctgcc atcgtccccc cgtgcgaaac ctgcacgtcc 2520
gcgtcaaaga aataaccggc acctcttgct gtttttatca gttgagggct tgacggatcc 2580
gcctcaagtt tgcggcgcag ccgcaaaatg agaacatcta tactcctgtc gtaaacctcc 2640
tcgtcgcgta ctcgactggc aatgagaagt tgctcgcgcg atagaacgtc gcggggtttc 2700
tctaaaaacg cgaggagaag attgaactca cctgccgtaa gtttcacctc accgccagct 2760
tcggacatca agcgacgttg cctgagatta agtgtccagt cagtaaaaca aaaagaccgt 2820
cggtctttgg agcggacaac gttggggcgc acgcgcaagg caacccgaat gcgtgcaaga 2880
aactctctcg tactaaacgg cttagcgata aaatcacttg ctcctagctc gagtgcaaca 2940
actttatccg tctcctcaag gcggtcgcca ctgataatta tgattggaat atcagacttt 3000
gccgccagat ttcgaacgat ctcaagccca tcttcacgac ctaaatttag atcaacaacc 3060
acgacatcga ccgtcgcgga agagagtact ctagtgaact gggtgctgtc ggctaccgcg 3120
gtcactttga aggcgtggat cgtaaggtat tcgataataa gatgccgcat agcgacatcg 3180
tcatcgataa gaagaacgtg tttcaacggc tcacctttca atctaaaatc tgaacccttg 3240
ttcacagcgc ttgagaaatt ttcacgtgaa ggatgtacaa tcatctccag ctaaatgggc 3300
agttcgtcag aattgcggct gaccgcggat gacgaaaatg cgaaccaagt atttcaattt 3360
tatgacaaaa gttctcaatc gttgttacaa gtgaaacgct tcgaggttac agctactatt 3420
gattaaggag atcgcctatg gtctcgcccc ggcgtcgtgc gtccgccgcg agccagatct 3480
cgcctacttc ataaacgtcc tcataggcac ggaatggaat gatgacatcg atcgccgtag 3540
agagcatgtc aatcagtgtg cgatcttcca agctagcacc ttgggcgcta cttttgacaa 3600
gggaaaacag tttcttgaat ccttggattg gattcgcgcc gtgtattgtt gaaatcgatc 3660
ccggatgtcc cgagacgact tcactcagat aagcccatgc tgcatcgtcg cgcatctcgc 3720
caagcaatat ccggtccggc cgcatacgca gacttgcttg gagcaagtgc tcggcgctca 3780
cagcacccag cccagcaccg ttcttggagt agagtagtct aacatgatta tcgtgtggaa 3840
tgacgagttc gagcgtatct tctatggtga ttagcctttc ctgggggggg atggcgctga 3900
tcaaggtctt gctcattgtt gtcttgccgc ttccggtagg gccacatagc aacatcgtca 3960
gtcggctgac gacgcatgcg tgcagaaacg cttccaaatc cccgttgtca aaatgctgaa 4020
ggatagcttc atcatcctga ttttggcgtt tccttcgtgt ctgccactgg ttccacctcg 4080
aagcatcata acgggaggag acttctttaa gaccagaaac acgcgagctt ggccgtcgaa 4140
tggtcaagct gacggtgccc gagggaacgg tcggcggcag acagatttgt agtcgttcac 4200
caccaggaag ttcagtggcg cagagggggt tacgtggtcc gacatcctgc tttctcagcg 4260
cgcccgctaa aatagcgata tcttcaagat catcataaga gacgggcaaa ggcatcttgg 4320

-continued

```
taaaaatgcc ggcttggcgc acaaatgcct ctccaggtcg attgatcgca atttcttcag   4380
tcttcgggtc atcgagccat tccaaaatcg gcttcagaag aaagcgtagt tgcggatcca   4440
cttccattta caatgtatcc tatctctaag cggaaatttg aattcattaa gagcggcggt   4500
tcctcccccg cgtggcgccg ccagtcaggc ggagctggta aacaccaaag aaatcgaggt   4560
cccgtgctac gaaaatggaa acggtgtcac cctgattctt cttcagggtt ggcggtatgt   4620
tgatggttgc cttaagggct gtctcagttg tctgctcacc gttattttga aagctgttga   4680
agctcatccc gccacccgag ctgccggcgt aggtgctagc tgcctggaag gcgccttgaa   4740
caacactcaa gagcatagct ccgctaaaac gctgccagaa gtggctgtcg accgagcccg   4800
gcaatcctga gcgaccgagt tcgtccgcgc ttggcgatgt taacgagatc atcgcatggt   4860
caggtgtctc ggcgcgatcc cacaacacaa aaacgcgccc atctccctgt tgcaagccac   4920
gctgtatttc gccaacaacg gtggtgccac gatcaagaag cacgatattg ttcgttgttc   4980
cacgaatatc ctgaggcaag acacacttta catagcctgc caaatttgtg tcgattgcgg   5040
tttgcaagat gcacggaatt attgtccctt gcgttaccat aaaatcgggg tgcggcaaga   5100
gcgtggcgct gctgggctgc agctcggtgg gtttcatacg tatcgacaaa tcgttctcgc   5160
cggacacttc gccattcggc aaggagttgt cgtcacgctt gccttcttgt cttcggcccg   5220
tgtcgccctg aatggcgcgt ttgctgaccc cttgatcgcc gctgctatat gcaaaaatcg   5280
gtgtttcttc cggccgtggc tcatgccgct ccggttcgcc cctcggcggt agaggagcag   5340
caggctgaac agcctcttga accgctggag gatccggcgg cacctcaatc ggagctggat   5400
gaaatggctt ggtgtttgtt gcgatcaaag ttgacggcga tgcgttctca ttcaccttct   5460
tttggcgccc acctagccaa atgaggctta atgataacgc gagaacgaca cctccgacga   5520
tcaatttctg agaccccgaa agacgccggc gatgtttgtc ggagaccagg gatccagatg   5580
catcaacctc atgtgccgct tgctgactat cgttattcat cccttcgccc ccttcaggac   5640
gcgtttcaca tcgggcctca ccgtgcccgt ttgcggcctt tggccaacgg gatcgtaagc   5700
ggtgttccag atacatagta ctgtgtggcc atccctcaga cgccaacctc gggaaaccga   5760
agaaatctcg acatcgctcc ctttaactga atagttggca acagcttcct tgccatcagg   5820
attgatggtg tagatggagg gtatgcgtac attgcccgga aagtggaata ccgtcgtaaa   5880
tccattgtcg aagacttcga gtggcaacag cgaacgatcg ccttgggcga cgtagtgcca   5940
attactgtcc gccgcaccaa gggctgtgac aggctgatcc aataaattct cagctttccg   6000
ttgatattgt gcttccgcgt gtagtctgtc cacaacagcc ttctgttgtg cctcccttcg   6060
ccgagccgcc gcatcgtcgg cggggtaggc gaattggacg ctgtaataga gatcgggctg   6120
ctctttatcg aggtgggaca gagtcttgga acttatactg aaaacataac ggcgcatccc   6180
ggagtcgctt gcggttagca cgattactgg ctgaggcgtg aggacctggc ttgccttgaa   6240
aaatagataa tttccccgcg gtagggctgc tagatctttg ctatttgaaa cggcaaccgc   6300
tgtcaccgtt tcgttcgtgg cgaatgttac gaccaaagta gctccaaccg ccgtcgagag   6360
gcgcaccact tgatcgggat tgtaagccaa ataacgcatg cgcggatcta gcttgcccgc   6420
cattggagtg tcttcagcct ccgcaccagt cgcagcggca aataaacatg ctaaaatgaa   6480
aagtgctttt ctgatcatgg ttcgctgtgg cctacgtttg aaacggtatc ttccgatgtc   6540
tgataggagg tgacaaccag acctgccggg ttggttagtc tcaatctgcc gggcaagctg   6600
gtcacctttt cgtagcgaac tgtcgcggtc cacgtactca ccacaggcat tttgccgtca   6660
acgacgaggg tccttttata gcgaatttgc tgcgtgcttg gagttacatc atttgaagcg   6720
```

-continued

```
atgtgctcga cctccaccct gccgcgtttg ccaagaatga cttgaggcga actgggattg   6780
ggatagttga agaattgctg gtaatcctgg cgcactgttg ggcactgaa gttcgatacc   6840
aggtcgtagg cgtactgagc ggtgtcggca tcataactct cgcgcaggcg aacgtactcc   6900
cacaatgagg cgttaacgac ggcctcctct tgagttgcag gcaatcgcga gacagacacc   6960
tcgctgtcaa cggtgccgtc cggccgtatc catagatata cgggcacaag cctgctcaac   7020
ggcaccattg tggctatagc gaacgcttga gcaacatttc ccaaaatcgc gatagctgcg   7080
acagctgcaa tgagtttgga gagacgtcgc gccgatttcg ctcgcgcggt ttgaaaggct   7140
tctacttcct tatagtgctc ggcaaggctt tcgcgcgcca ctagcatggc atattcaggc   7200
cccgtcatag cgtccacccg aattgccgag ctgaagatct gacggagtag gctgccatcg   7260
ccccacattc agcgggaaga tcgggccttt gcagctcgct aatgtgtcgt ttgtctggca   7320
gccgctcaaa gcgacaacta ggcacagcag gcaatacttc atagaattct ccattgaggc   7380
gaatttttgc gcgacctagc ctcgctcaac ctgagcgaag cgacggtaca agctgctggc   7440
agattgggtt gcgccgctcc agtaactgcc tccaatgttg ccggcgatcg ccggcaaagc   7500
gacaatgagc gcatcccctg tcagaaaaaa catatcgagt tcgtaaagac caatgatctt   7560
ggccgcggtc gtaccggcga aggtgattac accaagcata agggtgagcg cagtcgcttc   7620
ggttaggatg acgatcgttg ccacgaggtt taagaggaga agcaagagac cgtaggtgat   7680
aagttgcccg atccacttag ctgcgatgtc ccgcgtgcga tcaaaaatat atccgacgag   7740
gatcagaggc ccgatcgcga gaagcacttt cgtgagaatt ccaacggcgt cgtaaactcc   7800
gaaggcagac cagagcgtgc cgtaaaggac ccactgtgcc ccttggaaag caaggatgtc   7860
ctggtcgttc atcggaccga tttcggatgc gattttctga aaaacggcct gggtcacggc   7920
gaacattgta tccaactgtg ccggaacagt ctgcagaggc aagccggtta cactaaactg   7980
ctgaacaaag tttgggaccg tcttttcgaa gatggaaacc acatagtctt ggtagttagc   8040
ctgcccaaca attagagcaa caacgatggt gaccgtgatc acccgagtga taccgctacg   8100
ggtatcgact tcgccgcgta tgactaaaat accctgaaca ataatccaaa gagtgacaca   8160
ggcgatcaat ggcgcactca ccgcctcctg gatagtctca agcatcgagt ccaagcctgt   8220
cgtgaaggct acatcgaaga tcgtatgaat ggccgtaaac ggcgccggaa tcgtgaaatt   8280
catcgattgg acctgaactt gactggtttg tcgcataatg ttggataaaa tgagctcgca   8340
ttcggcgagg atgcgggcgg atgaacaaat cgcccagcct taggggaggg caccaaagat   8400
gacagcggtc ttttgatgct ccttgcgttg agcggccgcc tcttccgcct cgtgaaggcc   8460
ggcctgcgcg gtagtcatcg ttaataggct tgtcgcctgt acattttgaa tcattgcgtc   8520
atggatctgc ttgagaagca aaccattggt cacggttgcc tgcatgatat tgcgagatcg   8580
ggaaagctga gcagacgtat cagcattcgc cgtcaagcgt ttgtccatcg tttccagatt   8640
gtcagccgca atgccagcgc tgtttgcgga accggtgatc tgcgatcgca acaggtccgc   8700
ttcagcatca ctacccacga ctgcacgatc tgtatcgctg gtgatcgcac gtgccgtggt   8760
cgacattggc attcgcggcg aaaacatttc attgtctagg tccttcgtcg aaggatactg   8820
atttttctgg ttgagcgaag tcagtagtcc agtaacgccg taggccgacg tcaacatcgt   8880
aaccatcgct atagtctgag tgagattctc cgcagtcgcg agcgcagtcg cgagcgtctc   8940
agcctccgtt gccgggtcgc taacaacaaa ctgcgcccgc gcgggctgaa tatatagaaa   9000
gctgcaggtc aaaactgttg caataagttg cgtcgtcttc atcgtttcct accttatcaa   9060
tcttctgcct cgtggtgacg ggccatgaat tcgctgagcc agccagatga gttgccttct   9120
```

-continued

```
tgtgcctcgc gtagtcgagt tgcaaagcgc accgtgttgg cacgccccga aagcacggcg   9180
acatattcac gcatatcccg cagatcaaat tcgcagatga cgcttccact ttctcgttta   9240
agaagaaact tacggctgcc gaccgtcatg tcttcacgga tcgcctgaaa ttccttttcg   9300
gtacatttca gtccatcgac ataagccgat cgatctgcgg ttggtgatgg atagaaaatc   9360
ttcgtcatac attgcgcaac caagctggct cctagcggcg attccagaac atgctctggt   9420
tgctgcgttg ccagtattag catcccgttg ttttttcgaa cggtcaggag gaatttgtcg   9480
acgacagtcg aaaatttagg gtttaacaaa taggcgcgaa actcatcgca gctcatcaca   9540
aaacggcggc cgtcgatcat ggctccaatc cgatgcagga gatatgctgc agcgggagcg   9600
catacttcct cgtattcgag aagatgcgtc atgtcgaagc cggtaatcga cggatctaac   9660
tttacttcgt caacttcgcc gtcaaatgcc cagccaagcg catggccccg gcaccagcgt   9720
tggagccgcg ctcctgcgcc ttcggcgggc ccatgcaaca aaaattcacg taaccccgcg   9780
attgaacgca tttgtggatc aaacgagagc tgacgatgga taccacggac cagacggcgg   9840
ttctcttccg gagaaatccc accccgacca tcactctcga tgagagccac gatccattcg   9900
cgcagaaaat cgtgtgaggc tgctgtgttt tctaggccac gcaacggcgc caacccgctg   9960
ggtgtgcctc tgtgaagtgc caaatatgtt cctcctgtgg cgcgaaccag caattcgcca  10020
ccccggtcct tgtcaaagaa cacgaccgta cctgcacggt cgaccatgct ctgttcgagc  10080
atggctagaa caaacatcat gagcgtcgtc ttacccctcc cgataggccc gaatattgcc  10140
gtcatgccaa catcgtgctc atgcgggata tagtcgaaag gcgttccgcc attggtacga  10200
aatcgggcaa tcgcgttgcc ccagtggcct gagctggcgc cctctggaaa gttttcgaaa  10260
gagacaaacc ctgcgaaatt gcgtgaagtg attgcgccag ggcgtgtgcg ccacttaaaa  10320
ttccccggca attgggacca ataggccgct tccataccaa taccttcttg gacaaccacg  10380
gcacctgcat ccgccattcg tgtccgagcc cgcgcgcccc tgtccccaag actattgaga  10440
tcgtctgcat agacgcaaag gctcaaatga tgtgagccca taacgaattc gttgctcgca  10500
agtgcgtcct cagcctcgga taatttgccg atttgagtca cggctttatc gccggaactc  10560
agcatctggc tcgatttgag gctaagtttc gcgtgcgctt gcgggcgagt caggaacgaa  10620
aaactctgcg tgagaacaag tggaaaatcg agggatagca gcgcgttgag catgcccggc  10680
cgtgtttttg cagggtattc gcgaaacgaa tagatggatc caacgtaact gtcttttggc  10740
gttctgatct cgagtcctcg cttgccgcaa atgactctgt cggtataaat cgaagcgccg  10800
agtgagccgc tgacgaccgg aaccggtgtg aaccgaccag tcatgatcaa ccgtagcgct  10860
tcgccaattt cggtgaagag cacaccctgc ttctcgcgga tgccaagacg atgcaggcca  10920
tacgctttaa gagagccagc gacaacatgc caaagatctt ccatgttcct gatctggccc  10980
gtgagatcgt tttccctttt tccgcttagc ttggtgaacc tcctctttac cttccctaaa  11040
gccgcctgtg ggtagacaat caacgtaagg aagtgttcat tgcggaggag ttggccggag  11100
agcacgcgct gttcaaaagc ttcgttcagg ctagcggcga aaacactacg gaagtgtcgc  11160
ggcgccgatg atggcacgtc ggcatgacgt acgaggtgag catatattga cacatgatca  11220
tcagcgatat tgcgcaacag cgtgttgaac gcacgacaac gcgcattgcg catttcagtt  11280
tcctcaagct cgaatgcaac gccatcaatt ctcgcaatgg tcatgatcga tccgtcttca  11340
agaaggacga tatggtcgct gaggtggcca atataaggga gatagatctc accggatctt  11400
tcggtcgttc cactcgcgcc gagcatcaca ccattcctct ccctcgtggg ggaaccctaa  11460
ttggatttgg gctaacagta gcgccccccc aaactgcact atcaatgctt cttcccgcgg  11520
```

-continued

```
tccgcaaaaa tagcaggacg acgctcgccg cattgtagtc tcgctccacg atgagccggg  11580
ctgcaaacca taacggcacg agaacgactt cgtagagcgg gttctgaacg ataacgatga  11640
caaagccggc gaacatcatg aataaccctg ccaatgtcag tggcacccca agaaacaatg  11700
cgggccgtgt ggctgcgagg taaagggtcg attcttccaa acgatcagcc atcaactacc  11760
gccagtgagc gtttggccga ggaagctcgc cccaaacatg ataacaatgc cgccgacgac  11820
gccggcaacc agcccaagcg aagcccgccc gaacatccag gagatcccga tagcgacaat  11880
gccgagaaca gcgagtgact ggccgaacgg accaaggata aacgtgcata tattgttaac  11940
cattgtggcg gggtcagtgc cgccacccgc agattgcgct gcggcgggtc cggatgagga  12000
aatgctccat gcaattgcac cgcacaagct tggggcgcag ctcgatatca cgcgcatcat  12060
cgcattcgag agcgagaggc gatttagatg taaacggtat ctctcaaagc atcgcatcaa  12120
tgcgcacctc cttagtataa gtcgaataag acttgattgt cgtctgcgga tttgccgttg  12180
tcctggtgtg gcggtggcgg agcgattaaa ccgccagcgc catcctcctg cgagcggcgc  12240
tgatatgacc cccaaacatc ccacgtctct tcggatttta gcgcctcgtg atcgtctttt  12300
ggaggctcga ttaacgcggg caccagcgat tgagcagctg tttcaacttt tcgcacgtag  12360
ccgtttgcaa aaccgccgat gaaattaccg gtgttgtaag cggagatcgc ccgacgaagc  12420
gcaaattgct tctcgtcaat cgtttcgccg cctgcataac gacttttcag catgtttgca  12480
gcggcagata atgatgtgca cgcctggagc gcaccgtcag gtgtcagacc gagcatagaa  12540
aaatttcgag agtttatttg catgaggcca acatccagcg aatgccgtgc atcgagacgg  12600
tgcctgacga cttgggttgc ttggctgtga tcttgccagt gaagcgtttc gccggtcgtg  12660
ttgtcatgaa tcgctaaagg atcaaagcga ctctccacct tagctatcgc cgcaagcgta  12720
gatgtcgcaa ctgatggggc acacttgcga gcaacatggt caaactcagc agatgagagt  12780
ggcgtggcaa ggctcgacga acagaaggag accatcaagg caagagaaag cgaccccgat  12840
ctcttaagca taccttatct ccttagctcg caactaacac cgcctctccc gttggaagaa  12900
gtgcgttgtt ttatgttgaa gattatcggg agggtcggtt actcgaaaat tttcaattgc  12960
ttctttatga tttcaattga agcgagaaac ctcgcccggc gtcttggaac gcaacatgga  13020
ccgagaaccg cgcatccatg actaagcaac cggatcgacc tattcaggcc gcagttggtc  13080
aggtcaggct cagaacgaaa atgctcggcg aggttacgct gtctgtaaac ccattcgatg  13140
aacgggaagc ttccttccga ttgctcttgg caggaatatt ggcccatgcc tgcttgcgct  13200
ttgcaaatgc tcttatcgcg ttggtatcat atgccttgtc cgccagcaga aacgcactct  13260
aagcgattat ttgtaaaaat gtttcggtca tgcggcggtc atgggcttga cccgctgtca  13320
gcgcaagacg gatcggtcaa ccgtcggcat cgacaacagc gtgaatcttg gtggtcaaac  13380
cgccacggga acgtcccata cagccatcgt cttgatcccg ctgtttcccg tcgccgcatg  13440
ttggtggacg cggacacagg aactgtcaat catgacgaca ttctatcgaa agccttggaa  13500
atcacactca gaatatgatc ccagacgtct gcctcacgcc atcgtacaaa gcgattgtag  13560
caggttgtac aggaaccgta tcgatcagga acgtctgccc agggcgggcc cgtccggaag  13620
cgccacaaga tgacattgat cacccgcgtc aacgcgcggc acgcgacgcg gcttatttgg  13680
gaacaaagga ctgaacaaca gtccattcga aatcggtgac atcaaagcgg ggacgggtta  13740
tcagtggcct ccaagtcaag cctcaatgaa tcaaaatcag accgatttgc aaacctgatt  13800
tatgagtgtg cggcctaaat gatgaaatcg tccttctaga tcgcctccgt ggtgtagcaa  13860
cacctcgcag tatcgccgtg ctgaccttgg ccagggaatt gactggcaag ggtgctttca  13920
```

-continued

```
catgaccgct cttttggccg cgatagatga tttcgttgct gctttgggca cgtagaagga  13980
gagaagtcat atcggagaaa ttcctcctgg cgcgagagcc tgctctatcg cgacggcatc  14040
ccactgtcgg gaacagaccg gatcattcac gaggcgaaag tcgtcaacac atgcgttata  14100
ggcatcttcc cttgaaggat gatcttgttg ctgccaatct ggaggtgcgg cagccgcagg  14160
cagatgcgat ctcagcgcaa cttgcggcaa aacatctcac tcacctgaaa accactagcg  14220
agtctcgcga tcagacgaag gccttttact taacgacaca atatccgatg tctgcatcac  14280
aggcgtcgct atcccagtca atactaaagc ggtgcaggaa ctaaagatta ctgatgactt  14340
aggcgtgcca cgaggcctga gacgacgcgc gtagacagtt ttttgaaatc attatcaaag  14400
tgatggcctc cgctgaagcc tatcacctct gcgccggtct gtcggagaga tgggcaagca  14460
ttattacggt cttcgcgccc gtacatgcat tggacgattg cagggtcaat ggatctgaga  14520
tcatccagag gattgccgcc cttaccttcc gtttcgagtt ggagccagcc cctaaatgag  14580
acgacatagt cgacttgatg tgacaatgcc aagagagaga tttgcttaac ccgatttttt  14640
tgctcaagcg taagcctatt gaagcttgcc ggcatgacgt ccgcgccgaa agaatatcct  14700
acaagtaaaa cattctgcac accgaaatgc ttggtgtaga catcgattat gtgaccaaga  14760
tccttagcag tttcgcttgg ggaccgctcc gaccagaaat accgaagtga actgacgcca  14820
atgacaggaa tcccttccgt ctgcagatag gtaccatcga tagatctgct gcctcgcgcg  14880
tttcggtgat gacggtgaaa acctctgaca catgcagctc ccggagacgg tcacagcttg  14940
tctgtaagcg gatgccggga gcagacaagc ccgtcagggc gcgtcagcgg gtgttggcgg  15000
gtgtcggggc gcagccatga cccagtcacg tagcgatagc ggagtgtata ctggcttaac  15060
tatgcggcat cagagcagat tgtactgaga gtgcaccata tgcggtgtga aataccgcac  15120
agatgcgtaa ggagaaaata ccgcatcagg cgctcttccg cttcctcgct cactgactcg  15180
ctgcgctcgg tcgttcggct gcggcgagcg gtatcagctc actcaaaggc ggtaatacgg  15240
ttatccacag aatcagggga taacgcagga aagaacatgt gagcaaaagg ccagcaaaag  15300
gccaggaacc gtaaaaaggc cgcgttgctg gcgtttttcc ataggctccg cccccctgac  15360
gagcatcaca aaaatcgacg ctcaagtcag aggtggcgaa acccgacagg actataaaga  15420
taccaggcgt ttccccctgg aagctccctc gtgcgctctc ctgttccgac cctgccgctt  15480
accggatacc tgtccgcctt tctcccttcg ggaagcgtgg cgctttctca tagctcacgc  15540
tgtaggtatc tcagttcggt gtaggtcgtt cgctccaagc tgggctgtgt gcacgaaccc  15600
cccgttcagc ccgaccgctg cgccttatcc ggtaactatc gtcttgagtc caacccggta  15660
agacacgact tatcgccact ggcagcagcc actggtaaca ggattagcag agcgaggtat  15720
gtaggcggtg ctacagagtt cttgaagtgg tggcctaact acggctacac tagaaggaca  15780
gtatttggta tctgcgctct gctgaagcca gttaccttcg gaaaaagagt tggtagctct  15840
tgatccggca aacaaaccac cgctggtagc ggtggttttt ttgtttgcaa gcagcagatt  15900
acgcgcagaa aaaaaggatc tcaagaagat cctttgatct tttctacggg gtctgacgct  15960
cagtggaacg aaaactcacg ttaagggatt ttggtcatga gattatcaaa aaggatcttc  16020
acctagatcc ttttaaatta aaaatgaagt tttaaatcaa tctaaagtat atatgagtaa  16080
acttggtctg acagttacca atgcttaatc agtgaggcac ctatctcagc gatctgtcta  16140
tttcgttcat ccatagttgc ctgactcccc gtcgtgtaga taactacgat acgggagggc  16200
ttaccatctg gccccagtgc tgcaatgata ccgcgagacc cacgctcacc ggctccagat  16260
ttatcagcaa taaaccagcc agccggaagg gccgagcgca gaagtggtcc tgcaacttta  16320
```

-continued

```
tccgcctcca tccagtctat taattgttgc cgggaagcta gagtaagtag ttcgccagtt  16380
aatagtttgc gcaacgttgt tgccattgct gcaggggggg gggggggggg gttccattgt  16440
tcattccacg gacaaaaaca gagaaaggaa acgacagagg ccaaaaagct cgctttcagc  16500
acctgtcgtt tcctttcttt tcagagggta ttttaaataa aaacattaag ttatgacgaa  16560
gaagaacgga aacgccttaa accggaaaat ttcataaat agcgaaaacc cgcgaggtcg  16620
ccgccccgta acctgtcgga tcaccggaaa ggacccgtaa agtgataatg attatcatct  16680
acatatcaca acgtgcgtgg aggccatcaa accacgtcaa ataatcaatt atgacgcagg  16740
tatcgtatta attgatctgc atcaacttaa cgtaaaaaca acttcagaca atacaaatca  16800
gcgacactga atacggggca acctcatgtc cccccccccc cccccctgc aggcatcgtg  16860
gtgtcacgct cgtcgtttgg tatggcttca ttcagctccg gttcccaacg atcaaggcga  16920
gttacatgat cccccatgtt gtgcaaaaaa gcggttagct ccttcggtcc tccgatcgtt  16980
gtcagaagta agttggccgc agtgttatca ctcatggtta tggcagcact gcataattct  17040
cttactgtca tgccatccgt aagatgcttt tctgtgactg gtgagtactc aaccaagtca  17100
ttctgagaat agtgtatgcg gcgaccgagt tgctcttgcc cggcgtcaac acgggataat  17160
accgcgccac atagcagaac tttaaaagtg ctcatcattg gaaaacgttc ttcggggcga  17220
aaactctcaa ggatcttacc gctgttgaga tccagttcga tgtaacccac tcgtgcaccc  17280
aactgatctt cagcatcttt tactttcacc agcgtttctg ggtgagcaaa aacaggaagg  17340
caaaatgccg caaaaaaggg aataagggcg acacggaaat gttgaatact catactcttc  17400
ctttttcaat attattgaag catttatcag ggttattgtc tcatgagcgg atacatattt  17460
gaatgtattt agaaaaataa acaaataggg gttccgcgca catttccccg aaaagtgcca  17520
cctgacgtct aagaaaccat tattatcatg acattaacct ataaaaatag gcgtatcacg  17580
aggccctttc gtcttcaaga attcggagct tttgccattc tcaccggatt cagtcgtcac  17640
tcatggtgat ttctcacttg ataaccttat ttttgacgag gggaaattaa taggttgtat  17700
tgatgttgga cgagtcggaa tcgcagaccg ataccaggat cttgccatcc tatggaactg  17760
cctcggtgag ttttctcctt cattacagaa acggcttttt caaaaatatg gtattgataa  17820
tcctgatatg aataaattgc agtttcattt gatgctcgat gagtttttct aatcagaatt  17880
ggttaattgg ttgtaacact ggcagagcat tacgctgact tgacgggacg gcggctttgt  17940
tgaataaatc gaacttttgc tgagttgaag gatcagatca cgcatcttcc cgacaacgca  18000
gaccgttccg tggcaaagca aaagttcaaa atcaccaact ggtccaccta caacaaagct  18060
ctcatcaacc gtggctccct cactttctgg ctggatgatg gggcgattca ggcctggtat  18120
gagtcagcaa caccttcttc acgaggcaga cctcagcgcc agaaggccgc cagagaggcc  18180
gagcgcggcc gtgaggcttg gacgctaggg cagggcatga aaaagcccgt agcgggctgc  18240
tacgggcgtc tgacgcggtg gaaagggga ggggatgttg tctacatggc tctgctgtag  18300
tgagtgggtt gcgctccggc agcggtcctg atcaatcgtc acccttttctc ggtccttcaa  18360
cgttcctgac aacgagcctc cttttcgcca atccatcgac aatcaccgcg agtccctgct  18420
cgaacgctgc gtccggaccg gcttcgtcga aggcgtctat cgcggcccgc aacagcggcg  18480
agagcggagc ctgttcaacg gtgccgccgc gctcgccggc atcgctgtcg ccggcctgct  18540
cctcaagcac ggccccaaca gtgaagtagc tgattgtcat cagcgcattg acggcgtccc  18600
cggccgaaaa acccgcctcg cagaggaagc gaagctgcgc gtcggccgtt tccatctgcg  18660
gtgcgcccgg tcgcgtgccg gcatggatgc gcgcgccatc gcggtaggcg agcagcgcct  18720
```

gcctgaagct gcgggcattc ccgatcagaa atgagcgcca gtcgtcgtcg gctctcggca 18780
ccgaatgcgt atgattctcc gccagcatgg cttcggccag tgcgtcgagc agcgcccgct 18840
tgttcctgaa gtgccagtaa agcgccggct gctgaacccc caaccgttcc gccagtttgc 18900
gtgtcgtcag accgtctacg ccgacctcgt tcaacaggtc cagggcggca cggatcactg 18960
tattcggctg caactttgtc atgcttgaca ctttatcact gataaacata atatgtccac 19020
caacttatca gtgataaaga atccgcgcgt tcaatcggac cagcggaggc tggtccggag 19080
gccagacgtg aaacccaaca taccccctgat cgtaattctg agcactgtcg cgctcgacgc 19140
tgtcggcatc ggcctgatta tgccggtgct gccgggcctc ctgcgcgatc tggttcactc 19200
gaacgacgtc accgcccact atggcattct gctggcgctg tatgcgttgg tgcaatttgc 19260
ctgcgcacct gtgctgggcg cgctgtcgga tcgtttcggg cggcggccaa tcttgctcgt 19320
ctcgctggcc ggcgccactg tcgactacgc catcatggcg acagcgcctt tcctttgggt 19380
tctctatatc gggcggatcg tggccggcat caccggggcg actggggcgg tagccggcgc 19440
ttatattgcc gatatcactg atggcgatga gcgcgcgcgg cacttcggct tcatgagcgc 19500
ctgtttcggg ttcgggatgg tcgcgggacc tgtgctcggt gggctgatgg gcggtttctc 19560
cccccacgct ccgttcttcg ccgcggcagc cttgaacggc ctcaatttcc tgacgggctg 19620
tttccttttg ccggagtcgc acaaaggcga acgccggccg ttacgccggg aggctctcaa 19680
cccgctcgct tcgttccggt gggcccgggg catgaccgtc gtcgccgccc tgatggcggt 19740
cttcttcatc atgcaacttg tcggacaggt gccggccgcg ctttgggtca ttttcggcga 19800
ggatcgcttt cactgggacg cgaccacgat cggcatttcg cttgccgcat ttggcattct 19860
gcattcactc gcccaggcaa tgatcaccgg ccctgtagcc gcccggctcg gcgaaaggcg 19920
ggcactcatg ctcggaatga ttgccgacgg cacaggctac atcctgcttg ccttcgcgac 19980
acggggatgg atggcgttcc cgatcatggt cctgcttgct tcgggtggca tcggaatgcc 20040
ggcgctgcaa gcaatgttgt ccaggcaggt ggatgaggaa cgtcaggggc agctgcaagg 20100
ctcactggcg gcgctcacca gcctgacctc gatcgtcgga cccctcctct tcacggcgat 20160
ctatgcggct tctataacaa cgtggaacgg gtgggcatgg attgcaggcg ctgccctcta 20220
cttgctctgc ctgccggcgc tgcgtcgcgg gctttggagc ggcgcagggc aacgagccga 20280
tcgctgatcg tggaaacgat aggcctatgc catgcgggtc aaggcgactt ccggcaagct 20340
atacgcgccc taggagtgcg gttggaacgt tggcccagcc agatactccc gatcacgagc 20400
aggacgccga tgatttgaag cgcactcagc gtctgatcca agaacaacca tcctagcaac 20460
acggcggtcc ccgggctgag aaagcccagt aaggaaacaa ctgtaggttc gagtcgcgag 20520
atcccccgga accaaaggaa gtaggttaaa cccgctccga tcaggccgag ccacgccagg 20580
ccgagaacat tggttcctgt aggcatcggg attggcggat caaacactaa agctactgga 20640
acgagcagaa gtcctccggc cgccagttgc caggcggtaa aggtgagcag aggcacggga 20700
ggttgccact tgcgggtcag cacggttccg aacgccatgg aaaccgcccc cgccaggccc 20760
gctgcgacgc cgacaggatc tagcgctgcg tttggtgtca acaccaacag cgccacgccc 20820
gcagttccgc aaatagcccc caggaccgcc atcaatcgta tcgggctacc tagcagagcg 20880
gcagagatga acacgaccat cagcggctgc acagcgccta ccgtcgccgc gaccccgccc 20940
ggcaggcggt agaccgaaat aaacaacaag ctccagaata gcgaaatatt aagtgcgccg 21000
aggatgaaga tgcgcatcca ccagattccc gttggaatct gtcggacgat catcacgagc 21060
aataaacccg ccggcaacgc ccgcagcagc ataccggcga cccctcggcc tcgctgttcg 21120

-continued

```
ggctccacga aaacgccgga cagatgcgcc ttgtgagcgt ccttggggcc gtcctcctgt  21180
ttgaagaccg acagcccaat gatctcgccg tcgatgtagg cgccgaatgc cacggcatct  21240
cgcaaccgtt cagcgaacgc ctccatgggc tttttctcct cgtgctcgta aacggacccg  21300
aacatctctg gagctttctt cagggccgac aatcggatct cgcggaaatc ctgcacgtcg  21360
gccgctccaa gccgtcgaat ctgagcctta atcacaattg tcaattttaa tcctctgttt  21420
atcggcagtt cgtagagcgc gccgtgcgtc ccgagcgata ctgagcgaag caagtgcgtc  21480
gagcagtgcc cgcttgttcc tgaaatgcca gtaaagcgct ggctgctgaa cccccagccg  21540
gaactgaccc cacaaggccc tagcgtttgc aatgcaccag gtcatcattg acccaggcgt  21600
gttccaccag gccgctgcct cgcaactctt cgcaggcttc gccgacctgc tcgcgccact  21660
tcttcacgcg ggtggaatcc gatccgcaca tgaggcggaa ggtttccagc ttgagcgggt  21720
acggctcccg gtgcgagctg aaatagtcga acatccgtcg ggccgtcggc gacagcttgc  21780
ggtacttctc ccatatgaat ttcgtgtagt ggtcgccagc aaacagcacg acgatttcct  21840
cgtcgatcag gacctggcaa cgggacgttt tcttgccacg gtccaggacg cggaagcggt  21900
gcagcagcga caccgattcc aggtgcccaa cgcggtcgga cgtgaagccc atcgccgtcg  21960
cctgtaggcg cgacaggcat tcctcggcct tcgtgtaata ccggccattg atcgaccagc  22020
ccaggtcctg gcaaagctcg tagaacgtga aggtgatcgg ctcgccgata ggggtgcgct  22080
tcgcgtactc caacacctgc tgccacacca gttcgtcatc gtcggcccgc agctcgacgc  22140
cggtgtaggt gatcttcacg tccttgttga cgtggaaaat gaccttgttt tgcagcgcct  22200
cgcgcgggat tttcttgttg cgcgtggtga acagggcaga gcgggccgtg tcgtttggca  22260
tcgctcgcat cgtgtccggc cacggcgcaa tatcgaacaa ggaaagctgc atttccttga  22320
tctgctgctt cgtgtgtttc agcaacgcgg cctgcttggc ctcgctgacc tgttttgcca  22380
ggtcctcgcc ggcggttttt cgcttcttgg tcgtcatagt tcctcgcgtg tcgatggtca  22440
tcgacttcgc caaacctgcc gcctcctgtt cgagacgacg cgaacgctcc acggcggccg  22500
atggcgcggg cagggcaggg ggagccagtt gcacgctgtc gcgctcgatc ttggccgtag  22560
cttgctggac catcgagccg acggactgga aggtttcgcg gggcgcacgc atgacggtgc  22620
ggcttgcgat ggtttcggca tcctcggcgg aaaacccccgc gtcgatcagt tcttgcctgt  22680
atgccttccg gtcaaacgtc cgattcattc accctccttg cgggattgcc ccgactcacg  22740
ccggggcaat gtgcccttat tcctgatttg acccgcctgg tgccttggtg tccagataat  22800
ccaccttatc ggcaatgaag tcggtcccgt agaccgtctg gccgtccttc tcgtacttgg  22860
tattccgaat cttgccctgc acgaatacca gcgacccctt gcccaaatac ttgccgtggg  22920
cctcggcctg agagccaaaa cacttgatgc ggaagaagtc ggtgcgctcc tgcttgtcgc  22980
cggcatcgtt gcgccactct tcattaaccg ctatatcgaa aattgcttgc ggcttgttag  23040
aattgccatg acgtacctcg gtgtcacggg taagattacc gataaactgg aactgattat  23100
ggctcatatc gaaagtctcc ttgagaaagg agactctagt ttagctaaac attggttccg  23160
ctgtcaagaa ctttagcggc taaaattttg cgggccgcga ccaaaggtgc gaggggcggc  23220
ttccgctgtg tacaaccaga tatttttcac caacatcctt cgtctgctcg atgagcgggg  23280
catgacgaaa catgagctgt cggagagggc aggggtttca atttcgtttt tatcagactt  23340
aaccaacggt aaggccaacc cctcgttgaa ggtgatggag gccattgccg acgccctgga  23400
aactccccta cctcttctcc tggagtccac cgaccttgac cgcgaggcac tcgcggagat  23460
tgcgggtcat cctttcaaga gcagcgtgcc gcccggatac gaacgcatca gtgtggtttt  23520
```

```
gccgtcacat aaggcgttta tcgtaaagaa atggggcgac gacacccgaa aaaagctgcg  23580
tggaaggctc tgacgccaag ggttagggct tgcacttcct tctttagccg ctaaaacggc  23640
cccttctctg cgggccgtcg gctcgcgcat catatcgaca tcctcaacgg aagccgtgcc  23700
gcgaatggca tcgggcgggt gcgctttgac agttgttttc tatcagaacc cctacgtcgt  23760
gcggttcgat tagctgtttg tcttgcaggc taaacacttt cggtatatcg tttgcctgtg  23820
cgataatgtt gctaatgatt tgttgcgtag gggttactga aaagtgagcg ggaaagaaga  23880
gtttcagacc atcaaggagc gggccaagcg caagctggaa cgcgacatgg gtgcggacct  23940
gttggccgcg ctcaacgacc cgaaaaccgt tgaagtcatg ctcaacgcgg acggcaaggt  24000
gtggcacgaa cgccttggcg agccgatgcg gtacatctgc gacatgcggc ccagccagtc  24060
gcaggcgatt atagaaacgg tggccggatt ccacggcaaa gaggtcacgc ggcattcgcc  24120
catcctggaa ggcgagttcc ccttggatgg cagccgcttt gccggccaat tgccgccggt  24180
cgtggccgcg ccaacctttg cgatccgcaa gcgcgcggtc gccatcttca cgctggaaca  24240
gtacgtcgag gcgggcatca tgacccgcga gcaatacgag gtcattaaaa gcgccgtcgc  24300
ggcgcatcga aacatcctcg tcattggcgg tactggctcg ggcaagacca cgctcgtcaa  24360
cgcgatcatc aatgaaatgg tcgccttcaa cccgtctgag cgcgtcgtca tcatcgagga  24420
caccggcgaa atccagtgcg ccgcagagaa cgccgtccaa taccacacca gcatcgacgt  24480
ctcgatgacg ctgctgctca agacaacgct gcgtatgcgc cccgaccgca tcctggtcgg  24540
tgaggtacgt ggccccgaag cccttgatct gttgatggcc tggaacaccg ggcatgaagg  24600
aggtgccgcc accctgcacg caaacaaccc caaagcgggc ctgagccggc tcgccatgct  24660
tatcagcatg cacccggatt caccgaaacc cattgagccg ctgattggcg aggcggttca  24720
tgtggtcgtc catatcgcca ggacccctag cggccgtcga gtgcaagaaa ttctcgaagt  24780
tcttggttac gagaacggcc agtacatcac caaaaccctg taaggagtat ttccaatgac  24840
aacggctgtt ccgttccgtc tgaccatgaa tcgcggcatt ttgttctacc ttgccgtgtt  24900
cttcgttctc gctctcgcgt tatccgcgca tccggcgatg gcctcggaag gcaccggcgg  24960
cagcttgcca tatgagagct ggctgacgaa cctgcgcaac tccgtaaccg gcccggtggc  25020
cttcgcgctg tccatcatcg gcatcgtcgt cgccggcggc gtgctgatct tcggcggcga  25080
actcaacgcc ttcttccgaa ccctgatctt cctggttctg gtgatggcgc tgctggtcgg  25140
cgcgcagaac gtgatgagca ccttcttcgg tcgtggtgcc gaaatcgcgg ccctcggcaa  25200
cggggcgctg caccaggtgc aagtcgcggc ggcggatgcc gtgcgtgcgg tagcggctgg  25260
acggctcgcc taatcatggc tctgcgcacg atccccatcc gtcgcgcagg caaccgagaa  25320
aacctgttca tgggtggtga tcgtgaactg gtgatgttct cgggcctgat ggcgtttgcg  25380
ctgattttca gcgcccaaga gctgcgggcc accgtggtcg gtctgatcct gtggttcggg  25440
gcgctctatg cgttccgaat catggcgaag gccgatccga agatgcggtt cgtgtacctg  25500
cgtcaccgcc ggtacaagcc gtattacccg gcccgctcga ccccgttccg cgagaacacc  25560
aatagccaag ggaagcaata ccgatgatcc aagcaattgc gattgcaatc gcgggcctcg  25620
gcgcgcttct gttgttcatc ctctttgccc gcatccgcgc ggtcgatgcc gaactgaaac  25680
tgaaaaagca tcgttccaag gacgccggcc tggccgatct gctcaactac gccgctgtcg  25740
tcgatgacgg cgtaatcgtg ggcaagaacg gcagctttat ggctgcctgg ctgtacaagg  25800
gcgatgacaa cgcaagcagc accgaccagc agcgcgaagt agtgtccgcc cgcatcaacc  25860
aggccctcgc gggcctggga agtgggtgga tgatccatgt ggacgccgtg cggcgtcctg  25920
```

```
ctccgaacta cgcggagcgg ggcctgtcgg cgttccctga ccgtctgacg gcagcgattg  25980
aagaagagcg ctcggtcttg ccttgctcgt cggtgatgta cttcaccagc tccgcgaagt  26040
cgctcttctt gatggagcgc atggggacgt gcttggcaat cacgcgcacc ccccggccgt  26100
tttagcggct aaaaaagtca tggctctgcc ctcgggcgga ccacgcccat catgaccttg  26160
ccaagctcgt cctgcttctc ttcgatcttc gccagcaggg cgaggatcgt ggcatcaccg  26220
aaccgcgccg tgcgcgggtc gtcggtgagc cagagtttca gcaggccgcc caggcggccc  26280
aggtcgccat tgatgcgggc cagctcgcgg acgtgctcat agtccacgac gcccgtgatt  26340
ttgtagccct ggccgacggc cagcaggtag gccgacaggc tcatgccggc cgccgccgcc  26400
ttttcctcaa tcgctcttcg ttcgtctgga aggcagtaca ccttgatagg tgggctgccc  26460
ttcctggttg gcttggtttc atcagccatc cgcttgccct catctgttac gccggcggta  26520
gccggccagc ctcgcagagc aggattcccg ttgagcaccg ccaggtgcga ataagggaca  26580
gtgaagaagg aacacccgct cgcgggtggg cctacttcac ctatcctgcc cggctgacgc  26640
cgttggatac accaaggaaa gtctacacga accctttggc aaaatcctgt atatcgtgcg  26700
aaaaaggatg gatataccga aaaaatcgct ataatgaccc cgaagcaggg ttatgcagcg  26760
gaaaagcgct gcttccctgc tgttttgtgg aatatctacc gactggaaac aggcaaatgc  26820
aggaaattac tgaactgagg ggacaggcga gagacgatgc caaagagcta caccgacgag  26880
ctggccgagt gggttgaatc ccgcgcggcc aagaagcgcc ggcgtgatga ggctgcggtt  26940
gcgttcctgg cggtgagggc ggatgtcgag gcggcgttag cgtccggcta tgcgctcgtc  27000
accatttggg agcacatgcg ggaaacgggg aaggtcaagt tctcctacga gacgttccgc  27060
tcgcacgcca ggcggcacat caaggccaag cccgccgatg tgcccgcacc gcaggccaag  27120
gctgcggaac ccgcgccggc acccaagacg ccggagccac ggcggccgaa gcagggggc  27180
aaggctgaaa agccggcccc cgctgcggcc ccgaccggct tcaccttcaa cccaacaccg  27240
gacaaaaagg atctactgta atggcgaaaa ttcacatggt tttgcagggc aagggcgggg  27300
tcggcaagtc ggccatcgcc gcgatcattg cgcagtacaa gatggacaag ggcagacac  27360
ccttgtgcat cgacaccgac ccggtgaacg cgacgttcga gggctacaag gccctgaacg  27420
tccgccggct gaacatcatg gccggcgacg aaattaactc gcgcaacttc gacaccctgg  27480
tcgagctgat tgcgccgacc aaggatgacg tggtgatcga caacggtgcc agctcgttcg  27540
tgcctctgtc gcattacctc atcagcaacc aggtgccggc tctgctgcaa gaaatggggc  27600
atgagctggt catccatacc gtcgtcaccg gcggccaggc tctcctggac acggtgagcg  27660
gcttcgccca gctcgccagc cagttcccgg ccgaagcgct tttcgtggtc tggctgaacc  27720
cgtattgggg gcctatcgag catgagggca agagctttga gcagatgaag gcgtacacgg  27780
ccaacaaggc ccgcgtgtcg tccatcatcc agattccggc cctcaaggaa gaaacctacg  27840
gccgcgattt cagcgacatg ctgcaagagc ggctgacgtt cgaccaggcg ctggccgatg  27900
aatcgctcac gatcatgacg cggcaacgcc tcaagatcgt gcggcgcggc ctgtttgaac  27960
agctcgacgc ggcggccgtg ctatgagcga ccagattgaa gagctgatcc gggagattgc  28020
ggccaagcac ggcatcgccg tcggccgcga cgacccggtg ctgatcctgc ataccatcaa  28080
cgcccggctc atggccgaca gtgcggccaa gcaagaggaa atccttgccg cgttcaagga  28140
agagctggaa gggatcgccc atcgttgggg cgaggacgcc aaggccaaag cggagcggat  28200
gctgaacgcg gccctggcgg ccagcaagga cgcaatggcg aaggtaatga aggacagcgc  28260
cgcgcaggcg gccgaagcga tccgcaggga aatcgacgac ggccttggcc gccagctcgc  28320
```

-continued

```
ggccaaggtc gcggacgcgc ggcgcgtggc gatgatgaac atgatcgccg gcggcatggt  28380
gttgttcgcg gccgccctgg tggtgtgggc ctcgttatga atcgcagagg cgcagatgaa  28440
aaagcccggc gttgccgggc tttgtttttg cgttagctgg gcttgtttga caggcccaag  28500
ctctgactgc gcccgcgctc gcgctcctgg gcctgtttct tctcctgctc ctgcttgcgc  28560
atcagggcct ggtgccgtcg ggctgcttca cgcatcgaat cccagtcgcc ggccagctcg  28620
ggatgctccg cgcgcatctt gcgcgtcgcc agttcctcga tcttgggcgc gtgaatgccc  28680
atgccttcct tgatttcgcg caccatgtcc agccgcgtgt gcagggtctg caagcgggct  28740
tgctgttggg cctgctgctg ctgccaggcg gcctttgtac gcggcaggga cagcaagccg  28800
ggggcattgg actgtagctg ctgcaaacgc gcctgctgac ggtctacgag ctgttctagg  28860
cggtcctcga tgcgctccac ctggtcatgc tttgcctgca cgtagagcgc aagggtctgc  28920
tggtaggtct gctcgatggg cgcggattct aagagggcct gctgttccgt ctcggcctcc  28980
tgggccgcct gtagcaaatc ctcgccgctg ttgccgctgg actgctttac tgccggggac  29040
tgctgttgcc ctgctcgcgc cgtcgtcgca gttcggcttg cccccactcg attgactgct  29100
tcatttcgag ccgcagcgat gcgatctcgg attgcgtcaa cggacggggc agcgcggagg  29160
tgtccggctt ctccttgggt gagtcggtcg atgccatagc caaaggtttc cttccaaaat  29220
gcgtccattg ctggaccgtg tttctcattg atgcccgcaa gcatcttcgg cttgaccgcc  29280
aggtcaagcg cgccttcatg ggcggtcatg acggacgccg ccatgacctt gccgccgttg  29340
ttctcgatgt agccgcgtaa tgaggcaatg gtgccgccca tcgtcagcgt gtcatcgaca  29400
acgatgtact tctggccggg gatcacctcc ccctcgaaag tcgggttgaa cgccaggcga  29460
tgatctgaac cggctccggt tcgggcgacc ttctcccgct gcacaatgtc cgtttcgacc  29520
tcaaggccaa ggcggtcggc cagaacgacc gccatcatgg ccggaatctt gttgttcccc  29580
gccgcctcga cggcgaggac tggaacgatg cggggcttgt cgtcgccgat cagcgtcttg  29640
agctgggcaa cagtgtcgtc cgaaatcagg cgctcgacca aattaagcgc cgcttccgcg  29700
tcgccctgct tcgcagcctg gtattcaggc tcgttggtca aagaaccaag gtcgccgttg  29760
cgaaccacct tcgggaagtc tccccacggt gcgcgctcgg ctctgctgta gctgctcaag  29820
acgcctccct ttttagccgc taaaactcta acgagtgcgc ccgcgactca acttgacgct  29880
ttcggcactt acctgtgcct tgccacttgc gtcataggtg atgcttttcg cactcccgat  29940
ttcaggtact ttatcgaaat ctgaccgggc gtgcattaca aagttcttcc ccacctgttg  30000
gtaaatgctg ccgctatctg cgtggacgat gctgccgtcg tggcgctgcg acttatcggc  30060
cttttgggcc atatagatgt tgtaaatgcc aggtttcagg gccccggctt tatctacctt  30120
ctggttcgtc catgcgcctt ggttctcggt ctggacaatt ctttgcccat tcatgaccag  30180
gaggcggtgt ttcattgggt gactcctgac ggttgcctct ggtgttaaac gtgtcctggt  30240
cgcttgccgg ctaaaaaaaa gccgacctcg gcagttcgag gccggctttc cctagagccg  30300
ggcgcgtcaa ggttgttcca tctattttag tgaactgcgt tcgatttatc agttactttc  30360
ctcccgcttt gtgtttcctc ccactcgttt ccgcgtctag ccgacccctc aacatagcgg  30420
cctcttcttg ggctgccttt gcctcttgcc gcgcttcgtc acgctcggct tgcaccgtcg  30480
taaagcgctc ggcctgcctg gccgcctctt gcgccgccaa cttcctttgc tcctggtggg  30540
cctcggcgtc ggcctgcgcc ttcgctttca ccgctgccaa ctccgtgcgc aaactctccg  30600
cttcgcgcct ggtggcgtcg cgctcgccgc gaagcgcctg catttcctgg ttggccgcgt  30660
ccagggtctt gcggctctct tctttgaatg cgcgggcgtc ctggtgagcg tagtccagct  30720
```

cggcgcgcag ctcctgcgct cgacgctcca cctcgtcggc ccgctgcgtc gccagcgcgg 30780
cccgctgctc ggctcctgcc agggcggtgc gtgcttcggc cagggcttgc cgctggcgtg 30840
cggccagctc ggccgcctcg gcggcctgct gctctagcaa tgtaacgcgc gcctgggctt 30900
cttccagctc gcgggcctgc gcctcgaagg cgtcggccag ctccccgcgc acggcttcca 30960
actcgttgcg ctcacgatcc cagccggctt gcgctgcctg caacgattca ttggcaaggg 31020
cctgggcggc ttgccagagg gcggccacgg cctggttgcc ggcctgctgc accgcgtccg 31080
gcacctggac tgccagcggg gcggcctgcg ccgtgcgctg gcgtcgccat tcgcgcatgc 31140
cggcgctggc gtcgttcatg ttgacgcggg cggccttacg cactgcatcc acggtcggga 31200
agttctcccg gtcgccttgc tcgaacagct cgtccgcagc cgcaaaaatg cggtcgcgcg 31260
tctctttgtt cagttccatg ttggctccgg taattggtaa gaataataat actcttacct 31320
accttatcag cgcaagagtt tagctgaaca gttctcgact taacggcagg tttttagcg 31380
gctgaagggc aggcaaaaaa agccccgcac ggtcggcggg ggcaaagggt cagcgggaag 31440
gggattagcg ggcgtcgggc ttcttcatgc gtcggggccg cgcttcttgg gatggagcac 31500
gacgaagcgc gcacgcgcat cgtcctcggc cctatcggcc cgcgtcgcgg tcaggaactt 31560
gtcgcgcgct aggtcctccc tggtgggcac caggggcatg aactcggcct gctcgatgta 31620
ggtccactcc atgaccgcat cgcagtcgag gccgcgttcc ttcaccgtct cttgcaggtc 31680
gcggtacgcc cgctcgttga gcggctggta acgggccaat tggtcgtaaa tggctgtcgg 31740
ccatgagcgg cctttcctgt tgagccagca gccgacgacg aagccggcaa tgcaggcccc 31800
tggcacaacc aggccgacgc cgggggcagg ggatggcagc agctcgccaa ccaggaaccc 31860
cgccgcgatg atgccgatgc cggtcaacca gcccttgaaa ctatccggcc ccgaaacacc 31920
cctgcgcatt gcctggatgc tgcgccggat agcttgcaac atcaggagcc gtttcttttg 31980
ttcgtcagtc atggtccgcc ctcaccagtt gttcgtatcg gtgtcggacg aactgaaatc 32040
gcaagagctg ccggtatcgg tccagccgct gtccgtgtcg ctgctgccga agcacggcga 32100
ggggtccgcg aacgccgcag acggcgtatc cggccgcagc gcatcgccca gcatggcccc 32160
ggtcagcgag ccgccggcca ggtagcccag catggtgctg ttggtcgccc cggccaccag 32220
ggccgacgtg acgaaatcgc cgtcattccc tctggattgt tcgctgctcg gcggggcagt 32280
gcgccgcgcc ggcggcgtcg tggatggctc gggttggctg gcctgcgacg gccggcgaaa 32340
ggtgcgcagc agctcgttat cgaccggctg cggcgtcggg gccgccgcct tgcgctgcgg 32400
tcggtgttcc ttcttcggct cgcgcagctt gaacagcatg atcgcggaaa ccagcagcaa 32460
cgccgcgcct acgcctcccg cgatgtagaa cagcatcgga ttcattcttc ggtcctcctt 32520
gtagcggaac cgttgtctgt gcggcgcggg tggcccgcgc cgctgtcttt ggggatcagc 32580
cctcgatgag cgcgaccagt ttcacgtcgg caaggttcgc ctcgaactcc tggccgtcgt 32640
cctcgtactt caaccaggca tagccttccg ccggcggccg acggttgagg ataaggcggg 32700
cagggcgctc gtcgtgctcg acctggacga tggccttttt cagcttgtcc gggtccggct 32760
ccttcgcgcc cttttccttg gcgtccttac cgtcctggtc gccgtcctcg ccgtcctggc 32820
cgtcgccggc ctccgcgtca cgctcggcat cagtctggcc gttgaaggca tcgacggtgt 32880
tgggatcgcg gcccttctcg tccaggaact cgcgcagcag cttgaccgtg ccgcgcgtga 32940
tttcctgggt gtcgtcgtca agccacgcct cgacttcctc cgggcgcttc ttgaaggccg 33000
tcaccagctc gttcaccacg gtcacgtcgc gcacgcggcc ggtgttgaac gcatcggcga 33060
tcttctccgg caggtccagc agcgtgacgt gctgggtgat gaacgccggc gacttgccga 33120

```
tttccttggc gatatcgcct ttcttcttgc ccttcgccag ctcgcggcca atgaagtcgg  33180
caatttcgcg cggggtcagc tcgttgcgtt gcaggttctc gataacctgg tcggcttcgt  33240
tgtagtcgtt gtcgatgaac gccgggatgg acttcttgcc ggcccacttc gagccacggt  33300
agcggcgggc gccgtgattg atgatatagc ggcccggctg ctcctggttc tcgcgcaccg  33360
aaatgggtga cttcaccccg cgctctttga tcgtggcacc gatttccgcg atgctctccg  33420
gggaaaagcc ggggttgtcg gccgtccgcg gctgatgcgg atcttcgtcg atcaggtcca  33480
ggtccagctc gatagggccg gaaccgccct gagacgccgc aggagcgtcc aggaggctcg  33540
acaggtcgcc gatgctatcc aaccccaggc cggacggctg cgccgcgcct gcggcttcct  33600
gagcggccgc agcggtgttt ttcttggtgg tcttggcttg agccgcagtc attgggaaat  33660
ctccatcttc gtgaacacgt aatcagccag ggcgcgaacc tctttcgatg ccttgcgcgc  33720
ggccgttttc ttgatcttcc agaccggcac accggatgcg agggcatcgg cgatgctgct  33780
gcgcaggcca acggtggccg gaatcatcat cttggggtac gcggccagca gctcggcttg  33840
gtggcgcgcg tggcgcggat tccgcgcatc gaccttgctg ggcaccatgc caaggaattg  33900
cagcttggcg ttcttctggc gcacgttcgc aatggtcgtg accatcttct tgatgccctg  33960
gatgctgtac gcctcaagct cgatggggga cagcacatag tcggccgcga agagggcggc  34020
cgccaggccg acgccaaggg tcggggccgt gtcgatcagg cacacgtcga agccttggtt  34080
cgccagggcc ttgatgttcg ccccgaacag ctcgcgggcg tcgtccagcg acagccgttc  34140
ggcgttcgcc agtaccgggt tggactcgat gagggcgagg cgcgcggcct ggccgtcgcc  34200
ggctgcgggt gcggtttcgg tccagccgcc ggcagggaca gcgccgaaca gcttgcttgc  34260
atgcaggccg gtagcaaagt ccttgagcgt gtaggacgca ttgccctggg ggtccaggtc  34320
gatcacggca acccgcaagc cgcgctcgaa aaagtcgaag gcaagatgca caagggtcga  34380
agtcttgccg acgccgcctt tctggttggc cgtgaccaaa gttttcatcg tttggtttcc  34440
tgtttttttct tggcgtccgc ttcccacttc cggacgatgt acgcctgatg ttccggcaga  34500
accgccgtta cccgcgcgta cccctcgggc aagttcttgt cctcgaacgc ggcccacacg  34560
cgatgcaccg cttgcgacac tgcgcccctg gtcagtccca gcgacgttgc gaacgtcgcc  34620
tgtggcttcc catcgactaa gacgccccgc gctatctcga tggtctgctg ccccacttcc  34680
agcccctgga tcgcctcctg gaactggctt tcggtaagcc gtttcttcat ggataacacc  34740
cataatttgc tccgcgcctt ggttgaacat agcggtgaca gccgccagca catgagagaa  34800
gtttagctaa acatttctcg cacgtcaaca cctttagccg ctaaaactcg tccttggcgt  34860
aacaaaacaa aagcccggaa accgggcttt cgtctcttgc cgcttatggc tctgcacccg  34920
gctccatcac caacaggtcg cgcacgcgct tcactcggtt gcggatcgac actgccagcc  34980
caacaaagcc ggttgccgcc gccgccagga tcgcgccgat gatgccggcc acaccggcca  35040
tcgcccacca ggtcgccgcc ttccggttcc attcctgctg gtactgcttc gcaatgctgg  35100
acctcggctc accataggct gaccgctcga tggcgtatgc cgcttctccc cttggcgtaa  35160
aacccagcgc cgcaggcggc attgccatgc tgcccgccgc tttcccgacc acgacgcgcg  35220
caccaggctt gcggtccaga ccttcggcca cggcgagctg cgcaaggaca taatcagccg  35280
ccgacttggc tccacgcgcc tcgatcagct cttgcactcg cgcgaaatcc ttggcctcca  35340
cggccgccat gaatcgcgca cgcggcgaag gctccgcagg gccggcgtcg tgatcgccgc  35400
cgagaatgcc cttcaccaag ttcgacgaca cgaaaatcat gctgacggct atcaccatca  35460
tgcagacgga tcgcacgaac ccgctgaatt gaacacgagc acggcacccg cgaccactat  35520
```

gccaagaatg cccaaggtaa aaattgccgg ccccgccatg aagtccgtga atgccccgac 35580
ggccgaagtg aagggcaggc cgccacccag gccgccgccc tcactgcccg gcacctggtc 35640
gctgaatgtc gatgccagca cctgcggcac gtcaatgctt ccgggcgtcg cgctcgggct 35700
gatcgcccat cccgttactg ccccgatccc ggcaatggca aggactgcca gcgctgccat 35760
ttttggggtg aggccgttcg cggccgaggg gcgcagcccc tggggggatg ggaggcccgc 35820
gttagcgggc cgggagggtt cgagaagggg gggcaccccc cttcggcgtg cgcggtcacg 35880
cgcacagggc gcagccctgg ttaaaaacaa ggtttataaa tattggttta aaagcaggtt 35940
aaaagacagg ttagcggtgg ccgaaaaacg ggcggaaacc cttgcaaatg ctggattttc 36000
tgcctgtgga cagcccctca aatgtcaata ggtgcgcccc tcatctgtca gcactctgcc 36060
cctcaagtgt caaggatcgc gcccctcatc tgtcagtagt cgcgcccctc aagtgtcaat 36120
accgcagggc acttatcccc aggcttgtcc acatcatctg tgggaaactc gcgtaaaatc 36180
aggcgttttc gccgatttgc gaggctggcc agctccacgt cgccggccga aatcgagcct 36240
gcccctcatc tgtcaacgcc gcgccgggtg agtcggcccc tcaagtgtca acgtccgccc 36300
ctcatctgtc agtgagggcc aagttttccg cgaggtatcc acaacgccgg cggccgcggt 36360
gtctcgcaca cggcttcgac ggcgtttctg gcgcgtttgc agggccatag acggccgcca 36420
gcccagcggc gagggcaacc agcccggtga gcgtcggaaa ggcgctggaa gccccgtagc 36480
gacgcggaga ggggcgagac aagccaaggg cgcaggctcg atgcgcagca cgacatagcc 36540
ggttctcgca aggacgagaa tttccctgcg gtgcccctca agtgtcaatg aaagtttcca 36600
acgcgagcca ttcgcgagag ccttgagtcc acgctagatg agagctttgt tgtaggtgga 36660
ccagttggtg attttgaact tttgctttgc cacggaacgg tctgcgttgt cgggaagatg 36720
cgtgatctga tccttcaact cagcaaaagt tcgatttatt caacaaagcc acgttgtgtc 36780
tcaaaatctc tgatgttaca ttgcacaaga taaaaatata tcatcatgaa caataaaact 36840
gtctgcttac ataaacagta atacaagggg tgttatgagc catattcaac gggaaacgtc 36900
ttgctcgac 36909

<210> SEQ ID NO 38
<211> LENGTH: 13019
<212> TYPE: DNA
<213> ORGANISM: Artificial
<220> FEATURE:
<223> OTHER INFORMATION: Destination vector PHP23235

<400> SEQUENCE: 38
gttacccgga ccgaagctta gcccgggcat gcctgcagtg cagcgtgacc cggtcgtgcc 60
cctctctaga gataatgagc attgcatgtc taagttataa aaaattacca catatttttt 120
ttgtcacact tgtttgaagt gcagtttatc tatctttata catatattta aactttactc 180
tacgaataat ataatctata gtactacaat aatatcagtg ttttagagaa tcatataaat 240
gaacagttag acatggtcta aaggacaatt gagtattttg acaacaggac tctacagttt 300
tatcttttta gtgtgcatgt gttctccttt ttttttgcaa atagcttcac ctatataata 360
cttcatccat tttattagta catccattta gggtttaggg ttaatggttt ttatagacta 420 attttttag tacatctatt ttattctatt ttagcctcta aattaagaaa actaaaactc 480
tattttagtt tttttattta ataatttaga tataaaatag aataaaataa agtgactaaa 540
aattaaacaa ataccettta agaaattaaa aaaactaagg aaacattttt cttgtttcga 600
gtagataatg ccagcctgtt aaacgccgtc gacgagtcta acggacacca accagcgaac 660

```
cagcagcgtc gcgtcgggcc aagcgaagca gacggcacgg catctctgtc gctgcctctg    720
gacccctctc gagagttccg ctccaccgtt ggacttgctc cgctgtcggc atccagaaat    780
tgcgtggcgg agcggcagac gtgagccggc acggcaggcg gcctcctcct cctctcacgg    840
cacggcagct acgggggatt cctttcccac cgctccttcg ctttcccttc ctcgcccgcc    900
gtaataaata gacacccct ccacaccctc tttccccaac ctcgtgttgt tcggagcgca     960
cacacacaca accagatctc ccccaaatcc acccgtcggc acctccgctt caaggtacgc   1020
cgctcgtcct cccccccccc ccctctctac cttctctaga tcggcgttcc ggtccatggt   1080
tagggcccgg tagttctact tctgttcatg tttgtgttag atccgtgttt gtgttagatc   1140
cgtgctgcta gcgttcgtac acggatgcga cctgtacgtc agacacgttc tgattgctaa   1200
cttgccagtg tttctctttg gggaatcctg ggatggctct agccgttccg cagacgggat   1260
cgatttcatg attttttttg tttcgttgca tagggtttgg tttgcccttt tcctttattt   1320
caatatatgc cgtgcacttg tttgtcgggt catcttttca tgcttttttt tgtcttggtt   1380
gtgatgatgt ggtctggttg ggcggtcgtt ctagatcgga gtagaattct gtttcaaact   1440
acctggtgga tttattaatt ttggatctgt atgtgtgtgc catacatatt catagttacg   1500
aattgaagat gatggatgga aatatcgatc taggataggt atacatgttg atgcgggttt   1560
tactgatgca tatacagaga tgctttttgt tcgcttggtt gtgatgatgt ggtgtggttg   1620
ggcggtcgtt cattcgttct agatcggagt agaatactgt ttcaaactac ctggtgtatt   1680
tattaatttt ggaactgtat gtgtgtgtca tacatcttca tagttacgag tttaagatgg   1740
atggaaatat cgatctagga taggtataca tgttgatgtg ggttttactg atgcatatac   1800
atgatggcat atgcagcatc tattcatatg ctctaacctt gagtacctat ctattataat   1860
aaacaagtat gttttataat tattttgatc ttgatatact tggatgatgg catatgcagc   1920
agctatatgt ggattttttt agccctgcct tcatacgcta tttatttgct tggtactgtt   1980
tcttttgtcg atgctcaccc tgttgtttgg tgttacttct gcaggtcgac tctagaggat   2040
ccacaagttt gtacaaaaaa gctgaacgag aaacgtaaaa tgatataaat atcaatatat   2100
taaattagat tttgcataaa aaacagacta cataatactg taaaacacaa catatccagt   2160
cactatggcg gccgcattag gcaccccagg ctttacactt tatgcttccg gctcgtataa   2220
tgtgtggatt ttgagttagg atttaaatac gcgttgatcc ggcttactaa aagccagata   2280
acagtatgcg tatttgcgcg ctgatttttg cggtataaga atatatactg atatgtatac   2340
ccgaagtatg tcaaaaagag gtatgctatg aagcagcgta ttacagtgac agttgacagc   2400
gacagctatc agttgctcaa ggcatatatg atgtcaatat ctccggtctg gtaagcacaa   2460
ccatgcagaa tgaagcccgt cgtctgcgtg ccgaacgctg gaaagcggaa aatcaggaag   2520
ggatggctga ggtcgcccgg tttattgaaa tgaacggctc ttttgctgac gagaacaggg   2580
gctggtgaaa tgcagtttaa ggtttacacc tataaaagag agagccgtta tcgtctgttt   2640
gtggatgtac agagtgatat cattgacacg cccggtcgac ggatggtgat ccccctggcc   2700
agtgcacgtc tgctgtcaga taaagtctcc cgtgaacttt acccggtggt gcatatcggg   2760
gatgaaagct ggcgcatgat gaccaccgat atggccagtg tgccggtctc cgttatcggg   2820
gaagaagtgg ctgatctcag ccaccgcgaa aatgacatca aaaacgccat taacctgatg   2880
ttctggggaa tataaatgtc aggctccctt atacacagcc agtctgcagg tcgaccatag   2940
tgactggata tgttgtgttt tacagtatta tgtagtctgt tttttatgca aaatctaatt   3000
taatatattg atatttatat cattttacgt ttctcgttca gctttcttgt acaaagtggt   3060
```

-continued

```
gttaacctag acttgtccat cttctggatt ggccaactta attaatgtat gaaataaaag   3120
gatgcacaca tagtgacatg ctaatcacta taatgtgggc atcaaagttg tgtgttatgt   3180
gtaattacta gttatctgaa taaaagagaa agagatcatc catatttctt atcctaaatg   3240
aatgtcacgt gtctttataa ttctttgatg aaccagatgc atttcattaa ccaaatccat   3300
atacatataa atattaatca tatataatta atatcaattg ggttagcaaa acaaatctag   3360
tctaggtgtg ttttgcgaat tgcggccgcc accgcggtgg agctcgaatt ccggtccggg   3420
tcacctttgt ccaccaagat ggaactgcgg ccgctcatta attaagtcag gcgcgcctct   3480
agttgaagac acgttcatgt cttcatcgta agaagacact cagtagtctt cggccagaat   3540
ggccatctgg attcagcagg cctagaaggc catttaaatc ctgaggatct ggtcttccta   3600
aggacccggg atatcggacc gattaaactt taattcggtc cgaagcttgc atgcctgcag   3660
tgcagcgtga cccggtcgtg cccctctcta gagataatga gcattgcatg tctaagttat   3720
aaaaaattac cacatatttt ttttgtcaca cttgtttgaa gtgcagttta tctatcttta   3780
tacatatatt taaactttac tctacgaata atataatcta tagtactaca ataatatcag   3840
tgttttagag aatcatataa atgaacagtt agacatggtc taaaggacaa ttgagtattt   3900
tgacaacagg actctacagt tttatctttt tagtgtgcat gtgttctcct ttttttttgc   3960
aaatagcttc acctatataa tacttcatcc attttattag tacatccatt tagggtttag   4020
ggttaatggt ttttatagac taattttttt agtacatcta ttttattcta ttttagcctc   4080
taaattaaga aaactaaaac tctattttag ttttttttatt taataattta gatataaaat   4140
agaataaaat aaagtgacta aaaattaaac aaataccctt taagaaatta aaaaaactaa   4200
ggaaacattt ttcttgtttc gagtagataa tgccagcctg ttaaacgccg tcgacgagtc   4260
taacggacac caaccagcga accagcagcg tcgcgtcggg ccaagcgaag cagacggcac   4320
ggcatctctg tcgctgcctc tggacccctc tcgagagttc cgctccaccg ttggacttgc   4380
tccgctgtcg gcatccagaa attgcgtggc ggagcggcag acgtgagccg gcacggcagg   4440
cggcctcctc ctcctctcac ggcaccggca gctacggggg attcctttcc caccgctcct   4500
tcgctttccc ttcctcgccc gccgtaataa atagacaccc cctccacacc ctctttcccc   4560
aacctcgtgt tgttcggagc gcacacacac acaaccagat ctcccccaaa tccacccgtc   4620
ggcacctccg cttcaaggta cgccgctcgt cctccccccc cccctctct accttctcta   4680
gatcggcgtt ccggtccatg catggttagg gcccggtagt tctacttctg ttcatgtttg   4740
tgttagatcc gtgtttgtgt tagatccgtg ctgctagcgt tcgtacacgg atgcgacctg   4800
tacgtcagac acgttctgat tgctaacttg ccagtgtttc tctttgggga atcctgggat   4860
ggctctagcc gttccgcaga cgggatcgat ttcatgattt tttttgtttc gttgcatagg   4920
gtttggtttg cccttttcct ttatttcaat atatgccgtg cacttgtttg tcgggtcatc   4980
ttttcatgct ttttttgtc ttggttgtga tgatgtggtc tggttgggcg gtcgttctag   5040
atcggagtag aattctgttt caaactacct ggtggattta ttaattttgg atctgtatgt   5100
gtgtgccata catattcata gttacgaatt gaagatgatg gatggaaata tcgatctagg   5160
ataggtatac atgttgatgc gggttttact gatgcatata cagagatgct tttgttcgc   5220
ttggttgtga tgatgtggtg tggttgggcg gtcgttcatt cgttctagat cggagtagaa   5280
tactgtttca aactacctgg tgtatttatt aattttggaa ctgtatgtgt gtgtcataca   5340
tcttcatagt tacgagttta agatggatgg aaatatcgat ctaggatagg tatacatgtt   5400
gatgtgggtt ttactgatgc atatacatga tggcatatgc agcatctatt catatgctct   5460
```

-continued

```
aaccttgagt acctatctat tataataaac aagtatgttt tataattatt ttgatcttga   5520

tatacttgga tgatggcata tgcagcagct atatgtggat ttttttagcc ctgccttcat   5580

acgctattta tttgcttggt actgtttctt ttgtcgatgc tcaccctgtt gtttggtgtt   5640

acttctgcag gtcgacttta acttagccta ggatccacac gacaccatgt cccccgagcg   5700

ccgccccgtc gagatccgcc cggccaccgc cgccgacatg gccgccgtgt gcgacatcgt   5760

gaaccactac atcgagacct ccaccgtgaa cttccgcacc gagccgcaga ccccgcagga   5820

gtggatcgac gacctggagc gcctccagga ccgctacccg tggctcgtgg ccgaggtgga   5880

gggcgtggtg gccggcatcg cctacgccgg cccgtggaag gcccgcaacg cctacgactg   5940

gaccgtggag tccaccgtgt acgtgtccca ccgccaccag cgcctcggcc tcggctccac   6000

cctctacacc cacctcctca agagcatgga ggcccagggc ttcaagtccg tggtggccgt   6060

gatcggcctc ccgaacgacc cgtccgtgcg cctccacgag gccctcggct acaccgcccg   6120

cggcaccctc cgcgccgccg gctacaagca cggcggctgg cacgacgtcg gcttctggca   6180

gcgcgacttc gagctgccgg ccccgccgcg cccggtgcgc ccggtgacgc agatctgagt   6240

cgaaacctag acttgtccat cttctggatt ggccaactta attaatgtat gaaataaaag   6300

gatgcacaca tagtgacatg ctaatcacta taatgtgggc atcaaagttg tgtgttatgt   6360

gtaattacta gttatctgaa taaaagagaa agagatcatc catatttctt atcctaaatg   6420

aatgtcacgt gtctttataa ttctttgatg aaccagatgc atttcattaa ccaaatccat   6480

atacatataa atattaatca tatataatta atatcaattg ggttagcaaa acaaatctag   6540

tctaggtgtg ttttgcgaat tgcggccgcc accgcggtgg agctcgaatt cattccgatt   6600

aatcgtggcc tcttgctctt caggatgaag agctatgttt aaacgtgcaa gcgctactag   6660

acaattcagt acattaaaaa cgtccgcaat gtgttattaa gttgtctaag cgtcaatttg   6720

tttacaccac aatatatcct gccaccagcc agccaacagc tccccgaccg gcagctcggc   6780

acaaaatcac cactcgatac aggcagccca tcagtccggg acggcgtcag cgggagagcc   6840

gttgtaaggc ggcagacttt gctcatgtta ccgatgctat tcggaagaac ggcaactaag   6900

ctgccgggtt tgaaacacgg atgatctcgc ggagggtagc atgttgattg taacgatgac   6960

agagcgttgc tgcctgtgat caaatatcat ctccctcgca gagatccgaa ttatcagcct   7020

tcttattcat ttctcgctta accgtgacag gctgtcgatc ttgagaacta tgccgacata   7080

ataggaaatc gctggataaa gccgctgagg aagctgagtg gcgctatttc tttagaagtg   7140

aacgttgacg atcgtcgacc gtaccccgat gaattaattc ggacgtacgt tctgaacaca   7200

gctggatact tacttgggcg attgtcatac atgacatcaa caatgtaccc gtttgtgtaa   7260

ccgtctcttg gaggttcgta tgacactagt ggttcccctc agcttgcgac tagatgttga   7320

ggcctaacat tttattagag agcaggctag ttgcttagat acatgatctt caggccgtta   7380

tctgtcaggg caagcgaaaa ttggccattt atgacgacca atgccccgca gaagctccca   7440

tctttgccgc catagacgcc gcgccccccct tttggggtgt agaacatcct tttgccagat   7500

gtggaaaaga agttcgttgt cccattgttg gcaatgacgt agtagccggc gaaagtgcga   7560

gacccatttg cgctatatat aagcctacga tttccgttgc gactattgtc gtaattggat   7620

gaactattat cgtagttgct ctcagagttg tcgtaatttg atggactatt gtcgtaattg   7680

cttatggagt tgtcgtagtt gcttggagaa atgtcgtagt tggatgggga gtagtcatag   7740

ggaagacgag cttcatccac taaaacaatt ggcaggtcag caagtgcctg ccccgatgcc   7800

atcgcaagta cgaggcttag aaccaccttc aacagatcgc gcatagtctt ccccagctct   7860
```

ctaacgcttg agttaagccg cgccgcgaag cggcgtcggc ttgaacgaat tgttagacat 7920
tatttgccga ctaccttggt gatctcgcct ttcacgtagt gaacaaattc ttccaactga 7980
tctgcgcgcg aggccaagcg atcttcttgt ccaagataag cctgcctagc ttcaagtatg 8040
acgggctgat actgggccgg caggcgctcc attgcccagt cggcagcgac atccttcggc 8100
gcgattttgc cggttactgc gctgtaccaa atgcgggaca acgtaagcac tacatttcgc 8160
tcatcgccag cccagtcggg cggcgagttc catagcgtta aggtttcatt tagcgcctca 8220
aatagatcct gttcaggaac cggatcaaag agttcctccg ccgctggacc taccaaggca 8280
acgctatgtt ctcttgcttt tgtcagcaag atagccagat caatgtcgat cgtggctggc 8340
tcgaagatac ctgcaagaat gtcattgcgc tgccattctc caaattgcag ttcgcgctta 8400
gctggataac gccacggaat gatgtcgtcg tgcacaacaa tggtgacttc tacagcgcgg 8460
agaatctcgc tctctccagg ggaagccgaa gtttccaaaa ggtcgttgat caaagctcgc 8520
cgcgttgttt catcaagcct tacagtcacc gtaaccagca aatcaatatc actgtgtggc 8580
ttcaggccgc catccactgc ggagccgtac aaatgtacgg ccagcaacgt cggttcgaga 8640
tggcgctcga tgacgccaac tacctctgat agttgagtcg atacttcggc gatcaccgct 8700
tccctcatga tgtttaactc ctgaattaag ccgcgccgcg aagcggtgtc ggcttgaatg 8760
aattgttagg cgtcatcctg tgctcccgag aaccagtacc agtacatcgc tgtttcgttc 8820
gagacttgag gtctagtttt atacgtgaac aggtcaatgc cgccgagagt aaagccacat 8880
tttgcgtaca aattgcaggc aggtacattg ttcgtttgtg tctctaatcg tatgccaagg 8940
agctgtctgc ttagtgccca ctttttcgca aattcgatga gactgtgcgc gactcctttg 9000
cctcggtgcg tgtgcgacac aacaatgtgt tcgatagagg ctagatcgtt ccatgttgag 9060
ttgagttcaa tcttcccgac aagctcttgg tcgatgaatg cgccatagca agcagagtct 9120
tcatcagagt catcatccga gatgtaatcc ttccggtagg ggctcacact tctggtagat 9180
agttcaaagc cttggtcgga taggtgcaca tcgaacactt cacgaacaat gaaatggttc 9240
tcagcatcca atgtttccgc cacctgctca gggatcaccg aaatcttcat atgacgccta 9300
acgcctggca cagcggatcg caaacctggc gcggcttttg gcacaaaagg cgtgacaggt 9360
ttgcgaatcc gttgctgcca cttgttaacc cttttgccag atttggtaac tataatttat 9420
gttagaggcg aagtcttggg taaaaactgg cctaaaattg ctggggattt caggaaagta 9480
aacatcacct tccggctcga tgtctattgt agatatatgt agtgtatcta cttgatcggg 9540
ggatctgctg cctcgcgcgt ttcggtgatg acggtgaaaa cctctgacac atgcagctcc 9600
cggagacggt cacagcttgt ctgtaagcgg atgccgggag cagacaagcc cgtcagggcg 9660
cgtcagcggg tgttggcggg tgtcggggcg cagccatgac ccagtcacgt agcgatagcg 9720
gagtgtatac tggcttaact atgcggcatc agagcagatt gtactgagag tgcaccatat 9780
gcggtgtgaa ataccgcaca gatgcgtaag gagaaaatac cgcatcaggc gctcttccgc 9840
ttcctcgctc actgactcgc tgcgctcggt cgttcggctg cggcgagcgg tatcagctca 9900
ctcaaaggcg gtaatacggt tatccacaga atcaggggat aacgcaggaa agaacatgtg 9960
agcaaaaggc cagcaaaagg ccaggaaccg taaaaaggcc gcgttgctgg cgtttttcca 10020
taggctccgc ccccctgacg agcatcacaa aaatcgacgc tcaagtcaga ggtggcgaaa 10080
cccgacagga ctataaagat accaggcgtt tccccctgga agctccctcg tgcgctctcc 10140
tgttccgacc ctgccgctta ccggatacct gtccgccttt ctcccttcgg gaagcgtggc 10200
gctttctcat agctcacgct gtaggtatct cagttcggtg taggtcgttc gctccaagct 10260

```
gggctgtgtg cacgaacccc ccgttcagcc cgaccgctgc gccttatccg gtaactatcg  10320
tcttgagtcc aacccggtaa gacacgactt atcgccactg gcagcagcca ctggtaacag  10380
gattagcaga gcgaggtatg taggcggtgc tacagagttc ttgaagtggt ggcctaacta  10440
cggctacact agaaggacag tatttggtat ctgcgctctg ctgaagccag ttaccttcgg  10500
aaaaagagtt ggtagctctt gatccggcaa acaaaccacc gctggtagcg gtggtttttt  10560
tgtttgcaag cagcagatta cgcgcagaaa aaaaggatct caagaagatc ctttgatctt  10620
ttctacgggg tctgacgctc agtggaacga aaactcacgt taagggattt tggtcatgag  10680
attatcaaaa aggatcttca cctagatcct tttaaattaa aaatgaagtt ttaaatcaat  10740
ctaaagtata tatgagtaaa cttggtctga cagttaccaa tgcttaatca gtgaggcacc  10800
tatctcagcg atctgtctat ttcgttcatc catagttgcc tgactccccg tcgtgtagat  10860
aactacgata cgggagggct taccatctgg ccccagtgct gcaatgatac cgcgagaccc  10920
acgctcaccg gctccagatt tatcagcaat aaaccagcca gccggaaggg ccgagcgcag  10980
aagtggtcct gcaactttat ccgcctccat ccagtctatt aattgttgcc gggaagctag  11040
agtaagtagt tcgccagtta atagtttgcg caacgttgtt gccattgctg caggggggggg  11100
gggggggggg gacttccatt gttcattcca cggacaaaaa cagagaaagg aaacgacaga  11160
ggccaaaaag cctcgctttc agcacctgtc gtttcctttc ttttcagagg gtattttaaa  11220
taaaaacatt aagttatgac gaagaagaac ggaaacgcct taaaccggaa aattttcata  11280
aatagcgaaa acccgcgagg tcgccgcccc gtaacctgtc ggatcaccgg aaaggacccg  11340
taaagtgata atgattatca tctacatatc acaacgtgcg tggaggccat caaaccacgt  11400
caaataatca attatgacgc aggtatcgta ttaattgatc tgcatcaact taacgtaaaa  11460
acaacttcag acaatacaaa tcagcgacac tgaatacggg gcaacctcat gtcccccccc  11520
cccccccccc tgcaggcatc gtggtgtcac gctcgtcgtt tggtatggct tcattcagct  11580
ccggttccca acgatcaagg cgagttacat gatcccccat gttgtgcaaa aaagcggtta  11640
gctccttcgg tcctccgatc gttgtcagaa gtaagttggc cgcagtgtta tcactcatgg  11700
ttatggcagc actgcataat tctcttactg tcatgccatc cgtaagatgc ttttctgtga  11760
ctggtgagta ctcaaccaag tcattctgag aatagtgtat gcggcgaccg agttgctctt  11820
gcccggcgtc aacacgggat aataccgcgc cacatagcag aactttaaaa gtgctcatca  11880
ttggaaaacg ttcttcgggg cgaaaactct caaggatctt accgctgttg agatccagtt  11940
cgatgtaacc cactcgtgca cccaactgat cttcagcatc ttttactttc accagcgttt  12000
ctgggtgagc aaaaacagga aggcaaaatg ccgcaaaaaa gggaataagg gcgacacgga  12060
aatgttgaat actcatactc ttcctttttc aatattattg aagcatttat cagggttatt  12120
gtctcatgag cggatacata tttgaatgta tttagaaaaa taaacaaata ggggttccgc  12180
gcacatttcc ccgaaaagtg ccacctgacg tctaagaaac cattattatc atgacattaa  12240
cctataaaaa taggcgtatc acgaggccct ttcgtcttca agaattggtc gacgatcttg  12300
ctgcgttcgg atattttcgt ggagttcccg ccacagaccc ggattgaagg cgagatccag  12360
caactcgcgc cagatcatcc tgtgacggaa ctttggcgcg tgatgactgg ccaggacgtc  12420
ggccgaaaga gcgacaagca gatcacgctt ttcgacagcg tcggatttgc gatcgaggat  12480
ttttcggcgc tgcgctacgt ccgcgaccgc gttgagggat caagccacag cagcccactc  12540
gaccttctag ccgacccaga cgagccaagg gatctttttg gaatgctgct ccgtcgtcag  12600
gctttccgac gtttgggtgg ttgaacagaa gtcattatcg tacggaatgc caagcactcc  12660
```

cgaggggaac cctgtggttg gcatgcacat acaaatggac gaacggataa accttttcac 12720
gcccttttaa atatccgtta ttctaataaa cgctcttttc tcttaggttt acccgccaat 12780
atatcctgtc aaacactgat agtttaaact gaaggcggga aacgacaatc tgatcatgag 12840
cggagaatta agggagtcac gttatgaccc ccgccgatga cgcgggacaa gccgttttac 12900
gtttggaact gacagaaccg caacgttgaa ggagccactc agcaagctgg tacgattgta 12960
atacgactca ctatagggcg aattgagcgc tgtttaaacg ctcttcaact ggaagagcg 13019

<210> SEQ ID NO 39
<211> LENGTH: 15663
<212> TYPE: DNA
<213> ORGANISM: Artificial
<220> FEATURE:
<223> OTHER INFORMATION: Destination vector PHP28647

<400> SEQUENCE: 39
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagcaag 180
ctggtacgat tgtaatacga ctcactatag ggcgaattga gcgctgttta aacgctcttc 240
aactggaaga gcggttaccc ggaccgaagc ttgcatgcct gcagtgcagc gtgacccggt 300
cgtgcccctc tctagagata atgagcattg catgtctaag ttataaaaaa ttaccacata 360 tttttttgt cacacttgtt tgaagtgcag tttatctatc tttatacata tatttaaact 420
ttactctacg aataatataa tctatagtac tacaataata tcagtgtttt agagaatcat 480
ataaatgaac agttagacat ggtctaaagg acaattgagt attttgacaa caggactcta 540
cagttttatc tttttagtgt gcatgtgttc tccttttttt ttgcaaatag cttcacctat 600
ataatacttc atccatttta ttagtacatc catttagggt ttagggttaa tggtttttat 660
agactaattt ttttagtaca tctattttat tctattttag cctctaaatt aagaaaacta 720
aaactctatt ttagtttttt tatttaataa tttagatata aaatagaata aaataaagtg 780
actaaaaatt aaacaaatac cctttaagaa attaaaaaaa ctaaggaaac atttttcttg 840
tttcgagtag ataatgccag cctgttaaac gccgtcgacg agtctaacgg acaccaacca 900
gcgaaccagc agcgtcgcgt cgggccaagc gaagcagacg gcacggcatc tctgtcgctg 960
cctctggacc cctctcgaga gttccgctcc accgttggac ttgctccgct gtcggcatcc 1020
agaaattgcg tggcggagcg gcagacgtga gccggcacgg caggcggcct cctcctcctc 1080
tcacggcacg gcagctacgg gggattcctt tcccaccgct ccttcgcttt cccttcctcg 1140
cccgccgtaa taaatagaca ccccctccac accctctttc cccaacctcg tgttgttcgg 1200
agcgcacaca cacacaacca gatctccccc aaatccaccc gtcggcacct ccgcttcaag 1260
gtacgccgct cgtcctcccc ccccccccct ctctaccttc tctagatcgg cgttccggtc 1320
catggttagg gcccggtagt tctacttctg ttcatgtttg tgttagatcc gtgtttgtgt 1380
tagatccgtg ctgctagcgt tcgtacacgg atgcgacctg tacgtcagac acgttctgat 1440
tgctaacttg ccagtgtttc tctttgggga atcctgggat ggctctagcc gttccgcaga 1500
cgggatcgat ttcatgattt tttttgtttc gttgcatagg gtttggtttg cccttttcct 1560
ttatttcaat atatgccgtg cacttgtttg tcgggtcatc ttttcatgct tttttttgtc 1620
ttggttgtga tgatgtggtc tggttgggcg gtcgttctag atcggagtag aattctgttt 1680
caaactacct ggtggattta ttaattttgg atctgtatgt gtgtgccata catattcata 1740

```
gttacgaatt gaagatgatg gatggaaata tcgatctagg ataggtatac atgttgatgc   1800
gggttttact gatgcatata cagagatgct tttgttcgc ttggttgtga tgatgtggtg   1860
tggttgggcg gtcgttcatt cgttctagat cggagtagaa tactgtttca aactacctgg   1920
tgtatttatt aattttggaa ctgtatgtgt gtgtcataca tcttcatagt tacgagttta   1980
agatggatgg aaatatcgat ctaggatagg tatacatgtt gatgtgggtt ttactgatgc   2040
atatacatga tggcatatgc agcatctatt catatgctct aaccttgagt acctatctat   2100
tataataaac aagtatgttt tataattatt ttgatcttga tatacttgga tgatggcata   2160
tgcagcagct atatgtggat ttttttagcc ctgccttcat acgctattta tttgcttggt   2220
actgtttctt ttgtcgatgc tcaccctgtt gtttggtgtt acttctgcag gtcgactcta   2280
gaggatctac aagtttgtac aaaaaagctg aacgagaaac gtaaaatgat ataaatatca   2340
atatattaaa ttagattttg cataaaaaac agactacata atactgtaaa acacaacata   2400
tccagtcact atggcggccg cattaggcac cccaggcttt acactttatg cttccggctc   2460
gtataatgtg tggattttga gttaggatcc ggcgagattt tcaggagcta aggaagctaa   2520
aatggagaaa aaaatcactg gatataccac cgttgatata tcccaatggc atcgtaaaga   2580
acattttgag gcatttcagt cagttgctca atgtacctat aaccagaccg ttcagctgga   2640
tattacggcc tttttaaaga ccgtaaagaa aaataagcac aagttttatc cggcctttat   2700
tcacattctt gcccgcctga tgaatgctca tccggaattc cgtatggcaa tgaaagacgg   2760
tgagctggtg atatgggata gtgttcaccc ttgttacacc gttttccatg agcaaactga   2820
aacgttttca tcgctctgga gtgaatacca cgacgatttc cggcagtttc tacacatata   2880
ttcgcaagat gtggcgtgtt acggtgaaaa cctggcctat ttccctaaag ggtttattga   2940
gaatatgttt ttcgtctcag ccaatccctg ggtgagtttc accagttttg atttaaacgt   3000
ggccaatatg gacaacttct tcgcccccgt tttcaccatg ggcaaatatt atacgcaagg   3060
cgacaaggtg ctgatgccgc tggcgattca ggttcatcat gccgtctgtg atggcttcca   3120
tgtcggcaga atgcttaatg aattacaaca gtactgcgat gagtggcagg gcggggcgta   3180
aacgcgtgga tccggcttac taaaagccag ataacagtat gcgtatttgc gcgctgattt   3240
ttgcggtata agaatatata ctgatatgta tacccgaagt atgtcaaaaa gaggtatgct   3300
atgaagcagc gtattacagt gacagttgac agcgacagct atcagttgct caaggcatat   3360
atgatgtcaa tatctccggt ctggtaagca caaccatgca gaatgaagcc cgtcgtctgc   3420
gtgccgaacg ctggaaagcg gaaaatcagg aagggatggc tgaggtcgcc cggtttattg   3480
aaatgaacgg ctcttttgct gacgagaaca ggggctggtg aaatgcagtt taaggtttac   3540
acctataaaa gagagagccg ttatcgtctg tttgtggatg tacagagtga tattattgac   3600
acgcccgggc gacggatggt gatccccctg gccagtgcac gtctgctgtc agataaagtc   3660
tcccgtgaac tttacccggt ggtgcatatc ggggatgaaa gctggcgcat gatgaccacc   3720
gatatggcca gtgtgccggt ctccgttatc ggggaagaag tggctgatct cagccaccgc   3780
gaaaatgaca tcaaaaacgc cattaacctg atgttctggg gaatataaat gtcaggctcc   3840
cttatacaca gccagtctgc aggtcgacca tagtgactgg atatgttgtg ttttacagta   3900
ttatgtagtc tgttttttat gcaaaatcta atttaatata ttgatattta tatcatttta   3960
cgtttctcgt tcagctttct tgtacaaagt ggtgttaacc tagacttgtc catcttctgg   4020
attggccaac ttaattaatg tatgaaataa aaggatgcac acatagtgac atgctaatca   4080
ctataatgtg ggcatcaaag ttgtgtgtta tgtgtaatta ctagttatct gaataaaaga   4140
```

-continued

```
gaaagagatc atccatattt cttatcctaa atgaatgtca cgtgtcttta taattctttg   4200
atgaaccaga tgcatttcat taaccaaatc catatacata taaatattaa tcatatataa   4260
ttaatatcaa ttgggttagc aaaacaaatc tagtctaggt gtgttttgcg aattgcggcc   4320
gccaccgcgg tggagctcga attccggtcc gggtcacctt tgtccaccaa gatggaactg   4380
cggccgctca ttaattaagt caggcgcgcc tctagttgaa gacacgttca tgtcttcatc   4440
gtaagaagac actcagtagt cttcggccag aatggccatc tggattcagc aggcctagaa   4500
ggccatttaa atcctgagga tctggtcttc ctaaggaccc gggatatcgg accgaagctg   4560
gccgctctag aactagtgga tctcgatgtg tagtctacga gaagggttaa ccgtctcttc   4620
gtgagaataa ccgtggccta aaaataagcc gatgaggata aataaaatgt ggtggtacag   4680
tacttcaaga ggtttactca tcaagaggat gcttttccga tgagctctag tagtacatcg   4740
gacctcacat acctccattg tggtgaaata ttttgtgctc atttagtgat gggtaaattt   4800
tgtttatgtc actctaggtt ttgacatttc agttttgcca ctcttaggtt ttgacaaata   4860
atttccattc cgcggcaaaa gcaaaacaat tttattttac ttttaccact cttagctttc   4920
acaatgtatc acaaatgcca ctctagaaat tctgtttatg ccacagaatg tgaaaaaaaa   4980
cactcactta tttgaagcca aggtgttcat ggcatggaaa tgtgacataa agtaacgttc   5040
gtgtataaga aaaaattgta ctcctcgtaa caagagacgg aaacatcatg agacaatcgc   5100
gtttggaagg ctttgcatca cctttggatg atgcgcatga atggagtcgt ctgcttgcta   5160
gccttcgcct accgcccact gagtccgggc ggcaactacc atcggcgaac gacccagctg   5220
acctctaccg accggacttg aatgcgctac cttcgtcagc gacgatggcc gcgtacgctg   5280
gcgacgtgcc cccgcatgca tggcggcaca tggcgagctc agaccgtgcg tggctggcta   5340
caaatacgta ccccgtgagt gccctagcta gaaacttaca cctgcaactg cgagagcgag   5400
cgtgtgagtg tagccgagta gatcccccgg gctgcaggtc gactctagag gatccaccgg   5460
tcgccaccat ggcctcctcc gagaacgtca tcaccgagtt catgcgcttc aaggtgcgca   5520
tggagggcac cgtgaacggc cacgagttcg agatcgaggg cgagggcgag ggccgcccct   5580
acgagggcca caacaccgtg aagctgaagg tgacgaaggg cggccccctg cccttcgcct   5640
gggacatcct gtcccccag ttccagtacg gctccaaggt gtacgtgaag caccccgccg    5700
acatccccga ctacaagaag ctgtccttcc ccgagggctt caagtgggag cgcgtgatga   5760
acttcgagga cggcggcgtg gcgaccgtga cccaggactc ctccctgcag gacggctgct   5820
tcatctacaa ggtgaagttc atcggcgtga acttcccctc cgacggcccc gtgatgcaga   5880
agaagaccat gggctgggag gcctccaccg agcgcctgta cccccgcgac ggcgtgctga   5940
agggcgagac ccacaaggcc ctgaagctga aggacggcgg ccactacctg gtggagttca   6000
agtccatcta catggccaag aagcccgtgc agctgcccgg ctactactac gtggacgcca   6060
agctggacat cacctcccac aacgaggact acaccatcgt ggagcagtac gagcgcaccg   6120
agggccgcca ccacctgttc ctgtagcggc ccatggatat tcgaacgcgt aggtaccaca   6180
tggttaacct agacttgtcc atcttctgga ttggccaact taattaatgt atgaaataaa   6240
aggatgcaca catagtgaca tgctaatcac tataatgtgg gcatcaaagt tgtgtgttat   6300
gtgtaattac tagttatctg aataaaagag aaagagatca tccatatttc ttatcctaaa   6360
tgaatgtcac gtgtctttat aattctttga tgaaccagat gcatttcatt aaccaaatcc   6420
atatacatat aaatattaat catatataat taatatcaat tgggttagca aaacaaatct   6480
agtctaggtg tgttttgcga atgcggccgc caccgcggtg gagctcgaat tccggtccga   6540
```

```
agcttgcatg cctgcagtgc agcgtgaccc ggtcgtgccc ctctctagag ataatgagca   6600
ttgcatgtct aagttataaa aaattaccac atattttttt tgtcacactt gtttgaagtg   6660
cagtttatct atctttatac atatatttaa actttactct acgaataata taatctatag   6720
tactacaata atatcagtgt tttagagaat catataaatg aacagttaga catggtctaa   6780
aggacaattg agtattttga caacaggact ctacagtttt atctttttag tgtgcatgtg   6840
ttctcctttt tttttgcaaa tagcttcacc tatataatac ttcatccatt ttattagtac   6900
atccatttag ggtttagggt taatggtttt tatagactaa ttttttttagt acatctattt   6960
tattctattt tagcctctaa attaagaaaa ctaaaactct attttagttt ttttatttaa   7020
taatttagat ataaaataga ataaaataaa gtgactaaaa attaaacaaa taccctttaa   7080
gaaattaaaa aaactaagga aacatttttc ttgtttcgag tagataatgc cagcctgtta   7140
aacgccgtcg acgagtctaa cggacaccaa ccagcgaacc agcagcgtcg cgtcgggcca   7200
agcgaagcag acggcacggc atctctgtcg ctgcctctgg acccctctcg agagttccgc   7260
tccaccgttg gacttgctcc gctgtcggca tccagaaatt gcgtggcgga gcggcagacg   7320
tgagccggca cggcaggcgg cctcctcctc ctctcacggc accggcagct acgggggatt   7380
cctttcccac cgctccttcg ctttcccttc ctcgcccgcc gtaataaata gacacccccct   7440
ccacaccctc tttccccaac ctcgtgttgt tcggagcgca cacacacaca accagatctc   7500
ccccaaatcc acccgtcggc acctccgctt caaggtacgc cgctcgtcct cccccccccc   7560
cctctctacc ttctctagat cggcgttccg gtccatgcat ggttagggcc cggtagttct   7620
acttctgttc atgtttgtgt tagatccgtg tttgtgttag atccgtgctg ctagcgttcg   7680
tacacggatg cgacctgtac gtcagacacg ttctgattgc taacttgcca gtgtttctct   7740
ttggggaatc ctgggatggc tctagccgtt ccgcagacgg gatcgatttc atgatttttt   7800
ttgtttcgtt gcatagggtt tggtttgccc ttttccttta tttcaatata tgccgtgcac   7860
ttgtttgtcg ggtcatcttt tcatgctttt ttttgtcttg gttgtgatga tgtggtctgg   7920
ttgggcggtc gttctagatc ggagtagaat tctgtttcaa actacctggt ggatttatta   7980
attttggatc tgtatgtgtg tgccatacat attcatagtt acgaattgaa gatgatggat   8040
ggaaatatcg atctaggata ggtatacatg ttgatgcggg ttttactgat gcatatacag   8100
agatgctttt tgttcgcttg gttgtgatga tgtggtgtgg ttgggcggtc gttcattcgt   8160
tctagatcgg agtagaatac tgtttcaaac tacctggtgt atttattaat tttggaactg   8220
tatgtgtgtg tcatacatct tcatagttac gagtttaaga tggatggaaa tatcgatcta   8280
ggataggtat acatgttgat gtgggtttta ctgatgcata tacatgatgg catatgcagc   8340
atctattcat atgctctaac cttgagtacc tatctattat aataaacaag tatgttttat   8400
aattattttg atcttgatat acttggatga tggcatatgc agcagctata tgtggatttt   8460
tttagccctg ccttcatacg ctatttattt gcttggtact gtttcttttg tcgatgctca   8520
ccctgttgtt tggtgttact tctgcaggtc gactttaact tagcctagga tccacacgac   8580
accatgtccc ccgagcgccg ccccgtcgag atccgcccgg ccaccgccgc cgacatggcc   8640
gccgtgtgcg acatcgtgaa ccactacatc gagacctcca ccgtgaactt ccgcaccgag   8700
ccgcagaccc cgcaggagtg gatcgacgac ctggagcgcc tccaggaccg ctacccgtgg   8760
ctcgtggccg aggtggaggg cgtggtggcc ggcatcgcct acgccggccc gtggaaggcc   8820
cgcaacgcct acgactggac cgtggagtcc accgtgtacg tgtcccaccg ccaccagcgc   8880
ctcggcctcg gctccaccct ctacacccac ctcctcaaga gcatggaggc ccagggcttc   8940
```

-continued

```
aagtccgtgg tggccgtgat cggcctcccg aacgacccgt ccgtgcgcct ccacgaggcc   9000
ctcggctaca ccgcccgcgg caccctccgc gccgccggct acaagcacgg cggctggcac   9060
gacgtcggct tctggcagcg cgacttcgag ctgccggccc cgccgcgccc ggtgcgcccg   9120
gtgacgcaga tctgagtcga aacctagact tgtccatctt ctggattggc caacttaatt   9180
aatgtatgaa ataaaaggat gcacacatag tgacatgcta atcactataa tgtgggcatc   9240
aaagttgtgt gttatgtgta attactagtt atctgaataa aagagaaaga gatcatccat   9300
atttcttatc ctaaatgaat gtcacgtgtc tttataattc tttgatgaac cagatgcatt   9360
tcattaacca aatccatata catataaata ttaatcatat ataattaata tcaattgggt   9420
tagcaaaaca aatctagtct aggtgtgttt tgcgaattgc ggccgccacc gcggtggagc   9480
tcgaattcat tccgattaat cgtggcctct tgctcttcag gatgaagagc tatgtttaaa   9540
cgtgcaagcg ctactagaca attcagtaca ttaaaaacgt ccgcaatgtg ttattaagtt   9600
gtctaagcgt caatttgttt acaccacaat atatcctgcc accagccagc caacagctcc   9660
ccgaccggca gctcggcaca aaatcaccac tcgatacagg cagcccatca gtccgggacg   9720
gcgtcagcgg gagagccgtt gtaaggcggc agactttgct catgttaccg atgctattcg   9780
gaagaacggc aactaagctg ccgggtttga aacacggatg atctcgcgga gggtagcatg   9840
ttgattgtaa cgatgacaga gcgttgctgc ctgtgatcaa atatcatctc cctcgcagag   9900
atccgaatta tcagccttct tattcatttc tcgcttaacc gtgacaggct gtcgatcttg   9960
agaactatgc cgacataata ggaaatcgct ggataaagcc gctgaggaag ctgagtggcg  10020
ctatttcttt agaagtgaac gttgacgatc gtcgaccgta ccccgatgaa ttaattcgga  10080
cgtacgttct gaacacagct ggatacttac ttgggcgatt gtcatacatg acatcaacaa  10140
tgtacccgtt tgtgtaaccg tctcttggag gttcgtatga cactagtggt tcccctcagc  10200
ttgcgactag atgttgaggc ctaacatttt attagagagc aggctagttg cttagataca  10260
tgatcttcag gccgttatct gtcagggcaa gcgaaaattg gccatttatg acgaccaatg  10320
ccccgcagaa gctcccatct ttgccgccat agacgccgcg ccccccttt  ggggtgtaga  10380
acatcctttt gccagatgtg gaaaagaagt tcgttgtccc attgttggca atgacgtagt  10440
agccggcgaa agtgcgagac ccatttgcgc tatatataag cctacgattt ccgttgcgac  10500
tattgtcgta attggatgaa ctattatcgt agttgctctc agagttgtcg taatttgatg  10560
gactattgtc gtaattgctt atggagttgt cgtagttgct tggagaaatg tcgtagttgg  10620
atggggagta gtcataggga agacgagctt catccactaa aacaattggc aggtcagcaa  10680
gtgcctgccc cgatgccatc gcaagtacga ggcttagaac caccttcaac agatcgcgca  10740
tagtcttccc cagctctcta acgcttgagt taagccgcgc cgcgaagcgg cgtcggcttg  10800
aacgaattgt tagacattat ttgccgacta ccttggtgat ctcgcctttc acgtagtgaa  10860
caaattcttc caactgatct gcgcgcgagg ccaagcgatc ttcttgtcca agataagcct  10920
gcctagcttc aagtatgacg ggctgatact gggccggcag gcgctccatt gcccagtcgg  10980
cagcgacatc cttcggcgcg attttgccgg ttactgcgct gtaccaaatg cgggacaacg  11040
taagcactac atttcgctca tcgccagccc agtcgggcgg cgagttccat agcgttaagg  11100
tttcatttag cgcctcaaat agatcctgtt caggaaccgg atcaaagagt tcctccgccg  11160
ctggacctac caaggcaacg ctatgttctc ttgcttttgt cagcaagata gccagatcaa  11220
tgtcgatcgt ggctggctcg aagatacctg caagaatgtc attgcgctgc cattctccaa  11280
attgcagttc gcgcttagct ggataacgcc acggaatgat gtcgtcgtgc acaacaatgg  11340
```

-continued

```
tgacttctac agcgcggaga atctcgctct ctccagggga agccgaagtt tccaaaaggt  11400
cgttgatcaa agctcgccgc gttgtttcat caagccttac agtcaccgta accagcaaat  11460
caatatcact gtgtggcttc aggccgccat ccactgcgga gccgtacaaa tgtacggcca  11520
gcaacgtcgg ttcgagatgg cgctcgatga cgccaactac ctctgatagt tgagtcgata  11580
cttcggcgat caccgcttcc ctcatgatgt ttaactcctg aattaagccg cgccgcgaag  11640
cggtgtcggc ttgaatgaat tgttaggcgt catcctgtgc tcccgagaac cagtaccagt  11700
acatcgctgt ttcgttcgag acttgaggtc tagttttata cgtgaacagg tcaatgccgc  11760
cgagagtaaa gccacatttt gcgtacaaat tgcaggcagg tacattgttc gtttgtgtct  11820
ctaatcgtat gccaaggagc tgtctgctta gtgcccactt tttcgcaaat tcgatgagac  11880
tgtgcgcgac tcctttgcct cggtgcgtgt gcgacacaac aatgtgttcg atagaggcta  11940
gatcgttcca tgttgagttg agttcaatct tcccgacaag ctcttggtcg atgaatgcgc  12000
catagcaagc agagtcttca tcagagtcat catccgagat gtaatccttc cggtaggggc  12060
tcacacttct ggtagatagt tcaaagcctt ggtcggatag gtgcacatcg aacacttcac  12120
gaacaatgaa atggttctca gcatccaatg tttccgccac ctgctcaggg atcaccgaaa  12180
tcttcatatg acgcctaacg cctggcacag cggatcgcaa acctggcgcg gcttttggca  12240
caaaaggcgt gacaggtttg cgaatccgtt gctgccactt gttaaccctt ttgccagatt  12300
tggtaactat aatttatgtt agaggcgaag tcttgggtaa aaactggcct aaaattgctg  12360
gggatttcag gaaagtaaac atcaccttcc ggctcgatgt ctattgtaga tatatgtagt  12420
gtatctactt gatcggggga tctgctgcct cgcgcgtttc ggtgatgacg gtgaaaacct  12480
ctgacacatg cagctcccgg agacggtcac agcttgtctg taagcggatg ccgggagcag  12540
acaagcccgt cagggcgcgt cagcgggtgt tggcgggtgt cggggcgcag ccatgaccca  12600
gtcacgtagc gatagcggag tgtatactgg cttaactatg cggcatcaga gcagattgta  12660
ctgagagtgc accatatgcg gtgtgaaata ccgcacagat gcgtaaggag aaaataccgc  12720
atcaggcgct cttccgcttc ctcgctcact gactcgctgc gctcggtcgt tcggctgcgg  12780
cgagcggtat cagctcactc aaaggcggta atacggttat ccacagaatc aggggataac  12840
gcaggaaaga acatgtgagc aaaaggccag caaaaggcca ggaaccgtaa aaaggccgcg  12900
ttgctggcgt ttttccatag gctccgcccc cctgacgagc atcacaaaaa tcgacgctca  12960
agtcagaggt ggcgaaaccc gacaggacta taaagatacc aggcgtttcc ccctggaagc  13020
tccctcgtgc gctctcctgt tccgaccctg ccgcttaccg gatacctgtc cgcctttctc  13080
ccttcgggaa gcgtggcgct ttctcatagc tcacgctgta ggtatctcag ttcggtgtag  13140
gtcgttcgct ccaagctggg ctgtgtgcac gaaccccccg ttcagcccga ccgctgcgcc  13200
ttatccggta actatcgtct tgagtccaac ccggtaagac acgacttatc gccactggca  13260
gcagccactg gtaacaggat tagcagagcg aggtatgtag gcggtgctac agagttcttg  13320
aagtggtggc ctaactacgg ctacactaga aggacagtat ttggtatctg cgctctgctg  13380
aagccagtta ccttcggaaa aagagttggt agctcttgat ccggcaaaca aaccaccgct  13440
ggtagcggtg gtttttttgt ttgcaagcag cagattacgc gcagaaaaaa aggatctcaa  13500
gaagatcctt tgatcttttc tacggggtct gacgctcagt ggaacgaaaa ctcacgttaa  13560
gggattttgg tcatgagatt atcaaaaagg atcttcacct agatcctttt aaattaaaaa  13620
tgaagtttta aatcaatcta aagtatatat gagtaaactt ggtctgacag ttaccaatgc  13680
ttaatcagtg aggcacctat ctcagcgatc tgtctatttc gttcatccat agttgcctga  13740
```

-continued ctccccgtcg tgtagataac tacgatacgg gagggcttac catctggccc cagtgctgca 13800
atgataccgc gagacccacg ctcaccggct ccagatttat cagcaataaa ccagccagcc 13860
ggaagggccg agcgcagaag tggtcctgca actttatccg cctccatcca gtctattaat 13920
tgttgccggg aagctagagt aagtagttcg ccagttaata gtttgcgcaa cgttgttgcc 13980
attgctgcag gggggggggg ggggggggac ttccattgtt cattccacgg acaaaaacag 14040
agaaaggaaa cgacagaggc caaaaagcct cgctttcagc acctgtcgtt tcctttcttt 14100
tcagagggta ttttaaataa aaacattaag ttatgacgaa gaagaacgga aacgccttaa 14160
accggaaaat ttcataaat agcgaaaacc cgcgaggtcg ccgccccgta acctgtcgga 14220
tcaccggaaa ggacccgtaa agtgataatg attatcatct acatatcaca acgtgcgtgg 14280
aggccatcaa accacgtcaa ataatcaatt atgacgcagg tatcgtatta attgatctgc 14340
atcaacttaa cgtaaaaaca acttcagaca atacaaatca gcgacactga atacggggca 14400
acctcatgtc cccccccccc cccccccctgc aggcatcgtg gtgtcacgct cgtcgtttgg 14460
tatggcttca ttcagctccg gttcccaacg atcaaggcga gttacatgat cccccatgtt 14520
gtgcaaaaaa gcggttagct ccttcggtcc tccgatcgtt gtcagaagta agttggccgc 14580
agtgttatca ctcatggtta tggcagcact gcataattct cttactgtca tgccatccgt 14640
aagatgcttt tctgtgactg gtgagtactc aaccaagtca ttctgagaat agtgtatgcg 14700
gcgaccgagt tgctcttgcc cggcgtcaac acgggataat accgcgccac atagcagaac 14760
tttaaaagtg ctcatcattg gaaaacgttc ttcggggcga aaactctcaa ggatcttacc 14820
gctgttgaga tccagttcga tgtaacccac tcgtgcaccc aactgatctt cagcatcttt 14880
tactttcacc agcgtttctg ggtgagcaaa aacaggaagg caaaatgccg caaaaaaggg 14940
aataagggcg acacggaaat gttgaatact catactcttc ctttttcaat attattgaag 15000
catttatcag ggttattgtc tcatgagcgg atacatattt gaatgtattt agaaaaataa 15060
acaaataggg gttccgcgca catttccccg aaaagtgcca cctgacgtct aagaaaccat 15120
tattatcatg acattaacct ataaaaatag gcgtatcacg aggccctttc gtcttcaaga 15180
attggtcgac gatcttgctg cgttcggata ttttcgtgga gttcccgcca cagacccgga 15240
ttgaaggcga gatccagcaa ctcgcgccag atcatcctgt gacggaactt tggcgcgtga 15300
tgactggcca ggacgtcggc cgaaagagcg acaagcagat cacgcttttc gacagcgtcg 15360
gatttgcgat cgaggatttt tcggcgctgc gctacgtccg cgaccgcgtt gagggatcaa 15420
gccacagcag cccactcgac cttctagccg acccagacga gccaagggat ctttttggaa 15480
tgctgctccg tcgtcaggct ttccgacgtt tgggtggttg aacagaagtc attatcgtac 15540
ggaatgccaa gcactcccga ggggaaccct gtggttggca tgcacataca aatggacgaa 15600
cggataaacc ttttcacgcc cttttaaata tccgttattc taataaacgc tcttttctct 15660
tag 15663

<210> SEQ ID NO 40
<211> LENGTH: 25
<212> TYPE: DNA
<213> ORGANISM: Artificial
<220> FEATURE:
<223> OTHER INFORMATION: attB1 site

<400> SEQUENCE: 40
acaagtttgt acaaaaaagc aggct 25

<210> SEQ ID NO 41

<211> LENGTH: 25
<212> TYPE: DNA
<213> ORGANISM: Artificial
<220> FEATURE:
<223> OTHER INFORMATION: attB2 site

<400> SEQUENCE: 41
accactttgt acaagaaagc tgggt 25

<210> SEQ ID NO 42
<211> LENGTH: 55
<212> TYPE: DNA
<213> ORGANISM: Artificial
<220> FEATURE:
<223> OTHER INFORMATION: At5g26030-5'attB forward primer

<400> SEQUENCE: 42
ttaaacaagt ttgtacaaaa aagcaggctc aacaatgcag gcaacggctt tatca 55

<210> SEQ ID NO 43
<211> LENGTH: 50
<212> TYPE: DNA
<213> ORGANISM: Artificial
<220> FEATURE:
<223> OTHER INFORMATION: At5g26030-3'attB reverse primer

<400> SEQUENCE: 43
ttaaaccact ttgtacaaga aagctgggtc tataggttcc ggaacgcatg 50

<210> SEQ ID NO 44
<211> LENGTH: 55
<212> TYPE: DNA
<213> ORGANISM: Artificial
<220> FEATURE:
<223> OTHER INFORMATION: At2g30390-5'attB forward primer

<400> SEQUENCE: 44
ttaaacaagt ttgtacaaaa aagcaggctc aacaatgaat tgcccagcca tgact 55

<210> SEQ ID NO 45
<211> LENGTH: 50
<212> TYPE: DNA
<213> ORGANISM: Artificial
<220> FEATURE:
<223> OTHER INFORMATION: At2g30390-3'attB reverse primer

<400> SEQUENCE: 45
ttaaaccact ttgtacaaga aagctgggtt tataatgaag gcaagatgcc 50

<210> SEQ ID NO 46
<211> LENGTH: 54
<212> TYPE: DNA
<213> ORGANISM: Artificial
<220> FEATURE:
<223> OTHER INFORMATION: VC062 primer

<400> SEQUENCE: 46
ttaaacaagt ttgtacaaaa aagcaggctg caattaaccc tcactaaagg gaac 54

<210> SEQ ID NO 47
<211> LENGTH: 53
<212> TYPE: DNA
<213> ORGANISM: Artificial
<220> FEATURE:
<223> OTHER INFORMATION: VC063 primer

<400> SEQUENCE: 47
ttaaaccact ttgtacaaga aagctgggtg cgtaatacga ctcactatag ggc 53

<210> SEQ ID NO 48
<211> LENGTH: 484
<212> TYPE: PRT
<213> ORGANISM: Hordeum vulgare

<400> SEQUENCE: 48

Met Glu Cys Val Arg Ser Gly Ala Leu Asp Leu Gly Arg Ser Gly Asn
1 5 10 15

Phe Leu Gly Lys Ser Gly Ser Thr Thr Ser Cys Gly Lys Val Arg Cys
20 25 30

Ser Thr Asn Leu Ala Gly Ser Thr Lys Cys Glu Gln Asn Leu His Gly
35 40 45

Lys Ala Lys Pro Leu Leu Leu Ser Ala Ser Gly Lys Ala Arg Gly Thr
50 55 60

Ser Gly Leu Val His Arg Ser Pro Val Leu Lys His Gln His His Leu
65 70 75 80

Ser Val Arg Ser Thr Ser Thr Asp Val Cys Thr Thr Phe Asp Glu Asp
85 90 95

Val Lys Gly Val Ser Ser His Ala Val Glu Glu Lys Val Gly Val Leu
100 105 110

Leu Leu Asn Leu Gly Gly Pro Glu Thr Leu Asn Asp Val Gln Pro Phe
115 120 125

Leu Phe Asn Leu Phe Ala Asp Pro Asp Ile Ile Arg Leu Pro Arg Leu
130 135 140

Phe Arg Phe Leu Gln Arg Pro Leu Ala Lys Leu Ile Ser Thr Phe Arg
145 150 155 160

Ala Pro Lys Ser Lys Glu Gly Tyr Ala Ser Ile Gly Gly Gly Ser Pro
165 170 175

Leu Arg Lys Ile Thr Asp Glu Gln Ala Asn Ala Leu Lys Val Ala Leu
180 185 190

Lys Ser Lys Asn Leu Glu Ala Asp Ile Tyr Val Gly Met Arg Tyr Trp
195 200 205

Tyr Pro Phe Thr Glu Glu Ala Ile Asp Gln Ile Lys Lys Asp Lys Ile
210 215 220

Thr Lys Leu Val Val Leu Pro Leu Tyr Pro Gln Tyr Ser Ile Ser Thr
225 230 235 240

Ser Gly Ser Ser Ile Arg Val Leu Gln Asn Ile Val Lys Glu Asp Pro
245 250 255

Tyr Phe Ala Gly Leu Pro Ile Ser Ile Ile Glu Ser Trp Tyr Gln Arg
260 265 270

Glu Gly Tyr Val Lys Ser Met Ala Asp Leu Ile Glu Lys Glu Leu Ser
275 280 285

Val Phe Ser Asn Pro Glu Glu Val Met Ile Phe Phe Ser Ala His Gly
290 295 300

Val Pro Leu Thr Tyr Val Lys Asp Ala Gly Asp Pro Tyr Arg Asp Gln
305 310 315 320

Met Glu Asp Cys Ile Ala Leu Ile Met Glu Glu Leu Lys Ser Arg Gly
325 330 335

Thr Leu Asn Asp His Thr Leu Ala Tyr Gln Ser Arg Val Gly Pro Val
340 345 350

Gln Trp Leu Lys Pro Tyr Thr Asp Glu Val Leu Val Glu Leu Gly Gln
355 360 365

Lys Gly Val Lys Ser Leu Leu Ala Val Pro Val Ser Phe Val Ser Glu

```
    370                 375                 380

His Ile Glu Thr Leu Glu Glu Ile Asp Met Glu Tyr Arg Glu Leu Ala
385                 390                 395                 400

Leu Glu Ser Gly Ile Glu Asn Trp Gly Arg Val Pro Ala Leu Gly Cys
                405                 410                 415

Thr Ser Ser Phe Ile Ser Asp Leu Ala Asp Ala Val Val Glu Ala Leu
            420                 425                 430

Pro Ser Ala Ser Ala Met Ala Thr Arg Lys Val Lys Asp Thr Asp Ser
        435                 440                 445

Asp Met Asp Met Met His Tyr Leu Thr Lys Met Phe Leu Gly Ser Val
    450                 455                 460

Leu Ala Phe Phe Leu Leu Leu Ser Pro Arg Leu Val Ser Ala Phe Arg
465                 470                 475                 480
Asn Thr Leu Gln


<210> SEQ ID NO 49
<211> LENGTH: 482
<212> TYPE: PRT
<213> ORGANISM: Oryza sativa

<400> SEQUENCE: 49

Met Glu Cys Val Arg Ser Gly Ser Gly Val Leu Asp Pro Arg Cys Ser
1               5                   10                  15

Pro Arg Phe Leu Gly Lys Lys Gly Gly Ser Leu Thr Ser Cys Gly Lys
            20                  25                  30

Ala Thr Ser Thr Asn Leu Ala Ile Cys Thr Lys His Glu Gln Asn Leu
        35                  40                  45

His Gly Asn Val Lys Pro Ser Gln Leu Ala Ala Ser Gly Ser Ser Tyr
    50                  55                  60

Ser Val His Arg Ser Pro Val Leu Lys Gln Arg Gln Asn Leu Ser Ala
65                  70                  75                  80

Arg Ser Thr Ser Ala Asp Val Tyr Thr Thr Phe Asp Glu Asn Val Arg
                85                  90                  95

Ala Val Ser Ser His Ala Ala Glu Glu Lys Val Gly Val Leu Leu Leu
            100                 105                 110

Asn Leu Gly Gly Pro Glu Thr Leu Asp Asp Val Gln Pro Phe Leu Phe
        115                 120                 125

Asn Leu Phe Ala Asp Pro Asp Ile Ile Arg Leu Pro Arg Leu Phe Arg
    130                 135                 140

Phe Leu Gln Arg Pro Leu Ala Lys Leu Ile Ser Thr Phe Arg Ala Pro
145                 150                 155                 160

Lys Ser Lys Glu Gly Tyr Ala Ser Ile Gly Gly Gly Ser Pro Leu Arg
                165                 170                 175

Lys Ile Thr Asp Glu Gln Ala Asn Ala Leu Lys Val Ala Leu Lys Lys
            180                 185                 190

Lys Asn Leu Asn Ala Asn Ile Tyr Val Gly Met Arg Tyr Trp Tyr Pro
        195                 200                 205

Phe Thr Glu Glu Ala Ile Asp Gln Ile Lys Lys Asp Lys Ile Thr Lys
    210                 215                 220

Leu Val Val Leu Pro Leu Tyr Pro Gln Tyr Ser Ile Ser Thr Ser Gly
225                 230                 235                 240

Ser Ser Ile Arg Val Leu Gln Asn Ile Val Lys Glu Asp Ser Tyr Phe
                245                 250                 255

Ala Gly Leu Pro Ile Ser Ile Ile Glu Ser Trp Tyr Gln Arg Asp Gly
            260                 265                 270
```

```
Tyr Val Lys Ser Met Ala Asp Leu Ile Glu Lys Glu Leu Ser Ile Phe
        275                 280                 285

Ser Asn Pro Glu Glu Val Met Ile Phe Phe Ser Ala His Gly Val Pro
    290                 295                 300

Leu Thr Tyr Val Thr Asp Ala Gly Asp Pro Tyr Arg Asp Gln Met Glu
305                 310                 315                 320

Asp Cys Ile Ala Leu Ile Met Gly Glu Leu Lys Ser Arg Gly Ile Leu
                325                 330                 335

Asn Ser His Thr Leu Ala Tyr Gln Ser Arg Val Gly Pro Val Gln Trp
            340                 345                 350

Leu Lys Pro Tyr Thr Asp Glu Val Leu Val Glu Leu Gly Gln Gln Gly
        355                 360                 365

Val Lys Ser Leu Leu Ala Val Pro Val Ser Phe Val Ser Glu His Ile
    370                 375                 380

Glu Thr Leu Glu Glu Ile Asp Met Glu Tyr Lys Glu Leu Ala Leu Glu
385                 390                 395                 400

Ser Gly Ile Glu Asn Trp Gly Arg Val Pro Ala Leu Gly Cys Thr Ser
                405                 410                 415

Ser Phe Ile Ser Asp Leu Ala Asp Ala Val Val Glu Ala Leu Pro Ser
            420                 425                 430

Ala Ser Ala Leu Val Thr Lys Lys Val Asp Glu Ser Asp Ser Asp Met
        435                 440                 445

Asp Leu Met His Tyr Leu Ser Lys Met Phe Phe Gly Ser Ile Leu Ala
    450                 455                 460

Phe Val Leu Leu Leu Ser Pro Arg Leu Ile Ser Ala Phe Arg Asn Thr
465                 470                 475                 480

Leu Leu


<210> SEQ ID NO 50
<211> LENGTH: 445
<212> TYPE: PRT
<213> ORGANISM: Vitis vinifera

<400> SEQUENCE: 50

Met Glu Ala Val Ser Thr Ser Ser Ile Leu Pro His Gly Lys Val Ser
1               5                   10                  15

Gly Leu Asn His Arg Ser Phe Asn Gln Lys Ser Ser Ile Arg Ser Ser
            20                  25                  30

Pro Trp Lys Gly Lys Gly Lys Glu Lys Leu Ser Phe Val Leu Thr Phe
        35                  40                  45

Gln Arg Gly Ala Tyr Thr Tyr Val Gly Ser Ala Val Glu Ser Pro Thr
    50                  55                  60

His Ala Val Glu Glu Lys Val Gly Val Leu Leu Leu Asn Leu Gly Gly
65                  70                  75                  80

Pro Glu Thr Leu His Asp Val Gln Pro Phe Leu Phe Asn Leu Phe Ala
                85                  90                  95

Asp Pro Asp Ile Ile Arg Leu Pro Arg Leu Phe Gln Phe Leu Gln Arg
            100                 105                 110

Pro Leu Ala Gln Leu Ile Ser Val Ile Arg Ala Pro Lys Ser Lys Glu
        115                 120                 125

Gly Tyr Ala Ala Ile Gly Gly Gly Ser Pro Leu Arg Lys Ile Thr Asp
    130                 135                 140

Glu Gln Ala His Ala Ile Lys Ala Ala Leu Glu Ala Lys Asn Met His
145                 150                 155                 160

Val Asn Val Tyr Val Gly Met Arg Tyr Trp Tyr Pro Phe Thr Glu Glu
```

```
                165                 170                 175

Ala Ile Glu Gln Ile Lys Lys Asp Lys Ile Thr Arg Leu Val Val Leu
            180                 185                 190

Pro Leu Tyr Pro Gln Phe Ser Ile Ser Thr Thr Gly Ser Ser Ile Arg
        195                 200                 205

Val Leu Glu Ser Ile Phe Arg Glu Asp Ala Tyr Leu Ser Arg Leu Pro
    210                 215                 220

Val Ser Ile Ile Gln Cys Trp Tyr Gln Arg Gln Gly Tyr Ile Asn Ser
225                 230                 235                 240

Met Ala Asp Leu Ile Glu Glu Glu Leu Gln Ile Phe Ser Lys Pro Lys
                245                 250                 255

Glu Val Met Ile Phe Phe Ser Ala His Gly Val Pro Val Ser Tyr Val
            260                 265                 270

Glu Asp Ala Gly Asp Pro Tyr Arg Asp Gln Met Glu Glu Cys Ile Tyr
        275                 280                 285

Leu Ile Met Gln Glu Leu Lys Ala Arg Gly Ile Ser Asn Lys His Thr
    290                 295                 300

Leu Ala Tyr Gln Ser Arg Val Gly Pro Val Gln Trp Leu Lys Pro Tyr
305                 310                 315                 320

Thr Asp Glu Val Leu Val Glu Leu Gly Gln Lys Gly Val Lys Ser Leu
                325                 330                 335

Leu Ala Val Pro Val Ser Phe Val Ser Glu His Ile Glu Thr Leu Glu
            340                 345                 350

Glu Ile Asp Met Glu Tyr Lys His Leu Ala Leu Glu Ser Gly Ile Glu
        355                 360                 365

Asn Trp Gly Arg Val Pro Ala Leu Gly Cys Thr Ser Ser Phe Ile Thr
    370                 375                 380

Asp Leu Ala Asp Ala Val Ile Glu Ala Leu Pro Ala Ala Lys Ala Met
385                 390                 395                 400

Thr Thr Gln Ser Thr Ser Lys Glu Phe Asn Met Asp Pro Val Asn Tyr
                405                 410                 415

Ala Ile Lys Met Phe Phe Gly Ser Ile Leu Ala Phe Val Leu Leu Leu
            420                 425                 430

Ser Pro Lys Met Ile Ser Lys Phe Lys Asn Gln Leu Phe
        435                 440                 445


<210> SEQ ID NO 51
<211> LENGTH: 526
<212> TYPE: PRT
<213> ORGANISM: Oryza sativa

<400> SEQUENCE: 51

Met Trp Ser Ser Ser Gln Ala Ser Thr Arg Gly Val Ile Glu Val Gly
1               5                   10                  15

Arg Val Glu Ala Gly Pro Ser His Phe Pro Lys Arg Pro Ala Pro Arg
            20                  25                  30

Asn Ser Ser Arg Val Asn Leu Ser Arg Thr Tyr Ala Ile Lys Ser Cys
        35                  40                  45

Ser Val Ser Ser Arg Thr Gly Leu Cys Leu Gly Gln Cys Tyr His Lys
    50                  55                  60

Lys Ser Ser Ala Cys Lys Cys Lys Leu Gly Trp Ser Ser Gln Pro Leu
65                  70                  75                  80

Ser Ser Leu Arg His His Leu Arg Val His Ser Ser Ala Ser Glu Ala
                85                  90                  95

Val Leu Thr Ser Gln Ser Asp Phe Thr Lys Leu Leu Val Gly Asn Glu
```

```
            100                 105                 110

Lys Ile Gly Val Leu Leu Leu Asn Leu Gly Gly Pro Glu Thr Leu Asp
        115                 120                 125

Asp Val Gln Pro Phe Leu Phe Asn Leu Phe Ala Asp Pro Asp Ile Ile
    130                 135                 140

Arg Leu Pro Arg Leu Phe Arg Phe Leu Gln Lys Pro Leu Ala Gln Phe
145                 150                 155                 160

Ile Ser Val Val Arg Ala Pro Lys Ser Lys Glu Gly Tyr Ala Ser Ile
                165                 170                 175

Gly Gly Gly Ser Pro Leu Arg Gln Ile Thr Asp Ala Gln Ala Glu Ala
            180                 185                 190

Leu Arg Lys Ala Leu Cys Asp Lys Asp Ile Pro Ala Lys Val Tyr Val
        195                 200                 205

Gly Met Arg Tyr Trp His Pro Phe Thr Glu Glu Ala Ile Glu Gln Ile
    210                 215                 220

Lys Arg Asp Gly Ile Thr Lys Leu Val Val Leu Pro Leu Tyr Pro Gln
225                 230                 235                 240

Phe Ser Ile Ser Thr Ser Gly Ser Ser Leu Arg Leu Leu Glu Gly Ile
                245                 250                 255

Phe Arg Glu Asp Glu Tyr Leu Val Asn Met Gln His Thr Val Ile Pro
            260                 265                 270

Ser Trp Tyr Gln Arg Glu Gly Tyr Ile Lys Ala Met Ala Thr Leu Ile
        275                 280                 285

Glu Lys Glu Leu Arg Thr Phe Ser Glu Pro Gln Lys Val Met Ile Phe
    290                 295                 300

Phe Ser Ala His Gly Val Pro Leu Ala Tyr Val Glu Glu Ala Gly Asp
305                 310                 315                 320

Pro Tyr Lys Ala Glu Met Glu Glu Cys Val Asp Leu Ile Met Glu Glu
                325                 330                 335

Leu Glu Lys Arg Gly Ile Thr Asn Ser Cys Thr Leu Ala Tyr Gln Ser
            340                 345                 350

Arg Val Gly Pro Val Glu Trp Leu Arg Pro Tyr Thr Asp Glu Thr Ile
        355                 360                 365

Ile Glu Leu Gly Gln Lys Gly Val Lys Ser Leu Leu Ala Val Pro Ile
    370                 375                 380

Ser Phe Val Ser Glu His Ile Glu Thr Leu Glu Glu Ile Asp Val Glu
385                 390                 395                 400

Tyr Lys Glu Leu Ala Leu Glu Ser Gly Ile Lys His Trp Gly Arg Val
                405                 410                 415

Pro Ala Leu Gly Cys Glu Pro Thr Phe Ile Thr Asp Leu Ala Asp Ala
            420                 425                 430

Val Ile Glu Ser Leu Pro Tyr Val Gly Ala Met Ala Val Ser Asn Leu
        435                 440                 445

Glu Ala Arg Gln Pro Leu Val Pro Leu Gly Ser Val Glu Glu Leu Leu
    450                 455                 460

Ala Ala Tyr Asp Ser Lys Arg Asp Glu Leu Pro Pro Pro Val Thr Val
465                 470                 475                 480

Trp Glu Trp Gly Trp Thr Lys Ser Ala Glu Thr Trp Asn Gly Arg Ala
                485                 490                 495

Ala Met Leu Ala Val Leu Ala Leu Leu Val Leu Glu Val Thr Thr Gly
            500                 505                 510

Glu Gly Phe Leu His Gln Trp Gly Ile Leu Pro Leu Phe His
        515                 520                 525
```

<210> SEQ ID NO 52
<211> LENGTH: 522
<212> TYPE: PRT
<213> ORGANISM: Cucumis sativus

<400> SEQUENCE: 52

```
Met Asp Ser Ala Ile Gln Ala Ser Ser Ser Pro Ala Ser Ser Ser Ala
1               5                   10                  15

Phe Arg Ser Pro Cys Leu Thr Ser Ala Ser Gln Asn Cys Lys Phe Pro
            20                  25                  30

Leu Pro Thr Ser Arg Val Val Gly Ser Lys Arg His Arg Ala Phe Arg
        35                  40                  45

Leu His Met Asp Ala Cys Pro Thr Lys Cys His Val Val Ser Arg Tyr
    50                  55                  60

Ser Phe Glu Leu Pro Asp Ser Gln Ser Ile Phe Ser Lys Lys Ser Ile
65                  70                  75                  80

Asn Lys Phe Phe Pro Pro Pro Arg Ala Leu Val Ala Ser Asn Thr Gln
                85                  90                  95

Asn Thr Ser Ala Ala Pro Leu Ile Gly Glu Asp Lys Val Gly Val Leu
            100                 105                 110

Leu Leu Asn Leu Gly Gly Pro Glu Thr Leu Asp Asp Val Gln Pro Phe
        115                 120                 125

Leu Phe Asn Leu Phe Ala Asp Pro Asp Ile Ile Arg Leu Pro Arg Leu
    130                 135                 140

Phe Arg Phe Leu Gln Arg Pro Leu Ala Arg Phe Ile Ser Val Leu Arg
145                 150                 155                 160

Ser Pro Lys Ser Arg Glu Gly Tyr Ala Ser Ile Gly Gly Gly Ser Pro
                165                 170                 175

Leu Arg Lys Ile Thr Asp Ala Gln Ala Glu Glu Leu Lys Lys Ala Leu
            180                 185                 190

Trp Gln Lys Asp Val Pro Ala Glu Val Tyr Val Gly Met Arg Tyr Trp
        195                 200                 205

His Pro Phe Thr Glu Glu Ala Ile Glu Gln Ile Lys Lys Asp Gly Ile
    210                 215                 220

Ser Lys Leu Val Val Leu Pro Leu Tyr Pro Gln Phe Ser Ile Ser Thr
225                 230                 235                 240

Ser Gly Ser Ser Leu Arg Leu Leu Glu Gly Ile Phe Arg Glu Asp Glu
                245                 250                 255

Tyr Leu Val Asn Met Gln His Thr Val Ile Pro Ser Trp Tyr Gln Arg
            260                 265                 270

Glu Gly Tyr Ile Lys Ala Met Ala Asp Leu Ile Glu Lys Glu Leu Lys
        275                 280                 285

Thr Phe Asp Phe Pro Glu Gln Val Met Val Phe Phe Ser Ala His Gly
    290                 295                 300

Val Pro Leu Ala Tyr Val Glu Glu Ala Gly Asp Pro Tyr Lys Ala Glu
305                 310                 315                 320

Met Glu Glu Cys Val Asp Leu Ile Met Glu Glu Leu Glu Lys Arg Arg
                325                 330                 335

Ile Thr Asn Ser Tyr Thr Leu Ala Tyr Gln Ser Arg Val Gly Pro Val
            340                 345                 350

Glu Trp Leu Lys Pro Tyr Thr Asp Glu Thr Ile Ile Glu Leu Gly Gln
        355                 360                 365

Lys Gly Val Lys Ser Leu Leu Ala Val Pro Ile Ser Phe Val Ser Glu
    370                 375                 380
```

His Ile Glu Thr Leu Glu Glu Ile Asp Val Glu Tyr Lys Glu Leu Ala
385 390 395 400

Leu Lys Ser Gly Ile Glu Lys Trp Gly Arg Val Pro Ala Leu Gly Cys
405 410 415

Glu Pro Thr Phe Ile Thr Asp Leu Ala Asp Ala Val Ile Glu Ser Leu
420 425 430

Pro Tyr Val Gly Ala Met Ala Val Ser Asn Leu Glu Ala Arg Gln Pro
435 440 445

Leu Val Pro Leu Gly Ser Val Glu Glu Leu Leu Ala Ala Tyr Asp Ser
450 455 460

Gln Arg Arg Gln Leu Pro Pro Pro Val Thr Val Trp Glu Trp Gly Trp
465 470 475 480

Thr Lys Ser Ala Glu Thr Trp Asn Gly Arg Ala Ala Met Leu Ala Val
485 490 495

Leu Val Leu Leu Val Leu Glu Val Thr Thr Gly Glu Gly Phe Leu His
500 505 510

Gln Trp Gly Ile Phe Pro Leu Phe His Gln
515 520

<210> SEQ ID NO 53
<211> LENGTH: 497
<212> TYPE: PRT
<213> ORGANISM: Nicotiana tabacum

<400> SEQUENCE: 53

Met Ala Gln Pro Val Ile Phe Cys Arg Glu Ile Ser Ala Ser Pro Ala
1 5 10 15

Asn Cys Thr Ser Tyr Ser Pro Phe His Gln Val Asp Gly Gln Ser Ser
20 25 30

Val Pro Phe Ala Ala Ser Cys Leu Arg Val Pro Lys Asn Cys Ser Leu
35 40 45

Val Ala Ala Arg Cys Ser Leu Lys Pro Ser Met Met Pro Ser Ala Leu
50 55 60

Val Thr Ser Arg Pro Gln Gln Val Ser Thr Asp Pro Val Asn Val Val
65 70 75 80

Cys Asp Gly Lys Ile Gly Val Leu Leu Leu Asn Leu Gly Gly Pro Glu
85 90 95

Ser Leu Glu Asp Val Gln Pro Phe Leu Phe Asn Leu Phe Ala Asp Pro
100 105 110

Asp Ile Ile Arg Leu Pro Arg Leu Phe Arg Phe Leu Gln Arg Pro Leu
115 120 125

Ala Gln Phe Ile Ser Val Ala Arg Ala Pro Lys Ser Lys Glu Gly Tyr
130 135 140

Ala Ser Ile Gly Gly Gly Ser Pro Leu Arg Arg Ile Thr Asp Ala Gln
145 150 155 160

Ala Glu Ala Leu Arg Lys Ala Leu Arg Glu Arg Asn Val Pro Ala Lys
165 170 175

Val Tyr Val Gly Met Arg Tyr Trp His Pro Phe Thr Glu Glu Ala Ile
180 185 190

Glu Leu Ile Lys Arg Asp Gly Ile Thr Lys Leu Val Val Leu Pro Leu
195 200 205

Tyr Pro Gln Phe Ser Ile Ser Thr Ser Gly Ser Ser Leu Arg Leu Leu
210 215 220

Glu Ser Ile Phe Arg Glu Asp Glu Tyr Leu Val Asn Met Gln His Thr
225 230 235 240

```
Val Ile Pro Ser Trp Tyr Gln Arg Glu Gly Tyr Ile Lys Ala Met Ala
                245                 250                 255

Asp Leu Met Glu Lys Glu Leu Lys Ser Phe Glu Arg Pro Gly Glu Val
            260                 265                 270

Met Ile Phe Phe Ser Ala His Gly Val Pro Leu Ala Tyr Val Glu Glu
        275                 280                 285

Ala Gly Asp Pro Tyr Lys Ala Glu Met Glu Glu Cys Val Asp Leu Ile
    290                 295                 300

Met Glu Glu Leu Glu Lys Arg Arg Val Tyr Asn Ala Tyr Thr Leu Ala
305                 310                 315                 320

Tyr Gln Ser Arg Val Gly Pro Val Glu Trp Leu Lys Pro Tyr Thr Asp
                325                 330                 335

Glu Thr Ile Ile Glu Leu Gly Lys Lys Gly Val Lys Ser Ile Leu Ala
            340                 345                 350

Val Pro Ile Ser Phe Val Ser Glu His Ile Glu Thr Leu Glu Glu Ile
        355                 360                 365

Asp Val Glu Tyr Lys Glu Leu Ala Leu Glu Ser Gly Ile Gln Asn Trp
    370                 375                 380

Ala Arg Val Pro Ala Leu Gly Val Glu Pro Thr Phe Ile Ser Asp Leu
385                 390                 395                 400

Ala Asp Ala Val Ile Glu Ser Leu Pro Tyr Val Gly Ala Met Ala Val
                405                 410                 415

Ser Asn Leu Glu Ala Arg Gln Ser Leu Val Pro Leu Gly Ser Val Glu
            420                 425                 430

Glu Leu Leu Ala Ala Tyr Asp Ser His Gly Arg Glu Leu Pro Pro Pro
        435                 440                 445

Val Thr Val Trp Glu Trp Gly Trp Thr Lys Ser Ala Glu Thr Trp Asn
    450                 455                 460

Gly Arg Ala Ala Met Leu Ala Val Leu Val Leu Leu Val Leu Glu Val
465                 470                 475                 480

Thr Thr Gly Glu Gly Phe Leu His Gln Trp Gly Ile Leu Pro Leu Phe
                485                 490                 495

Arg


<210> SEQ ID NO 54
<211> LENGTH: 387
<212> TYPE: PRT
<213> ORGANISM: Synechocystis PCC6803

<400> SEQUENCE: 54

Met Gly Arg Val Gly Val Leu Leu Leu Asn Leu Gly Gly Pro Glu Lys
1               5                   10                  15

Leu Glu Asp Val Arg Pro Phe Leu Phe Asn Leu Phe Ala Asp Pro Glu
            20                  25                  30

Ile Ile Arg Leu Pro Phe Pro Trp Leu Gln Lys Pro Leu Ala Trp Leu
        35                  40                  45

Ile Ser Thr Leu Arg Ala Lys Lys Ser Gln Ala Asn Tyr Ala Glu Ile
    50                  55                  60

Gly Gly Gly Ser Pro Leu Leu Gln Ile Thr Glu Ala Gln Ala Ser Ala
65                  70                  75                  80

Leu Thr Thr Arg Leu Glu Arg Leu Gly Gln Asp Ala Lys Val Tyr Ile
                85                  90                  95

Gly Met Arg Tyr Trp His Pro Phe Thr Glu Glu Ala Val Glu Lys Ile
            100                 105                 110

Lys Gly Asp Arg Leu Gln Arg Leu Val Ile Leu Pro Leu Tyr Pro His
```

```
        115                 120                 125

Phe Ser Ile Ser Thr Ser Gly Ser Ser Phe Arg Val Leu Glu Glu Met
    130                 135                 140

Trp His Asn Asp Pro Ser Leu Arg Gln Leu Asp Tyr Ser Leu Ile Pro
145                 150                 155                 160

Ser Trp Tyr Asp His Pro Gly Tyr Leu Gln Ala Met Ala Asp Leu Ile
                165                 170                 175

Ala Gln Glu Leu Lys Lys Phe Pro Asn Pro Asp Gln Ala His Ile Phe
            180                 185                 190

Phe Ser Ala His Gly Val Pro Gln Ser Tyr Val Asp Glu Ala Gly Asp
        195                 200                 205

Pro Tyr Gln Ala Glu Ile Glu Ala Cys Thr Arg Leu Ile Met Arg Thr
    210                 215                 220

Leu Asp Arg Pro Asn Gln Tyr Thr Leu Ala Tyr Gln Ser Arg Val Gly
225                 230                 235                 240

Pro Val Glu Trp Leu Lys Pro Tyr Thr Glu Glu Ala Leu Gln Lys Leu
                245                 250                 255

Gly Ala Glu Gly Ile Asp Asp Leu Leu Val Val Pro Ile Ser Phe Val
            260                 265                 270

Ser Glu His Ile Glu Thr Leu Gln Glu Ile Asp Ile Glu Tyr Arg Glu
        275                 280                 285

Ile Ala Glu Glu Ala Gly Ile Asp Asn Phe Gln Arg Val Pro Ala Leu
    290                 295                 300

Asn Thr His Pro Val Phe Ile Asp Ala Leu Ala Gln Met Val Met Asp
305                 310                 315                 320

Ser Leu Asn Asp Pro Pro Cys Thr Phe Glu Thr Val Pro His Pro Lys
                325                 330                 335

Lys Asn Met Lys Met Tyr Pro Gln Glu Arg Trp Glu Trp Gly Leu Thr
            340                 345                 350

Thr Ala Ala Glu Val Trp Asn Gly Arg Leu Ala Met Leu Gly Phe Ile
        355                 360                 365

Ala Leu Leu Val Glu Leu Ile Ser Gly Gln Gly Pro Leu His Phe Val
    370                 375                 380

Gly Leu Leu
385
```

<210> SEQ ID NO 55
<211> LENGTH: 4035
<212> TYPE: DNA
<213> ORGANISM: Artificial
<220> FEATURE:
<223> OTHER INFORMATION: Plasmid PHP30949, an entry clone containing the maize ferrochelatase-I protein.

<400> SEQUENCE: 55

```
aagggtgggc gcgccgaccc agctttcttg tacaaagttg gcattataag aaagcattgc      60

ttatcaattt gttgcaacga acaggtcact atcagtcaaa ataaaatcat tatttgccat     120

ccagctgata tcccctatag tgagtcgtat tacatggtca tagctgtttc ctggcagctc     180

tggcccgtgt ctcaaaatct ctgatgttac attgcacaag ataaaaatat atcatcatga     240

acaataaaac tgtctgctta cataaacagt aatacaaggg gtgttatgag ccatattcaa     300

cgggaaacgt cgaggccgcg attaaattcc aacatggatg ctgatttata tgggtataaa     360

tgggctcgcg ataatgtcgg gcaatcaggt gcgacaatct atcgcttgta tgggaagccc     420

gatgcgccag agttgtttct gaaacatggc aaaggtagcg ttgccaatga tgttacagat     480
```

-continued

```
gagatggtca gactaaactg gctgacggaa tttatgcctc ttccgaccat caagcatttt    540
atccgtactc ctgatgatgc atggttactc accactgcga tccccggaaa aacagcattc    600
caggtattag aagaatatcc tgattcaggt gaaaatattg ttgatgcgct ggcagtgttc    660
ctgcgccggt tgcattcgat tcctgtttgt aattgtcctt ttaacagcga tcgcgtattt    720
cgtctcgctc aggcgcaatc acgaatgaat aacggtttgg ttgatgcgag tgattttgat    780
gacgagcgta atggctggcc tgttgaacaa gtctggaaag aaatgcataa acttttgcca    840
ttctcaccgg attcagtcgt cactcatggt gatttctcac ttgataacct tatttttgac    900
gaggggaaat taataggttg tattgatgtt ggacgagtcg gaatcgcaga ccgataccag    960
gatcttgcca tcctatggaa ctgcctcggt gagttttctc cttcattaca gaaacggctt   1020
tttcaaaaat atggtattga taatcctgat atgaataaat tgcagtttca tttgatgctc   1080
gatgagtttt tctaatcaga attggttaat tggttgtaac actggcagag cattacgctg   1140
acttgacggg acggcgcaag ctcatgacca aaatccctta acgtgagtta cgcgtcgttc   1200
cactgagcgt cagaccccgt agaaaagatc aaaggatctt cttgagatcc tttttttctg   1260
cgcgtaatct gctgcttgca aacaaaaaaa ccaccgctac cagcggtggt ttgtttgccg   1320
gatcaagagc taccaactct ttttccgaag gtaactggct tcagcagagc gcagatacca   1380
aatactgtcc ttctagtgta gccgtagtta ggccaccact tcaagaactc tgtagcaccg   1440
cctacatacc tcgctctgct aatcctgtta ccagtggctg ctgccagtgg cgataagtcg   1500
tgtcttaccg ggttggactc aagacgatag ttaccggata aggcgcagcg gtcgggctga   1560
acggggggtt cgtgcacaca gcccagcttg gagcgaacga cctacaccga actgagatac   1620
ctacagcgtg agcattgaga aagcgccacg cttcccgaag ggagaaaggc ggacaggtat   1680
ccggtaagcg gcagggtcgg aacaggagag cgcacgaggg agcttccagg gggaaacgcc   1740
tggtatcttt atagtcctgt cgggtttcgc cacctctgac ttgagcgtcg atttttgtga   1800
tgctcgtcag gggggcggag cctatggaaa aacgccagca acgcggcctt tttacggttc   1860
ctggcctttt gctggccttt tgctcacatg ttctttcctg cgttatcccc tgattctgtg   1920
gataaccgta ttaccgcctt tgagtgagct gataccgctc gccgcagccg aacgaccgag   1980
cgcagcgagt cagtgagcga ggaagcggaa gagcgcccaa tacgcaaacc gcctctcccc   2040
gcgcgttggc cgattcatta atgcagctgg cacgacaggt ttcccgactg gaaagcgggc   2100
agtgagcgca acgcaattaa tacgcgtacc gctagccagg aagagtttgt agaaacgcaa   2160
aaaggccatc cgtcaggatg gccttctgct tagtttgatg cctggcagtt tatggcgggc   2220
gtcctgcccg ccaccctccg ggccgttgct tcacaacgtt caaatccgct cccggcggat   2280
ttgtcctact caggagagcg ttcaccgaca aacaacagat aaaacgaaag gcccagtctt   2340
ccgactgagc ctttcgtttt atttgatgcc tggcagttcc ctactctcgc gttaacgcta   2400
gcatggatgt tttcccagtc acgacgttgt aaaacgacgg ccagtcttaa gctcgggccc   2460
caaataatga ttttattttg actgatagtg acctgttcgt tgcaacaaat tgatgagcaa   2520
tgctttttta taatgccaac tttgtacaaa aaagcaggct ccgcggccgc cccctttcacc  2580
atgtcttcgt cgggcccctc cccggcgacg ggaatccacg cgtcgccgcc gttgggcctt   2640
ttgccggcga cgggaaccca tcacaccagg tcatggggca aaacaacctc cacaagtttt   2700
actggttcta ccaccaaaca tgagcagagc ttgcatggaa atgttaagcc gttgcaattg   2760
gcggcaaatg aatcctctcg tttggcttac agaagtccag cacttaaaaa ccagtggaat   2820
cttcctgcta gttcttcctc cactaatgtg gttaccacct ttgatgataa cgaacacgtg   2880
```

```
tcttccagtg ttattgaaga aaaagttgga gtactgttat taaaccttgg tggtccagag   2940

acacttgacg atgttcaacc atttttattc aacctatttg ctgatccaga tatcattcga   3000

ctccctaggc tcttcaggtt tcttcaaaga ccactggcca aacttatttc tacttttaga   3060

gctcctaaga gtaaagaagg gtatgcttca attggtggtg ggtcgccgtt aaggaaaatt   3120

actgatgaac aggcgaatgc tttgaagatt gccctggaaa agaaaaaatt gaacgcaaac   3180

atatatgttg ggatgcggta ttggtaccct ttcacagaag aggccattga tcaaattaaa   3240

aaggataaga ttaccaagct cgttgttctt cccctttacc ctcagtactc catatcaaca   3300

agtgggtcaa gcattcgtgt tctccaagac attgtcaagg aagattcata tttttctggt   3360

ttgccaattt ccattattga atcatggtac caacgagatg gctatgtgaa atcaatgtct   3420

gacctaattg aaaaggagct ctccgccttc tccaatcctg aagaggttat gatattcttc   3480

agtgcacatg gtgtgccact tacctatgtt gaggatgctg gagatcctta cagagatcag   3540

atggaggatt gtattgcttt gatcatgggg gagttaagat caagaggaat cttaaatagt   3600

cacactttgg cgtaccagag tcgggtgggg ccagttcaat ggctgaagcc atatactgat   3660

gaagttttag tagaacttgg tcaaaagggt gtgaagagcc tcctggctgt tccagtaagc   3720

tttgtgagtg agcacatcga gacattggaa gaaattgaca tggagtacaa ggagttggct   3780

ctggaatcag gcatcaagaa ctggggtcgg gttcctgctc ttggatgcac ttcaacattc   3840

atctccgacc ttgcagatgc tgtcgtcgaa gccctgccct ctgcttcagc gctcgcgacc   3900

agaaagcctg acgacatcga ttccagcatg gacctgacgc attacctcac caagatgctg   3960

tttggctcaa tcttggcatt tgtcctgctg ctatcaccaa ggctagtttc cgccttccgg   4020

agcaccatgc tttaa                                                    4035
```

<210> SEQ ID NO 56
<211> LENGTH: 1934
<212> TYPE: DNA
<213> ORGANISM: Zea mays

<400> SEQUENCE: 56

```
cgccactccc ccaatactca ggtgtcagga cagcgagcag gcacaagcag atctcactcc     60

acgttgctcc ttccgccctt cctctccgcc gctccccgaa aattcctgca ggaaggatca    120

tggagcgcgg gattcttggc tccaggggcg ccgtccaaat cttggggtcg aagaccgggg    180

ccgcgatgtc atgtggcaaa acaacctcta caagttttac ttgttctacc aaacacgagc    240

tgaacttgca tgtgaatgtt aagccgttgc aattggcaac agatggatcc tctcgtttgg    300

catacaaaac tccagtgctt aaaaatcagt ggaatctttc tgctagttct tcctctgcaa    360

atgtggttac cacttttgat gatgacaaag gtgtaccttc cagttttgct gaagaaaaga    420

tcggagtact gttattaaat cttggtggtc cagaaaccct agacgatgtt caaccattct    480

tgttcaacct atttgctgat ccagatatca ttcgactgcc taggctcttc aggttccttc    540

aaagaccact ggccaaactt atttctactt ttagagctcc taagagtaaa gaagggtatg    600

cttcaatcgg tggtgggtca ccattgagga aaattactga tgagcaggca aatgctttga    660

agattgctct ggaaaagaaa aaattgaacg caaatatata tgttgggatg cggtattggt    720

atcctttcac agaagaagcc attgatcaga ttaagaagga taatatttcc aagctcgttg    780

ttcttccact ctaccctcag tactccatat caacaagtgg gtcaagcatt cgtgttctcc    840

aaaatgttgt caaggaagat tcatattttt ctggcttgcc aatctccatt atcgaatcat    900

ggtaccaacg tgatggctat gtgaaatcaa tggctgacct aattgaaaaa gagctatctg    960
```

```
ccttttccaa tcctgaagag gtaatgatat tcttcagtgc acatggtgtg ccacttacct   1020
atgttcagga tgctggagat ccttacagag atcagatgga ggattgtatt tctttgatca   1080
tgggggagct gagatccaga ggaatcttaa atggtcacac tttggcgtat cagagtcggg   1140
tgggaccagt tcaatggctg aagccatata ctgatgaagt tttagtagaa cttggtcaga   1200
acggtgtgaa gagcctcctg gctgttccag taagcttcgt gagcgagcac attgagacac   1260
tggaagaaat agacatggag tacaaggagt tggctctgga atcaggcatt gagaactggg   1320
gccgggtccc tgctcttgga tgcacttcga ctttcatctc cgaccttgca gatgcggttg   1380
tcgaagccct cccatctgcc tcggcgctgg gaaccagaaa gcctgaagac accgattcca   1440
gcatggatct gatgcattac ctgaccaaga tgttcttcgg ctcaatcttg gcatttatcc   1500
tgctgttgtc accaagactg gtttctgctt tccggaacac catgctttag gtggttaggt   1560
aggtaagcaa aaagggaatg gtgtgatagg taattcttaa aaatttgaga ttaataatgg   1620
aaaaactgga gagagcttgg tgatagtaac tagagatcct ttaggctttg tttgggtact   1680
ctagtattga ccctaatccg tgtgttgaga tagattgagg tgtaaattag tttaagttat   1740
acctcaattc agctcagtac atatagattg agctcaatac tagaatactc aaactaggcc   1800
ttagtgcacg aggtagcagc ttgtaatttg ctgtttttga tattgttcac aggaaacatt   1860
ggtctcataa atgaatctgt gaaagcacat aacgttacaa atcaaaaaaa aaaaaaaaaa   1920
aaaaaaaaaa aaaa                                                     1934
```

<210> SEQ ID NO 57
<211> LENGTH: 481
<212> TYPE: PRT
<213> ORGANISM: Glycine max

<400> SEQUENCE: 57

```
Met Asn Ala Thr Ser Tyr Ser Ala Leu Pro Ser Thr Phe Arg Ser Leu
1               5                   10                  15

His His Arg Asn Phe Ser Ala Phe Cys Ser Asp Ile Gln Asn Pro Gly
            20                  25                  30

Tyr Val Asp Cys His Ser Asn Cys Asn Lys Ser Thr Ser Gln Ala Ser
        35                  40                  45

Leu Phe Leu Cys Ser Asp Ser Asn Ser Arg Arg Asn Gly Val Phe Gly
    50                  55                  60

Arg Pro Leu Cys Val Asn Pro Ser Gly Arg Arg Asn Leu Val Gly Pro
65                  70                  75                  80

Ala Phe Tyr Ser Leu Glu Thr Ser Ala Tyr Asp Val Ala Ala Leu Glu
                85                  90                  95

Ser Pro Ser Arg Val Ala Glu Glu Lys Val Gly Val Leu Leu Leu Asn
            100                 105                 110

Leu Gly Gly Pro Glu Thr Leu Ser Asp Val Gln Pro Phe Leu Phe Asn
        115                 120                 125

Leu Phe Ala Asp Pro Asp Ile Ile Arg Leu Pro Arg Leu Phe Arg Phe
    130                 135                 140

Leu Gln Arg Pro Leu Ala Lys Leu Ile Ser Val Leu Arg Ala Pro Lys
145                 150                 155                 160

Ser Lys Glu Gly Tyr Ala Ala Ile Gly Gly Gly Ser Pro Leu Arg Lys
                165                 170                 175

Ile Thr Asp Asp Gln Ala Leu Ala Ile Lys Met Ala Leu Glu Ala Lys
            180                 185                 190

Gly Ile Ser Ser Asn Val Tyr Val Gly Met Arg Tyr Trp Tyr Pro Phe
        195                 200                 205
```

```
Thr Glu Glu Ala Ile Gln Gln Ile Lys Arg Asp Arg Ile Thr Arg Leu
    210                 215                 220

Val Val Leu Pro Leu Tyr Pro Gln Phe Ser Ile Ser Thr Thr Gly Ser
225                 230                 235                 240

Ser Ile Arg Val Leu Glu His Ile Phe Arg Glu Asp Ala Tyr Leu Ser
                245                 250                 255

Lys Leu Pro Val Ser Ile Ile Asn Ser Trp Tyr Gln Arg Glu Gly Tyr
            260                 265                 270

Ile Lys Ser Met Ala Asn Leu Ile Gln Lys Glu Leu Gln Ser Phe Ser
        275                 280                 285

Glu Pro Lys Glu Val Met Ile Phe Phe Ser Ala His Gly Val Pro Val
    290                 295                 300

Ser Tyr Val Glu Glu Ala Gly Asp Pro Tyr Arg Asp Gln Met Glu Glu
305                 310                 315                 320

Cys Ile Phe Leu Ile Met Gln Glu Leu Lys Ala Arg Gly Ile Ser Asn
                325                 330                 335

Glu His Thr Leu Ala Tyr Gln Ser Arg Val Gly Pro Val Gln Trp Leu
            340                 345                 350

Lys Pro Tyr Thr Asp Glu Val Leu Val Glu Leu Gly Gln Lys Gly Val
        355                 360                 365

Lys Ser Leu Leu Ala Val Pro Val Ser Phe Val Ser Glu His Ile Glu
    370                 375                 380

Thr Leu Glu Glu Ile Asp Met Glu Tyr Lys Glu Leu Ala Leu Glu Ser
385                 390                 395                 400

Gly Ile Lys Asn Trp Ala Arg Val Pro Ala Leu Gly Val Thr Pro Ser
                405                 410                 415

Phe Ile Thr Asp Leu Ala Asp Ala Val Ile Glu Ala Leu Pro Ser Ala
            420                 425                 430

Thr Ala Ile Tyr Ala Pro Thr Arg Thr Ser Glu Asp Val Asp His Asp
        435                 440                 445

Pro Val Arg Tyr Phe Ile Lys Met Phe Phe Gly Ser Ile Leu Ala Phe
    450                 455                 460

Ile Leu Phe Leu Ser Pro Lys Met Ile Thr Ala Phe Arg Asn His Val
465                 470                 475                 480

Ile


<210> SEQ ID NO 58
<211> LENGTH: 466
<212> TYPE: PRT
<213> ORGANISM: Arabidopsis thaliana

<400> SEQUENCE: 58

Met Gln Ala Thr Ala Leu Ser Ser Gly Phe Asn Pro Leu Thr Lys Arg
1               5                   10                  15

Lys Asp His Arg Phe Pro Arg Ser Cys Ser Gln Arg Asn Ser Leu Ser
            20                  25                  30

Leu Ile Gln Cys Asp Ile Lys Glu Arg Ser Phe Gly Glu Ser Met Thr
        35                  40                  45

Ile Thr Asn Arg Gly Leu Ser Phe Lys Thr Asn Val Phe Glu Gln Ala
    50                  55                  60

Arg Ser Val Thr Gly Asp Cys Ser Tyr Asp Glu Thr Ser Ala Lys Ala
65                  70                  75                  80

Arg Ser His Val Val Ala Glu Asp Lys Ile Gly Val Leu Leu Leu Asn
                85                  90                  95
```

Leu Gly Gly Pro Glu Thr Leu Asn Asp Val Gln Pro Phe Leu Tyr Asn
100 105 110

Leu Phe Ala Asp Pro Asp Ile Ile Arg Leu Pro Arg Pro Phe Gln Phe
115 120 125

Leu Gln Gly Thr Ile Ala Lys Phe Ile Ser Val Val Arg Ala Pro Lys
130 135 140

Ser Lys Glu Gly Tyr Ala Ala Ile Gly Gly Gly Ser Pro Leu Arg Lys
145 150 155 160

Ile Thr Asp Glu Gln Ala Asp Ala Ile Lys Met Ser Leu Gln Ala Lys
165 170 175

Asn Ile Ala Ala Asn Val Tyr Val Gly Met Arg Tyr Trp Tyr Pro Phe
180 185 190

Thr Glu Glu Ala Val Gln Gln Ile Lys Lys Asp Lys Ile Thr Arg Leu
195 200 205

Val Val Leu Pro Leu Tyr Pro Gln Tyr Ser Ile Ser Thr Thr Gly Ser
210 215 220

Ser Ile Arg Val Leu Gln Asp Leu Phe Arg Lys Asp Pro Tyr Leu Ala
225 230 235 240

Gly Val Pro Val Ala Ile Ile Lys Ser Trp Tyr Gln Arg Arg Gly Tyr
245 250 255

Val Asn Ser Met Ala Asp Leu Ile Glu Lys Glu Leu Gln Thr Phe Ser
260 265 270

Asp Pro Lys Glu Val Met Ile Phe Phe Ser Ala His Gly Val Pro Val
275 280 285

Ser Tyr Val Glu Asn Ala Gly Asp Pro Tyr Gln Lys Gln Met Glu Glu
290 295 300

Cys Ile Asp Leu Ile Met Glu Glu Leu Lys Ala Arg Gly Val Leu Asn
305 310 315 320

Asp His Lys Leu Ala Tyr Gln Ser Arg Val Gly Pro Val Gln Trp Leu
325 330 335

Lys Pro Tyr Thr Asp Glu Val Leu Val Asp Leu Gly Lys Ser Gly Val
340 345 350

Lys Ser Leu Leu Ala Val Pro Val Ser Phe Val Ser Glu His Ile Glu
355 360 365

Thr Leu Glu Glu Ile Asp Met Glu Tyr Arg Glu Leu Ala Leu Glu Ser
370 375 380

Gly Val Glu Asn Trp Gly Arg Val Pro Ala Leu Gly Leu Thr Pro Ser
385 390 395 400

Phe Ile Thr Asp Leu Ala Asp Ala Val Ile Glu Ser Leu Pro Ser Ala
405 410 415

Glu Ala Met Ser Asn Pro Asn Ala Val Val Asp Ser Glu Asp Ser Glu
420 425 430

Ser Ser Asp Ala Phe Ser Tyr Ile Val Lys Met Phe Phe Gly Ser Ile
435 440 445

Leu Ala Phe Val Leu Leu Leu Ser Pro Lys Met Phe His Ala Phe Arg
450 455 460

Asn Leu
465

<210> SEQ ID NO 59
<211> LENGTH: 476
<212> TYPE: PRT
<213> ORGANISM: Zea mays

<400> SEQUENCE: 59

-continued

```
Met Glu Arg Gly Ile Leu Gly Ser Arg Gly Ala Val Gln Ile Leu Gly
1               5                   10                  15

Ser Lys Thr Gly Ala Ala Met Ser Cys Gly Lys Thr Thr Ser Thr Ser
            20                  25                  30

Phe Thr Cys Ser Thr Lys His Glu Leu Asn Leu His Val Asn Val Lys
        35                  40                  45

Pro Leu Gln Leu Val Thr Asp Gly Ser Ser Arg Leu Ala Tyr Lys Thr
    50                  55                  60

Pro Val Leu Lys Asn Gln Trp Asn Leu Ser Ala Ser Ser Ser Ser Ala
65                  70                  75                  80

Asn Val Val Thr Thr Phe Asp Asp Asp Lys Gly Val Pro Ser Ser Phe
                85                  90                  95

Ala Glu Glu Lys Ile Gly Val Leu Leu Leu Asn Leu Gly Gly Pro Glu
            100                 105                 110

Thr Leu Asp Asp Val Gln Pro Phe Leu Phe Asn Leu Phe Ala Asp Pro
        115                 120                 125

Asp Ile Ile Arg Leu Pro Arg Leu Phe Arg Phe Leu Gln Arg Pro Leu
    130                 135                 140

Ala Lys Leu Ile Ser Thr Phe Arg Ala Pro Lys Ser Lys Glu Gly Tyr
145                 150                 155                 160

Ala Ser Ile Gly Gly Gly Ser Pro Leu Arg Lys Ile Thr Asp Glu Gln
                165                 170                 175

Ala Asn Ala Leu Lys Ile Ala Leu Glu Lys Lys Lys Leu Asn Ala Asn
            180                 185                 190

Ile Tyr Val Gly Met Arg Tyr Trp Tyr Pro Phe Thr Glu Glu Ala Ile
        195                 200                 205

Asp Gln Ile Lys Lys Asp Asn Ile Ser Lys Leu Val Val Leu Pro Leu
    210                 215                 220

Tyr Pro Gln Tyr Ser Ile Ser Thr Ser Gly Ser Ser Ile Arg Val Leu
225                 230                 235                 240

Gln Asn Val Val Lys Glu Asp Ser Tyr Phe Ser Gly Leu Pro Ile Ser
                245                 250                 255

Ile Ile Glu Ser Trp Tyr Gln Arg Asp Gly Tyr Val Lys Ser Met Ala
            260                 265                 270

Asp Leu Ile Glu Lys Glu Leu Ser Ala Phe Ser Asn Pro Glu Glu Val
        275                 280                 285

Met Ile Phe Phe Ser Ala His Gly Val Pro Leu Thr Tyr Val Gln Asp
    290                 295                 300

Ala Gly Asp Pro Tyr Arg Asp Gln Met Glu Asp Cys Ile Ser Leu Ile
305                 310                 315                 320

Met Gly Glu Leu Arg Ser Arg Gly Ile Leu Asn Gly His Thr Leu Ala
                325                 330                 335

Tyr Gln Ser Arg Val Gly Pro Val Gln Trp Leu Lys Pro Tyr Thr Asp
            340                 345                 350

Glu Val Leu Val Glu Leu Gly Gln Asn Gly Val Lys Ser Leu Leu Ala
        355                 360                 365

Val Pro Val Ser Phe Val Ser Glu His Ile Glu Thr Leu Glu Glu Ile
    370                 375                 380

Asp Met Glu Tyr Lys Glu Leu Ala Leu Glu Ser Gly Ile Glu Asn Trp
385                 390                 395                 400

Gly Arg Val Pro Ala Leu Gly Cys Thr Ser Thr Phe Ile Ser Asp Leu
                405                 410                 415

Ala Asp Ala Val Val Glu Ala Leu Pro Ser Ala Ser Ala Leu Gly Thr
            420                 425                 430
```

Arg Lys Pro Glu Asp Thr Gly Ser Ser Met Asp Leu Met His Tyr Leu
435 440 445

Thr Lys Met Phe Phe Gly Ser Ile Leu Ala Phe Ile Leu Leu Leu Ser
450 455 460

Pro Arg Leu Val Ser Ala Phe Arg Asn Thr Thr Leu
465 470 475

<210> SEQ ID NO 60
<211> LENGTH: 484
<212> TYPE: PRT
<213> ORGANISM: Zea mays

<400> SEQUENCE: 60

Met Ser Ser Ser Gly Pro Ser Pro Ala Thr Gly Ile His Ala Ser Pro
1 5 10 15

Pro Leu Gly Leu Leu Pro Ala Thr Gly Thr His His Thr Arg Ser Trp
20 25 30

Gly Lys Thr Thr Ser Thr Ser Phe Thr Gly Ser Thr Thr Lys His Glu
35 40 45

Gln Ser Leu His Gly Asn Val Lys Pro Leu Gln Leu Ala Ala Asn Glu
50 55 60

Ser Ser Arg Leu Ala Tyr Arg Ser Pro Ala Leu Lys Asn Gln Trp Asn
65 70 75 80

Leu Pro Ala Ser Ser Ser Ser Thr Asn Val Val Thr Thr Phe Asp Asp
85 90 95

Asn Glu His Val Ser Ser Ser Val Ile Glu Glu Lys Val Gly Val Leu
100 105 110

Leu Leu Asn Leu Gly Gly Pro Glu Thr Leu Asp Asp Val Gln Pro Phe
115 120 125

Leu Phe Asn Leu Phe Ala Asp Pro Asp Ile Ile Arg Leu Pro Arg Leu
130 135 140

Phe Arg Phe Leu Gln Arg Pro Leu Ala Lys Leu Ile Ser Thr Phe Arg
145 150 155 160

Ala Pro Lys Ser Lys Glu Gly Tyr Ala Ser Ile Gly Gly Gly Ser Pro
165 170 175

Leu Arg Lys Ile Thr Asp Glu Gln Ala Asn Ala Leu Lys Ile Ala Leu
180 185 190

Glu Lys Lys Lys Leu Asn Ala Asn Ile Tyr Val Gly Met Arg Tyr Trp
195 200 205

Tyr Pro Phe Thr Glu Glu Ala Ile Asp Gln Ile Lys Lys Asp Lys Ile
210 215 220

Thr Lys Leu Val Val Leu Pro Leu Tyr Pro Gln Tyr Ser Ile Ser Thr
225 230 235 240

Ser Gly Ser Ser Ile Arg Val Leu Gln Asp Ile Val Lys Glu Asp Ser
245 250 255

Tyr Phe Ser Gly Leu Pro Ile Ser Ile Ile Glu Ser Trp Tyr Gln Arg
260 265 270

Asp Gly Tyr Val Lys Ser Met Ser Asp Leu Ile Glu Lys Glu Leu Ser
275 280 285

Ala Phe Ser Asn Pro Glu Glu Val Met Ile Phe Phe Ser Ala His Gly
290 295 300

Val Pro Leu Thr Tyr Val Glu Asp Ala Gly Asp Pro Tyr Arg Asp Gln
305 310 315 320

Met Glu Asp Cys Ile Ala Leu Ile Met Gly Glu Leu Arg Ser Arg Gly
325 330 335

Ile Leu Asn Ser His Thr Leu Ala Tyr Gln Ser Arg Val Gly Pro Val
340 345 350

Gln Trp Leu Lys Pro Tyr Thr Asp Glu Val Leu Val Glu Leu Gly Gln
355 360 365

Lys Gly Val Lys Ser Leu Leu Ala Val Pro Val Ser Phe Val Ser Glu
370 375 380

His Ile Glu Thr Leu Glu Glu Ile Asp Met Glu Tyr Lys Glu Leu Ala
385 390 395 400

Leu Glu Ser Gly Ile Lys Asn Trp Gly Arg Val Pro Ala Leu Gly Cys
405 410 415

Thr Ser Thr Phe Ile Ser Asp Leu Ala Asp Ala Val Val Glu Ala Leu
420 425 430

Pro Ser Ala Ser Ala Leu Ala Thr Arg Lys Pro Asp Asp Ile Asp Ser
435 440 445

Ser Met Asp Leu Thr His Tyr Leu Thr Lys Met Leu Phe Gly Ser Ile
450 455 460

Leu Ala Phe Val Leu Leu Leu Ser Pro Arg Leu Val Ser Ala Phe Arg
465 470 475 480

Ser Thr Met Leu

<210> SEQ ID NO 61
<211> LENGTH: 482
<212> TYPE: PRT
<213> ORGANISM: Oryza sativa

<400> SEQUENCE: 61

Met Glu Cys Val Arg Ser Gly Ser Gly Val Leu Asp Pro Arg Cys Ser
1 5 10 15

Pro Arg Phe Leu Gly Lys Lys Gly Gly Ser Leu Thr Ser Cys Gly Lys
20 25 30

Ala Thr Ser Thr Asn Leu Ala Ile Cys Thr Lys His Glu Gln Asn Leu
35 40 45

His Gly Asn Val Lys Pro Ser Gln Leu Ala Ala Ser Gly Ser Ser Tyr
50 55 60

Ser Val His Arg Ser Pro Val Leu Lys Gln Arg Gln Asn Leu Ser Ala
65 70 75 80

Arg Ser Thr Ser Ala Asp Val Tyr Thr Thr Phe Asp Glu Asn Val Arg
85 90 95

Ala Val Ser Ser His Ala Ala Glu Glu Lys Val Gly Val Leu Leu Leu
100 105 110

Asn Leu Gly Gly Pro Glu Thr Leu Asp Asp Val Gln Pro Phe Leu Phe
115 120 125

Asn Leu Phe Ala Asp Pro Asp Ile Ile Arg Leu Pro Arg Leu Phe Arg
130 135 140

Phe Leu Gln Arg Pro Leu Ala Lys Leu Ile Ser Thr Phe Arg Ala Pro
145 150 155 160

Lys Ser Lys Glu Gly Tyr Ala Ser Ile Gly Gly Gly Ser Pro Leu Arg
165 170 175

Lys Ile Thr Asp Glu Gln Ala Asn Ala Leu Lys Val Ala Leu Lys Lys
180 185 190

Lys Asn Leu Asn Ala Asn Ile Tyr Val Gly Met Arg Tyr Trp Tyr Pro
195 200 205

Phe Thr Glu Glu Ala Ile Asp Gln Ile Lys Lys Asp Lys Ile Thr Lys
210 215 220

```
Leu Val Val Leu Pro Leu Tyr Pro Gln Tyr Ser Ile Ser Thr Ser Gly
225                 230                 235                 240

Ser Ser Ile Arg Val Leu Gln Asn Ile Val Lys Glu Asp Ser Tyr Phe
                245                 250                 255

Ala Gly Leu Pro Ile Ser Ile Ile Glu Ser Trp Tyr Gln Arg Asp Gly
            260                 265                 270

Tyr Val Lys Ser Met Ala Asp Leu Ile Glu Lys Glu Leu Ser Ile Phe
        275                 280                 285

Ser Asn Pro Glu Glu Val Met Ile Phe Phe Ser Ala His Gly Val Pro
    290                 295                 300

Leu Thr Tyr Val Thr Asp Ala Gly Asp Pro Tyr Arg Asp Gln Met Glu
305                 310                 315                 320

Asp Cys Ile Ala Leu Ile Met Gly Glu Leu Lys Ser Arg Gly Ile Leu
                325                 330                 335

Asn Ser His Thr Leu Ala Tyr Gln Ser Arg Val Gly Pro Val Gln Trp
            340                 345                 350

Leu Lys Pro Tyr Thr Asp Glu Val Leu Val Glu Leu Gly Gln Gln Gly
        355                 360                 365

Val Lys Ser Leu Leu Ala Val Pro Val Ser Phe Val Ser Glu His Ile
    370                 375                 380

Glu Thr Leu Glu Glu Ile Asp Met Glu Tyr Lys Glu Leu Ala Leu Glu
385                 390                 395                 400

Ser Gly Ile Glu Asn Trp Gly Arg Val Pro Ala Leu Gly Cys Thr Ser
                405                 410                 415

Ser Phe Ile Ser Asp Leu Ala Asp Ala Val Val Glu Ala Leu Pro Ser
            420                 425                 430

Ala Ser Ala Leu Val Thr Lys Lys Val Asp Glu Ser Asp Ser Asp Met
        435                 440                 445

Asp Leu Met His Tyr Leu Ser Lys Met Phe Phe Gly Ser Ile Leu Ala
    450                 455                 460

Phe Val Leu Leu Leu Ser Pro Arg Leu Ile Ser Ala Phe Arg Asn Thr
465                 470                 475                 480

Leu Leu


<210> SEQ ID NO 62
<211> LENGTH: 526
<212> TYPE: PRT
<213> ORGANISM: Oryza sativa

<400> SEQUENCE: 62

Met Trp Ser Ser Ser Gln Ala Ser Thr Arg Gly Val Ile Glu Val Gly
1               5                   10                  15

Arg Val Glu Ala Gly Pro Ser His Phe Pro Lys Arg Pro Ala Pro Arg
            20                  25                  30

Asn Ser Ser Arg Val Asn Leu Ser Arg Thr Tyr Ala Ile Lys Ser Cys
        35                  40                  45

Ser Val Ser Ser Arg Thr Gly Leu Cys Leu Gly Gln Cys Tyr His Lys
    50                  55                  60

Lys Ser Ser Ala Cys Lys Cys Lys Leu Gly Trp Ser Ser Gln Pro Leu
65                  70                  75                  80

Ser Ser Leu Arg His His Leu Arg Val His Ser Ser Ala Ser Glu Ala
                85                  90                  95

Val Leu Thr Ser Gln Ser Asp Phe Thr Lys Leu Leu Val Gly Asn Glu
            100                 105                 110

Lys Ile Gly Val Leu Leu Leu Asn Leu Gly Gly Pro Glu Thr Leu Asp
```

```
        115                 120                 125

Asp Val Gln Pro Phe Leu Phe Asn Leu Phe Ala Asp Pro Asp Ile Ile
    130                 135                 140

Arg Leu Pro Arg Leu Phe Arg Phe Leu Gln Lys Pro Leu Ala Gln Phe
145                 150                 155                 160

Ile Ser Val Val Arg Ala Pro Lys Ser Lys Glu Gly Tyr Ala Ser Ile
                165                 170                 175

Gly Gly Gly Ser Pro Leu Arg Gln Ile Thr Asp Ala Gln Ala Glu Ala
            180                 185                 190

Leu Arg Lys Ala Leu Cys Asp Lys Asp Ile Pro Ala Lys Val Tyr Val
        195                 200                 205

Gly Met Arg Tyr Trp His Pro Phe Thr Glu Glu Ala Ile Glu Gln Ile
    210                 215                 220

Lys Arg Asp Gly Ile Thr Lys Leu Val Val Leu Pro Leu Tyr Pro Gln
225                 230                 235                 240

Phe Ser Ile Ser Thr Ser Gly Ser Ser Leu Arg Leu Leu Glu Gly Ile
                245                 250                 255

Phe Arg Glu Asp Glu Tyr Leu Val Asn Met Gln His Thr Val Ile Pro
            260                 265                 270

Ser Trp Tyr Gln Arg Glu Gly Tyr Ile Lys Ala Met Ala Thr Leu Ile
        275                 280                 285

Glu Lys Glu Leu Arg Thr Phe Ser Glu Pro Gln Lys Val Met Ile Phe
    290                 295                 300

Phe Ser Ala His Gly Val Pro Leu Ala Tyr Val Glu Glu Ala Gly Asp
305                 310                 315                 320

Pro Tyr Lys Ala Glu Met Glu Glu Cys Val Asp Leu Ile Met Glu Glu
                325                 330                 335

Leu Glu Lys Arg Gly Ile Thr Asn Ser Cys Thr Leu Ala Tyr Gln Ser
            340                 345                 350

Arg Val Gly Pro Val Glu Trp Leu Arg Pro Tyr Thr Asp Glu Thr Ile
        355                 360                 365

Ile Glu Leu Gly Gln Lys Gly Val Lys Ser Leu Leu Ala Val Pro Ile
    370                 375                 380

Ser Phe Val Ser Glu His Ile Glu Thr Leu Glu Glu Ile Asp Val Glu
385                 390                 395                 400

Tyr Lys Glu Leu Ala Leu Glu Ser Gly Ile Lys His Trp Gly Arg Val
                405                 410                 415

Pro Ala Leu Gly Cys Glu Pro Thr Phe Ile Thr Asp Leu Ala Asp Ala
            420                 425                 430

Val Ile Glu Ser Leu Pro Tyr Val Gly Ala Met Ala Val Ser Asn Leu
        435                 440                 445

Glu Ala Arg Gln Pro Leu Val Pro Leu Gly Ser Val Glu Glu Leu Leu
    450                 455                 460

Ala Ala Tyr Asp Ser Lys Arg Asp Glu Leu Pro Pro Pro Val Thr Val
465                 470                 475                 480

Trp Glu Trp Gly Trp Thr Lys Ser Ala Glu Thr Trp Asn Gly Arg Ala
                485                 490                 495

Ala Met Leu Ala Val Leu Ala Leu Leu Val Leu Glu Val Thr Thr Gly
            500                 505                 510

Glu Gly Phe Leu His Gln Trp Gly Ile Leu Pro Leu Phe His
        515                 520                 525
```

<210> SEQ ID NO 63
<211> LENGTH: 591

<212> TYPE: PRT
<213> ORGANISM: Zea mays

<400> SEQUENCE: 63

Phe Pro Leu Val Ser Ser Arg Leu Val Pro Tyr Ser Arg Pro Val Arg
1 5 10 15

Leu His Leu Arg Ser Pro Gly Pro Asp Thr Pro Leu Tyr Gln Ser Arg
20 25 30

Pro Pro Ala His Phe Ser His Pro Arg Ala Ala Ser Gly Ala Gly Glu
35 40 45

Pro Ser Arg Arg Ser Ser Asn Asp Pro Ser Leu Ser Arg Pro Val Ser
50 55 60

Leu Pro Leu Pro Ala Gln Gly Glu Glu Arg Glu Arg Met Trp Ser Ser
65 70 75 80

Ser Gln Ala Ser Thr Arg Gly Val Val Glu Met Gly Arg Val Glu Ala
85 90 95

Gly Pro Ser His Phe Pro Lys Arg Pro Ala Pro Gln Asn Ser Ala Arg
100 105 110

Val Asn Leu Ser Arg Thr His Thr Val Lys Pro Thr Ser Ala Gly Asp
115 120 125

Arg Ser Gly Ile Ser Val Lys Cys Asn Leu Gly Trp Ser Ser Gln Pro
130 135 140

Ser Pro Asp Leu Arg His His Phe Arg Gly Tyr Ser Ser Ala Ser Glu
145 150 155 160

Ala Val Leu Thr Ser Gln Ser Asp Val Arg Lys Leu Phe Val Gly Asn
165 170 175

Glu Lys Ile Gly Val Leu Leu Leu Asn Leu Gly Gly Pro Glu Thr Leu
180 185 190

Asp Asp Val Gln Pro Phe Leu Phe Asn Leu Phe Ala Asp Pro Asp Ile
195 200 205

Ile Arg Leu Pro Arg Leu Phe Arg Phe Leu Gln Lys Pro Leu Ala Lys
210 215 220

Phe Ile Ser Glu Val Arg Ala Pro Lys Ser Lys Glu Gly Tyr Ala Ser
225 230 235 240

Ile Gly Gly Gly Ser Pro Leu Arg Gln Ile Thr Asp Ala Gln Ala Glu
245 250 255

Ala Leu Arg Glu Ala Leu His Gly Lys Asp Val Pro Ala Asn Val Tyr
260 265 270

Val Gly Met Arg Tyr Trp His Pro Phe Thr Glu Glu Ala Ile Glu Gln
275 280 285

Ile Lys Arg Asp Gly Ile Thr Lys Leu Val Val Leu Pro Leu Tyr Pro
290 295 300

Gln Phe Ser Ile Ser Thr Ser Gly Ser Ser Leu Arg Leu Leu Glu Ser
305 310 315 320

Ile Ser Arg Glu Asp Glu Tyr Leu Val Asn Met Gln His Thr Val Ile
325 330 335

Pro Ser Trp Tyr Gln Arg Glu Gly Tyr Ile Lys Ala Met Ala Thr Leu
340 345 350

Ile Glu Asn Glu Leu Thr Lys Phe Gln Glu Pro Gln Lys Val Met Ile
355 360 365

Phe Phe Ser Ala His Gly Val Pro Leu Ala Tyr Val Glu Glu Ala Gly
370 375 380

Asp Pro Tyr Lys Ala Glu Met Glu Glu Cys Ile Asp Leu Ile Met Glu
385 390 395 400

-continued

```
Glu Leu Glu Lys Arg Gly Ile Thr Asn Pro Cys Ile Leu Ala Tyr Gln
                405                 410                 415

Ser Arg Val Gly Pro Val Glu Trp Leu Lys Pro Tyr Thr Asp Glu Thr
            420                 425                 430

Ile Ile Glu Leu Gly Gln Lys Gly Val Lys Ser Leu Leu Ala Val Pro
        435                 440                 445

Ile Ser Phe Val Ser Glu His Ile Lys Thr Leu Glu Glu Ile Asp Val
    450                 455                 460

Glu Tyr Lys Glu Leu Ala Leu Glu Ser Gly Ile Lys His Trp Gly Arg
465                 470                 475                 480

Val Pro Ala Leu Gly Cys Glu Pro Thr Phe Ile Ser Asp Leu Ala Asp
                485                 490                 495

Ala Val Ile Glu Ser Leu Pro Tyr Val Gly Ala Met Ala Val Ser Asn
            500                 505                 510

Leu Glu Ala Arg Gln Ser Leu Val Pro Leu Gly Ser Val Glu Glu Leu
        515                 520                 525

Leu Ala Ala Tyr Asp Ser Lys Arg Asp Glu Leu Pro Pro Pro Val Ile
    530                 535                 540

Val Trp Glu Trp Gly Trp Thr Lys Ser Ala Glu Thr Trp Asn Gly Arg
545                 550                 555                 560

Ala Ala Met Leu Ala Val Leu Ala Leu Leu Val Leu Glu Val Thr Thr
                565                 570                 575

Gly Glu Gly Phe Leu His Gln Trp Gly Ile Leu Pro Leu Phe Arg
            580                 585                 590
```

DROUGHT TOLERANT PLANTS AND RELATED CONSTRUCTS AND METHODS INVOLVING GENE ENCODING FERROCHELATASES

This application claims the benefit of U.S. Provisional Application No. 60/991,859, filed Dec. 3, 2007, the entire content of which is herein incorporated by reference.

FIELD OF THE INVENTION

The field of invention relates to plant breeding and genetics and, in particular, relates to recombinant DNA constructs useful in plants for conferring tolerance to drought.

BACKGROUND OF THE INVENTION

Abiotic stressors significantly limit crop production worldwide. Cumulatively, these factors are estimated to be responsible for an average 70% reduction in agricultural production (Bresson, 1999).

Drought stress, in particular, not only causes a reduction in the average yield for crops but also causes yield instability through high interannual yield variation. Globally, about 35-40% of arable land falls under arid or semiarid classification. Even in non-arid regions where soils are nutrient-rich, drought stress occurs regularly for brief periods or at moderate levels. Moreover, it has been predicted that in the coming years rainfall patterns will shift and become more variable due to increased global temperatures.

U.S. studies have shown that the ten most important kinds of cultivated plants (corn, soybeans, wheat, tomatoes, etc.) produced only about 50% of the genetically possible yields on average per year; two thirds of the losses were due to the frequent combination of heat stress and water shortage (G. Schütte, S. Stirn, and V. Beusmann, Transgene Pflanzen-Sicherheitsforschung, Risikoabschätzung and Nachzulassungs-Monitoring. Birkhäuser Verlag AG, Basel-Boston-Berlin, 2001).

Plants are sessile and have to adjust to the prevailing environmental conditions of their surroundings. This has led to their development of a great plasticity in gene regulation, morphogenesis, and metabolism. Adaptation and defense strategies involve the activation of genes encoding proteins important in the acclimation or defense towards the different stressors. Some of the molecular responses to abiotic stress factors such as drought are specific, but it has also been shown that similar genes are activated by several stressors (Royal Society of London, *Transgenic Plants and World Agriculture,* 2000, National Academy Press, Washington, D.C.). It is believed that about 15 percent of a plant's genome is devoted to stress perception and adaptation (see e.g., Cushman and Bohnert, 2000).

Earlier work on molecular aspects of abiotic stress responses was accomplished by differential and/or subtractive analysis (e.g., see Bray, 1993, Shinozaki and Yamaguchi-Shinozaki, 1997, Zhu et al., 1997, Thomashow, 1999). Other methods include selection of candidate genes (e.g., selection of genes from a particular known module and analyzing expression of such a gene or its active product under stresses, or by functional complementation in a stressor system that is well defined, see Xiong and Zhu, 2001). Additionally, forward and reverse genetic studies involving the identification and isolation of mutations in regulatory genes have also been used to provide evidence for observed changes in gene expression under stress or exposure (Xiong and Zhu, 2001).

Activation tagging can be utilized to identify genes with the ability to affect a trait. This approach has been used in the model plant species *Arabidopsis thaliana* (Weigel et al., *Plant Physiol.* 122:1003-1013 (2000)). Insertions of transcriptional enhancer elements can dominantly activate and/or elevate the expression of nearby endogenous genes. This method can be used to select genes involved in agronomically important phenotypes, including stress tolerance.

SUMMARY OF THE INVENTION

The present invention includes:

In one embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NO:2, 4, 6, 8, 10, 12, 14, 16, 18, 20, 22, 24, 26, 28 or 30, and wherein said plant exhibits increased drought tolerance when compared to a control plant not comprising said recombinant DNA construct.

In another embodiment, a method of increasing drought tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:2, 4, 6, 8, 10, 12, 14, 16, 18, 20, 22, 24, 26, 28 or 30; (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct; and optionally, (c) obtaining a progeny plant derived from the transgenic plant, wherein said progeny plant comprises in its genome the recombinant DNA construct and exhibits increased drought tolerance when compared to a control plant not comprising the recombinant DNA construct.

In another embodiment, a method of evaluating drought tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:2, 4, 6, 8, 10, 12, 14, 16, 18, 20, 22, 24, 26, 28 or 30; (b) regenerating a transgenic plant from the regenerable plant cell after step (a), wherein the transgenic plant comprises in its genome the recombinant DNA construct; and (c) evaluating the transgenic plant for drought tolerance compared to a control plant not comprising the recombinant DNA construct; and optionally, (d) obtaining a progeny plant derived from the transgenic plant, wherein the progeny plant comprises in its genome the recombinant DNA construct; and optionally, (e) evaluating the progeny plant for drought tolerance compared to a control plant not comprising the recombinant DNA construct.

In another embodiment, a method of evaluating drought tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:2, 4, 6, 8, 10, 12, 14, 16, 18, 20, 22, 24, 26, 28 or 30; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for drought tolerance compared to a control plant not comprising the recombinant DNA construct.

In another embodiment, the present invention includes any of the methods of the present invention wherein the plant is a maize plant or a soybean plant.

In another embodiment, the present invention includes an isolated polynucleotide comprising: (a) a nucleotide sequence encoding a ferrochelatase, wherein the polypeptide has an amino acid sequence of at least 90% or 95% sequence identity, based on the Clustal V method of alignment, when compared to one of SEQ ID NO:4, 6, 8, 10, 12, 14, 16, 18, 24, 26, 28 or 30, or (b) a full complement of the nucleotide sequence, wherein the full complement and the nucleotide sequence consist of the same number of nucleotides and are 100% complementary. The polypeptide may comprise the amino acid sequence of SEQ ID NO:4, 6, 8, 10, 12, 14, 16, 18, 24, 26, 28 or 30. The nucleotide sequence may comprise the nucleotide sequence of SEQ ID NO:3, 5, 7, 9, 11, 13, 15, 17, 23, 25, 27 or 29.

In another embodiment, the present invention concerns a recombinant DNA construct comprising any of the isolated polynucleotides of the present invention operably linked to at least one regulatory sequence, and a cell, a plant, and a seed comprising the recombinant DNA construct.

In another embodiment, the present invention includes a vector comprising any of the isolated polynucleotides of the present invention.

In another embodiment, the present invention concerns a cell, plant or seed comprising any of the recombinant DNA constructs of the present invention. The cell may be eukaryotic, e.g., a yeast, insect or plant cell, or prokaryotic, e.g., a bacterium.

BRIEF DESCRIPTION OF THE FIGURES AND SEQUENCE LISTING

The invention can be more fully understood from the following detailed description and the accompanying drawings and Sequence Listing which form a part of this application.

Figure 10A:
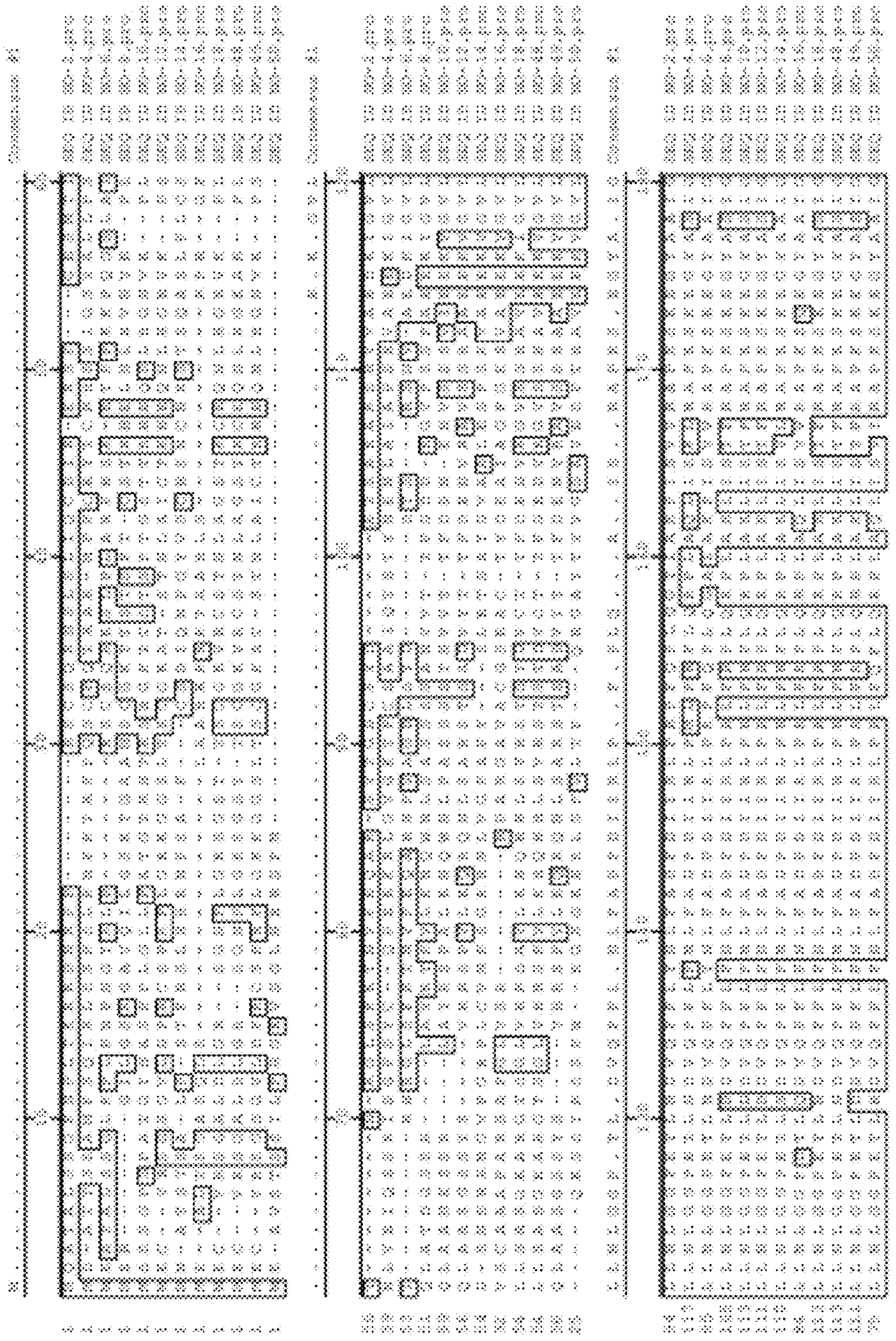
Figure 10B:
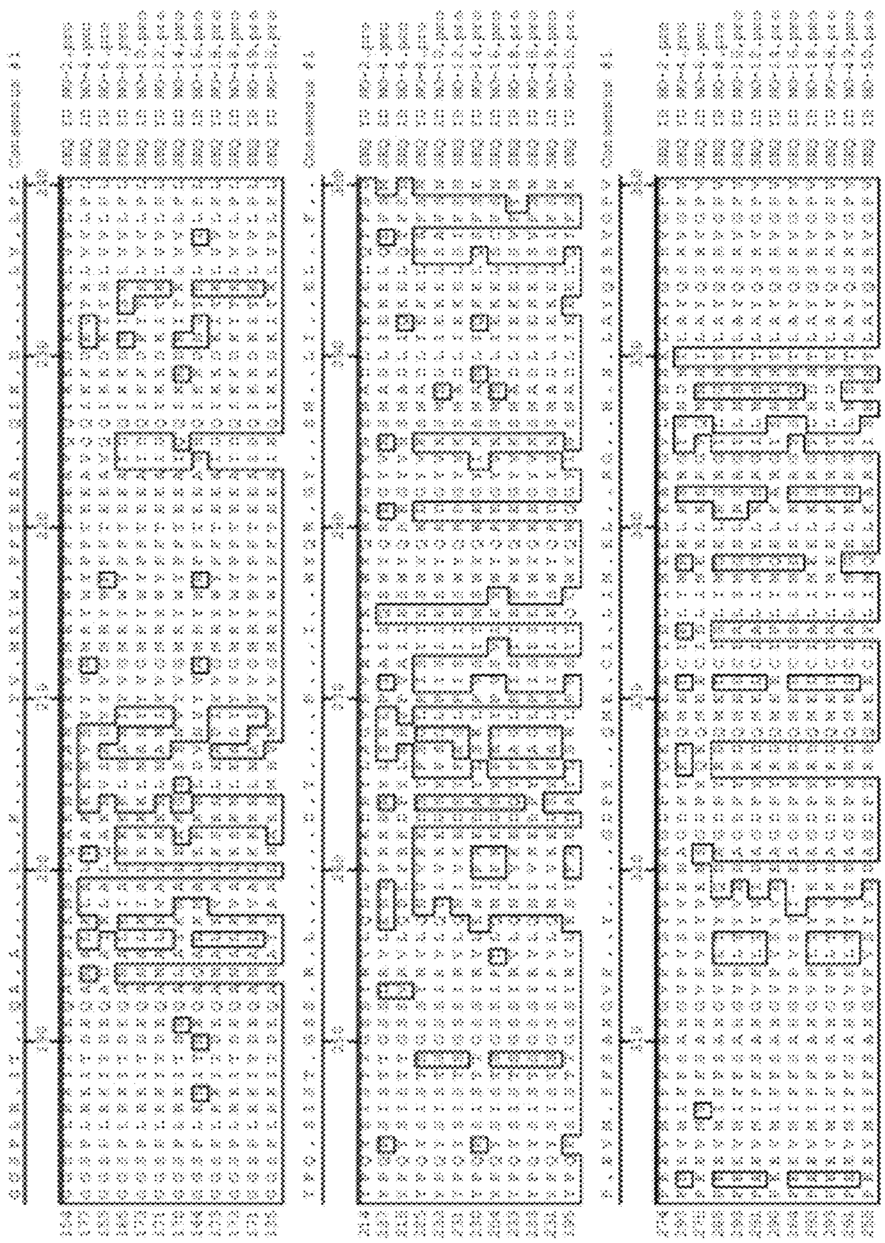
Figure 10C:
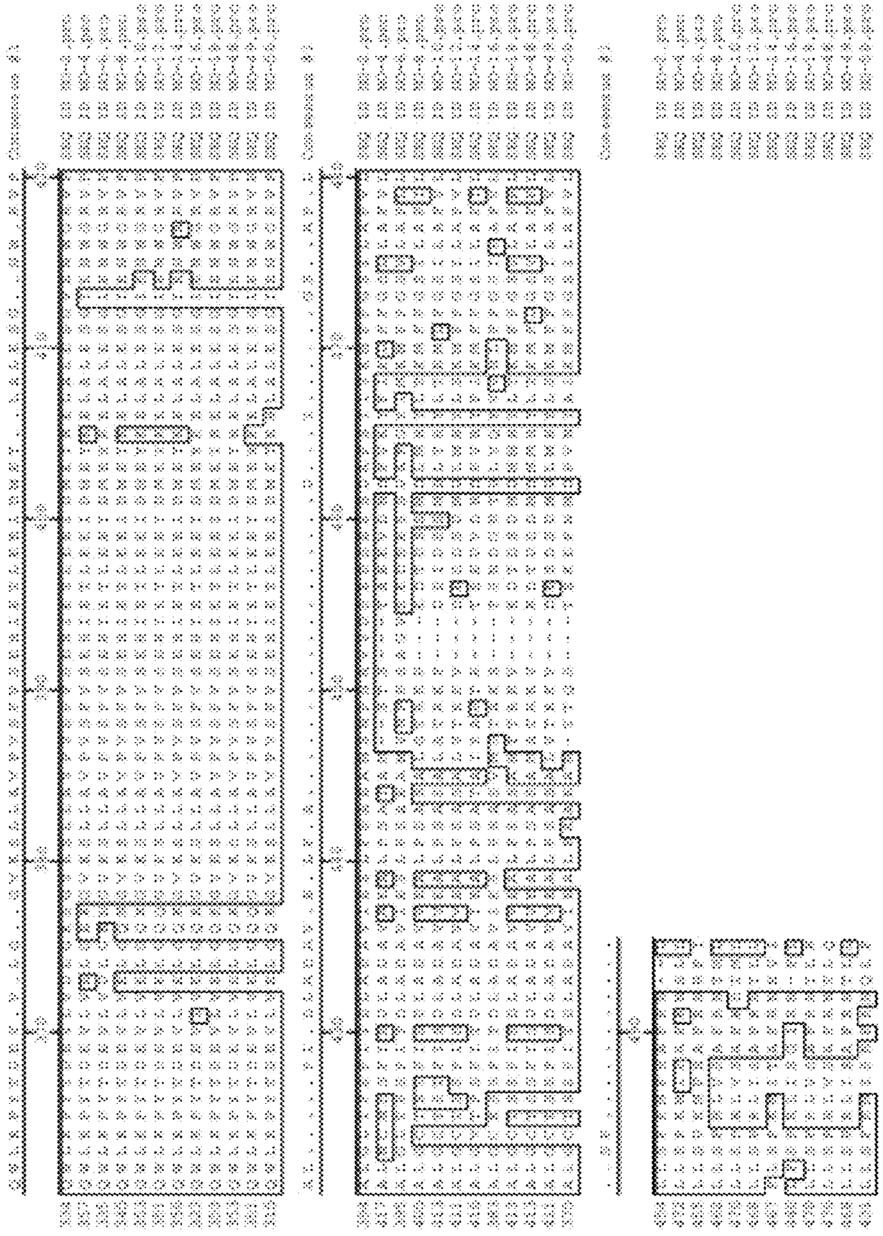

FIGS. 10A-10C show the multiple alignment of the amino acid sequences of the ferrochelatase-I proteins of SEQ ID NOs:2, 4, 6, 8, 10, 12, 14, 16, 18, 48, 49 and 50. Residues that are identical to the residue of SEQ ID NO:2 at a given position are enclosed in a box. A consensus sequence is presented where a residue is shown if identical in all sequences, otherwise, a period is shown.

FIG. 11 shows the percent sequence identity and the divergence values for each pair of amino acids sequences of ferrochelatases displayed in FIGS. 10A-10C.

Figure 12A:
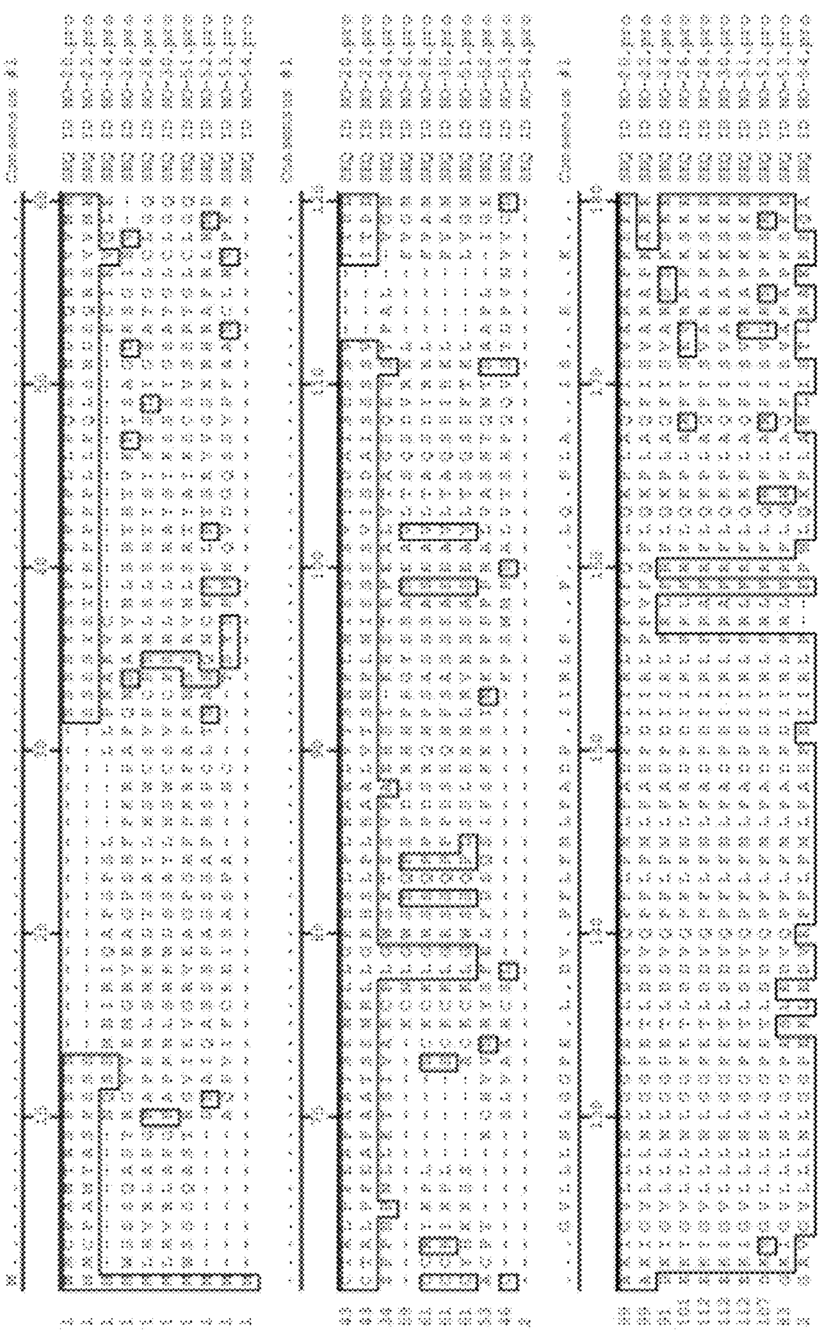
Figure 12B:
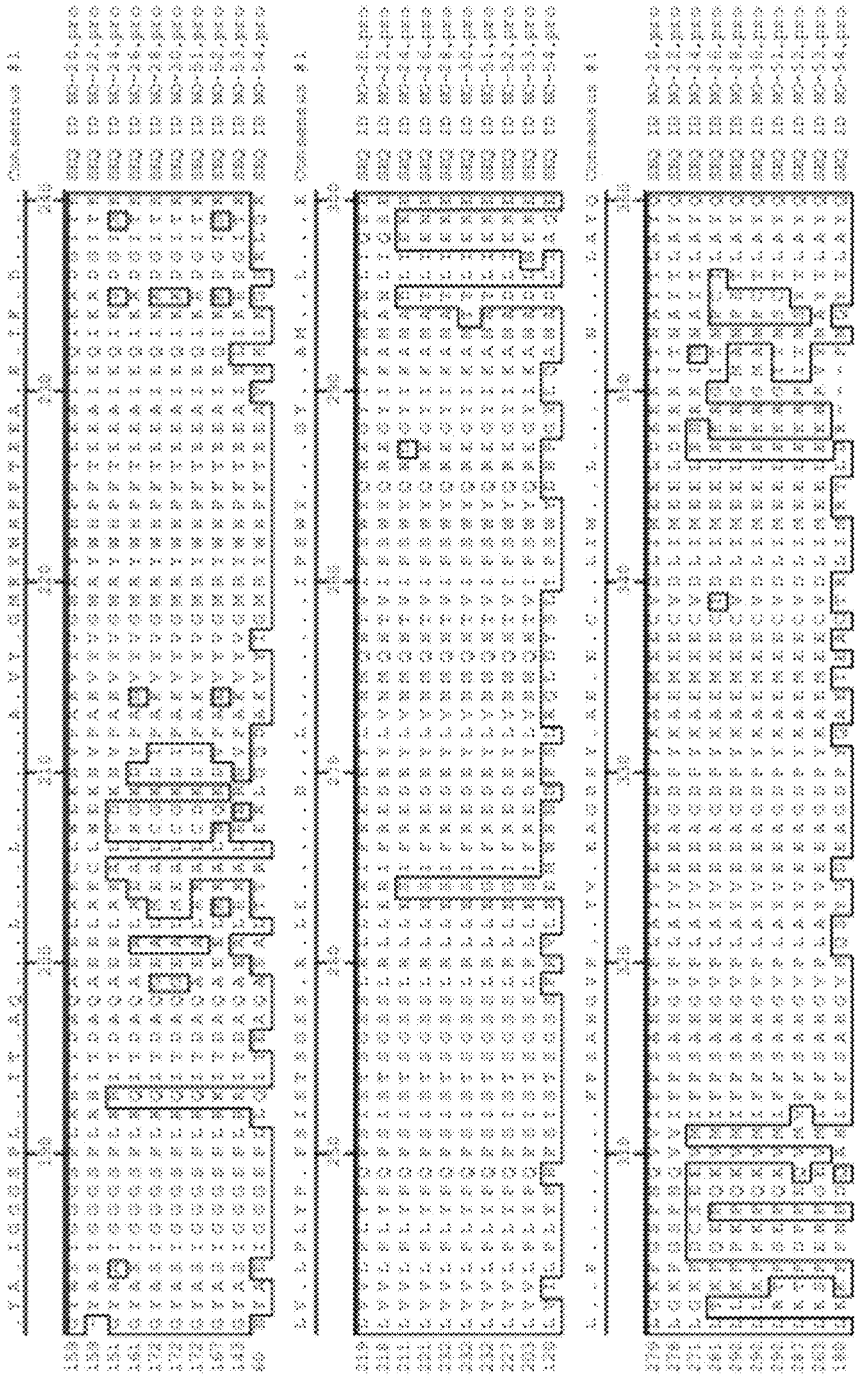
Figure 12C:
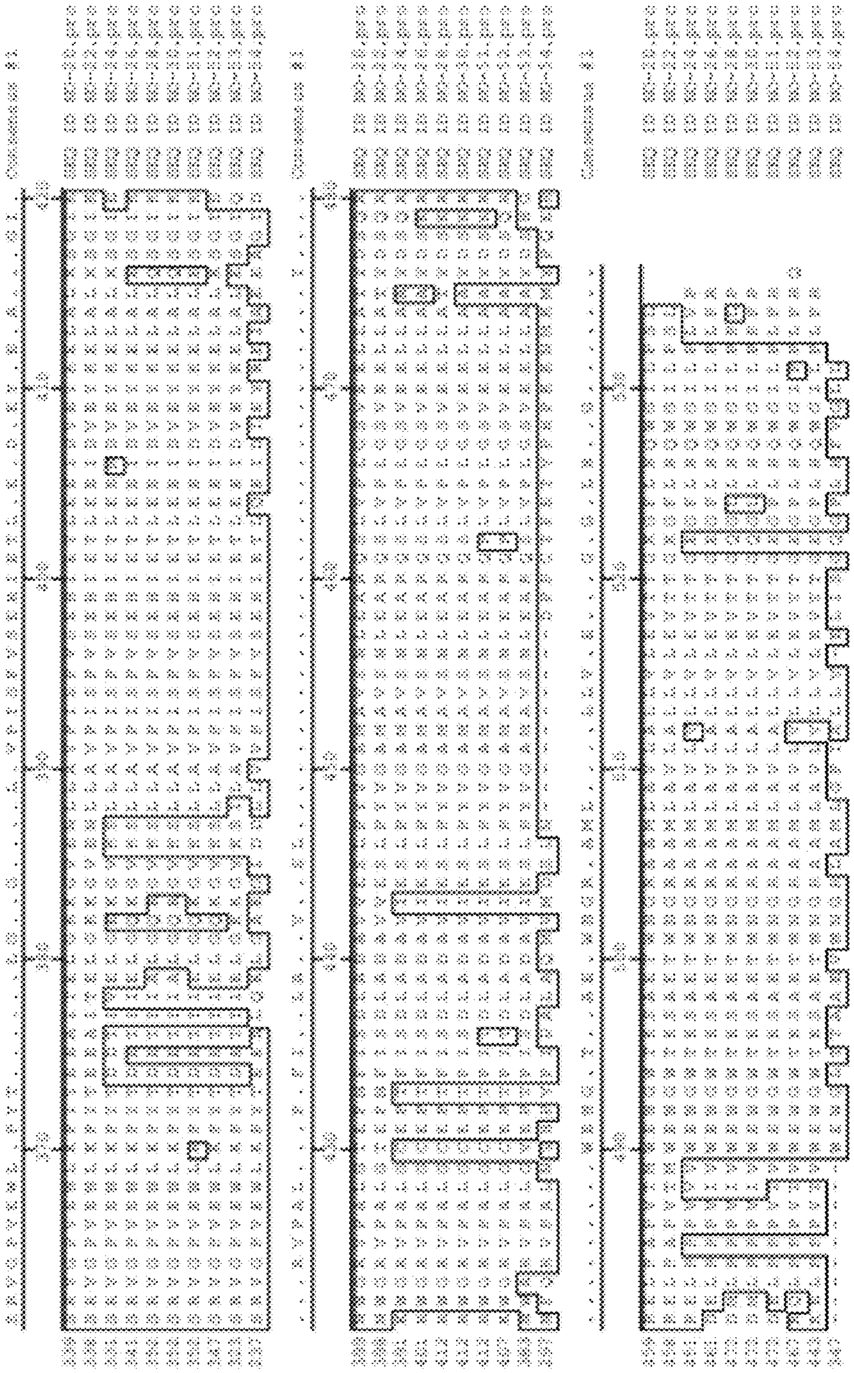

FIGS. 12A-12C show the multiple alignment of the amino acid sequences of the ferrochelatase-II proteins of SEQ ID NOs:20, 22, 24, 26, 28, 30, 51, 52, 53 and 54. Residues that are identical to the residue of SEQ ID NO:20 at a given position are enclosed in a box. A consensus sequence is presented where a residue is shown if identical in all sequences, otherwise, a period is shown.

FIG. 13 shows the percent sequence identity and the divergence values for each pair of amino acids sequences of ferrochelatases displayed in FIGS. 12A-12C.

FIGS. 14A-14B show an evaluation of individual Gaspe Flint derived maize lines transformed with PHP31419.

FIG. 15 shows a summary evaluation of Gaspe Flint derived maize lines transformed with PHP31419.

FIGS. 16A-16B show an evaluation of individual Gaspe Flint derived maize lines transformed with PHP33089.

FIG. 17 shows a summary evaluation of Gaspe Flint derived maize lines transformed with PHP33089.

FIGS. 18A-18B show an evaluation of individual Gaspe Flint derived maize lines transformed with PHP30829.

FIG. 19 shows a summary evaluation of Gaspe Flint derived maize lines transformed with PHP30829.

FIGS. 20A-20B show an evaluation of individual Gaspe Flint derived maize lines transformed with PHP30745.

FIG. 21 shows a summary evaluation of Gaspe Flint derived maize lines transformed with PHP30745.

FIGS. 22A-22B show an evaluation of individual Gaspe Flint derived maize lines transformed with PHP30761.

FIG. 23 shows a summary evaluation of Gaspe Flint derived maize lines transformed with PHP30761.

SEQ ID NO:1 corresponds to NCBI GI No. 511080 which is the nucleotide sequence of a cDNA fragment encoding an *Arabidopsis* ferrochelatase-I protein (locus At5g26030).

SEQ ID NO:2 corresponds to NCBI GI No. 511081, which is the amino acid sequence of the *Arabidopsis* ferrochelatase-I protein encoded by SEQ ID NO:1.

TABLE 1

| cDNAs Encoding Ferrochelatase-I (FeC-I) | | | |
|---|---|---|---|
| Plant | Clone Designation | SEQ ID NO: (Nucleotide) | SEQ ID NO: (Amino Acid) |
| Sugar Beet | ebs1c.pk002.n16 (FIS) | 3 | 4 |
| *Brassica* | ebb1c.pk006.j11 (FIS) | 5 | 6 |
| Maize | cfp3n.pk004.f12 (FIS) | 7 | 8 |
| Maize | cfp5n.pk009.j16 (FIS) | 9 | 10 |
| Rice | rl0n.pk117.h21 (FIS) | 11 | 12 |
| Soybean | se3.pk0034.e10 (FIS) | 13 | 14 |
| Tulip | etb1n.pk002.n16 (FIS) | 15 | 16 |
| Wheat | wlp1c.pk002.p10 (FIS) | 17 | 18 |

SEQ ID NO:19 corresponds to NCBI GI No. 30684569 which is the nucleotide sequence of a cDNA fragment encoding a first allele of an *Arabidopsis* ferrochelatase-II protein (locus At2g30390).

SEQ ID NO:20 corresponds to NCBI GI No. 15227742, which is the amino acid sequence of the *Arabidopsis* ferrochelatase-II protein encoded by SEQ ID NO:19.

SEQ ID NO:21 corresponds to NCBI GI No. 2623989, which is the nucleotide sequence of a cDNA fragment encoding a second allele of an *Arabidopsis* ferrochelatase-II protein (locus At2g30390).

SEQ ID NO:22 corresponds to NCBI GI No. 2623990, which is the amino acid sequence of the *Arabidopsis* ferrochelatase-II protein encoded by SEQ ID NO:21.

TABLE 2

| cDNAs Encoding Ferrochelatase-II (FeC-II) | | | |
|---|---|---|---|
| Plant | Clone Designation | SEQ ID NO: (Nucleotide) | SEQ ID NO: (Amino Acid) |
| Catmint | ecl1c.pk005.l15 (FIS) | 23 | 24 |
| Maize | cfp6n.pk072.n9 (FIS) | 25 | 26 |
| Wheat | Wlp1c.pk004.d13 (FIS) | 27 | 28 |
| Wheat | wpa1c.pk014.g4 (FIS) | 29 | 30 |

SEQ ID NO:31 is the nucleotide sequence of the pHSbarENDs2 activation tagging vector.

SEQ ID NO:32 is the nucleotide sequence of the GATEWAY® donor vector pDONR™/Zeo.

SEQ ID NO:33 is the nucleotide sequence of the GATEWAY® donor vector pDONR™221.

SEQ ID NO:34 is the nucleotide sequence of pBC-yellow, a destination vector for use with *Arabidopsis.*

SEQ ID NO:35 is the nucleotide sequence of PHP27840, a destination vector for use with soybean.

SEQ ID NO:36 is the nucleotide sequence of PHP23236, a destination vector for use with Gaspe Flint derived maize lines.

SEQ ID NO:37 is the nucleotide sequence of PHP10523 (Komari et al., *Plant J.* 10:165-174 (1996); NCBI General Identifier No. 59797027).

SEQ ID NO:38 is the nucleotide sequence of PHP23235, a destination vector for use with Gaspe Flint derived lines.

SEQ ID NO:39 is the nucleotide sequence of PHP28647, a destination vector for use with maize inbred-derived lines.

SEQ ID NO:40 is the nucleotide sequence of the attB1 site.

SEQ ID NO:41 is the nucleotide sequence of the attB2 site.

SEQ ID NO:42 is the nucleotide sequence of the At5g26030-5' attB forward primer, containing the attB1 sequence, used to amplify the At5g26030 protein-coding region.

SEQ ID NO:43 is the nucleotide sequence of the At5g26030-3' attB reverse primer, containing the attB2 sequence, used to amplify the At5g26030 protein-coding region.

SEQ ID NO:44 is the nucleotide sequence of the At2g30390-5' attB forward primer, containing the attB1 sequence, used to amplify the At2g30390 protein-coding region.

SEQ ID NO:45 is the nucleotide sequence of the At2g30390-3' attB reverse primer, containing the attB2 sequence, used to amplify the At2g30390 protein-coding region.

SEQ ID NO:46 is the nucleotide sequence of the VC062 primer, containing the T3 promoter and attB1 site, useful to amplify cDNA inserts cloned into a Bluescript® II SK(+) vector (Stratagene).

SEQ ID NO:47 is the nucleotide sequence of the VC063 primer, containing the T7 promoter and attB2 site, useful to amplify cDNA inserts cloned into a Bluescript® II SK(+) vector (Stratagene).

SEQ ID NO:48 is the amino acid sequence of a *Hordeum vulgare* ferrochelatase-I protein (NCBI GI NO. 2460251).

SEQ ID NO:49 is the amino acid sequence of a rice ferrochelatase-I protein (NCBI GI NO. 113631036).

SEQ ID NO:50 is the amino acid sequence of a *Vitis vinifera* ferrochelatase-I protein (NCBI GI NO. 147818793).

SEQ ID NO:51 is the amino acid sequence of a rice ferrochelatase-II protein (NCBI GI NO. 115463419).

SEQ ID NO:52 is the amino acid sequence of a *Cucumis sativus* ferrochelatase-II protein (NCBI GI NO. 12082085).

SEQ ID NO:53 is the amino acid sequence of a *Nicotiana tabacum* ferrochelatase-II protein (NCBI GI NO. 15147828).

SEQ ID NO:54 is the amino acid sequence of a *Synechocystis* ferrochelatase protein (NCBI GI NO. 1708186).

SEQ ID NO:55 is the nucleotide acid sequence of plasmid PHP30949, an entry clone containing the maize ferrochelatase-I protein (SEQ ID NO:10).

SEQ ID NO:56 is the nucleotide sequence of the cDNA insert of cfp5n.pk064.n7 and encodes a maize ferrochelatase-II protein (SEQ ID NO:8). SEQ ID NO:56 differs from the nucleotide sequence of cfp3n.pk004.f12 (SEQ ID NO:7) in that it contains a 12 base pair insertion in the 5'-UTR, 8 nucleotides before the ATG start codon.

SEQ ID NO:57 is the amino acid sequence presented in SEQ ID NO:240025 of US Patent Publication No. US2004031072.

SEQ ID NO:58 is the amino acid sequence presented in SEQ ID NO:20 of Japanese Patent Publication No. JP2001190168-A.

SEQ ID NO:59 is the amino acid sequence presented in SEQ ID NO:13029 of US Patent Publication No. US2006150283.

SEQ ID NO:60 is the amino acid sequence presented in SEQ ID NO:7745 of US Patent Publication No. US2006150283.

SEQ ID NO:61 is the amino acid sequence presented in SEQ ID NO:46156 of Japanese Patent Publication No. JP2005185101.

SEQ ID NO:62 is the amino acid sequence presented in SEQ ID NO:52154 of Japanese Patent Publication No. JP2005185101.

SEQ ID NO:63 is the amino acid sequence presented in SEQ ID NO:72746 of US Patent Publication No. US2004034888-A1.

The sequence descriptions and Sequence Listing attached hereto comply with the rules governing nucleotide and/or amino acid sequence disclosures in patent applications as set forth in 37 C.F.R. §1.821-1.825.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF EMBODIMENTS

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

"Ferrochelatase" (protoheme ferrolyase; EC 4.99.1.1) is the terminal enzyme of the biosynthetic pathway of heme; it catalyses the chelation of ferrous ion into the protoporphyrin IX ring to form protoheme In higher plants there is evidence for two isoforms of this enzyme, ferrochelatase-1 and ferrochelatase-2 (Suzuki et al. 2002 J Biol Chem 277:4731-4737). The terms "ferrochelatase-I", "ferrochelatase-1", "FeC-I" and "FeC-1" are used interchangeably herein. The terms "ferrochelatase-II", "ferrochelatase-2", "FeC-II" and "FeC-2" are used interchangeably herein.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Agronomic characteristic" is a measurable parameter including but not limited to, greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height and ear length.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to the embodiments:

Embodiments include isolated polynucleotides and polypeptides, recombinant DNA constructs useful for conferring drought tolerance, compositions (such as plants or seeds) comprising these recombinant DNA constructs, and methods utilizing these recombinant DNA constructs.

Isolated Polynucleotides and Polypeptides:

The present invention includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:4, 6, 8, 10, 12, 14, 16, 18, 24, 26, 28 or 30; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs (including suppression DNA constructs) of the present invention. The polypeptide is preferably a ferrochelatase.

An isolated polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:4, 6, 8, 10, 12, 14, 16, 18, 24, 26, 28 or 30. The polypeptide is preferably a ferrochelatase.

An isolated polynucleotide comprising (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:3, 5, 7, 9, 11, 13, 15, 17, 23, 25, 27 or 29; or (ii) a full complement of the nucleic acid sequence of (i). Any of the foregoing isolated polynucleotides may be utilized in any recombinant DNA constructs (including suppression DNA constructs) of the present invention. The isolated polynucleotide preferably encodes a ferrochelatase.

Recombinant DNA Constructs and Suppression DNA Constructs:

In one aspect, the present invention includes recombinant DNA constructs (including suppression DNA constructs).

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 1, 3, 5, 7, 9, 11, 13, 15, 17, 19, 21, 23, 25, 27 or 29; or (ii) a full complement of the nucleic acid sequence of (i).

FIGS. 10A-10C show the multiple alignment of the amino acid sequences of the ferrochelatases of SEQ ID NO:2, 4, 6, 8, 10, 12, 14, 16, 18, 48, 49 and 50. The multiple alignment of the sequences was performed using the Megalign® program of the LASERGENE® bioinformatics computing suite (DNASTAR® Inc., Madison, Wis.); in particular, using the Clustal V method of alignment (Higgins and Sharp (1989) *CABIOS.* 5:151-153) with the multiple alignment default parameters of GAP PENALTY=10 and GAP LENGTH PENALTY=10, and the pairwise alignment default parameters of KTUPLE=1, GAP PENALTY=3, WINDOW=5 and DIAGONALS SAVED=5.

FIG. 11 shows the percent sequence identity and the divergence values for each pair of amino acids sequences displayed in FIGS. 10A-10C.

FIGS. 12A-12C show the multiple alignment of the amino acid sequences of the ferrochelatases of SEQ ID NO:20, 22, 24, 26, 28, 30, 51, 52, 53 and 54. The multiple alignment of the sequences was performed using the Megalign® program of the LASERGENE® bioinformatics computing suite (DNASTAR® Inc., Madison, Wis.); in particular, using the Clustal V method of alignment (Higgins and Sharp (1989) CABIOS. 5:151-153) with the multiple alignment default parameters of GAP PENALTY=10 and GAP LENGTH PENALTY=10, and the pairwise alignment default parameters of KTUPLE=1, GAP PENALTY=3, WINDOW=5 and DIAGONALS SAVED=5.

FIG. 13 shows the percent sequence identity and the divergence values for each pair of amino acids sequences displayed in FIGS. 12A-12C.

In another embodiment, a recombinant DNA construct comprises a polynucleotide operably linked to at least one regulatory sequence (e.g., a promoter functional in a plant), wherein said polynucleotide encodes a ferrochelatase. The ferrochelatase may be from *Arabidopsis thaliana, Zea mays, Glycine max, Glycine tabacina, Glycine soja* and *Glycine tomentella.*

In another aspect, the present invention includes suppression DNA constructs.

A suppression DNA construct may comprise at least one regulatory sequence (e.g., a promoter functional in a plant) operably linked to (a) all or part of: (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a ferrochelatase; or (c) all or part of: (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 1, 3, 5, 7, 9, 11, 13, 15, 17, 19, 21, 23, 25, 27 or 29, or (ii) a full complement of the nucleic acid sequence of (c)(i). The suppression DNA construct may comprise a cosuppression construct, antisense construct, viral-suppression construct, hairpin suppression construct, stem-loop suppression construct, double-stranded RNA-producing construct, RNAi construct, or small RNA construct (e.g., an siRNA construct or an miRNA construct).

It is understood, as those skilled in the art will appreciate, that the invention encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)).

Another variation describes the use of plant viral sequences to direct the suppression of proximal mRNA encoding sequences (PCT Publication No. WO 98/36083 published on Aug. 20, 1998).

Previously described is the use of "hairpin" structures that incorporate all, or part, of an mRNA encoding sequence in a complementary orientation that results in a potential "stem-loop" structure for the expressed RNA (PCT Publication No. WO 99/53050 published on Oct. 21, 1999). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression see Wesley, S. V. et al. (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (PCT Publication No. WO 99/61632 published on Dec. 2, 1999).

The use of poly-T and poly-A sequences to generate the stem in the stem-loop structure has also been described (PCT Publication No. WO 02/00894 published Jan. 3, 2002).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication No. WO 02/00904, published Jan. 3, 2002.

RNA interference refers to the process of sequence-specific post-transcriptional gene silencing in animals mediated by short interfering RNAs (siRNAs) (Fire et al., *Nature* 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein et al., *Nature* 409:363 (2001)). Short interfering RNAs derived from dicer activity are typically about 21 to about 23 nucleotides in length and comprise about 19 base pair duplexes (Elbashir et al., *Genes Dev.* 15:188 (2001)). Dicer has also been implicated in the excision of 21- and 22-nucleotide small temporal RNAs (stRNAs) from precursor RNA of conserved structure that are implicated in translational control (Hutvagner et al., *Science* 293:834 (2001)). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex. In addition, RNA interference can also involve small RNA (e.g., miRNA) mediated gene silencing, presumably through cellular mechanisms that regulate chromatin structure and thereby prevent transcription of target gene sequences (see, e.g., Allshire, *Science* 297:1818-1819 (2002); Volpe et al., *Science* 297:1833-1837 (2002); Jenuwein, *Science* 297:2215-2218 (2002); and Hall et al., *Science* 297:2232-2237 (2002)). As such, miRNA molecules of the invention can be used to mediate gene silencing via interaction with RNA transcripts or alternately by interaction with particular gene sequences, wherein such interaction results in gene silencing either at the transcriptional or post-transcriptional level.

RNAi has been studied in a variety of systems. Fire et al. (*Nature* 391:806 (1998)) were the first to observe RNAi in *Caenorhabditis elegans*. Wianny and Goetz (*Nature Cell Biol.* 2:70 (1999)) describe RNAi mediated by dsRNA in mouse embryos. Hammond et al. (*Nature* 404:293 (2000)) describe RNAi in *Drosophila* cells transfected with dsRNA. Elbashir et al., (*Nature* 411:494 (2001)) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

It is thought that sequence complementarity between small RNAs and their RNA targets helps to determine which mechanism, RNA cleavage or translational inhibition, is employed. It is believed that siRNAs which are perfectly complementary with their targets, work by RNA cleavage. Some miRNAs have perfect or near-perfect complementarity with their targets, and RNA cleavage has been demonstrated for at least a few of these miRNAs. Other miRNAs have several mismatches with their targets, and apparently inhibit their targets at the translational level. Again, without being held to a particular theory on the mechanism of action, a general rule is emerging that perfect or near-perfect complementarity causes RNA cleavage, whereas translational inhibition is favored when the miRNA/target duplex contains many mismatches. The apparent exception to this is microRNA 172 (miR172) in plants. One of the targets of miR172 is APETALA2 (AP2), and although miR172 shares near-perfect complementarity with AP2 it appears to cause translational inhibition of AP2 rather than RNA cleavage.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures. In animals, the enzyme involved in processing miRNA precursors is called dicer, an RNAse III-like protein (Grishok et al., *Cell* 106:23-34 (2001); Hutvagner et al., *Science* 293:834-838 (2001); Ketting et al., *Genes. Dev.* 15:2654-2659 (2001)). Plants also have a dicer-like enzyme, DCL1 (previously named CARPEL FACTORY/SHORT INTEGUMENTS1/SUSPENSOR1), and recent evidence indicates that it, like dicer, is involved in processing the hairpin precursors to generate mature miRNAs (Park et al., *Curr. Biol.* 12:1484-1495 (2002); Reinhart et al., *Genes Dev.* 16:1616-1626 (2002)). Furthermore, it is becoming clear from recent work that at least some miRNA hairpin precursors originate as longer polyadenylated transcripts, and several different miRNAs and associated hairpins can be present in a single transcript (Lagos-Quintana et al., *Science* 294:853-858 (2001); Lee et al., *EMBO J.* 21:4663-4670 (2002)). Recent work has also examined the selection of the miRNA strand from the dsRNA product arising from processing of the hairpin by DICER (Schwartz et al., *Cell* 115:199-208 (2003)). It appears that the stability (i.e. G:C versus A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

MicroRNAs (miRNAs) appear to regulate target genes by binding to complementary sequences located in the transcripts produced by these genes. In the case of lin-4 and let-7, the target sites are located in the 3' UTRs of the target mRNAs (Lee et al., *Cell* 75:843-854 (1993); Wightman et al., *Cell* 75:855-862 (1993); Reinhart et al., *Nature* 403:901-906 (2000); Slack et al., *Mol. Cell.* 5:659-669 (2000)), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (Olsen and Ambros, *Dev. Biol.* 216:671-680 (1999)). On the other hand, recent evidence suggests that miRNAs can in some cases cause specific RNA cleavage of the target transcript within the target site, and this cleavage step appears to require 100% complementarity between the miRNA and the target transcript (Hutvagner and Zamore,

*Science* 297:2056-2060 (2002); Llave et al., *Plant Cell* 14:1605-1619 (2002)). It seems likely that miRNAs can enter at least two pathways of target gene regulation: (1) protein downregulation when target complementarity is <100%; and (2) RNA cleavage when target complementarity is 100%. MicroRNAs entering the RNA cleavage pathway are analogous to the 21-25 nt short interfering RNAs (siRNAs) generated during RNA interference (RNAi) in animals and post-transcriptional gene silencing (PTGS) in plants, and likely are incorporated into an RNA-induced silencing complex (RISC) that is similar or identical to that seen for RNAi.

Identifying the targets of miRNAs with bioinformatics has not been successful in animals, and this is probably due to the fact that animal miRNAs have a low degree of complementarity with their targets. On the other hand, bioinformatic approaches have been successfully used to predict targets for plant miRNAs (Llave et al., *Plant Cell* 14:1605-1619 (2002); Park et al., *Curr. Biol.* 12:1484-1495 (2002); Rhoades et al., *Cell* 110:513-520 (2002)), and thus it appears that plant miRNAs have higher overall complementarity with their putative targets than do animal miRNAs. Most of these predicted target transcripts of plant miRNAs encode members of transcription factor families implicated in plant developmental patterning or cell differentiation.

Regulatory Sequences:

A recombinant DNA construct (including a suppression DNA construct) of the present invention may comprise at least one regulatory sequence.

A regulatory sequence may be a promoter.

A number of promoters can be used in recombinant DNA constructs of the present invention. The promoters can be selected based on the desired outcome, and may include constitutive, tissue-specific, inducible, or other promoters for expression in the host organism.

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to enhance drought tolerance. This effect has been observed in *Arabidopsis* (Kasuga et al. (1999) Nature Biotechnol. 17:287-91).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., Nature 313:810-812 (1985)); rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo-specific and may be useful in the invention include soybean Kunitz trypsin inhibitor (Kti3, Jofuku and Goldberg, Plant Cell 1:1079-1093 (1989)), patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259: 149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol. Biol. 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., Bio/Technology 7:L929-932 (1989)), bean lectin and bean beta-phaseolin promoters to express luciferase (Riggs et al., Plant Sci. 63:47-57 (1989)), and wheat glutenin promoters to express chloramphenicol acetyl transferase (Colot et al., EMBO J. 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in the current invention include the following: 1) the stress-inducible RD29A promoter (Kasuga et al. (1999) Nature Biotechnol. 17:287-91); 2) the barley promoter, B22E; expression of B22E is specific to the pedicel in developing maize kernels ("Primary Structure of a Novel Barley Gene Differentially Expressed in Immature Aleurone Layers". Klemsdal, S. S. et al., Mol. Gen. Genet. 228(1/2):9-16 (1991)); and 3) maize promoter, Zag2 ("Identification and molecular characterization of ZAG1, the maize homolog of the *Arabidopsis* floral homeotic gene AGAMOUS", Schmidt, R. J. et al., Plant Cell 5(7):729-737 (1993); "Structural characterization, chromosomal localization and phylogenetic evaluation of two pairs of AGAMOUS-like MADS-box genes from maize", Theissen et al. Gene 156(2):155-166 (1995); NCBI GenBank Accession No. X80206)). Zag2 transcripts can be detected 5 days prior to pollination to 7 to 8 days after pollination ("DAP"), and directs expression in the carpel of developing female inflorescences and Ciml which is specific to the nucleus of developing maize kernels. Ciml transcript is detected 4 to 5 days before pollination to 6 to 8 DAP. Other useful promoters include any promoter which can be derived from a gene whose expression is maternally associated with developing female florets.

Additional promoters for regulating the expression of the nucleotide sequences of the present invention in plants are stalk-specific promoters. Such stalk-specific promoters include the alfalfa S2A promoter (GenBank Accession No.

EF030816; Abrahams et al., Plant Mol. Biol. 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B., Biochemistry of Plants 15:1-82 (1989).

Promoters for use in the current invention may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (Genbank accession number EF030817), and the constitutive promoter GOS2 from *Zea mays*. Other promoters include root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CR1B10 promoter (WO06055487, published May 26, 2006), the CRWAQ81 (WO05035770, published Apr. 21, 2005) and the maize ZRP2.47 promoter (NCBI accession number: U38790; GI No. 1063664), Recombinant DNA constructs of the present invention may also include other regulatory sequences, including but not limited to, translation leader sequences, introns, and polyadenylation recognition sequences. In another embodiment of the present invention, a recombinant DNA construct of the present invention further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell. Biol.* 8:4395-4405 (1988); Callis et al., *Genes Dev.* 1:1183-1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994).

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or from a non-plant eukaryotic gene.

A translation leader sequence is a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) Molecular Biotechnology 3:225).

Any plant can be selected for the identification of regulatory sequences and ferrochelatase genes to be used in recombinant DNA constructs of the present invention. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassaya, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

Compositions:

A composition of the present invention is a plant comprising in its genome any of the recombinant DNA constructs (including any of the suppression DNA constructs) of the present invention (such as any of the constructs discussed above). Compositions also include any progeny of the plant, and any seed obtained from the plant or its progeny, wherein the progeny or seed comprises within its genome the recombinant DNA construct (or suppression DNA construct). Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit an altered agronomic characteristic (e.g., an increased agronomic characteristic optionally under water limiting conditions), or used in a breeding program to produce hybrid seed, which can be grown to produce plants that would exhibit such an altered agronomic characteristic. The seeds may be maize seeds.

The plant may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley or millet.

The recombinant DNA construct may be stably integrated into the genome of the plant.

Particularly embodiments include but are not limited to the following:

1. A plant (for example, a maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, and wherein said plant exhibits increased drought tolerance when compared to a control plant not comprising said recombinant DNA construct. The plant may further exhibit an alteration of at least one agronomic characteristic when compared to the control plant.

2. A plant (for example, a maize or soybean plant) comprising in its genome a recombinant DNA construct comprising a polynucleotide operably linked to at least one regulatory sequence, wherein said polynucleotide encodes a ferrochelatase, and wherein said plant exhibits increased drought tolerance when compared to a control plant not comprising said recombinant DNA construct. The plant may further exhibit an alteration of at least one agronomic characteristic when compared to the control plant.

3. A plant (for example, a maize or soybean plant) comprising in its genome a recombinant DNA construct comprising a polynucleotide operably linked to at least one regulatory sequence, wherein said polynucleotide encodes a ferrochelatase, and wherein said plant exhibits an alteration of at least one agronomic characteristic when compared to a control plant not comprising said recombinant DNA construct.

4. A plant (for example, a maize or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, and wherein said plant exhibits an alteration of at least one agronomic characteristic when compared to a control plant not comprising said recombinant DNA construct.

5. A plant (for example, a maize or soybean plant) comprising in its genome a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a ferrochelatase, and wherein said plant exhibits an alteration of at least one agronomic characteristic when compared to a control plant not comprising said suppression DNA construct.

6. A plant (for example, a maize or soybean plant) comprising in its genome a suppression DNA construct comprising at least one regulatory element operably linked to all or part of (a) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, or (b) a full complement of the nucleic acid sequence of (a), and wherein said plant exhibits an alteration of at least one agronomic characteristic when compared to a control plant not comprising said suppression DNA construct.

7. Any progeny of the above plants in embodiments 1-6, any seeds of the above plants in embodiments 1-6, any seeds of progeny of the above plants in embodiments 1-6, and cells from any of the above plants in embodiments 1-6 and progeny thereof.

In any of the foregoing embodiments 1-7 or any other embodiments of the present invention, the ferrochelatase may be from *Arabidopsis thaliana, Zea mays, Glycine max, Glycine tabacina, Glycine soja* or *Glycine tomentella.*

In any of the foregoing embodiments 1-7 or any other embodiments of the present invention, the recombinant DNA construct (or suppression DNA construct) may comprise at least a promoter functional in a plant as a regulatory sequence.

In any of the foregoing embodiments 1-7 or any other embodiments of the present invention, the alteration of at least one agronomic characteristic is either an increase or decrease.

In any of the foregoing embodiments 1-7 or any other embodiments of the present invention, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height and ear length. For example, the alteration of at least one agronomic characteristic may be an increase in yield, greenness or biomass.

In any of the foregoing embodiments 1-7 or any other embodiments of the present invention, the plant may exhibit the alteration of at least one agronomic characteristic when compared, under water limiting conditions, to a control plant not comprising said recombinant DNA construct (or said suppression DNA construct).

"Drought" refers to a decrease in water availability to a plant that, especially when prolonged, can cause damage to the plant or prevent its successful growth (e.g., limiting plant growth or seed yield).

"Drought tolerance" is a trait of a plant to survive under drought conditions over prolonged periods of time without exhibiting substantial physiological or physical deterioration.

"Increased drought tolerance" of a plant is measured relative to a reference or control plant, and is a trait of the plant to survive under drought conditions over prolonged periods of time, without exhibiting the same degree of physiological or physical deterioration relative to the reference or control plant grown under similar drought conditions. Typically, when a transgenic plant comprising a recombinant DNA construct or suppression DNA construct in its genome exhibits increased drought tolerance relative to a reference or control plant, the reference or control plant does not comprise in its genome the recombinant DNA construct or suppression DNA construct.

One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color or leaf area size. Other techniques for evaluating drought tolerance include measuring chlorophyll fluorescence, photosynthetic rates and gas exchange rates.

A drought stress experiment may involve a chronic stress (i.e., slow dry down) and/or may involve two acute stresses (i.e., abrupt removal of water) separated by a day or two of recovery. Chronic stress may last 8-10 days. Acute stress may last 3-5 days. The following variables may be measured during drought stress and well watered treatments of transgenic plants and relevant control plants:

The variable "% area chg_start chronic-acute2" is a measure of the percent change in total area determined by remote visible spectrum imaging between the first day of chronic stress and the day of the second acute stress The variable "% area chg_start chronic-end chronic" is a measure of the percent change in total area determined by remote visible spectrum imaging between the first day of chronic stress and the last day of chronic stress The variable "% area chg_start chronic-harvest" is a measure of the percent change in total area determined by remote visible spectrum imaging between the first day of chronic stress and the day of harvest The variable "% area chg_start chronic-recovery24 hr" is a measure of the percent change in total area determined by remote visible spectrum imaging between the first day of chronic stress and 24 hrs into the recovery (24 hrs after acute stress 2)

The variable "psii_acute1" is a measure of Photosystem II (PSII) efficiency at the end of the first acute stress period. It provides an estimate of the efficiency at which light is absorbed by PSII antennae and is directly related to carbon dioxide assimilation within the leaf.

The variable "psii_acute2" is a measure of Photosystem II (PSII) efficiency at the end of the second acute stress period. It provides an estimate of the efficiency at which light is absorbed by PSII antennae and is directly related to carbon dioxide assimilation within the leaf.

The variable "fv/fm_acute1" is a measure of the optimum quantum yield (Fv/Fm) at the end of the first acute stress–(variable fluorescence difference between the maximum and minimum fluorescence/maximum fluorescence)

The variable "fv/fm_acute2" is a measure of the optimum quantum yield (Fv/Fm) at the end of the second acute stress–(variable flourescence difference between the maximum and minimum fluorescence/maximum fluorescence)

The variable "leaf rolling_harvest" is a measure of the ratio of top image to side image on the day of harvest.

The variable "leaf rolling_recovery24 hr" is a measure of the ratio of top image to side image 24 hours into the recovery.

The variable "Specific Growth Rate (SGR)" represents the change in total plant surface area (as measured by Lemna Tec Instrument) over a single day ($Y(t)=Y0*e^{r*t}$). $Y(t)=Y0*e^{r*t}$ is equivalent to % change in $Y/\Delta t$ where the individual terms are as follows: Y(t)=Total surface area at t; Y0=Initial total surface area (estimated); r=Specific Growth Rate $day^{-1}$, and t=Days After Planting ("DAP")

The variable "shoot dry weight" is a measure of the shoot weight 96 hours after being placed into a 104° C. oven The variable "shoot fresh weight" is a measure of the shoot weight immediately after being cut from the plant The Examples below describe some representative protocols and techniques for simulating drought conditions and/or evaluating drought tolerance.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring drought conditions (e.g., by measuring for substantially equivalent yield under drought conditions compared to non-drought conditions, or by measuring for less yield loss under drought conditions compared to a control or reference plant).

One of ordinary skill in the art would readily recognize a suitable control or reference plant to be utilized when assessing or measuring an agronomic characteristic or phenotype of a transgenic plant in any embodiment of the present invention in which a control plant is utilized (e.g., compositions or methods as described herein). For example, by way of non-limiting illustrations:

1. Progeny of a transformed plant which is hemizygous with respect to a recombinant DNA construct (or suppression DNA construct), such that the progeny are segregating into plants either comprising or not comprising the recombinant DNA construct (or suppression DNA construct): the progeny comprising the recombinant DNA construct (or suppression DNA construct) would be typically measured relative to the progeny not comprising the recombinant DNA construct (or suppression DNA construct) (i.e., the progeny not comprising the recombinant DNA construct (or the suppression DNA construct) is the control or reference plant).

2. Introgression of a recombinant DNA construct (or suppression DNA construct) into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct (or suppression DNA construct): the second hybrid line would typically be measured relative to the first hybrid line (i.e., the first hybrid line is the control or reference plant).

4. A plant comprising a recombinant DNA construct (or suppression DNA construct): the plant may be assessed or measured relative to a control plant not comprising the recombinant DNA construct (or suppression DNA construct) but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct (or suppression DNA construct)). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Methods:

Methods include but are not limited to methods for increasing drought tolerance in a plant, methods for evaluating drought tolerance in a plant, methods for altering an agronomic characteristic in a plant, methods for determining an alteration of an agronomic characteristic in a plant, and methods for producing seed. The plant may be a monocotyledonous or dicotyledonous plant, for example, a maize or soybean plant. The plant may also be sunflower, sorghum, canola, wheat, alfalfa, cotton, rice, barley or millet. The seed is may be a maize or soybean seed, for example, a maize hybrid seed or maize inbred seed.

Methods include but are not limited to the following:

A method for transforming a cell comprising transforming a cell with any of the isolated polynucleotides of the present invention. The cell transformed by this method is also included. In particular embodiments, the cell is eukaryotic cell, e.g., a yeast, insect or plant cell, or prokaryotic, e.g., a bacterium.

A method for producing a transgenic plant comprising transforming a plant cell with any of the isolated polynucleotides or recombinant DNA constructs of the present invention and regenerating a transgenic plant from the transformed plant cell. The invention is also directed to the transgenic plant produced by this method, and transgenic seed obtained from this transgenic plant.

A method for isolating a polypeptide of the invention from a cell or culture medium of the cell, wherein the cell comprises a recombinant DNA construct comprising a polynucleotide of the invention operably linked to at least one regulatory sequence, and wherein the transformed host cell is grown under conditions that are suitable for expression of the recombinant DNA construct.

A method of altering the level of expression of a polypeptide of the invention in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the polypeptide of the invention in the transformed host cell.

A method of increasing drought tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30; and (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct. The method may further comprise (c) obtaining a progeny plant derived from the transgenic plant, wherein said progeny plant comprises in its genome the recombinant DNA construct and exhibits increased drought tolerance when compared to a control plant not comprising the recombinant DNA construct.

A method of increasing drought tolerance in a plant, comprising: (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, or (ii) a full complement of the nucleic acid sequence of (a)(i); and (b) regenerating a transgenic plant from the regenerable plant cell after step (a), wherein the transgenic plant comprises in its genome the suppression DNA construct and exhibits increased drought tolerance when compared to a control plant not comprising the suppression DNA construct. The method may further comprise (c) obtaining a progeny plant derived from the transgenic plant, wherein said progeny plant comprises in its genome the suppression DNA construct and exhibits increased drought tolerance when compared to a control plant not comprising the suppression DNA construct.

A method of increasing drought tolerance in a plant, comprising: (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a ferrochelatase; and (b) regenerating a transgenic plant from the regenerable plant cell after step (a), wherein the transgenic plant comprises in its genome the suppression DNA construct and exhibits increased drought tolerance when compared to a control plant not comprising the suppression DNA construct. The method may further comprise (c) obtaining a progeny plant derived from the transgenic plant, wherein said progeny plant comprises in its genome the suppression DNA construct and exhibits increased drought tolerance when compared to a control plant not comprising the suppression DNA construct.

A method of evaluating drought tolerance in a plant, comprising (a) introducing into a regenerable plant cell a recombinant DNA construct comprising a polynucleotide operably linked to at least on regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30; (b) regenerating a transgenic plant from the regenerable plant cell after step (a), wherein the transgenic plant comprises in its genome the recombinant DNA construct; and (c) evaluating the transgenic plant for drought tolerance compared to a control plant not comprising the recombinant DNA construct. The method may further comprise (d) obtaining a progeny plant derived from the transgenic plant, wherein the progeny plant comprises in its genome the recombinant DNA construct; and (e) evaluating the progeny plant for drought tolerance compared to a control plant not comprising the recombinant DNA construct.

A method of evaluating drought tolerance in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, or (ii) a full complement of the nucleic acid sequence of (a)(i); (b) regenerating a transgenic plant from the regenerable plant cell after step (a), wherein the transgenic plant comprises in its genome the suppression DNA construct; and (c) evaluating the transgenic plant for drought tolerance compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for drought tolerance compared to a control plant not comprising the suppression DNA construct.

A method of evaluating drought tolerance in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a ferrochelatase; (b) regenerating a transgenic plant from the regenerable plant cell after step (a), wherein the transgenic plant comprises in its genome the suppression DNA construct; and (c) evaluating the transgenic plant for drought tolerance compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for drought tolerance compared to a control plant not comprising the suppression DNA construct.

A method of evaluating drought tolerance in a plant, comprising (a) introducing into a regenerable plant cell a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30; (b) regenerating a transgenic plant from the regenerable plant cell after step (a), wherein the transgenic plant comprises in its genome the recombinant DNA construct; (c) obtaining a progeny plant derived from said transgenic plant, wherein the progeny plant comprises in its genome the recombinant DNA construct; and (d) evaluating the progeny plant for drought tolerance compared to a control plant not comprising the recombinant DNA construct.

A method of evaluating drought tolerance in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, or (ii) a full complement of the nucleic acid sequence of (a)(i); (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) evaluating the progeny plant for drought tolerance compared to a control plant not comprising the suppression DNA construct.

A method of evaluating drought tolerance in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a ferrochelatase; (b) regenerating a transgenic plant from the regenerable plant cell after step (a), wherein the transgenic plant comprises in its genome the suppression DNA construct; (c) obtaining a progeny plant derived from the transgenic plant, wherein the progeny plant comprises in its genome the suppression DNA construct; and (d) evaluating the progeny plant for drought tolerance compared to a control plant not comprising the suppression DNA construct.

A method of determining an alteration of an agronomic characteristic in a plant, comprising (a) introducing into a regenerable plant cell a recombinant DNA construct comprising a polynucleotide operably linked to at least on regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30; (b) regenerating a transgenic plant from the regenerable plant cell after step (a), wherein the transgenic plant comprises in its genome said recombinant DNA construct; and (c) determining whether the transgenic plant exhibits an alteration in at least one agronomic characteristic when compared, optionally under water limiting conditions, to a control plant not comprising the recombinant DNA construct. The method may further comprise (d) obtaining a progeny plant derived from the transgenic plant, wherein the progeny plant comprises in its genome the recombinant DNA construct; and (e) determining whether the progeny plant exhibits an alteration in at least one agronomic characteristic when compared, optionally under water limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, or (ii) a full complement of the nucleic acid sequence of (i); (b) regenerating a transgenic plant from the regenerable plant cell after step (a), wherein the transgenic plant comprises in its genome the suppression DNA construct; and (c) determining whether the transgenic plant exhibits an alteration in at least one agronomic characteristic when compared, optionally under water limiting conditions, to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration in at least one agronomic characteristic when compared, optionally under water limiting conditions, to a control plant not comprising the suppression DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a ferrochelatase; (b) regenerating a transgenic plant from the regenerable plant cell after step (a), wherein the transgenic plant comprises in its genome the suppression DNA construct; and (c) determining whether the transgenic plant exhibits an alteration in at least one agronomic characteristic when compared, optionally under water limiting conditions, to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration in at least one agronomic characteristic when compared, optionally under water limiting conditions, to a control plant not comprising the suppression DNA construct.

A method of determining an alteration of an agronomic characteristic in a plant, comprising (a) introducing into a regenerable plant cell a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30; (b) regenerating a transgenic plant from the regenerable plant cell after step (a), wherein the transgenic plant comprises in its genome said recombinant DNA construct; (c) obtaining a progeny plant derived from said transgenic plant, wherein the progeny plant comprises in its genome the recombinant DNA construct; and (d) determining whether the progeny plant exhibits an alteration in at least one agronomic characteristic when compared, optionally under water limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, or (ii) a full complement of the nucleic acid sequence of (i); (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration in at least one agronomic characteristic when compared, optionally under water limiting conditions, to a control plant not comprising the suppression DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a ferrochelatase; (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration in at least one agronomic characteristic when compared, optionally under water limiting conditions, to a control plant not comprising the suppression DNA construct.

A method of producing seed (for example, seed that can be sold as a drought tolerant product offering) comprising any of the preceding methods, and further comprising obtaining seeds from said progeny plant, wherein said seeds comprise in their genome said recombinant DNA construct (or suppression DNA construct).

In any of the preceding methods or any other embodiments of methods of the present invention, in said introducing step said regenerable plant cell may comprise a callus cell, an embryogenic callus cell, a gametic cell, a meristematic cell, or a cell of an immature embryo. The regenerable plant cells may derive from an inbred maize plant.

In any of the preceding methods or any other embodiments of methods of the present invention, said regenerating step may comprise the following: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present invention, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, amino acid content in a vegetative tissue, total plant protein content, fruit protein content, seed protein content, protein content in a vegetative tissue, drought tolerance, nitrogen uptake, root lodging, harvest index, stalk lodging, plant height, ear height and ear length. The alteration of at least one agronomic characteristic may be an increase in yield, greenness or biomass.

In any of the preceding methods or any other embodiments of methods of the present invention, the plant may exhibit the alteration of at least one agronomic characteristic when compared, under water limiting conditions, to a control plant not comprising said recombinant DNA construct (or said suppression DNA construct).

In any of the preceding methods or any other embodiments of methods of the present invention, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant invention.

The introduction of recombinant DNA constructs of the present invention into plants may be carried out by any suitable technique, including but not limited to direct DNA uptake, chemical treatment, electroporation, microinjection, cell fusion, infection, vector-mediated DNA transfer, bombardment, or *Agrobacterium*-mediated transformation.

Techniques are set forth below in the Examples below for transformation of maize plant cells and soybean plant cells.

Other methods for transforming dicots, primarily by use of *Agrobacterium tumefaciens*, and obtaining transgenic plants include those published for cotton (U.S. Pat. Nos. 5,004,863, 5,159,135, 5,518,908); soybean (U.S. Pat. Nos. 5,569,834 , 5,416,011, McCabe et. al., BiolTechnology 6:923 (1988), Christou et al., Plant Physiol. 87:671 674 (1988)); *Brassica* (U.S. Pat. No. 5,463,174); peanut (Cheng et al., Plant Cell Rep. 15:653 657 (1996), McKently et al., Plant Cell Rep. 14:699 703 (1995)); papaya; and pea (Grant et al., Plant Cell Rep. 15:254 258, (1995)).

Transformation of monocotyledons using electroporation, particle bombardment, and *Agrobacterium* have also been reported, for example, transformation and plant regeneration as achieved in asparagus (Bytebier et al., Proc. Natl. Acad. Sci. (USA) 84:5354, (1987)); barley (Wan and Lemaux, Plant Physiol 104:37 (1994)); maize (Rhodes et al., Science 240: 204 (1988), Gordon-Kamm et al., Plant Cell 2:603 618 (1990), Fromm et al., BiolTechnology 8:833 (1990), Koziel et al., BiolTechnology 11: 194, (1993), Armstrong et al., Crop Science 35:550 557 (1995)); oat (Somers et al., BiolTechnology 10: 15 89 (1992)); orchard grass (Horn et al., Plant Cell Rep. 7:469 (1988)); rice (Toriyama et al., TheorAppl. Genet. 205:34, (1986); Part et al., Plant Mol. Biol. 32:1135 1148, (1996); Abedinia et al., Aust. J. Plant Physiol. 24:133 141 (1997); Zhang and Wu, Theor. Appl. Genet. 76:835 (1988); Zhang et al. Plant Cell Rep. 7:379, (1988); Battraw and Hall, Plant Sci. 86:191 202 (1992); Christou et al., Bio/Technology 9:957 (1991)); rye (De la Pena et al., Nature 325:274 (1987)); sugarcane (Bower and Birch, Plant J. 2:409 (1992)); tall fescue (Wang et al., BiolTechnology 10:691 (1992)), and wheat (Vasil et al., Bio/Technology 10:667 (1992); U.S. Pat. No. 5,631,152).

There are a variety of methods for the regeneration of plants from plant tissue. The particular method of regeneration will depend on the starting plant tissue and the particular plant species to be regenerated.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

EXAMPLES

The present invention is further illustrated in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Creation of an *Arabidopsis* Population with Activation-Tagged Genes

Figure 1:
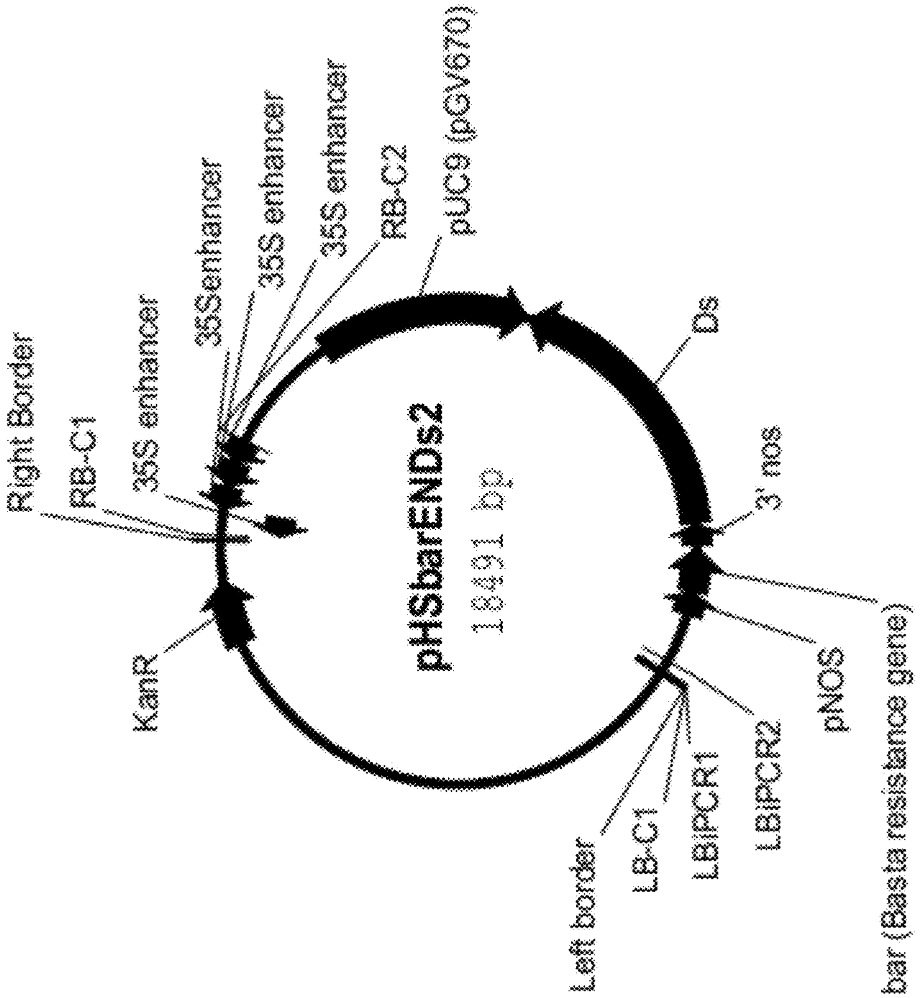
FIG. 1 shows a schematic of the pHSbarENDs2 activation tagging construct (SEQ ID NO:31) used to make the *Arabidopsis* populations.

An 18.5-kb T-DNA based binary construct was created, pHSbarENDs2 (FIG. 1; SEQ ID NO:31), that contains four multimerized enhancer elements derived from the Cauliflower Mosaic Virus 35S promoter (corresponding to sequences −341 to −64, as defined by Odell et al., *Nature* 313:810-812 (1985)). The construct also contains vector sequences (pUC9) and a polylinker to allow plasmid rescue, transposon sequences (Ds) to remobilize the T-DNA, and the bar gene to allow for glufosinate selection of transgenic plants. In principle, only the 10.8-kb segment from the right border (RB) to left border (LB) inclusive will be transferred into the host plant genome. Since the enhancer elements are located near the RB, they can induce cis-activation of genomic loci following T-DNA integration.

*Arabidopsis* activation-tagged populations were created by whole plant *Agrobacterium* transformation. The pHSbarENDs2 construct was transformed into *Agrobacterium tumefaciens* strain C58, grown in LB at 25° C. to OD600 ~1.0. Cells were then pelleted by centrifugation and resuspended in an equal volume of 5% sucrose/0.05% Silwet L-77 (OSI Specialties, Inc). At early bolting, soil grown *Arabidopsis thaliana* ecotype Col-0 were top watered with the *Agrobacterium* suspension. A week later, the same plants were top watered again with the same *Agrobacterium* strain in sucrose/Silwet. The plants were then allowed to set seed as normal. The resulting T1 seed were sown on soil, and transgenic seedlings were selected by spraying with glufosinate (Finale®; AgrEvo; Bayer Environmental Science). A total of 100,000 glufosinate resistant T1 seedlings were selected. T2 seed from each line was kept separate.

Example 2

Screens to Identify Lines with Enhanced Drought Tolerance

Quantitative Drought Screen: From each of 96,000 separate T1 activation-tagged lines, nine glufosinate resistant T2 plants are sown, each in a single pot on Scotts® Metro-Mix® 200 soil. Flats are configured with 8 square pots each. Each of the square pots is filled to the top with soil. Each pot (or cell) is sown to produce 9 glufosinate resistant seedlings in a 3×3 array.

The soil is watered to saturation and then plants are grown under standard conditions (i.e., 16 hour light, 8 hour dark cycle; 22° C.; ~60% relative humidity). No additional water is given.

Digital images of the plants are taken at the onset of visible drought stress symptoms. Images are taken once a day (at the same time of day), until the plants appear dessicated. Typically, four consecutive days of data is captured. Color analysis is employed for identifying potential drought tolerant lines.

Color analysis can be used to measure the increase in the percentage of leaf area that falls into a yellow color bin. Using hue, saturation and intensity data ("HSI"), the yellow color bin consists of hues 35 to 45.

Maintenance of leaf area is also used as another criterion for identifying potential drought tolerant lines, since *Arabidopsis* leaves wilt during drought stress. Maintenance of leaf area can be measured as reduction of rosette leaf area over time.

Leaf area is measured in terms of the number of green pixels obtained using the LemnaTec imaging system. Activation-tagged and control (e.g., wild-type) plants are grown side by side in flats that contain 72 plants (9 plants/pot). When wilting begins, images are measured for a number of days to monitor the wilting process. From these data wilting profiles are determined based on the green pixel counts obtained over four consecutive days for activation-tagged and accompanying control plants. The profile is selected from a series of measurements over the four day period that gives the largest degree of wilting. The ability to withstand drought is measured by the tendency of activation-tagged plants to resist wilting compared to control plants.

LemnaTec HTSBonitUV software is used to analyze CCD images. Estimates of the leaf area of the *Arabidopsis* plants are obtained in terms of the number of green pixels. The data for each image is averaged to obtain estimates of mean and standard deviation for the green pixel counts for activation-tagged and wild-type plants. Parameters for a noise function are obtained by straight line regression of the squared deviation versus the mean pixel count using data for all images in a batch. Error estimates for the mean pixel count data are calculated using the fit parameters for the noise function. The mean pixel counts for activation-tagged and wild-type plants are summed to obtain an assessment of the overall leaf area for each image. The four-day interval with maximal wilting is obtained by selecting the interval that corresponds to the maximum difference in plant growth. The individual wilting responses of the activation-tagged and wild-type plants are obtained by normalization of the data using the value of the green pixel count of the first day in the interval. The drought tolerance of the activation-tagged plant compared to the wild-type plant is scored by summing the weighted difference between the wilting response of activation-tagged plants and wild-type plants over day two to day four; the weights are estimated by propagating the error in the data. A positive drought tolerance score corresponds to an activation-tagged plant with slower wilting compared to the wild-type plant. Significance of the difference in wilting response between activation-tagged and wild-type plants is obtained from the weighted sum of the squared deviations.

Lines with a significant delay in yellow color accumulation and/or with significant maintenance of rosette leaf area, when compared to the average of the whole flat, are designated as Phase 1 hits. Phase 1 hits are re-screened in duplicate under the same assay conditions. When either or both of the Phase 2 replicates show a significant difference (score of greater than 0.9) from the whole flat mean, the line is then considered a validated drought tolerant line.

Example 3

Identification of Activation-Tagged Genes

Genes flanking the T-DNA insert in drought tolerant lines are identified using one, or both, of the following two standard procedures: (1) thermal asymmetric interlaced (TAIL) PCR (Liu et al., (1995), *Plant J.* 8:457-63); and (2) SAIFF PCR (Siebert et al., (1995) *Nucleic Acids Res.* 23:1087-1088). In lines with complex multimerized T-DNA inserts, TAIL PCR and SAIFF PCR may both prove insufficient to identify candidate genes. In these cases, other procedures, including inverse PCR, plasmid rescue and/or genomic library construction, can be employed.

A successful result is one where a single TAIL or SAIFF PCR fragment contains a T-DNA border sequence and *Arabidopsis* genomic sequence.

Once a tag of genomic sequence flanking a T-DNA insert is obtained, candidate genes are identified by alignment to publicly available *Arabidopsis* genome sequence.

Specifically, the annotated gene nearest the 35S enhancer elements/T-DNA RB are candidates for genes that are activated.

To verify that an identified gene is truly near a T-DNA and to rule out the possibility that the TAIL/SAIFF fragment is a chimeric cloning artifact, a diagnostic PCR on genomic DNA is done with one oligo in the T-DNA and one oligo specific for the candidate gene. Genomic DNA samples that give a PCR product are interpreted as representing a T-DNA insertion. This analysis also verifies a situation in which more than one insertion event occurs in the same line, e.g., if multiple differing genomic fragments are identified in TAIL and/or SAIFF PCR analyses.

Example 4A

Identification of Activation-Tagged Ferrochelatase-I (FeC-I) Gene

An activation-tagged line (No. 105998) showing drought tolerance was further analyzed. DNA from the line was extracted, and genes flanking the T-DNA insert in the mutant line were identified using SAIFF PCR (Siebert et al., *Nucleic Acids Res.* 23:1087-1088 (1995)). A PCR amplified fragment was identified that contained T-DNA border sequence and *Arabidopsis* genomic sequence. Genomic sequences flanking the T-DNA insert was obtained, and the candidate gene was identified by alignment to the completed *Arabidopsis* genome. For a given T-DNA integration event, the annotated gene nearest the 35S enhancer elements/T-DNA RB was the candidate for gene that is activated in the line. In the case of line 105998, the gene nearest the 35S enhancers at the integration site was At5g26030 (SEQ ID NO:1; NCBI GI No. 511080), encoding a ferrochelatase-I protein (SEQ ID NO:2; NCBI GI No. 511081).

Example 4B

Assay for Expression Level of Candidate Drought Tolerance Genes

A functional activation-tagged allele should result in either up-regulation of the candidate gene in tissues where it is normally expressed, ectopic expression in tissues that do not normally express that gene, or both. Expression levels of the candidate genes in the cognate mutant line vs. wild-type are compared. A standard RT-PCR procedure, such as the QuantiTect® Reverse Transcription Kit from Qiagen®, is used. RT-PCR of the actin gene is used as a control to show that the amplification and loading of samples from the mutant line and wild-type are similar.

Assay conditions are optimized for each gene. Expression levels are checked in mature rosette leaves. If the activation-tagged allele results in ectopic expression in other tissues (e.g., roots), it is not detected by this assay. As such, a positive result is useful but a negative result does not eliminate a gene from further analysis.

Example 5A

Validation of *Arabidopsis* Candidate Gene At5g26030 (Ferrochelatase-I) Via Transformation into *Arabidopsis*

Candidate genes can be transformed into *Arabidopsis* and overexpressed under the 35S promoter. If the same or similar phenotype is observed in the transgenic line as in the parent activation-tagged line, then the candidate gene is considered to be a validated "lead gene" in *Arabidopsis*.

The candidate *Arabidopsis* ferrochelatase-I gene (At5g26030; SEQ ID NO:1; NCBI GI No. 511080) was tested for its ability to confer drought tolerance in the following manner.

Figure 4:
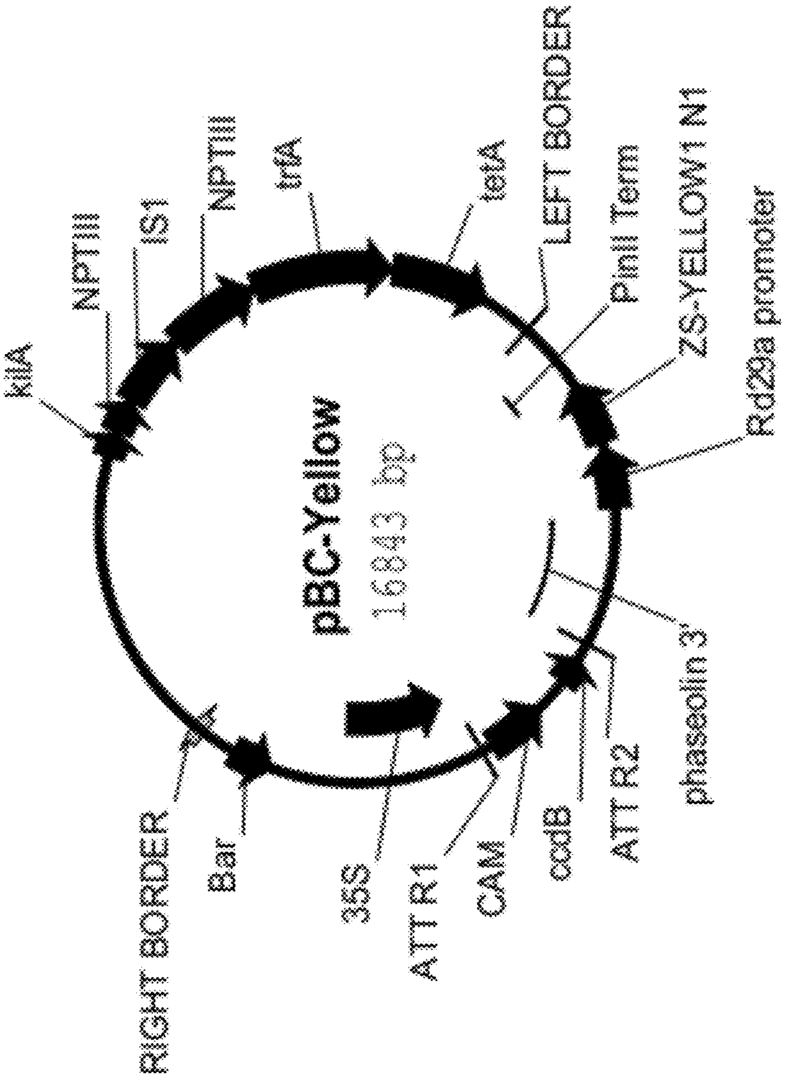
FIG. 4 shows a map of the vector pBC-yellow (SEQ ID NO:34), a destination vector for use in construction of expression vectors for *Arabidopsis*. The attR1 site is at nucleotides 11276-11399 (complementary strand); the attR2 site is at nucleotides 9695-9819 (complementary strand).

A 16.8-kb T-DNA based binary vector, called pBC-yellow (SEQ ID NO:34; FIG. 4), was constructed with a 1.3-kb 35S promoter immediately upstream of the INVITROGEN™ GATEWAY® Cl conversion insert. The vector also contains the RD29a promoter driving expression of the gene for ZS-Yellow (INVITROGENT™), which confers yellow fluorescence to transformed seed.

The At5g26030 cDNA protein-coding region was amplified by RT-PCR with the following primers:

(1) At5g26030-5' attB forward primer (SEQ ID NO:42):

```
TTAAACAAGTTTGTACAAAAAAGCAGGCTCAACAATGCAGGCAACGG
CTTTATCA
```

(2) At5g26030-3' attB reverse primer (SEQ ID NO:43):

```
TTAAACCACTTTGTACAAGAAAGCTGGGTCTATAGGTTCCGGAACGC
ATG
```

The forward primer contains the attB1 sequence (ACAAGTTTGTACAAAAAAGCAGGCT; SEQ ID NO:40) and a consensus Kozak sequence (CAACA) adjacent to the first 21 nucleotides of the protein-coding region, beginning with the ATG start codon, of said cDNA.

The reverse primer contains the attB2 sequence (ACCACTTTGTACAAGAAAGCTGGGT; SEQ ID NO:41) adjacent to the reverse complement of the last 21 nucleotides of the protein-coding region, beginning with the reverse complement of the stop codon, of said cDNA.

Figure 2:
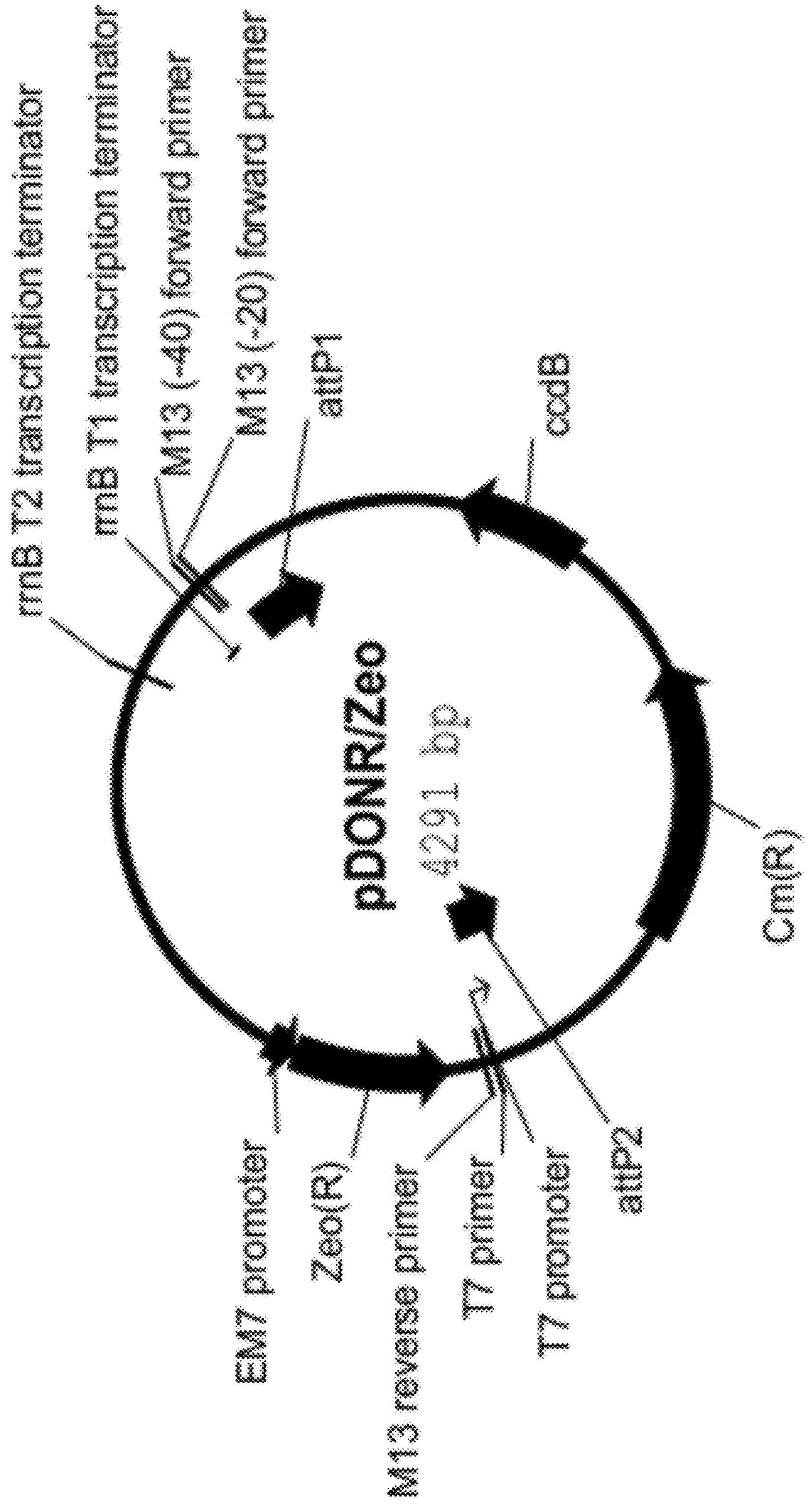
FIG. 2 shows a map of the vector pDONR™/Zeo (SEQ ID NO:32). The attP1 site is at nucleotides 570-801; the attP2 site is at nucleotides 2754-2985 (complementary strand).

Using the INVITROGEN™ GATEWAY® CLONASE™ technology, a BP Recombination Reaction was performed with pDONR™/Zeo (SEQ ID NO:32; FIG. 2). This process removed the bacteria lethal ccdB gene, as well as the chloramphenicol resistance gene (CAM) from pDONR™/Zeo and directionally cloned the PCR product with flanking attB1 and attB2 sites creating an entry clone, PHP31052. This entry clone was used for a subsequent LR Recombination Reaction with a destination vector, as follows.

A 16.8-kb T-DNA based binary vector (destination vector), called pBC-yellow (SEQ ID NO:34; FIG. 4), was constructed with a 1.3-kb 35S promoter immediately upstream of the INVITROGEN™ GATEWAY® C1 conversion insert, which contains the bacterial lethal ccdB gene as well as the chloramphenicol resistance gene (CAM) flanked by attR1 and attR2 sequences. The vector also contains the RD29a promoter driving expression of the gene for ZS-Yellow (INVITROGEN™), which confers yellow fluorescence to transformed seed. Using the INVITROGEN™ GATEWAY® technology, an LR Recombination Reaction was performed on the PHP31052 entry clone, containing the directionally cloned PCR product, and pBC-yellow. This allowed for rapid and directional cloning of the candidate gene behind the 35S promoter in pBC-yellow to create the 35S promoter::At5g26030 expression construct, pBC-Yellow-At5g26030.

Applicants then introduced the 35S promoter::At5g26030 expression construct into wild-type *Arabidopsis* ecotype Col-0, using the same *Agrobacterium*-mediated transformation procedure described in Example 1. Transgenic T1 seeds were selected by yellow fluorescence, and T1 seeds were plated next to wild-type seeds and grown under water limiting conditions. Growth conditions and imaging analysis were as described in Example 2. It was found that the original drought tolerance phenotype from activation tagging could be recapitulated in wild-type *Arabidopsis* plants that were transformed with a construct where At5g26030 was directly expressed by the 35S promoter. The drought tolerance score, as determined by the method of Example 2, was 5.3.

Example 5B

Validation of *Arabidopsis* Candidate Gene At2g30390 (Ferrochelatase-II) Via Transformation into *Arabidopsis*

A cDNA encoding ferrochelatase-I from *Arabidopsis* was previously cloned by functional complementation of a yeast mutant (Smith et al. 1994 J Biol Chem 269:13405-13413). Subsequently, a second ferrochelatase isoform, ferrochelatase-II, was found in *Arabidopsis* (Chow et al. 1998 Plant J 15:531-541). Two forms of ferrochelatase also have been identified in cucumber, *Cucumis sativus* (Miyamoto et al. 1994 Plant Physiol 105:769-770; and Suzuki et al. 2002 J Biol Chem 277:4731-4737). The C-terminal region of ferrochelatase-II, but not ferrochelatase-I, contains a conserved motif found in light-harvesting chlorophyll proteins (Suzuki et al. 2002 J Biol Chem 277:4731-4737). The C-terminal region of the ferrochelatase from the cyanobacteria *Synechocystis* (NCBI GI NO. 1708186) has sequence homology to this conserved motif.

The *Arabidopsis* ferrochelatase-II gene (At2g30390) was selected as a second candidate gene, and was tested for its ability to confer drought tolerance in the following manner.

A 16.8-kb T-DNA based binary vector, called pBC-yellow (SEQ ID NO:34; FIG. 4), was constructed with a 1.3-kb 35S promoter immediately upstream of the INVITROGEN™ GATEWAY® C1 conversion insert. The vector also contains the RD29a promoter driving expression of the gene for ZS-Yellow (INVITROGENT™), which confers yellow fluorescence to transformed seed.

The At2g30390 cDNA protein-coding region was amplified by RT-PCR with the following primers:

(3) At2g30390-5' attB forward primer (SEQ ID NO:44):

TTAAACAAGTTTGTACAAAAAAGCAGGCTCAACAATGAATTGCCCAG
CCATGACT (4) At2g30390-3' attB reverse primer (SEQ ID NO:45):

TTAAACCACTTTGTACAAGAAAGCTGGGTTTATAATGAAGGCAAGAT
GCC

The forward primer contains the attB1 sequence (ACAAGTTTGTACAAAAAAGCAGGCT; SEQ ID NO:40) and a consensus Kozak sequence (CAACA) adjacent to the first 21 nucleotides of the protein-coding region, beginning with the ATG start codon, of said cDNA.

The reverse primer contains the attB2 sequence (ACCACTTTGTACAAGAAAGCTGGGT; SEQ ID NO:41) adjacent to the reverse complement of the last 21 nucleotides of the protein-coding region, beginning with the reverse complement of the stop codon, of said cDNA.

Using the INVITROGEN™ GATEWAY® CLONASE™ technology, a BP Recombination Reaction was performed with pDONR™/Zeo (SEQ ID NO:32; FIG. 2). This process removed the bacteria lethal ccdB gene, as well as the chloramphenicol resistance gene (CAM) from pDONR™/Zeo and directionally cloned the PCR product with flanking attB1 and attB2 sites creating an entry clone, PHP-Entry-At2g30390. This entry clone was used for a subsequent LR Recombination Reaction with a destination vector, as follows.

A 16.8-kb T-DNA based binary vector (destination vector), called pBC-yellow (SEQ ID NO:34; FIG. 4), was constructed with a 1.3-kb 35S promoter immediately upstream of the INVITROGEN™ GATEWAY® C1 conversion insert, which contains the bacterial lethal ccdB gene as well as the chloramphenicol resistance gene (CAM) flanked by attR1 and attR2 sequences. The vector also contains the RD29a promoter driving expression of the gene for ZS-Yellow (INVITROGEN™), which confers yellow fluorescence to transformed seed. Using the INVITROGEN™ GATEWAY® technology, an LR Recombination Reaction was performed on the PHP-Entry-At2g30390 entry clone, containing the directionally cloned PCR product, and pBC-yellow. This allowed for rapid and directional cloning of the candidate gene behind the 35S promoter in pBC-yellow to create the 35S promoter::At2g30390 expression construct, pBC-Yellow-At2g30390.

Applicants then introduced the 35S promoter::At2g30390 expression construct into wild-type *Arabidopsis* ecotype Col-0, using the same *Agrobacterium*-mediated transformation procedure described in Example 1. Transgenic T1 seeds were selected by yellow fluorescence, and T1 seeds were plated next to wild-type seeds and grown under water limiting conditions. Growth conditions and imaging analysis were as described in Example 2. It was found that the original drought tolerance phenotype from activation tagging could be recapitulated in wild-type *Arabidopsis* plants that were transformed with a construct where At2g30390 was directly expressed by the 35S promoter. The drought tolerance score, as determined by the method of Example 2, was 3.7.

Example 6A

Preparation of cDNA Libraries and Isolation and Sequencing of cDNA Clones cDNA libraries may be prepared by any one of many methods available. For example, the cDNAs may be introduced into plasmid vectors by first preparing the cDNA libraries in UNI-ZAP™ XR vectors according to the manufacturer's protocol (Stratagene Cloning Systems, La Jolla, Calif.). The UNI-ZAP™ XR libraries are converted into plasmid libraries according to the protocol provided by Stratagene. Upon conversion, cDNA inserts will be contained in the plasmid vector pBluescript®. In addition, the cDNAs may be introduced directly into precut Bluescript® II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript® plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism® dye-terminator ReadyReaction mix) outward from the transposition event site, utilizing unique primers specific to the binding sites within the transposon.

Sequence data is collected (ABI Prism® Collections) and assembled using Phred and Phrap (Ewing et al. (1998) *Genome Res.* 8:175-185; Ewing and Green (1998) *Genome Res.* 8:186-194). Phred is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (Gordon et al. (1998) *Genome Res.* 8:195-202).

In some of the clones the cDNA fragment may correspond to a portion of the 3'-terminus of the gene and does not cover the entire open reading frame. In order to obtain the upstream information one of two different protocols is used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript® vector using a commercial kit and following the manufacturer's protocol. This kit is selected from many available from several vendors including INVITROGEN™ (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 7

Identification of cDNA Clones cDNA clones encoding ferrochelatases can be identified by conducting BLAST (Basic Local Alignment Search Tool; Altschul et al. (1993) *J. Mol. Biol.* 215:403-410; see also the explanation of the BLAST algorithm on the world wide web site for the National Center for Biotechnology Information at the National Library of Medicine of the National Institutes of Health) searches for similarity to amino acid sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The DNA sequences from clones can be translated in all reading frames and compared for similarity to all publicly available protein sequences contained in the "nr" database using the BLASTX algorithm (Gish and States (1993) *Nat. Genet.* 3:266-272) provided by the NCBI. The polypeptides encoded by the cDNA sequences can be analyzed for similarity to all publicly available amino acid sequences contained in the "nr" database using the BLASTP algorithm provided by the National Center for Biotechnology Information (NCBI). For convenience, the P-value (probability) or the E-value (expectation) of observing a match of a cDNA-encoded sequence to a sequence contained in the searched databases merely by chance as calculated by BLAST are reported herein as "pLog" values, which represent the negative of the logarithm of the reported P-value or E-value. Accordingly, the greater the pLog value, the greater the likelihood that the cDNA-encoded sequence and the BLAST "hit" represent homologous proteins.

ESTs sequences can be compared to the Genbank database as described above. ESTs that contain sequences more 5- or 3-prime can be found by using the BLASTn algorithm (Altschul et al (1997) *Nucleic Acids Res.* 25:3389-3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described above. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 8

Characterization of cDNA Clones Encoding Ferrochetalases cDNA libraries representing mRNAs from various tissues of Sugar Beet, Canola, Maize, Rice, Soybean, Wheat and Catmint were prepared and cDNA clones encoding ferrochelatases were identified. The characteristics of the libraries are described below.

TABLE 3 cDNA Libraries from Sugar Beet, Canola, Maize, Rice, Soybean, Wheat and Catmint

| Library | Description | Clone |
|---|---|---|
| ebs1c | Sugar Beet, shoot and phloem specific genes | ebs1c.pk002.n16:fis |
| ebb1c | Immature buds of Canola, Rf gene knock out mutant line, 02SM2 | ebb1c.pk006.j11:fis |
| cfp3n | Maize Ear, pooled V10-V14-v16-VT, Full-length enriched normalized | cfp3n.pk004.f12:fis |
| cfp5n | Maize Kernel, pooled stages, Full-length enriched, normalized | cfp5n.pk009.j16:fis |
| rl0n | Rice 15 Day Old Leaf* | rl0n.pk117.h21:fis |
| se3 | Soybean Embryo, 17 Days After Flowering | se3.pk0034.e10:fis |
| etb1n | Normalized tulip bulb library | etb1n.pk002.n16:fis |
| wlp1c | Wheat (*Triticum aestivum*, Hi Line) lemma and palea | wlp1c.pk002.p10:fis |
| ecl1c | Catmint (*Nepeta racemosa*) cDNA library from young leaf tissue | ecl1c.pk005.l15:fis |
| cfp6n | Maize Leaf and Seed pooled, Full-length enriched normalized | cfp6n.pk072.n9:fis |
| wlp1c | Wheat (*Triticum aestivum*, Hi Line) lemma and palea | wlp1c.pk004.d13:fis |
| wpa1c | Wheat (*Triticum aestivum*) pre-meiotic anthers | wpa1c.pk014.g4:fis |

*These libraries were normalized essentially as described in U.S. Pat. No. 5,482,845

Two of the cDNA clones listed in Table 3 had anomalies. The clone ebb1c.pk006.j11:fis contains an unspliced intron at nucleotides 386-481 of SEQ ID NO:5. The polypeptide encoded by the two exons surrounding the intron is given in SEQ ID NO:6. Additionally, the clone ecl1c.pk005.115:fis has a single base deletion at nucleotide 442, which results in a frame-shift in the corresponding translation. Based on comparison to a highly similar clone cDNA clone from grape, veb1c.pk008.p6 (411 base pairs), a "T" nucleotide was added to the ecl1c.pk005.115:fis sequence at position 442. The modified nucleotide sequence is presented in SEQ ID NO:23, which encodes the amino acid sequence of SEQ ID NO:24.

The BLAST search using the sequences from clones listed in Table 3 revealed similarity of the polypeptides encoded by the cDNAs to the ferrochelatases from various organisms. As shown in Table 4 and FIGS. 10A-10C, certain cDNAs encoded polypeptides similar to ferrochelatase-1 proteins from *Arabidopsis* (GI No. 511081; SEQ ID NO:2; FeC-I), barley (GI No. 2460251; SEQ ID NO:48; FeC-I), rice (GI No. 113631036; SEQ ID NO:49; FeC-I), and grape (GI No. 147818793; SEQ ID NO:50; FeC-I). As shown in Table 6 and FIGS. 12A-12C, certain cDNAs encoded polypeptides similar to ferrochelatase-II proteins from *Arabidopsis* (GI No. 15227742; SEQ ID NO:20; FeC-II), rice (GI No. 115463419; SEQ ID NO:51; FeC-II), cucumber (GI No. 12082085; SEQ ID NO:52; FeC-II), tobacco (GI No. 15147828; SEQ ID NO:53; FeC-II) and a ferrochelatse-II-like protein from *Synechocystis* (GI No. 1708186; SEQ ID NO:54; FeC-II-like).

Shown in Tables 4 and 6 (non-patent literature) and Tables 5 and 7 (patent literature) are the BLASTP results for the amino acid sequences derived from the nucleotide sequences of the entire cDNA inserts ("Full-Insert Sequence" or "FIS") of the clones listed in Table 3. Each cDNA insert encodes an entire or functional protein ("Complete Gene Sequence" or "CGS"). Also shown in Tables 4-7 are the percent sequence identity values for each pair of amino acid sequences:

TABLE 4

BLASTP Results for Ferrochelatase-I Polypeptides

| Sequence (SEQ ID NO) | Status | NCBI GI No. (SEQ ID NO) | BLASTP pLog of E-value | Percent Sequence Identity |
|---|---|---|---|---|
| ebs1c.pk002.n16 (FIS) (SEQ ID NO: 4) | CGS | 147818793 (SEQ ID NO: 50) | >180 | 72.6 |
| ebb1c.pk006.j11 (FIS) (SEQ ID NO: 6) | CGS | 511081 (SEQ ID NO: 2) | >180 | 83.3 |
| cfp3n.pk004.f12 (FIS) (SEQ ID NO: 8) | CGS | 113631036 (SEQ ID NO: 49) | >180 | 84.0 |
| cfp5n.pk009.j16 (FIS) (SEQ ID NO: 10) | CGS | 113631036 (SEQ ID NO: 49) | >180 | 81.7 |
| rl0n.pk117.h21 (FIS) (SEQ ID NO: 12) | CGS | 113631036 (SEQ ID NO: 49) | >180 | 100 |
| se3.pk0034.e10 (FIS) (SEQ ID NO: 14) | CGS | 147818793 (SEQ ID NO: 50) | >180 | 74.2 |
| etb1n.pk002.n16 (FIS) (SEQ ID NO: 16) | CGS | 113631036 (SEQ ID NO: 49) | 180 | 69.5 |
| wlp1c.pk002.p10 (FIS) (SEQ ID NO: 18) | CGS | 2460251 (SEQ ID NO: 48) | >180 | 98.3 |

TABLE 5

BLASTP Results for Ferrochelatase-I Polypeptides

| Sequence (SEQ ID NO) | Status | Reference (SEQ ID NO) | BLASTP pLog of E-value | Percent Sequence Identity |
|---|---|---|---|---|
| ebs1c.pk002.n16 (FIS) (SEQ ID NO: 4) | CGS | SEQ ID NO: 240025 of US2004031072 (SEQ ID NO: 57) | >180 | 68.8 |
| ebb1c.pk006.j11 (FIS) (SEQ ID NO: 6) | CGS | SEQ ID NO: 20 of JP2001190168-A (SEQ ID NO: 58) | >180 | 83.3 |
| cfp3n.pk004.f12 (FIS) (SEQ ID NO: 8) | CGS | SEQ ID NO: 13029 of US2006150283 (SEQ ID NO: 59) | >180 | 99.4 |
| cfp5n.pk009.j16 (FIS) (SEQ ID NO: 10) | CGS | SEQ ID NO: 7745 of US2006150283 (SEQ ID NO: 60) | >180 | 100 |
| rl0n.pk117.h21 (FIS) (SEQ ID NO: 12) | CGS | SEQ ID NO: 46156 of JP2005185101 (SEQ ID NO: 61) | >180 | 100 |
| se3.pk0034.e10 (FIS) (SEQ ID NO: 14) | CGS | SEQ ID NO: 240025 of US2004031072 (SEQ ID NO: 57) | >180 | 100 |
| etb1n.pk002.n16 (FIS) (SEQ ID NO: 16) | CGS | SEQ ID NO: 46156 of JP2005185101 (SEQ ID NO: 61) | >180 | 69.5 |
| wlp1c.pk002.p10 (FIS) (SEQ ID NO: 18) | CGS | SEQ ID NO: 46156 of JP2005185101 (SEQ ID NO: 61) | >180 | 84.6 |

TABLE 6

BLASTP Results for Ferrochelatase-II Polypeptides

| Sequence (SEQ ID NO) | Status | NCBI GI No. (SEQ ID NO) | BLASTP pLog of E-value | Percent Sequence Identity |
|---|---|---|---|---|
| ecl1c.pk005.l15 (FIS) (SEQ ID NO: 24) | CGS | 12082085 (SEQ ID NO: 52) | >180 | 78.6 |
| cfp6n.pk072.n9 (FIS) (SEQ ID NO: 26) | CGS | 115463419 (SEQ ID NO: 51) | >180 | 90.5 |
| wlp1c.pk004.d13 (FIS) (SEQ ID NO: 28) | CGS | 115463419 (SEQ ID NO: 51) | >180 | 82.9 |
| wpa1c.pk014.g4 (FIS) (SEQ ID NO: 30) | CGS | 115463419 (SEQ ID NO: 51) | >180 | 83.3 |

TABLE 7

BLASTP Results for Ferrochelatase-II Polypeptides

| Sequence (SEQ ID NO) | Status | Reference (SEQ ID NO) | BLASTP pLog of E-value | Percent Sequence Identity |
|---|---|---|---|---|
| ecl1c.pk005.l15 (FIS) (SEQ ID NO: 24) | CGS | SEQ ID NO: 52154 of JP2005185101 (SEQ ID NO: 62) | >180 | 77.4 |
| cfp6n.pk072.n9 (FIS) (SEQ ID NO: 26) | CGS | SEQ ID NO: 72746 of US2004034888 (SEQ ID NO: 63) | >180 | 99.6 |
| wlp1c.pk004.d13 (FIS) (SEQ ID NO: 28) | CGS | SEQ ID NO: 52154 of JP2005185101 (SEQ ID NO: 62) | >180 | 82.9 |
| wpa1c.pk014.g4 (FIS) (SEQ ID NO: 30) | CGS | SEQ ID NO: 52154 of JP2005185101 (SEQ ID NO: 62) | >180 | 83.3 |

FIGS. 10A-10C present an alignment of the amino acid sequences of ferrochelatase-I proteins set forth in SEQ ID NOs:2, 4, 6, 8, 10, 12, 14, 16, 18, 48, 49 and 50. FIG. 11 presents the percent sequence identities and divergence values for each sequence pair presented in FIGS. 10A and 10B.

FIGS. 12A-12C present an alignment of the amino acid sequences of ferrochelatase-II proteins set forth in SEQ ID NOs:20, 22, 24, 26, 28, 30, 51, 52, 53 and 54. FIG. 13 presents the percent sequence identities and divergence values for each sequence pair presented in FIGS. 12A and 12B.

Sequence alignments and percent identity calculations were performed using the Megalign® program of the LASERGENE® bioinformatics computing suite (DNASTAR® Inc., Madison, Wis.). Multiple alignment of the sequences was performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5.

Import experiments into isolated chloroplasts and mitochondria showed that the *Arabidopsis* ferrochelatase-II gene encodes a precursor which is imported solely into the chloroplast, in contrast to *Arabidopsis* ferrochelatase-I which is targeted to both organelles (Chow et al. 1997 J Biol Chem 272:27565-27571; Chow et al. 1998 Plant J 15:531-541). The ferrochelatase from *Synechocystis* (GI No. 1708186; SEQ ID NO:54) is more similar to the ferrechelatase-II isoform.

Sequence alignments and BLAST scores and probabilities indicate that the nucleic acid fragments comprising the instant cDNA clones encode ferrochelatases.

Example 9

Preparation of a Plant Expression Vector Containing a Homolog to the *Arabidopsis* Lead Gene Sequences homologous to the *Arabidopsis* ferrochelatase-I polypeptide can be identified using sequence comparison algorithms such as BLAST (Basic Local Alignment Search Tool; Altschul et al., J. Mol. Biol. 215:403-410 (1993); see also the explanation of the BLAST algorithm on the world wide web site for the National Center for Biotechnology Information at the National Library of Medicine of the National Institutes of Health). Sequences encoding homologous ferrochelatases can be PCR-amplified by either of the following methods.

Method 1 (RNA-based): If the 5' and 3' sequence information for the protein-coding region of a gene encoding a ferrochelatase homolog is available, gene-specific primers can be designed as outlined in Example 5. RT-PCR can be used with plant RNA to obtain a nucleic acid fragment containing the protein-coding region flanked by attB1 (SEQ ID NO:40) and attB2 (SEQ ID NO:41) sequences. The primer may contain a consensus Kozak sequence (CAACA) upstream of the start codon.

Method 2 (DNA-based): Alternatively, if a cDNA clone is available for a gene encoding a ferrochelatase homolog, the entire cDNA insert (containing 5' and 3' non-coding regions) can be PCR amplified. Forward and reverse primers can be designed that contain either the attB1 sequence and vector-specific sequence that precedes the cDNA insert or the attB2 sequence and vector-specific sequence that follows the cDNA insert, respectively. For a cDNA insert cloned into the vector pBulescript SK+, the forward primer VC062 (SEQ ID NO:46) and the reverse primer VC063 (SEQ ID NO:47) can be used.

Methods 1 and 2 can be modified according to procedures known by one skilled in the art. For example, the primers of Method 1 may contain restriction sites instead of attB1 and attB2 sites, for subsequent cloning of the PCR product into a vector containing attB1 and attB2 sites. Additionally, Method 2 can involve amplification from a cDNA clone, a lambda clone, a BAC clone or genomic DNA.

Figure 3:
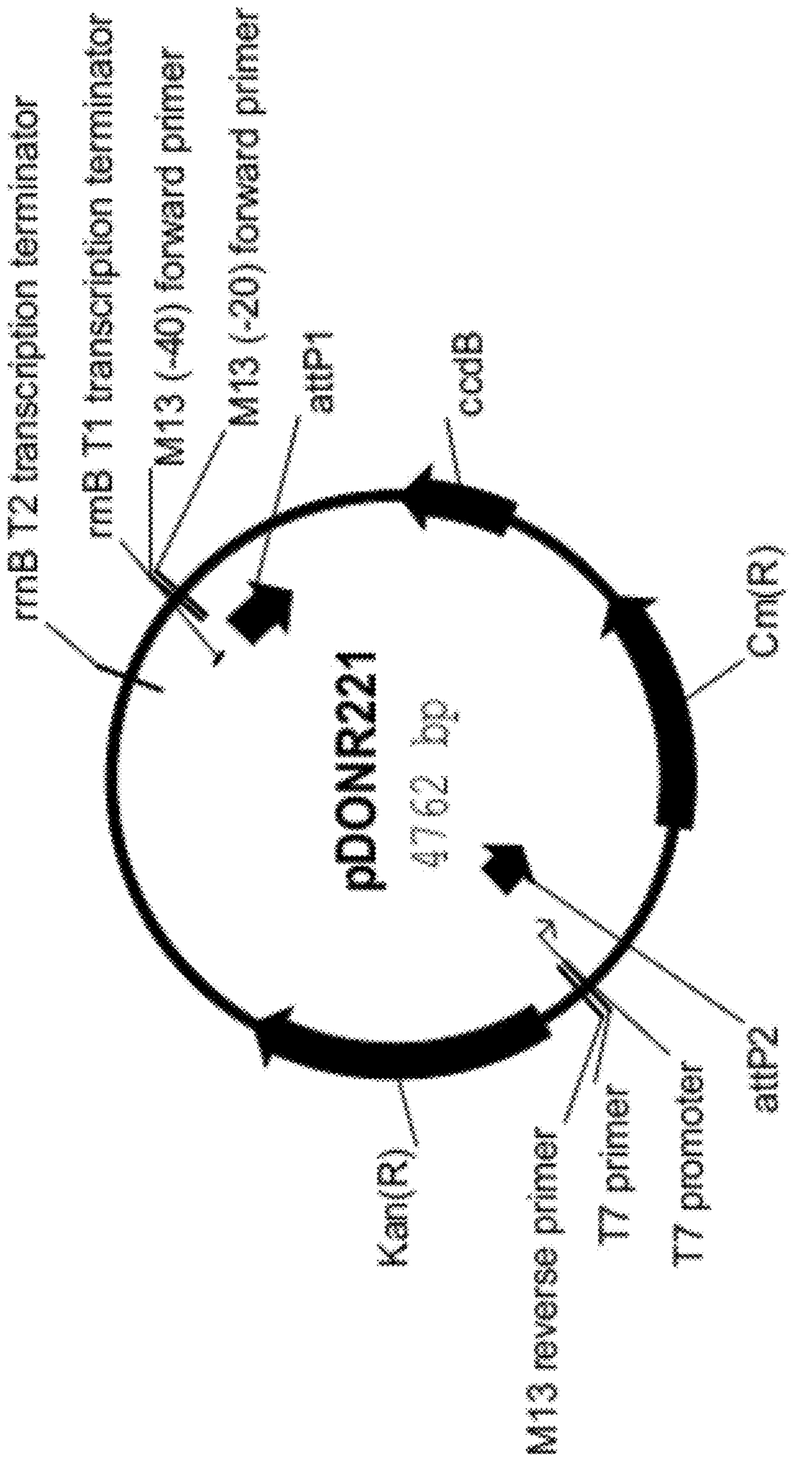
FIG. 3 shows a map of the vector pDONR™ 221 (SEQ ID NO:33). The attP1 site is at nucleotides 570-801; the attP2 site is at nucleotides 2754-2985 (complementary strand).

A PCR product obtained by either method above can be combined with the GATEWAY® donor vector, such as pDONR™/Zeo (INVITROGEN™; FIG. 2; SEQ ID NO:32) or pDONR™221 (INVITROGEN™; FIG. 3; SEQ ID NO:33), using a BP Recombination Reaction. This process removes the bacteria lethal ccdB gene, as well as the chloramphenicol resistance gene (CAM) from pDONR™221 and directionally clones the PCR product with flanking attB1 and attB2 sites to create an entry clone. Using the INVITROGEN™ GATEWAY® CLONASE™ technology, the sequence encoding the homologous ferrochelatase from the entry clone can then be transferred to a suitable destination vector, such as pBC-Yellow (FIG. 4; SEQ ID NO:34), PHP27840 (FIG. 5; SEQ ID NO:35) or PHP23236 (FIG. 6; SEQ ID NO:36), to obtain a plant expression vector for use with *Arabidopsis*, soybean and corn, respectively.

Figure 5:
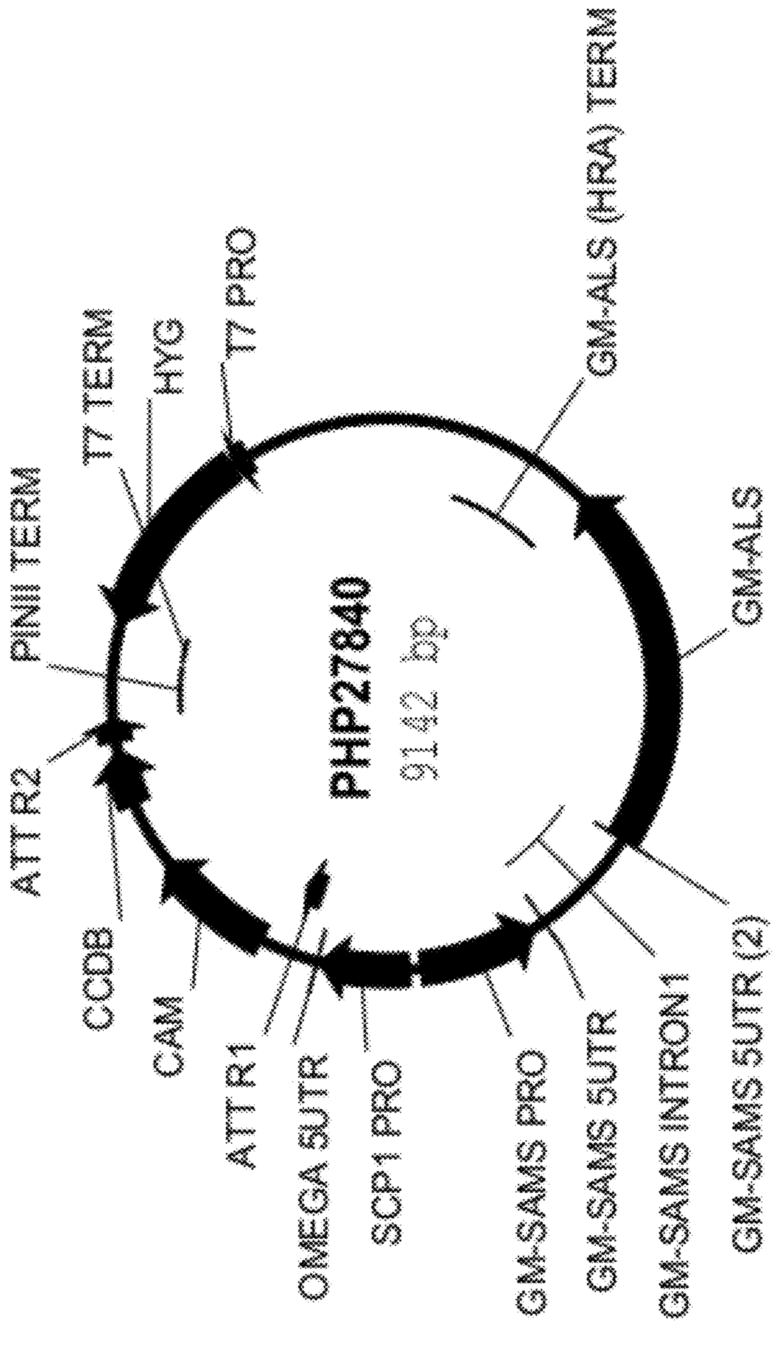
FIG. 5 shows a map of PHP27840 (SEQ ID NO:35), a destination vector for use in construction of expression vectors for soybean. The attR1 site is at nucleotides 7310-7434; the attR2 site is at nucleotides 8890-9014.
Figure 6:
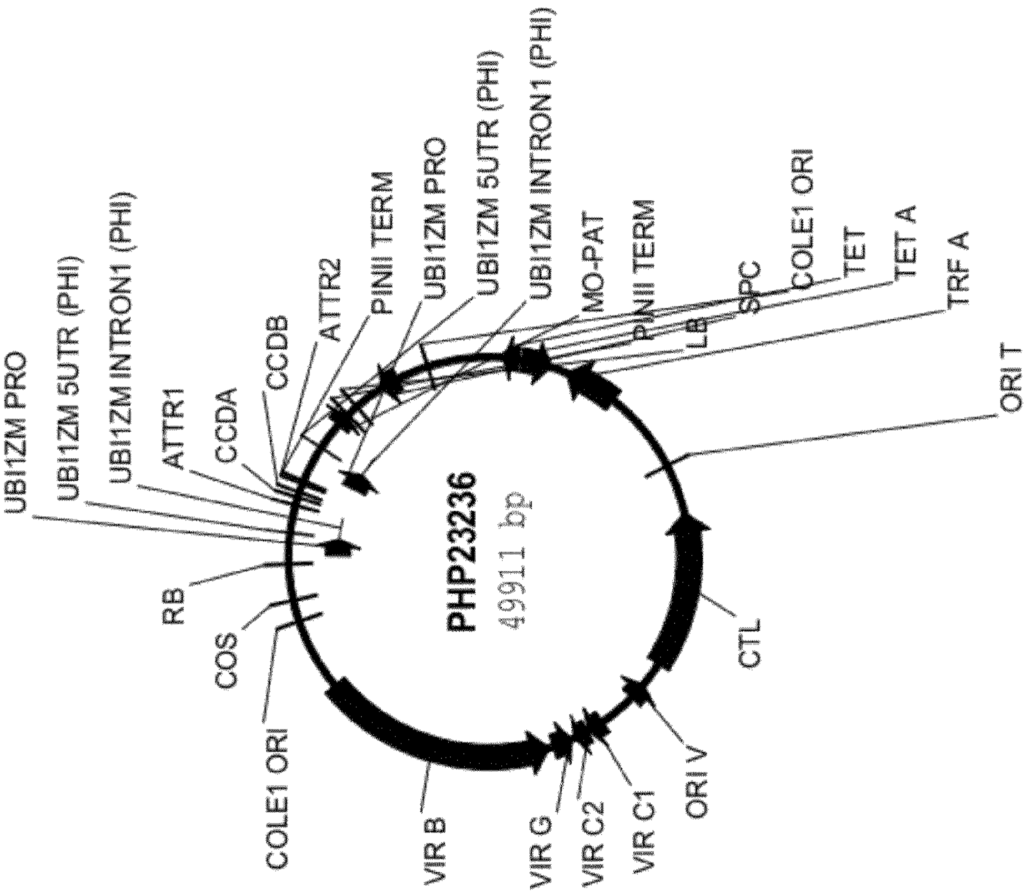
FIG. 6 shows a map of PHP23236 (SEQ ID NO:36), a destination vector for use in construction of expression vectors for Gaspe Flint derived maize lines. The attR1 site is at nucleotides 2006-2130; the attR2 site is at nucleotides 2899-3023.

The attP1 and attP2 sites of donor vectors pDONR™/Zeo or pDONR™221 are shown in FIGS. 2 and 3, respectively. The attR1 and attR2 sites of destination vectors pBC-Yellow, PHP27840 and PHP23236 are shown in FIGS. 4, 5 and 6, respectively.

Alternatively a MultiSite GATEWAY® LR recombination reaction between multiple entry clones and a suitable destination vector can be performed to create an expression vector.

Example 10

Preparation of Soybean Expression Vectors and Transformation of Soybean with Validated *Arabidopsis* Lead Genes Soybean plants can be transformed to overexpress a validated *Arabidopsis* lead gene or the corresponding homologs from various species in order to examine the resulting phenotype.

The same GATEWAY® entry clone described in Example 5 can be used to directionally clone each gene into the PHP27840 vector (SEQ ID NO:35; FIG. 5) such that expression of the gene is under control of the SCP1 promoter.

Soybean embryos may then be transformed with the expression vector comprising sequences encoding the instant polypeptides.

To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos, which produce secondary embryos, are then excised and placed into a suitable liquid medium. After repeated selection for clusters of somatic embryos which multiply as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium. Soybean embryogenic suspension cultures may then be transformed by the method of particle gun bombardment (Klein et al. (1987) Nature (London) 327:70-73, U.S. Pat. No. 4,945,050). A DUPONT™ BIOLISTIC™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. Another selectable marker gene which can be used to facilitate soybean transformation is an herbicide-resistant acetolactate synthase (ALS) gene from soybean or *Arabidopsis*. ALS is the first common enzyme in the biosynthesis of the branched-chain amino acids valine, leucine and isoleucine. Mutations in ALS have been identified that convey resistance to some or all of three classes of inhibitors of ALS (U.S. Pat. No. 5,013,659; the entire contents of which are herein incorporated by reference). Expression of the herbicide-resistant ALS gene can be under the control of a SAM synthetase promoter (U.S. Patent Application No.

US-2003-0226166-A1; the entire contents of which are herein incorporated by reference).

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly.

Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

T1 plants can be subjected to a soil-based drought stress. Using image analysis, plant area, volume, growth rate and color analysis can be taken at multiple times before and during drought stress. Overexpression constructs that result in a significant delay in wilting or leaf area reduction, yellow color accumulation and/or increased growth rate during drought stress will be considered evidence that the *Arabidopsis* gene functions in soybean to enhance drought tolerance.

Soybean plants transformed with validated genes can then be assayed under more vigorous field-based studies to study yield enhancement and/or stability under well-watered and water-limiting conditions.

Example 11

Transformation of Maize with Validated *Arabidopsis* Lead Genes Using Particle Bombardment Maize plants can be transformed to overexpress a validated *Arabidopsis* lead gene or the corresponding homologs from various species in order to examine the resulting phenotype.

The same GATEWAY® entry clone described in Example 5 can be used to directionally clone each gene into a maize transformation vector. Expression of the gene in the maize transformation vector can be under control of a constitutive promoter such as the maize ubiquitin promoter (Christensen et al., (1989) *Plant Mol. Biol.* 12:619-632 and Christensen et al., (1992) *Plant Mol. Biol.* 18:675-689)

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a KAPTON™ flying disc (Bio-Rad Labs). The particles are then accelerated into the corn tissue with a DUPONT™ BIOLISTIC™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialaphos (5 mg per liter) and lacks casein or proline. The tissue continues to grow slowly on this medium. After an additional 2 weeks the tissue can be transferred to fresh N6 medium containing bialaphos. After 6 weeks, areas of about 1 cm in diameter of actively growing callus can be identified on some of the plates containing the bialaphos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839). Transgenic T0 plants can be regenerated and their phenotype determined following high throughput ("HTP") procedures. T1 seed can be collected.

T1 plants can be subjected to a soil-based drought stress. Using image analysis, plant area, volume, growth rate and color analysis can be taken at multiple times before and during drought stress. Overexpression constructs that result in a significant delay in wilting or leaf area reduction, yellow color accumulation and/or increased growth rate during drought stress will be considered evidence that the *Arabidopsis* gene functions in maize to enhance drought tolerance.

Example 12

Electroporation of *Agrobacterium tumefaciens* LBA4404

Figure 7:
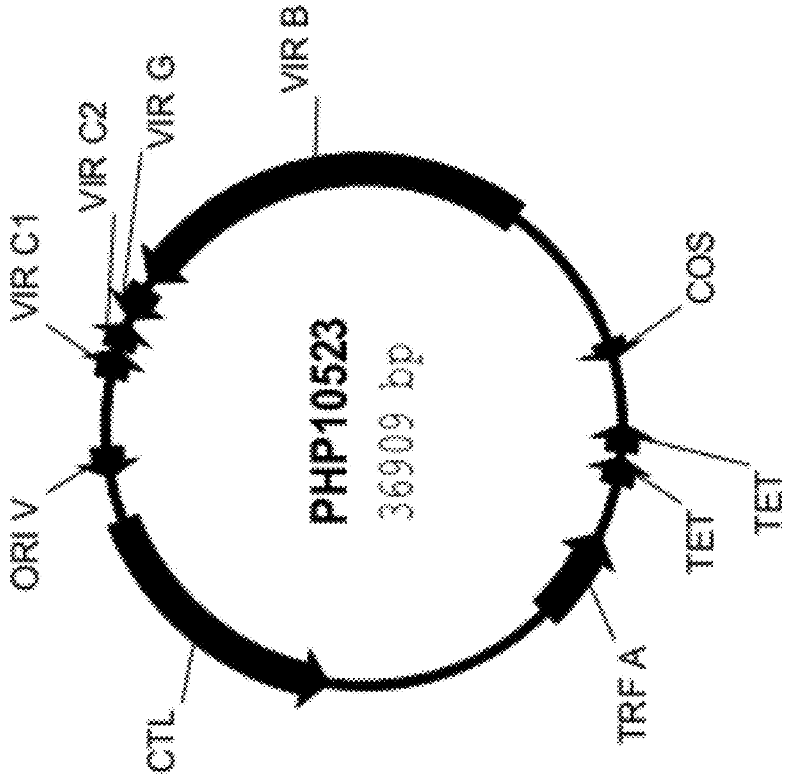
FIG. 7 shows a map of PHP10523 (SEQ ID NO:37), a plasmid DNA present in *Agrobacterium* strain LBA4404 (Komari et al., *Plant J.* 10:165-174 (1996); NCBI General Identifier No. 59797027).

Electroporation competent cells (40 μL), such as *Agrobacterium tumefaciens LBA*4404 containing PHP10523 (FIG. 7; SEQ ID NO:37), are thawed on ice (20-30 min). PHP10523 contains VIR genes for T-DNA transfer, an *Agrobacterium* low copy number plasmid origin of replication, a tetracycline resistance gene, and a Cos site for in vivo DNA bimolecular recombination. Meanwhile the electroporation cuvette is chilled on ice. The electroporator settings are adjusted to 2.1 kV. A DNA aliquot (0.5 μL parental DNA at a concentration of 0.2 μg-1.0 μg in low salt buffer or twice distilled $H_2O$) is mixed with the thawed *Agrobacterium tumefaciens* LBA4404 cells while still on ice. The mixture is transferred to the bottom of electroporation cuvette and kept at rest on ice for 1-2 min. The cells are electroporated (Eppendorf electroporator 2510) by pushing the "pulse" button twice (ideally achieving a 4.0 millisecond pulse). Subsequently, 0.5 mL of room temperature 2xYT medium (or SOC medium) are added to the cuvette and transferred to a 15 mL snap-cap tube (e.g., FALCON™ tube). The cells are incubated at 28-30° C., 200-250 rpm for 3 h.

Aliquots of 2504 are spread onto plates containing YM medium and 50 μg/mL spectinomycin and incubated three days at 28-30° C. To increase the number of transformants one of two optional steps can be performed:

Option 1: Overlay plates with 30 μL of 15 mg/mL rifampicin. LBA4404 has a chromosomal resistance gene for rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on plates containing AB minimal medium and 50 μg/mL spectinomycin for isolation of single colonies. The plates are incubated at 28° C. for two to three days. A single colony for each putative co-integrate is picked and inoculated with 4 mL of 10 g/L bactopeptone, 10 g/L yeast extract, 5 g/L sodium chloride and 50 mg/L spectinomycin. The mixture is incubated for 24 h at 28° C. with shaking. Plasmid DNA from 4 mL of culture is isolated using Qiagen® Miniprep and an optional Buffer PB wash. The DNA is eluted in 30 μL. Aliquots of 2 μL are used to electroporate 20 μL of DH10b+20 μL of twice distilled $H_2O$ as per above. Optionally a 15 μL aliquot can be used to transform 75-100 μL of INVITROGEN™ Library Efficiency DH5α. The cells are spread on plates containing LB medium and 50 μg/mL spectinomycin and incubated at 37° C. overnight.

Three to four independent colonies are picked for each putative co-integrate and inoculated 4 mL of 2xYT medium (10 g/L bactopeptone, 10 g/L yeast extract, 5 g/L sodium chloride) with 50 μg/mL spectinomycin. The cells are incubated at 37° C. overnight with shaking. Next, isolate the plasmid DNA from 4 mL of culture using QIAprep® Miniprep with optional Buffer PB wash (elute in 50 μL). Use 84 for digestion with SalI (using parental DNA and PHP10523 as controls). Three more digestions using restriction enzymes BamHI, EcoRI, and HindIII are performed for 4 plasmids that represent 2 putative co-integrates with correct SalI digestion pattern (using parental DNA and PHP10523 as controls). Electronic gels are recommended for comparison.

Example 13

Transformation of Maize Using *Agrobacterium*

Maize plants can be transformed to overexpress a validated *Arabidopsis* lead gene or the corresponding homologs from various species in order to examine the resulting phenotype.

*Agrobacterium*-mediated transformation of maize is performed essentially as described by Zhao et al. in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium innoculation, co-cultivation, resting, selection and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step:

PHI-A medium of (1) is removed with 1 mL micropipettor, and 1 mL of *Agrobacterium* suspension is added. The tube is gently inverted to mix. The mixture is incubated for 5 min at room temperature.

2.2 Co-culture Step:

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events:

To each plate of PHI-D medium in a 100×15 mm Petri dish, 10 embryos are transferred, maintaining orientation and the dishes are sealed with parafilm. The plates are incubated in darkness at 28° C. Actively growing putative events, as pale yellow embryonic tissue, are expected to be visible in six to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of T0 plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 µE from cool white or equivalent fluorescent lamps). In seven to ten days, regenerated plants, about 10 cm tall, are potted in horticultural mix and hardened-off using standard horticultural methods.

Media for Plant Transformation:

1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 µM acetosyringone (filter-sterilized).
2. PHI-B: PHI-A without glucose, increase 2,4-D to 2 mg/L, reduce sucrose to 30 g/L and supplemente with 0.85 mg/L silver nitrate (filter-sterilized), 3.0 g/L Gelrite®, 100 µM acetosyringone (filter-sterilized), pH 5.8.
3. PHI-C: PHI-B without Gelrite® and acetosyringonee, reduce 2,4-D to 1.5 mg/L and supplemente with 8.0 g/L agar, 0.5 g/L 2-[N-morpholino]ethane-sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat. No. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; reduce sucrose to 40 g/L; replacing agar with 1.5 g/L Gelrite®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined. T1 seed can be collected.

Furthermore, a recombinant DNA construct containing a validated *Arabidopsis* gene can be introduced into an elite maize inbred line either by direct transformation or introgression from a separately transformed line.

Transgenic plants, either inbred or hybrid, can undergo more vigorous field-based experiments to study yield enhancement and/or stability under water limiting and water non-limiting conditions.

Subsequent yield analysis can be done to determine whether plants that contain the validated *Arabidopsis* lead gene have an improvement in yield performance (under water limiting or non-limiting conditions), when compared to the control (or reference) plants that do not contain the validated *Arabidopsis* lead gene. Specifically, water limiting conditions can be imposed during the flowering and/or grain fill period for plants that contain the validated *Arabidopsis* lead gene and the control plants. Plants containing the validated *Arabidopsis* lead gene would have less yield loss relative to the control plants, for example, at least 50% less yield loss, under water limiting conditions, or would have increased yield relative to the control plants under water non-limiting conditions.

Example 14A

Preparation of *Arabidopsis* Lead Gene (At5q26030) Expression Vector for Transformation of Maize Using INVITROGEN's™ GATEWAY® technology, an LR Recombination Reaction was performed with an entry clone (PHP31052) and a destination vector (PHP28647) to create the precursor plasmid PHP31079. The vector PHP31079 contains the following expression cassettes:

1. Ubiquitin promoter::moPAT::PinII terminator; cassette expressing the PAT herbicide resistance gene used for selection during the transformation process.
2. LTP2 promoter::DS-RED2::PinII terminator; cassette expressing the DS-RED color marker gene used for seed sorting.
3. Ubiquitin promoter::At5g26030::PinII terminator; cassette overexpressing the gene of interest, *Arabidopsis* ferrochelatase-I.

Example 14B

Transformation of Maize with the *Arabidopsis* Lead Gene (At5g26030) Using *Agrobacterium*

The ferrochelatase-I expression cassette present in vector PHP31079 can be introduced into a maize inbred line, or a transformable maize line derived from an elite maize inbred line, using *Agrobacterium*-mediated transformation as described in Examples 12 and 13.

Vector PHP31079 can be electroporated into the LBA4404 *Agrobacterium* strain containing vector PHP10523 (FIG. 7; SEQ ID NO:37) to create the co-integrate vector PHP31217. The co-integrate vector is formed by recombination of the 2 plasmids, PHP31079 and PHP10523, through the COS recombination sites contained on each vector. The co-integrate vector PHP31217 contains the same 3 expression cassettes as above (Example 14A) in addition to other genes (TET, TET, TRFA, ORI terminator, CTL, ORI V, VIR C1, VIR C2, VIR G, VIR B) needed for the *Agrobacterium* strain and the *Agrobacterium*-mediated transformation.

Example 15

Figure 8:
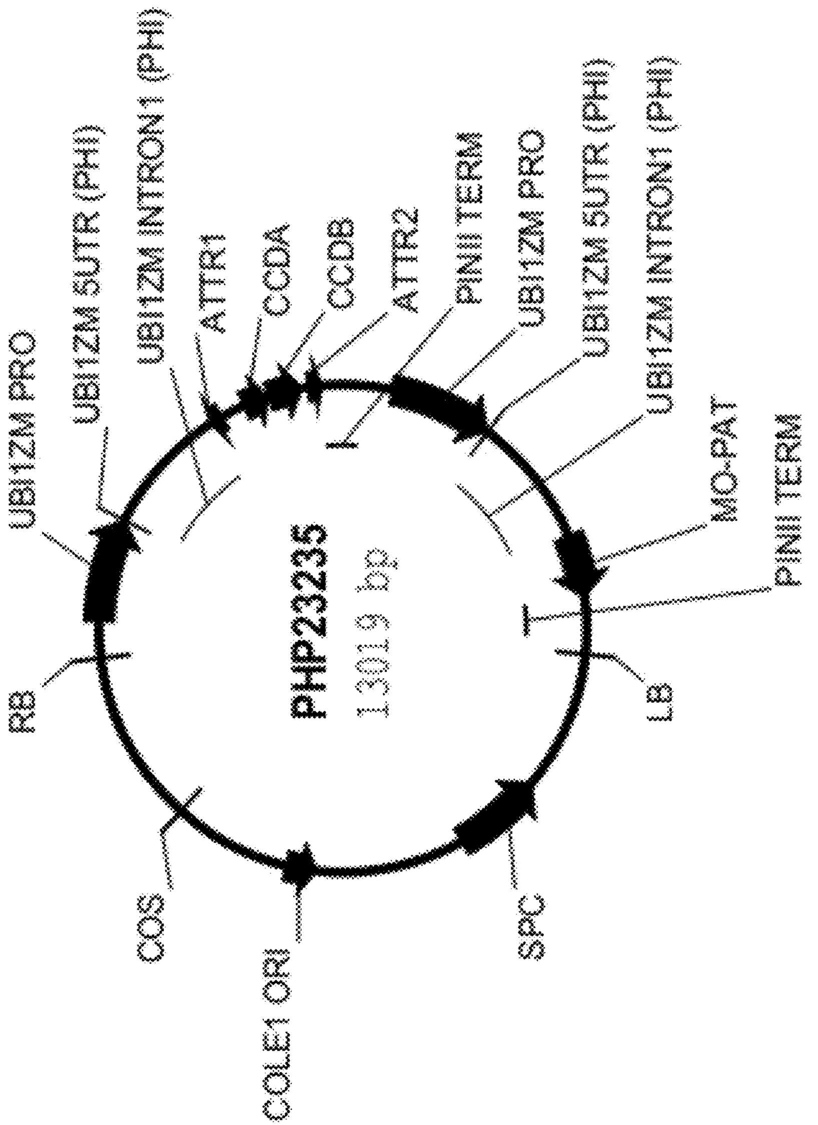
FIG. 8 shows a map of PHP23235 (SEQ ID NO:38), a vector used to construct the destination vector PHP23236.
Figure 9:
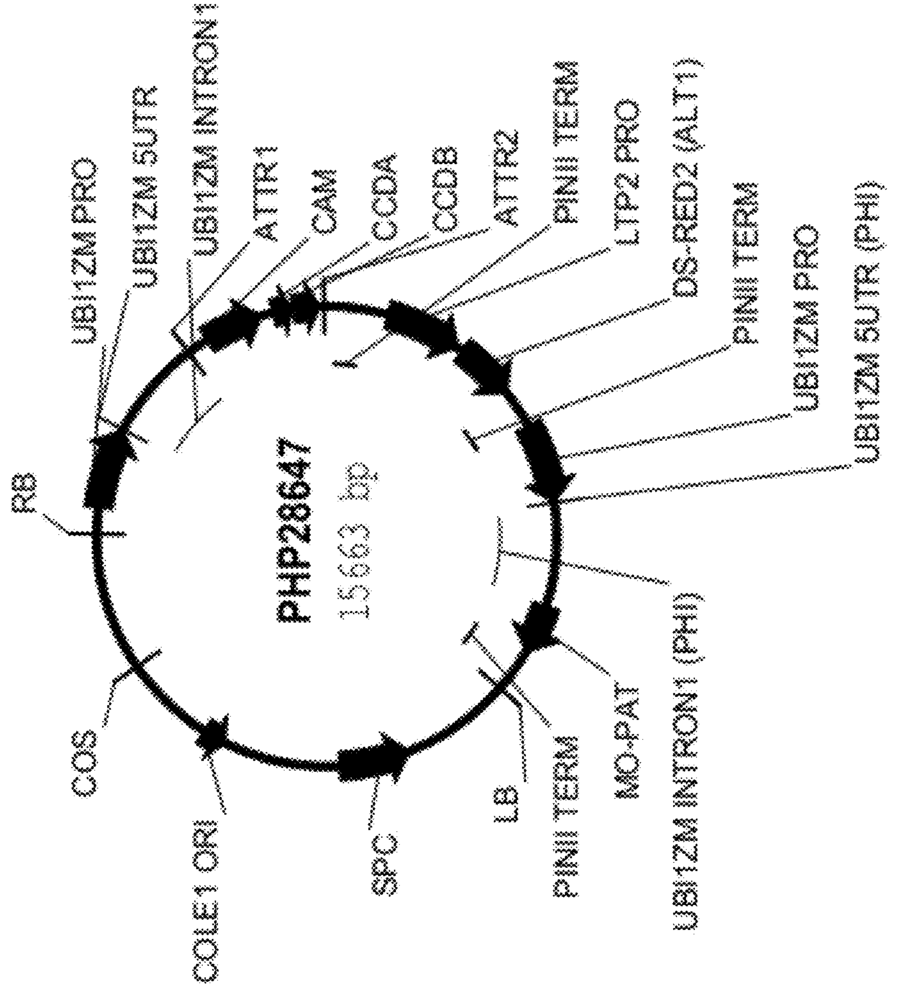
FIG. 9 shows a map of PHP28647 (SEQ ID NO:39), a destination vector for use with maize inbred-derived lines. The attR1 site is at nucleotides 2289-2413; the attR2 site is at nucleotides 3869-3993.

Preparation of the Destination Vector PHP23236 for Transformation into Gaspe Flint Derived Maize Lines Destination vector PHP23236 (FIG. 6, SEQ ID NO:36) was obtained by transformation of *Agrobacterium* strain LBA4404 containing plasmid PHP10523 (FIG. 7, SEQ ID NO:37) with plasmid PHP23235 (FIG. 8, SEQ ID NO:38) and isolation of the resulting co-integration product. Destination vector PHP23236, can be used in a recombination reaction with an entry clone as described in Example 16 to create a maize expression vector for transformation of Gaspe Flint-derived maize lines.

Example 16

Preparation of Plasmids for Transformation into Gaspe Flint Derived Maize Lines Using the INVITROGEN™ GATEWAY® LR Recombination technology, the same entry clone described in Example 5A, PHP31052, was directionally cloned into the destination vector PHP23236 (SEQ ID NO:36; FIG. 6) to create an expression vector, PHP31419. This expression vector contains the cDNA of interest, encoding AtFeC-I, under control of the UBI promoter and is a T-DNA binary vector for *Agrobacterium*-mediated transformation into corn as described, but not limited to, the examples described herein.

Using the INVITROGEN™ GATEWAY® LR Recombination technology, the same entry clone described in Example 5B, PHP-Entry-At2g30390, was directionally cloned into the destination vector PHP29634 to create an expression vector, PHP33089. Destination vector PHP29634 is similar to destination vector PHP23236, however, destination vector PHP29634 has site-specific recombination sites FRT1 and FRT87 and also encodes the GAT4602 selectable marker protein for selection of transformants using glyphosate. This expression vector contains the cDNA of interest, encoding AtFeC-II, under control of the UBI promoter and is a T-DNA binary vector for *Agrobacterium*-mediated transformation into corn as described, but not limited to, the examples described herein.

Example 17

Transformation of Gaspe Flint Derived Maize Lines with a Validated *Arabidopsis* Lead Gene Maize plants can be transformed to overexpress the *Arabidopsis* lead gene or the corresponding homologs from other species in order to examine the resulting phenotype.

Recipient Plants:

Recipient plant cells can be from a uniform maize line having a short life cycle ("fast cycling"), a reduced size, and high transformation potential. Typical of these plant cells for maize are plant cells from any of the publicly available Gaspe Flint (GBF) line varieties. One possible candidate plant line variety is the F1 hybrid of GBF×QTM (Quick Turnaround Maize, a publicly available form of Gaspe Flint selected for growth under greenhouse conditions) disclosed in Tomes et al. U.S. Patent Application Publication No. 2003/0221212. Transgenic plants obtained from this line are of such a reduced size that they can be grown in four inch pots (¼ the space needed for a normal sized maize plant) and mature in less than 2.5 months. (Traditionally 3.5 months is required to obtain transgenic T0 seed once the transgenic plants are acclimated to the greenhouse.) Another suitable line is a double haploid line of GS3 (a highly transformable line) X Gaspe Flint. Yet another suitable line is a transformable elite inbred line carrying a transgene which causes early flowering, reduced stature, or both.

Transformation Protocol:

Any suitable method may be used to introduce the transgenes into the maize cells, including but not limited to inoculation type procedures using *Agrobacterium* based vectors. Transformation may be performed on immature embryos of the recipient (target) plant.

Precision Growth and Plant Tracking:

The event population of transgenic (T0 ) plants resulting from the transformed maize embryos is grown in a controlled greenhouse environment using a modified randomized block design to reduce or eliminate environmental error. A randomized block design is a plant layout in which the experimental plants are divided into groups (e.g., thirty plants per group), referred to as blocks, and each plant is randomly assigned a location with the block.

For a group of thirty plants, twenty-four transformed, experimental plants and six control plants (plants with a set phenotype) (collectively, a "replicate group") are placed in pots which are arranged in an array (a.k.a. a replicate group or block) on a table located inside a greenhouse. Each plant, control or experimental, is randomly assigned to a location with the block which is mapped to a unique, physical greenhouse location as well as to the replicate group. Multiple replicate groups of thirty plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

An alternative to the addition of a specific control group is to identify those transgenic plants that do not express the gene of interest. A variety of techniques such as RT-PCR can be applied to quantitatively assess the expression level of the introduced gene. T0 plants that do not express the transgene can be compared to those which do.

Each plant in the event population is identified and tracked throughout the evaluation process, and the data gathered from that plant is automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor. See U.S. Published Patent Application No. 2004/0122592, incorporated herein by reference.

Phenotypic Analysis Using Three-Dimensional Imaging:

Each greenhouse plant in the T0event population, including any control plants, is analyzed for agronomic characteristics of interest, and the agronomic data for each plant is recorded or stored in a manner so that it is associated with the identifying data (see above) for that plant. Confirmation of a phenotype (gene effect) can be accomplished in the T1 generation with a similar experimental design to that described above.

The T0 plants are analyzed at the phenotypic level using quantitative, non-destructive imaging technology throughout the plant's entire greenhouse life cycle to assess the traits of interest. A digital imaging analyzer may be used for automatic multi-dimensional analyzing of total plants. The imaging may be done inside the greenhouse. Two camera systems, located at the top and side, and an apparatus to rotate the plant, are used to view and image plants from all sides. Images are acquired from the top, front and side of each plant. All three images together provide sufficient information to evaluate the biomass, size and morphology of each plant.

Due to the change in size of the plants from the time the first leaf appears from the soil to the time the plants are at the end of their development, the early stages of plant development are best documented with a higher magnification from the top. This may be accomplished by using a motorized zoom lens system that is fully controlled by the imaging software.

In a single imaging analysis operation, the following events occur: (1) the plant is conveyed inside the analyzer area, rotated 360 degrees so its machine readable label can be read, and left at rest until its leaves stop moving; (2) the side image is taken and entered into a database; (3) the plant is rotated 90 degrees and again left at rest until its leaves stop moving, and (4) the plant is transported out of the analyzer.

Plants are allowed at least six hours of darkness per twenty four hour period in order to have a normal day/night cycle.

Imaging Instrumentation:

Any suitable imaging instrumentation may be used, including but not limited to light spectrum digital imaging instrumentation commercially available from LemnaTec GmbH of Wurselen, Germany. The images are taken and analyzed with a LemnaTec Scanalyzer HTS LT-0001-2 having a ½" IT Progressive Scan IEE CCD imaging device. The imaging cameras may be equipped with a motor zoom, motor aperture and motor focus. All camera settings may be made using LemnaTec software. For example, the instrumental variance of the imaging analyzer is less than about 5% for major components and less than about 10% for minor components.

Software:

The imaging analysis system comprises a LemnaTec HTS Bonit software program for color and architecture analysis and a server database for storing data from about 500,000 analyses, including the analysis dates. The original images and the analyzed images are stored together to allow the user to do as much reanalyzing as desired. The database can be connected to the imaging hardware for automatic data collection and storage. A variety of commercially available software systems (e.g. Matlab, others) can be used for quantitative interpretation of the imaging data, and any of these software systems can be applied to the image data set.

Conveyor System:

A conveyor system with a plant rotating device may be used to transport the plants to the imaging area and rotate them during imaging. For example, up to four plants, each with a maximum height of 1.5 m, are loaded onto cars that travel over the circulating conveyor system and through the imaging measurement area. In this case the total footprint of the unit (imaging analyzer and conveyor loop) is about 5 m×5 m.

The conveyor system can be enlarged to accommodate more plants at a time. The plants are transported along the conveyor loop to the imaging area and are analyzed for up to 50 seconds per plant. Three views of the plant are taken. The conveyor system, as well as the imaging equipment, should be capable of being used in greenhouse environmental conditions.

Illumination:

Any suitable mode of illumination may be used for the image acquisition. For example, a top light above a black background can be used. Alternatively, a combination of top- and backlight using a white background can be used. The illuminated area should be housed to ensure constant illumination conditions. The housing should be longer than the measurement area so that constant light conditions prevail without requiring the opening and closing or doors. Alternatively, the illumination can be varied to cause excitation of either transgene (e.g., green fluorescent protein (GFP), red fluorescent protein (RFP)) or endogenous (e.g. Chlorophyll) fluorophores.

Biomass Estimation Based on Three-Dimensional Imaging:

For best estimation of biomass the plant images should be taken from at least three axes, for example, the top and two side (sides 1 and 2) views. These images are then analyzed to separate the plant from the background, pot and pollen control bag (if applicable). The volume of the plant can be estimated by the calculation:

$$\text{Volume(voxels)} = \sqrt{\text{TopArea(pixels)}} \times \sqrt{\text{Side1Area(pixels)}} \times \sqrt{\text{Side2Area(pixels)}}$$

In the equation above the units of volume and area are "arbitrary units". Arbitrary units are entirely sufficient to detect gene effects on plant size and growth in this system because what is desired is to detect differences (both positive-larger and negative-smaller) from the experimental mean, or control mean. The arbitrary units of size (e.g. area) may be trivially converted to physical measurements by the addition of a physical reference to the imaging process. For instance, a physical reference of known area can be included in both top and side imaging processes. Based on the area of these physical references a conversion factor can be determined to allow conversion from pixels to a unit of area such as square centimeters ($cm^2$). The physical reference may or may not be an independent sample. For instance, the pot, with a known diameter and height, could serve as an adequate physical reference.

Color Classification:

The imaging technology may also be used to determine plant color and to assign plant colors to various color classes. The assignment of image colors to color classes is an inherent feature of the LemnaTec software. With other image analysis software systems color classification may be determined by a variety of computational approaches.

For the determination of plant size and growth parameters, a useful classification scheme is to define a simple color scheme including two or three shades of green and, in addition, a color class for chlorosis, necrosis and bleaching, should these conditions occur. A background color class which includes non plant colors in the image (for example pot and soil colors) is also used and these pixels are specifically excluded from the determination of size. The plants are analyzed under controlled constant illumination so that any change within one plant over time, or between plants or different batches of plants (e.g. seasonal differences) can be quantified.

In addition to its usefulness in determining plant size growth, color classification can be used to assess other yield component traits. For these other yield component traits additional color classification schemes may be used. For instance, the trait known as "staygreen", which has been associated with improvements in yield, may be assessed by a color classification that separates shades of green from shades of yellow and brown (which are indicative of senescing tissues). By applying this color classification to images taken toward the end of the T0 or T1 plants' life cycle, plants that have increased amounts of green colors relative to yellow and brown colors (expressed, for instance, as Green/Yellow Ratio) may be identified. Plants with a significant difference in this Green/Yellow ratio can be identified as carrying transgenes which impact this important agronomic trait.

The skilled plant biologist will recognize that other plant colors arise which can indicate plant health or stress response (for instance anthocyanins), and that other color classification schemes can provide further measures of gene action in traits related to these responses.

Plant Architecture Analysis:

Transgenes which modify plant architecture parameters may also be identified using the present invention, including such parameters as maximum height and width, internodal distances, angle between leaves and stem, number of leaves starting at nodes and leaf length. The LemnaTec system software may be used to determine plant architecture as follows. The plant is reduced to its main geometric architecture in a first imaging step and then, based on this image, parameterized identification of the different architecture parameters can be performed. Transgenes that modify any of these architecture parameters either singly or in combination can be identified by applying the statistical approaches previously described.

Pollen Shed Date:

Pollen shed date is an important parameter to be analyzed in a transformed plant, and may be determined by the first appearance on the plant of an active male flower. To find the male flower object, the upper end of the stem is classified by color to detect yellow or violet anthers. This color classification analysis is then used to define an active flower, which in turn can be used to calculate pollen shed date.

Alternatively, pollen shed date and other easily visually detected plant attributes (e.g. pollination date, first silk date) can be recorded by the personnel responsible for performing plant care. To maximize data integrity and process efficiency this data is tracked by utilizing the same barcodes utilized by the LemnaTec light spectrum digital analyzing device. A computer with a barcode reader, a palm device, or a notebook PC may be used for ease of data capture recording time of observation, plant identifier, and the operator who captured the data.

Orientation of the Plants:

Mature maize plants grown at densities approximating commercial planting often have a planar architecture. That is, the plant has a clearly discernable broad side, and a narrow side. The image of the plant from the broadside is determined. To each plant a well defined basic orientation is assigned to obtain the maximum difference between the broadside and edgewise images. The top image is used to determine the main axis of the plant, and an additional rotating device is used to turn the plant to the appropriate orientation prior to starting the main image acquisition.

Example 18

Screening of Gaspe Flint Derived Maize Lines for Drought Tolerance

Transgenic Gaspe Flint derived maize lines containing the candidate gene can be screened for tolerance to drought stress in the following manner.

Transgenic maize plants are subjected to well-watered conditions (control) and to drought-stressed conditions. Transgenic maize plants are screened at the T1 stage or later.

Stress is imposed starting at 10 to 14 days after sowing (DAS) or 7 days after transplanting, and is continued through to silking. Pots are watered by an automated system fitted to timers to provide watering at 25 or 50% of field capacity during the entire period of drought-stress treatment. The intensity and duration of this stress will allow identification of the impact on vegetative growth as well as on the anthesis-silking interval.

Potting mixture: A mixture of ⅓ TURFACE® (Profile Products LLC, IL, USA), ⅓ sand and ⅓ SB300 (Sun Gro Horticulture, WA, USA) can be used. The SB300 can be replaced with Fafard Fine-Germ (Conrad Fafard, Inc., MA, USA) and the proportion of sand in the mixture can be reduced. Thus, a final potting mixture can be ⅜ (37.5%) TURFACE®, ⅜ (37.5%) Fafard and ¼ (25%) sand.

Field Capacity Determination: The weight of the soil mixture (w1) to be used in one S200 pot (minus the pot weight) is measured. If all components of the soil mix are not dry, the soil is dried at 100° C. to constant weight before determining w1. The soil in the pot is watered to full saturation and all the gravitational water is allowed to drain out. The weight of the soil (w2) after all gravitational water has seeped out (minus the pot weight) is determined. Field capacity is the weight of the water remaining in the soil obtained as w2−w1. It can be written as a percentage of the oven-dry soil weight.

Stress Treatment: During the early part of plant growth (10 DAS to 21 DAS), the well-watered control has a daily watering of 75% field capacity and the drought-stress treatment has a daily watering of 25% field capacity, both as a single daily dose at or around 10 AM. As the plants grow bigger, by 21 DAS, it will become necessary to increase the daily watering of the well-watered control to full field capacity and the drought stress treatment to 50% field capacity.

Nutrient Solution: A modified Hoagland's solution at 1/16 dilution with tap water is used for irrigation.

TABLE 8

Preparation of 20 L of Modified Hoagland's Solution Using the Following Recipe:

| Component | Amount/20 L |
|---|---|
| 10X Micronutrient Solution | 16 mL |
| $KH_2PO_4$ (MW: 136.02) | 22 g |
| $MgSO_4$ (MW: 120.36) | 77 g |
| $KNO_3$ (MW: 101.2) | 129.5 g |
| $Ca(NO_3)_2{\bullet}4H_20$ (MW: 236.15) | 151 g |
| $NH_4NO_3$ (MW: 80.04) | 25.6 g |
| Sprint 330 (Iron chelate) | 32 g |

TABLE 9

Preparation of 1 L of 10X Micronutrient Solution Using the Following Recipe:

| Component | mg/L | Concentration |
|---|---|---|
| $H_3BO_3$ | 1854 | 30 mM |
| $MnCl_2{\bullet}4H_20$ | 1980 | 10 mM |
| $ZnSO_4{\bullet}7H_20$ | 2874 | 10 mM |
| $CuSO_4{\bullet}5H_20$ | 250 | 1 mM |
| $H_2MoO_4{\bullet}H_20$ | 242 | 1 mM |

Fertilizer grade $KNO_3$ is used.

It is useful to add half a teaspoon of OSMOCOTE® (NPK 15:9:12) to the pot at the time of transplanting or after emergence (The Scotts Miracle-Gro Company, OH, USA).

Border plants: Place a row of border plants on bench-edges adjacent to the glass walls of the greenhouse or adjacent to other potential causes of microenvironment variability such as a cooler fan.

Automation: Watering can be done using PVC pipes with drilled holes to supply water to systematically positioned pots using a siphoning device. Irrigation scheduling can be done using timers.

Statistical analysis: Mean values for plant size, color and chlorophyll fluorescence recorded on transgenic events under different stress treatments will be exported to Spotfire (Spotfire, Inc., MA, USA). Treatment means will be evaluated for differences using Analysis of Variance.

Replications: Eight to ten individual plants are used per treatment per event.

Observations Made: Lemnatec measurements are made three times a week throughout growth to capture plant-growth rate. Leaf color determinations are made three times a week throughout the stress period using Lemnatec. Chlorophyll fluorescence is recorded as PhiPSII (which is indicative of the operating quantum efficiency of photosystem II photochemistry) and Fv'/Fm' (which is the maximum efficiency of photosystem II) two to four times during the experimental period, starting at 11 AM on the measurement days, using the Hansatech FMS2 instrument (LemnaTec GmbH, Wurselen, Germany). Measurements are started during the stress period at the beginning of visible drought stress symptoms, namely, leaf greying and the start of leaf rolling until the end of the experiment and measurements are recorded on the youngest most fully expanded leaf. The dates of tasseling and silking on individual plants are recorded, and the ASI is computed.

The above methods may be used to select transgenic plants with increased drought tolerance when compared to a control plant not comprising said recombinant DNA construct.

Example 19

Yield Analysis of Maize Lines with the *Arabidopsis* Lead Gene

A recombinant DNA construct containing a validated *Arabidopsis* gene can be introduced into an elite maize inbred line either by direct transformation or introgression from a separately transformed line.

Transgenic plants, either inbred or hybrid, can undergo more vigorous field-based experiments to study yield enhancement and/or stability under well-watered and water-limiting conditions.

Subsequent yield analysis can be done to determine whether plants that contain the validated *Arabidopsis* lead gene have an improvement in yield performance under water-limiting conditions, when compared to the control plants that do not contain the validated *Arabidopsis* lead gene. Specifically, drought conditions can be imposed during the flowering and/or grain fill period for plants that contain the validated *Arabidopsis* lead gene and the control plants. Reduction in yield can be measured for both. Plants containing the validated *Arabidopsis* lead gene have less yield loss relative to the control plants, for example, at least 50% less yield loss.

The above method may be used to select transgenic plants with increased yield, under water-limiting conditions and/or well-watered conditions, when compared to a control plant not comprising said recombinant DNA construct.

Example 20A

Preparation of Maize Ferrochelatase-I Lead Gene Expression Vector for Transformation of Maize Clone cfp5n.pk009.j16 encodes a maize ferrochelatase-I protein designated "ZmFeC-Ia" (SEQ ID NO:10). The protein-coding region of clone cfp5n.pk009.j16 was introduced into the INVITROGEN™ vector pENTR/D-TOPO® to create entry clone PHP30949 (SEQ ID NO:55).

Using INVITROGEN's™ GATEWAY® technology, an LR Recombination Reaction was performed with an entry clone (PHP30949) and a destination vector (PHP28647) to create the precursor plasmid PHP30963. The vector PHP30963 contains the following expression cassettes:

1. Ubiquitin promoter::moPAT::PinII terminator; cassette expressing the PAT herbicide resistance gene used for selection during the transformation process.

2. LTP2 promoter::DS-RED2::PinII terminator; cassette expressing the DS-RED color marker gene used for seed sorting.

3. Ubiquitin promoter:ZmFeC-1a::PinII terminator; cassette overexpressing the gene of interest, maize ferrochelatase-I.

Example 20B

Transformation of Maize with Maize Ferrochelatase-I Lead Gene Using *Agrobacterium*

The ZmFeC-1a expression cassette present in vector PHP30963 can be introduced into a maize inbred line, or a transformable maize line derived from an elite maize inbred line, using *Agrobacterium*-mediated transformation as described in Examples 12 and 13.

Vector PHP30963 can be electroporated into the LBA4404 *Agrobacterium* strain containing vector PHP10523 (FIG. 7; SEQ ID NO:37) to create the co-integrate vector PHP30976. The co-integrate vector is formed by recombination of the 2 plasmids, PHP30963 and PHP10523, through the COS recombination sites contained on each vector. The co-integrate vector PHP30976 contains the same 3 expression cassettes as above (Example 14A) in addition to other genes (TET, TET, TRFA, ORI terminator, CTL, ORI V, VIR C1, VIR C2, VIR G, VIR B) needed for the *Agrobacterium* strain and the *Agrobacterium*-mediated transformation.

Example 21

Preparation of Maize Expression Plasmids for Transformation into Gaspe Flint Derived Maize Lines Clone cfp5n.pk009.j16 encodes a complete maize ferrochelatase-I homolog designated "ZmFeC-Ia" (SEQ ID NO:10). Clone cfp3n.pk004.f12 encodes a different complete maize ferrochelatase-I homolog designated "ZmFeC-Ib" (SEQ ID NO:8). Clone cfp5n.pk064.n7 also encodes the ZmFeC-Ib protein (SEQ ID NO:8), however the nucleotide sequence of cfp5n.pk064.n7 (SEQ ID NO:56) differs from the nucleotide sequence of cfp3n.pk004.f12 (SEQ ID NO:7) in that it contains a 12 base pair insertion in the 5'-UTR, 8 nucleotides before the ATG start codon.

Using the INVITROGEN™ GATEWAY® Recombination technology described in Example 9, the three clones encoding maize ferrochelatase-I homologs were directionally cloned into the destination vector PHP23236 (SEQ ID NO:36; FIG. 6) to create the expression vectors listed in Table 10. Each expression vector contains the cDNA of interest under control of the UBI promoter and is a T-DNA binary vector for *Agrobacterium*-mediated transformation into corn as described, but not limited to, the examples described herein.

TABLE 10

Maize Ferrochelatase-I Expression Vectors

| Protein | Clone Origin | SEQ ID NO: (Amino Acid) | Expression Vector |
|---|---|---|---|
| ZmFeC-la | cfp5n.pk009.j16 (FIS) | 10 | PHP30829 |
| ZmFeC-lb | cfp3n.pk004.f12 (FIS) | 8 | PHP30745 |
| ZmFeC-lb | cfp5n.pk064.n7 (FIS) | 8 | PHP30761 |

Example 22

Transformation and Evaluation of Gaspe Flint Derived Maize Lines for Drought Tolerance Gaspe Flint derived maize lines were transformed via *Agrobacterium* using the following plasmid DNAs: PHP31419 (AtFeC-I; At5g26030); PHP33089 (AtFeC-II; At2g30390); PHP30829 (ZmFeC-1a; cfp5n.pk009.j16); PHP30745 (ZmFeC-Ib; cfp3n.pk004.f12) and PHP30761 (ZmFeC-Ib; cfp5n.pk064.n7). Four transformation events for each plasmid construct were evaluated for drought tolerance in the following manner. For plant growth, the soil mixture consisted of ⅓ TURFACE®, ⅓ SB300 and ⅓ sand. All pots were filled with the same amount of soil±10 grams. Pots were brought up to 100% field capacity ("FC") by hand watering. All plants were maintained at 60% FC using a 20-10-20 (N-P-K) 125 ppm N nutrient solution. Throughout the experiment pH was monitored at least three times weekly for each table. Starting at 13 days after planting (DAP), the experiment was divided into two treatment groups, well watered and reduce watered. All plants comprising the reduced watered treatment were maintained at 40% FC while plants in the well watered treatment were maintained at 80% FC. Reduced watered plants were grown for 10 days under chronic drought stress conditions (40% FC). All plants were imaged daily throughout chronic stress period. Plants were sampled for metabolic profiling analyses at the end of chronic drought period, 22 DAP. At the conclusion of the chronic stress period all plants were imaged and measured for chlorophyll fluorescence. Reduced watered plants were subjected to a severe drought stress period followed by a recovery period, 23-31 DAP and 32-34 DAP respectively. During the severe drought stress, water and nutrients were withheld until the plants reached 8% FC. At the conclusion of severe stress and recovery periods all plants were again imaged and measured for chlorophyll fluorescence. The probability of a greater Student's t Test was calculated for each transgenic mean compared to the appropriate null mean (either segregant null or construct null). A minimum (P<t) of 0.1 was used as a cut off for a statistically significant result.

Tables 11-20 show the variables for each transgenic event that were significantly altered, as compared to the segregant nulls. A "positive effect" was defined as statistically significant improvement in that variable for the transgenic event relative to the null control. A "negative effect" was defined as a statistically significant improvement in that variable for the null control relative to the transgenic event. Tables 11, 13, 15, 17, and 19 present the number of variable with a significant change for individual events transformed with each of the five plasmid DNA constructs. Tables 12, 14, 16, 18 and 20 present the number of events for each construct that showed a significant change for each individual variable.

TABLE 11

Number of Variables with a Significant Change* for Individual Events Transformed with PHP31419 Encoding AtFeC-I (At5g26030)

| | Reduced Water | | Well Watered | |
|---|---|---|---|---|
| Event | Positive Effect | Negative Effect | Positive Effect | Negative Effect |
| EA2392.498.1.2 | 2 | 1 | 4 | 0 |
| EA2392.498.1.3 | 3 | 1 | 1 | 3 |
| EA2392.498.1.5 | 0 | 0 | 3 | 0 |
| EA2392.498.1.6 | 12 | 0 | 3 | 0 |

*P-value less than or equal to 0.1

TABLE 12

Number of Events Transformed with PHP31419 Encoding AtFeC-I (At5g26030) with a Significant Change* for Individual Variables

| | Reduced Water | | Well Watered | |
|---|---|---|---|---|
| Variable | Positive Effect | Negative Effect | Positive Effect | Negative Effect |
| % area chg_start chronic - acute2 | 1 | 0 | 1 | 0 |
| % area chg_start chronic - end chronic | 1 | 0 | 2 | 0 |
| % area chg_start chronic - harvest | 1 | 0 | 1 | 0 |
| % area chg_start chronic - recovery 24 hr | 1 | 0 | 1 | 1 |
| fv/fm_acute1 | 2 | 0 | 2 | 0 |
| fv/fm_acute2 | 1 | 0 | 1 | 0 |
| leaf rolling_harvest | 2 | 0 | 0 | 0 |

TABLE 12-continued

Number of Events Transformed with PHP31419 Encoding AtFeC-I (At5g26030) with a Significant Change* for Individual Variables

| | Reduced Water | | Well Watered | |
|---|---|---|---|---|
| Variable | Positive Effect | Negative Effect | Positive Effect | Negative Effect |
| leaf rolling_recovery 24 hr | 2 | 0 | 1 | 0 |
| psii_acute1 | 2 | 0 | 2 | 0 |
| psii_acute2 | 1 | 0 | 0 | 0 |
| sgr - r2 > 0.9 | 2 | 0 | 0 | 0 |
| shoot dry weight | 0 | 1 | 0 | 1 |
| shoot fresh weight | 1 | 1 | 0 | 1 |

*P-value less than or equal to 0.1

TABLE 13

Number of Variables with a Significant Change* for Individual Events Transformed with PHP33089 Encoding AtFeC-II (At2g30390)

| | Reduced Water | | Well Watered | |
|---|---|---|---|---|
| Event | Positive Effect | Negative Effect | Positive Effect | Negative Effect |
| EA2534.088.2.2 | 0 | 3 | 1 | 0 |
| EA2534.088.2.4 | 3 | 1 | 2 | 2 |
| EA2534.088.2.5 | 6 | 0 | 2 | 2 |
| EA2534.088.2.8 | 1 | 3 | 0 | 2 |

*P-value less than or equal to 0.1

TABLE 14

Number of Events Transformed with PHP33089 Encoding AtFeC-II (At2g30390) with a Significant Change* for Individual Variables

| | Reduced Water | | Well Watered | |
|---|---|---|---|---|
| Variable | Positive Effect | Negative Effect | Positive Effect | Negative Effect |
| % area chg_start chronic - end chronic | 2 | 0 | 1 | 0 |
| % area chg_start chronic - end severe | 1 | 2 | 0 | 0 |
| % area chg_start chronic - recovery 48 hr | 0 | 1 | 0 | 0 |
| fv/fm_end severe | 1 | 2 | 1 | 0 |
| fv/fm_recovery 48 hr | 1 | 0 | 0 | 1 |
| fv/fm_start severe | 1 | 0 | 0 | 0 |
| leaf rolling_recovery 24 hr | 0 | 0 | 1 | 1 |
| psii_end severe | 1 | 2 | 1 | 0 |
| psii_recovery 48 hr | 1 | 0 | 0 | 2 |
| psii_start severe | 1 | 0 | 1 | 2 |
| sgr - r2 > 0.9 | 0 | 0 | 0 | 0 |
| shoot dry weight | 1 | 0 | 0 | 0 |
| shoot fresh weight | 0 | 0 | 0 | 0 |

*P-value less than or equal to 0.1

TABLE 15

Number of Variables with a Significant Change* for Individual Events Transformed with PHP30829 Encoding MzFeC-Ia (cfp5n.pk009.j16)

| | Reduced Water | | Well Watered | |
|---|---|---|---|---|
| Event | Positive Effect | Negative Effect | Positive Effect | Negative Effect |
| EA2391.472.1.10 | 0 | 5 | 3 | 3 |
| EA2391.472.1.2 | 0 | 2 | 6 | 1 |

TABLE 15-continued

Number of Variables with a Significant Change* for Individual Events Transformed with PHP30829 Encoding MzFeC-Ia (cfp5n.pk009.j16)

| | Reduced Water | | Well Watered | |
|---|---|---|---|---|
| Event | Positive Effect | Negative Effect | Positive Effect | Negative Effect |
| EA2391.472.1.3 | 0 | 4 | 2 | 0 |
| EA2391.472.1.4 | 2 | 2 | 3 | 0 |

*P-value less than or equal to 0.1

TABLE 16

Number of Events Transformed with PHP30829 Encoding MzFeC-Ia (cfp5n.pk009.j16) with a Significant Change* for Individual Variables

| | Reduced Water | | Well Watered | |
|---|---|---|---|---|
| Variable | Positive Effect | Negative Effect | Positive Effect | Negative Effect |
| % area chg_start chronic - end chronic | 0 | 2 | 0 | 0 |
| % area chg_start chronic - harvest | 0 | 1 | 3 | 0 |
| % area chg_start chronic - recovery 24 hr | 0 | 0 | 0 | 0 |
| % area chg_start chronic - recovery 48 hr | 0 | 1 | 0 | 0 |
| fv/fm_acute1 | 0 | 0 | 2 | 1 |
| fv/fm_acute2 | 1 | 1 | 2 | 0 |
| leaf rolling_recovery 24 hr | 0 | 1 | 1 | 0 |
| leaf rolling_recovery 48 hr | 0 | 2 | 1 | 0 |
| psii_acute1 | 0 | 0 | 2 | 1 |
| psii_acute2 | 1 | 1 | 1 | 1 |
| sgr - r2 > 0.9 | 0 | 2 | 1 | 0 |
| shoot dry weight | 0 | 1 | 0 | 1 |
| shoot fresh weight | 0 | 1 | 1 | 0 |

*P-value less than or equal to 0.1

TABLE 17

Number of Variables with a Significant Change* for Individual Events Transformed with PHP30745 Encoding MzFeC-Ib (cfp3n.pk004.f12)

| | Reduced Water | | Well Watered | |
|---|---|---|---|---|
| Event | Positive Effect | Negative Effect | Positive Effect | Negative Effect |
| EA2392.447.1.1 | 4 | 1 | 4 | 0 |
| EA2392.447.1.3 | 0 | 3 | 2 | 7 |
| EA2392.447.1.5 | 0 | 0 | 2 | 1 |
| EA2392.447.1.9 | 2 | 4 | 4 | 1 |

*P-value less than or equal to 0.1

TABLE 18

Number of Events Transformed with PHP30745 Encoding MzFeC-Ib (cfp3n.pk004.f12) with a Significant Change* for Individual Variables

| | Reduced Water | | Well Watered | |
|---|---|---|---|---|
| Variable | Positive Effect | Negative Effect | Positive Effect | Negative Effect |
| % area chg_start chronic - end chronic | 1 | 0 | 3 | 1 |
| % area chg_start chronic - end severe | 0 | 0 | 2 | 1 |
| % area chg_start chronic - recovery 48 hr | 0 | 0 | 2 | 1 |

TABLE 18-continued

Number of Events Transformed with PHP30745 Encoding MzFeC-Ib (cfp3n.pk004.f12) with a Significant Change* for Individual Variables

| | Reduced Water | | Well Watered | |
|---|---|---|---|---|
| Variable | Positive Effect | Negative Effect | Positive Effect | Negative Effect |
| fv/fm_end severe | 2 | 0 | 0 | 0 |
| fv/fm_recovery 48 hr | 1 | 1 | 0 | 1 |
| fv/fm_start severe | 0 | 1 | 0 | 1 |
| leaf rolling_recovery 48 hr | 0 | 0 | 0 | 0 |
| psii_end severe | 0 | 0 | 0 | 0 |
| psii_recovery 48 hr | 0 | 1 | 1 | 2 |
| psii_start severe | 0 | 2 | 0 | 1 |
| shoot dry weight | 2 | 0 | 2 | 1 |
| shoot fresh weight | 2 | 1 | 2 | 0 |

*P-value less than or equal to 0.1

TABLE 19

Number of Variables with a Significant Change* for Individual Events Transformed with PHP30761 Encoding MzFeC-Ib (cfp5n.pk064.n7)

| | Reduced Water | | Well Watered | |
|---|---|---|---|---|
| Event | Positive Effect | Negative Effect | Positive Effect | Negative Effect |
| EA2392.441.1.1 | 0 | 0 | 0 | 1 |
| EA2392.441.1.2 | 0 | 0 | 2 | 0 |
| EA2392.441.1.4 | 5 | 0 | 7 | 3 |
| EA2392.441.1.7 | 5 | 3 | 0 | 0 |

*P-value less than or equal to 0.1

TABLE 20

Number of Events Transformed with PHP30761 Encoding MzFeC-Ib (cfp5n.pk064.n7) with a Significant Change* for Individual Variables

| | Reduced Water | | Well Watered | |
|---|---|---|---|---|
| Variable | Positive Effect | Negative Effect | Positive Effect | Negative Effect |
| % area chg_start chronic - end chronic | 0 | 1 | 0 | 1 |
| % area chg_start chronic - end severe | 0 | 1 | 0 | 0 |
| % area chg_start chronic —recovery 48 hr | 0 | 0 | 0 | 0 |
| fv/fm_end severe | 2 | 0 | 1 | 0 |
| fv/fm_recovery 48 hr | 2 | 0 | 1 | 0 |
| fv/fm_start severe | 0 | 0 | 2 | 0 |
| leaf rolling_recovery 48 hr | 1 | 0 | 1 | 0 |
| psii_end severe | 2 | 0 | 1 | 0 |
| psii_recovery 48 hr | 2 | 0 | 1 | 0 |
| psii_start severe | 1 | 0 | 1 | 0 |
| sgr - r2 > 0.9 | 0 | 0 | 0 | 1 |
| shoot dry weight | 0 | 1 | 1 | 2 |
| shoot fresh weight | 0 | 0 | 0 | 0 |

*P-value less than or equal to 0.1

For each of the five constructs evaluated, the statistical value associated with each improved variable is presented in FIGS. 14A-23. A significant positive result had a P-value of less than or equal to 0.1. The results for individual transformed maize lines are presented in FIGS. 14A-14B, 16A-16B, 18A-18B, 20A-20B and 22A-22B. The summary evaluations for each of the five constructs are presented in FIGS. 15, 17, 19, 21, and 23.

Example 23

Screening of Inbred Derived Maize Lines for Drought Tolerance

A transformable maize line derived from an elite maize inbred line was transformed with PHP30829 which encodes the maize ferrochelatase-I protein, MzFeC-1a (SEQ ID NO:10). Seed of transgenic events from the PHP30829 transformation were separated into transgenic and null seed using a seed color marker. The Fv'/Fm' and Phi PSII data were collected from a drought seedling assay following a procedure similar to the one described in Example 18 with the following modifications: an elite maize hybrid seedling was used for the assay instead of a Gaspe Flint derived maize line; and the chlorophyll fluorescence data were collected only during recovery from moderate drought stress (or chronic drought stress). The experiment was designed and analyzed as a Randomized Complete Block Design with the events including the construct null as treatments. A number of individual events were found to have higher Fv'/Fm' and/or Phi PSII values during drought stress relative to the null segregant control. The data is presented in the Table below.

TABLE 21

Fv'/Fm' and Phi PSII Values For Individual Events Transformed With PHP30829 Encoding MzFeC-Ia (cfp5n.pk009.j16)

| Event | Fv'/Fm' | Phi PSII |
|---|---|---|
| E7733.78.1.1 | 0.421 | 0.330[a] |
| E7733.78.1.2 | 0.462 | 0.407[a] |
| E7733.78.2.20 | 0.520[a] | 0.420[a] |
| E7733.78.4.1 | 0.428 | 0.339[a] |
| E7733.78.2.10 | 0.475[a] | 0.398[a] |
| E7733.78.2.2 | 0.360[b] | 0.284 |
| E7733.78.2.6 | 0.373[b] | 0.289 |
| E7733.78.2.7 | 0.469[a] | 0.392[a] |
| 30976-CN[c] | 0.392 | 0.314 |

[a]Positive and statistically significant at the 0.1 level of confidence
[b]Negative and statistically significant at the 0.1 level of confidence
[c]Null segregant used as a control Example 24

Transformation and Evaluation of Soybean with Soybean Homologs of Validated Lead Genes Based on homology searches, one or several candidate soybean homologs of validated *Arabidopsis* lead genes can be identified and also be assessed for their ability to enhance drought tolerance in soybean. Vector construction, plant transformation and phenotypic analysis will be similar to that in previously described Examples.

Example 25

Transformation of *Arabidopsis* with Maize and Soybean Homologs of Validated Lead Genes Soybean and maize homologs to validated *Arabidopsis* lead genes can be transformed into *Arabidopsis* under control of the 35S promoter and assessed for their ability to enhance drought tolerance in *Arabidopsis*. Vector construction, plant transformation and phenotypic analysis will be similar to that in previously described Examples.

What is claimed is:

1. An isolated polynucleotide comprising:

(a) a nucleotide sequence encoding a polypeptide with ferrochelatase activity, wherein the polypeptide has an amino acid sequence of at least 95% sequence identity, based on the Clustal V method of alignment with pairwise alignment default parameters of KTUPLE=1, GAP PENALTY=3, WINDOW=5 and DIAGONALS SAVED=5, when compared to SEQ ID NO:28, or (b) the full complement of the nucleotide sequence of (a).

2. The polynucleotide of claim 1, wherein the polypeptide has an amino acid sequence of at least 97% sequence identity, based on the Clustal V method of alignment with the pairwise alignment default parameters, when compared to SEQ ID NO:28.

3. The polynucleotide of claim 1, wherein the amino acid sequence of the polypeptide comprises SEQ ID NO:28.

4. The polynucleotide of claim 1 wherein the nucleotide sequence comprises SEQ ID NO:27.

5. A vector comprising the polynucleotide of claim 1.

6. A recombinant DNA construct comprising the isolated polynucleotide of claim 1 operably linked to at least one regulatory sequence.

7. A cell comprising the recombinant DNA construct of claim 6, wherein the cell is selected from the group consisting of a bacterial cell, a yeast cell, and insect cell and a plant cell.

8. A plant or seed comprising the recombinant DNA construct of claim 6.

9. The plant or seed of claim 8 wherein the plant or seed is selected from the group consisting of: maize, soybean, sunflower, sorghum, canola, wheat, alfalfa, cotton, rice, barley and millet.

* * * * *